(12) United States Patent
Ting et al.

(10) Patent No.: US 8,759,482 B2
(45) Date of Patent: Jun. 24, 2014

(54) KINETICALLY EFFICIENT SUBSTRATE FOR LIPOIC ACID LIGASE

(75) Inventors: Alice Y. Ting, Allston, MA (US); Sujiet Puthenveetil, North Attleborough, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 292 days.

(21) Appl. No.: 12/907,470

(22) Filed: Oct. 19, 2010

(65) Prior Publication Data
US 2011/0130348 A1 Jun. 2, 2011

Related U.S. Application Data

(60) Provisional application No. 61/252,881, filed on Oct. 19, 2009.

(51) Int. Cl.
*A61K 38/00* (2006.01)
*C07K 7/08* (2006.01)

(52) U.S. Cl.
USPC ........... 530/327; 530/300; 530/328; 514/21.5

(58) Field of Classification Search
None
See application file for complete search history.

(56) References Cited

U.S. PATENT DOCUMENTS

| | | | |
|---|---|---|---|
| 5,252,466 A | 10/1993 | Cronan, Jr. | |
| 7,056,683 B2 | 6/2006 | Ting | |
| 7,172,877 B2 | 2/2007 | Ting | |
| 8,137,925 B2 * | 3/2012 | Ting et al. | 435/7.72 |
| 2004/0115777 A1 | 6/2004 | Budworth et al. | |
| 2005/0233389 A1 | 10/2005 | Ting et al. | |
| 2007/0099248 A1 | 5/2007 | Ting et al. | |
| 2007/0105162 A1 | 5/2007 | Ting et al. | |
| 2009/0149631 A1 | 6/2009 | Ting et al. | |
| 2012/0129159 A1 | 5/2012 | Ting et al. | |
| 2012/0214201 A1 | 8/2012 | Ting et al. | |

FOREIGN PATENT DOCUMENTS

WO  WO 2005/014570 A1  2/2005

OTHER PUBLICATIONS

Adams et al., New biarsenical ligands and tetracysteine motifs for protein labeling in vitro and in vivo: synthesis and biological applications. J Am Chem Soc. May 29, 2002;124(21):6063-76.
Agard et al., A comparative study of bioorthogonal reactions with azides. ACS Chem Biol. Nov. 21, 2006;1(10):644-8.
Ali et al., Isolation and characterization of lipoylated and unlipoylated domains of the E2p subunit of the pyruvate dehydrogenase complex of *Escherichia coli*. Biochem J. Oct. 1, 1990;271(1);139-45.
Alper et al., Metal catalyzed diazo transfer for the synthesis of azides from amines. Tetrahedron Letters. 1996;37:6029-6032.

Amano et al., Chemical xenobiotics and mitochondrial autoantigens in primary biliary cirrhosis: identification of antibodies against a common environmental, cosmetic, and food additive, 2-octynoic acid. J Immunol. May 1, 2005;174(9):5874-83.
Anderson et al., Surface distribution and recycling of the low density lipoprotein receptor as visualized with antireceptor antibodies. J Cell Biol. Jun. 1982;93(3):523-31.
Barak, et al., Fluorescent low density lipoprotein for observation of dynamics of individual receptor complexes on cultured human fibroblasts. J Cell Biol. Sep. 1981;90(3):595-604.
Baruah et al., An engineered aryl azide ligase for site-specific mapping of protein-protein interactions through photo-cross-linking. Angew Chem Int Ed Engl. 2008;47(37):7018-21.
Branden et al., Prediction, engineering and design of protein structures. Introduction to Protein Structure. Garland Publishing, Inc., New York. 1991: 247.
Brock et al., Comparison of fixation protocols for adherent cultured cells applied to a GFP fusion protein of the epidermal growth factor receptor. Cytometry. Apr. 1, 1999;35(4):353-62.
Chen et al., Phage display evolution of a peptide substrate for yeast biotin ligase and application to two-color quantum dot labeling of cell surface proteins. J Am Chem Soc. May 23, 2007;129(20):6619-25. Epub May 2, 2007.
Chen et al., Site-specific labeling of cell surface proteins with biophysical probes using biotin ligase. Nat Methods. Feb. 2005;2(2):99-104. Epub Jan. 21, 2005.
Cronan et al., Function, attachment and synthesis of lipoic acid in *Escherichia coli*. Adv Microb Physiol. 2005;50:103-46.
Cui et al., Identification and solution structures of a single domain biotin/lipoyl attachment protein from *Bacillus subtilis*. J Biol Chem. Jul. 21, 2006;281(29):20598-607. Epub May 14, 2006.
Dardel et al., Expression in *Escherichia coli* of a sub-gene encoding the lipoyl domain of the pyruvate dehydrogenase complex of *Bacillus stearothermophilus*. FEBS Lett. May 21, 1990;264(2):206-10. Erratum in: FEBS Lett Jul. 30, 1990;268(1):306.
Dardel et al., Three-dimensional structure of the lipoyl domain from *Bacillus stearothermophilus* pyruvate dehydrogenase multienzyme complex. J Mol Biol. Feb. 20, 1993;229(4):1037-48.
Debant et al., Receptor cross-linking restores an insulin metabolic effect altered by mutation on tyrosine 1162 and tyrosine 1163. Biochemistry. Jan. 10, 1989;28(1):14-7.
Deisseroth et al., Next-generation optical technologies for illuminating genetically targeted brain circuits. J Neurosci. Oct. 11, 2006;26(41):10380-6.
Devadas et al., Substrate specificity of *Saccharomyces cerevisiae* myristoyl-CoA: protein N-myristoyltransferase. Analysis of fatty acid analogs containing carbonyl groups, nitrogen heteroatoms, and nitrogen heterocycles in an in vitro enzyme assay and subsequent identification of inhibitors of human immunodeficiency virus I replication. J Biol Chem. Apr. 15, 1992;267(11):7224-39.
Dubois et al., Digital holographic microscopy for the three-dimensional dynamic analysis of in vitro cancer cell migration. J Biomed Opt. Sep.-Oct. 2006;11(5):054032-1-5.
Fernandez-Suarez et al., Redirecting lipoic acid ligase for cell surface protein labeling with small-molecule probes. Nat Biotechnol. Dec. 2007;25(12):1483-7. Epub Dec. 2, 2007. Supplementary Information 18 pages.

(Continued)

*Primary Examiner* — James H Alstrum Acevedo
*Assistant Examiner* — Li Lee
(74) *Attorney, Agent, or Firm* — Wolf, Greenfield & Sacks, P.C.

(57) ABSTRACT

The invention provides methods for identifying and optimizing peptide substrates for enzymes such as lipoic acid ligase (LplA).

19 Claims, 13 Drawing Sheets

(56) References Cited

OTHER PUBLICATIONS

Flanagan et al., The ephrins and Eph receptors in neural development. Annu Rev Neurosci. 1998;21:309-45. Review.

Fujiwara et al., Crystal structure of lipoate-protein ligase A from *Escherichia coli*. Determination of the lipoic acid-binding site. J Biol Chem. Sep. 30, 2005;280(39):33645-51. Epub Jul. 25, 2005.

Gama et al., Generation of epitope-tagged proteins by inverse polymerase chain reaction mutagenesis. Methods Mol Biol. 2002;182:77-83.

George, N. et al., Specific labeling of cell surface proteins with chemically diverse compounds. J Am Chem Soc. Jul. 28, 2004;126(29):8896-7.

Green et al., Purification and properties of the lipoate protein ligase of *Escherichia coli*. Biochem J. Aug. 1, 1995;309 ( Pt 3):853-62.

Green et al., Three-dimensional structure of a lipoyl domain from the dihydrolipoyl acetyltransferase component of the pyruvate dehydrogenase multienzyme complex of *Escherichia coli*. J Mol Biol. Apr. 28, 1995;248(2):328-43.

Griffin et al., Specific covalent labeling of recombinant protein molecules inside live cells. Science. Jul. 10, 1998;281(5374):269-72.

Griffin, The medicinal chemistry of the azido group. Prog Med Chem. 1994;31:121-232. Review.

Howard et al., Protein-protein interaction revealed by NMR T(2) relaxation experiments: the lipoyl domain and E1 component of the pyruvate dehydrogenase multienzyme complex of *Bacillus stearothermophilus*. J Mol Biol. Jan. 28, 2000;295(4):1023-37.

Howarth et al., A monovalent streptavidin with a single femtomolar biotin binding site. Nat Methods. Apr. 2006;3(4):267-73.

Howarth, et al., Targeting quantum dots to surface proteins in living cells with biotin ligase. Proc Natl Acad Sci U S A. May 24, 2005;102(21):7583-8. Epub May 16, 2005.

Jones et al., Restricted motion of the lipoyl-lysine swinging arm in the pyruvate dehydrogenase complex of *Escherichia coli*. Biochemistry. Jul. 25, 2000;39(29):8448-59.

Kiick et al., Incorporation of azides into recombinant proteins for chemoselective modification by the Staudinger ligation. Proc Natl Acad Sci U S A. Jan. 8, 2002;99(1):19-24. Epub Dec. 18, 2001.

Kim et al., Crystal structure of lipoate-protein ligase A bound with the activated intermediate: insights into interaction with lipoyl domains. J Biol Chem. Nov. 11, 2005;280(45):38081-9. Epub Sep. 2, 2005.

Lin et al., Transglutaminase-catalyzed site-specific conjugation of small-molecule probes to proteins in vitro and on the surface of living cells. J Am Chem Soc. Apr. 12, 2006;128(14):4542-3.

Marks et al., Chemical labeling strategies for cell biology. Nat Methods. Aug. 2006;3(8):591-6. Review.

McLean et al., Ligand regulation of green fluorescent protein-tagged forms of the human beta(1)- and beta(2)-adrenoceptors; comparisons with the unmodified receptors. Br J Pharmacol. Aug. 2000;130(8):1825-32.

Morris et al., Lipoic acid metabolism in *Escherichia coli:* the lplA and lipB genes define redundant pathways for ligation of lipoyl groups to apoprotein. J Bacteriol. Jan. 1995;177(1):1-10.

Nauman et al., Kinetic parameters for small-molecule drug delivery by covalent cell surface targeting. Biochim Biophys Acta. Dec. 5, 2001;1568(2):147-54.

Novis-Smith et al., Preparation of alkynes and dialkynes by reaction of mono-halo and dihaloalkanes with lithium acetylenide-ethylenediamine complex. Synthetic Communications. 1974; 441-442.

Pasquale, Eph receptor signalling casts a wide net on cell behaviour. Nat Rev Mol Cell Biol. Jun. 2005;6(6):462-75. Review. Erratum in: Nat Rev Mol Cell Biol. Jul. 2005;6(7):589.

Prescher et al., Chemistry in living systems. Nat Chem Biol. Jun. 2005;1(1):13-21. Review.

Puthenveetil et al., Yeast display evolution of a kinetically efficient 13-amino acid substrate for lipoic acid ligase. J Am Chem Soc. Nov. 18, 2009;131(45):16430-8. Epub Oct. 28, 2009.

Reche et al., Structure and selectivity in post-translational modification: attaching the biotinyl-lysine and lipoyl-lysine swinging arms in multifunctional enzymes. EMBO J. May 17, 1999;18(10):2673-82.

Ricaud et al., Three-dimensional structure of the lipoyl domain from the dihydrolipoyl succinyltransferase component of the 2-oxoglutarate dehydrogenase multienzyme complex of *Escherichia coli*. J Mol Biol. Nov. 22, 1996;264(1):179-90.

Saunders et al., Molecular cloning of a human homologue of *Drosophila* heterochromatin protein Hp1 using anti-centromere autoantibodies with anti-chromo specificity. J Cell Sci. Feb. 1993;104 ( Pt 2):573-82.

Scriven et al., Azides: their preparation and synthetic uses. Chemical Reviews. 1988;88:297-368.

Singh et al., Autocrine, paracrine and juxtacrine signaling by EGFR ligands. Cell Signal. Oct. 2005;17(10):1183-93. Review.

Tuli et al., Immunohistochemical localization of EGF, TGF-alpha, TGF-beta, and their receptors in rat corneas during healing of excimer laser ablation. Curr Eye Res. Sep. 2006;31(9):709-19.

UniProtKB Submission, Accession No. B2Q6T8; Sudarsunam et al.; Jun. 16, 2009.

Weiss et al., Signal transduction by lymphocyte antigen receptors. Cell. Jan. 28, 1994;76(2):263-74. Review.

Willnow, The low-density lipoprotein receptor gene family: multiple roles in lipid metabolism. J Mol Med. Mar. 1999;77(3):306-15. Review.

Wimmer-Kleikamp et al., Eph-modulated cell morphology, adhesion and motility in carcinogenesis. IUBMB Life. Jun. 2005;57(6):421-31. Review.

Yan et al., N-hydroxysuccinimide ester functionalized perfluorophenyl azides as novel photoactive heterobifunctional cross-linking reagents. The covalent immobilization of biomolecules to polymer surfaces. Bioconjug Chem. Mar.-Apr. 1994;5(2):151-7.

Zhou et al., Genetically encoded short peptide tags for orthogonal protein labeling by Sfp and AcpS phosphopantetheinyl transferases. ACS Chem Biol. May 22, 2007;2(5):337-46. Epub Apr. 27, 2007.

\* cited by examiner

A

B

C

A

| | Clone Name | Sequence | % Conversion by HPLC | N- or C-term fusion to HP1 |
|---|---|---|---|---|
| SEQ ID NO:1120 | LAP1 | GDEVLVEIETDKAVLEVP | 0.3 ± 0.1 | N |
| SEQ ID NO:1121 | LAP4.1 | GFELDKVWFDVDS | 47.2 ± 2.6 | N |
| SEQ ID NO:1122 | LAP4.2 | GFEIDKVWHDFPA | 23.6 ± 0.7 | N |
| SEQ ID NO:1123 | LAP4.3D | GFEHEKVWYDLDA | 55.9 ± 6.0 | N |
| SEQ ID NO:1 | LAP2 | GFEIDKVWYDLDA | 98.3 ± 0.8 | N |
| SEQ ID NO:1 | LAP2 | GFEIDKVWYDLDA | 64.0 ± 4.3 | C |
| SEQ ID NO:1124 | E2p | ...EQSLITVEGDKASMEVPAP... | 72.4 ± 2.8 | N/A |

B http://www.russell.embl-heidelberg.de/aas/other_images/lb3.gif

```
            (-) 54321*1234567  (+)
                GFEIDKVWYDLDA    SEQ ID NO:1
SEQ ID NO:1149  LDHN  IFHEIES    SEQ ID NO:1150
                 I LE  L F FY
                 V RY  F L VS
                    E  A I  T
                       S V  C
                         T  P
```

Lipoylation of 8-mer LAP2 substrates by LplA

```
                        SEQUENCE LISTING

<160> NUMBER OF SEQ ID NOS: 1222

<210> SEQ ID NO 1
<211> LENGTH: 13
<212> TYPE: PRT
<213> ORGANISM: artificial sequence
<220> FEATURE:
<223> OTHER INFORMATION: synthetic peptide

<400> SEQUENCE: 1

Gly Phe Glu Ile Asp Lys Val Trp Tyr Asp Leu Asp Ala
1               5                   10

<210> SEQ ID NO 2
<211> LENGTH: 11
<212> TYPE: PRT
<213> ORGANISM: artificial sequence
<220> FEATURE:
<223> OTHER INFORMATION: synthetic peptide

<400> SEQUENCE: 2

Phe Glu Ile Asp Lys Val Trp Tyr Asp Leu Asp
1               5                   10

<210> SEQ ID NO 3
<211> LENGTH: 12
<212> TYPE: PRT
<213> ORGANISM: artificial sequence
<220> FEATURE:
<223> OTHER INFORMATION: synthetic peptide

<400> SEQUENCE: 3

Gly Phe Glu Ile Asp Lys Val Trp Tyr Asp Leu Asp
1               5                   10

<210> SEQ ID NO 4
<211> LENGTH: 12
<212> TYPE: PRT
<213> ORGANISM: artificial sequence
<220> FEATURE:
<223> OTHER INFORMATION: synthetic peptide

<400> SEQUENCE: 4

Phe Glu Ile Asp Lys Val Trp Tyr Asp Leu Asp Ala
1               5                   10

<210> SEQ ID NO 5
<211> LENGTH: 13
<212> TYPE: PRT
<213> ORGANISM: artificial sequence
<220> FEATURE:
<223> OTHER INFORMATION: synthetic peptide

<400> SEQUENCE: 5

Gly Phe Glu Ile Asp Lys Ile Trp Tyr Asp Leu Asp Ala
1               5                   10
```

```
<210> SEQ ID NO 6
<211> LENGTH: 11
<212> TYPE: PRT
<213> ORGANISM: artificial sequence
<220> FEATURE:
<223> OTHER INFORMATION: synthetic peptide

<400> SEQUENCE: 6

Phe Glu Ile Asp Lys Ile Trp Tyr Asp Leu Asp
1               5                   10

<210> SEQ ID NO 7
<211> LENGTH: 12
<212> TYPE: PRT
<213> ORGANISM: artificial sequence
<220> FEATURE:
<223> OTHER INFORMATION: synthetic peptide

<400> SEQUENCE: 7

Gly Phe Glu Ile Asp Lys Ile Trp Tyr Asp Leu Asp
1               5                   10

<210> SEQ ID NO 8
<211> LENGTH: 12
<212> TYPE: PRT
<213> ORGANISM: artificial sequence
<220> FEATURE:
<223> OTHER INFORMATION: synthetic peptide

<400> SEQUENCE: 8

Phe Glu Ile Asp Lys Ile Trp Tyr Asp Leu Asp Ala
1               5                   10

<210> SEQ ID NO 9
<211> LENGTH: 13
<212> TYPE: PRT
<213> ORGANISM: artificial sequence
<220> FEATURE:
<223> OTHER INFORMATION: synthetic peptide

<400> SEQUENCE: 9

Gly Phe Glu Ile Asp Lys Leu Trp Tyr Asp Leu Asp Ala
1               5                   10

<210> SEQ ID NO 10
<211> LENGTH: 11
<212> TYPE: PRT
<213> ORGANISM: artificial sequence
<220> FEATURE:
<223> OTHER INFORMATION: synthetic peptide

<400> SEQUENCE: 10

Phe Glu Ile Asp Lys Leu Trp Tyr Asp Leu Asp
1               5                   10

<210> SEQ ID NO 11
<211> LENGTH: 12
<212> TYPE: PRT
<213> ORGANISM: artificial sequence
<220> FEATURE:
<223> OTHER INFORMATION: synthetic peptide

<400> SEQUENCE: 11

Gly Phe Glu Ile Asp Lys Leu Trp Tyr Asp Leu Asp
1               5                   10

<210> SEQ ID NO 12
```

```
<211> LENGTH: 12
<212> TYPE: PRT
<213> ORGANISM: artificial sequence
<220> FEATURE:
<223> OTHER INFORMATION: synthetic peptide

<400> SEQUENCE: 12

Phe Glu Ile Asp Lys Leu Trp Tyr Asp Leu Asp Ala
1               5                   10

<210> SEQ ID NO 13
<211> LENGTH: 13
<212> TYPE: PRT
<213> ORGANISM: artificial sequence
<220> FEATURE:
<223> OTHER INFORMATION: synthetic peptide

<400> SEQUENCE: 13

Gly Phe Glu Ile Asp Lys Phe Trp Tyr Asp Leu Asp Ala
1               5                   10

<210> SEQ ID NO 14
<211> LENGTH: 11
<212> TYPE: PRT
<213> ORGANISM: artificial sequence
<220> FEATURE:
<223> OTHER INFORMATION: synthetic peptide

<400> SEQUENCE: 14

Phe Glu Ile Asp Lys Phe Trp Tyr Asp Leu Asp
1               5                   10

<210> SEQ ID NO 15
<211> LENGTH: 12
<212> TYPE: PRT
<213> ORGANISM: artificial sequence
<220> FEATURE:
<223> OTHER INFORMATION: synthetic peptide

<400> SEQUENCE: 15

Gly Phe Glu Ile Asp Lys Phe Trp Tyr Asp Leu Asp
1               5                   10

<210> SEQ ID NO 16
<211> LENGTH: 12
<212> TYPE: PRT
<213> ORGANISM: artificial sequence
<220> FEATURE:
<223> OTHER INFORMATION: synthetic peptide

<400> SEQUENCE: 16

Phe Glu Ile Asp Lys Phe Trp Tyr Asp Leu Asp Ala
1               5                   10

<210> SEQ ID NO 17
<211> LENGTH: 13
<212> TYPE: PRT
<213> ORGANISM: artificial sequence
<220> FEATURE:
<223> OTHER INFORMATION: synthetic peptide

<400> SEQUENCE: 17

Gly Phe Glu Ile Asp Lys Ala Trp Tyr Asp Leu Asp Ala
1               5                   10

<210> SEQ ID NO 18
<211> LENGTH: 11
<212> TYPE: PRT
```

<213> ORGANISM: artificial sequence
<220> FEATURE:
<223> OTHER INFORMATION: synthetic peptide

<400> SEQUENCE: 18

Phe Glu Ile Asp Lys Ala Trp Tyr Asp Leu Asp
1               5                   10

<210> SEQ ID NO 19
<211> LENGTH: 12
<212> TYPE: PRT
<213> ORGANISM: artificial sequence
<220> FEATURE:
<223> OTHER INFORMATION: synthetic peptide

<400> SEQUENCE: 19

Gly Phe Glu Ile Asp Lys Ala Trp Tyr Asp Leu Asp
1               5                   10

<210> SEQ ID NO 20
<211> LENGTH: 12
<212> TYPE: PRT
<213> ORGANISM: artificial sequence
<220> FEATURE:
<223> OTHER INFORMATION: synthetic peptide

<400> SEQUENCE: 20

Phe Glu Ile Asp Lys Ala Trp Tyr Asp Leu Asp Ala
1               5                   10

<210> SEQ ID NO 21
<211> LENGTH: 13
<212> TYPE: PRT
<213> ORGANISM: artificial sequence
<220> FEATURE:
<223> OTHER INFORMATION: synthetic peptide

<400> SEQUENCE: 21

Gly Phe Glu Ile Asp Lys Ser Trp Tyr Asp Leu Asp Ala
1               5                   10

<210> SEQ ID NO 22
<211> LENGTH: 11
<212> TYPE: PRT
<213> ORGANISM: artificial sequence
<220> FEATURE:
<223> OTHER INFORMATION: synthetic peptide

<400> SEQUENCE: 22

Phe Glu Ile Asp Lys Ser Trp Tyr Asp Leu Asp
1               5                   10

<210> SEQ ID NO 23
<211> LENGTH: 12
<212> TYPE: PRT
<213> ORGANISM: artificial sequence
<220> FEATURE:
<223> OTHER INFORMATION: synthetic peptide

<400> SEQUENCE: 23

Gly Phe Glu Ile Asp Lys Ser Trp Tyr Asp Leu Asp
1               5                   10

<210> SEQ ID NO 24
<211> LENGTH: 12
<212> TYPE: PRT
<213> ORGANISM: artificial sequence
<220> FEATURE:

<223> OTHER INFORMATION: synthetic peptide

<400> SEQUENCE: 24

Phe Glu Ile Asp Lys Ser Trp Tyr Asp Leu Asp Ala
1               5                   10

<210> SEQ ID NO 25
<211> LENGTH: 13
<212> TYPE: PRT
<213> ORGANISM: artificial sequence
<220> FEATURE:
<223> OTHER INFORMATION: synthetic peptide

<400> SEQUENCE: 25

Gly Phe Glu Ile Asp Lys Val Phe Tyr Asp Leu Asp Ala
1               5                   10

<210> SEQ ID NO 26
<211> LENGTH: 11
<212> TYPE: PRT
<213> ORGANISM: artificial sequence
<220> FEATURE:
<223> OTHER INFORMATION: synthetic peptide

<400> SEQUENCE: 26

Phe Glu Ile Asp Lys Val Phe Tyr Asp Leu Asp
1               5                   10

<210> SEQ ID NO 27
<211> LENGTH: 12
<212> TYPE: PRT
<213> ORGANISM: artificial sequence
<220> FEATURE:
<223> OTHER INFORMATION: synthetic peptide

<400> SEQUENCE: 27

Gly Phe Glu Ile Asp Lys Val Phe Tyr Asp Leu Asp
1               5                   10

<210> SEQ ID NO 28
<211> LENGTH: 12
<212> TYPE: PRT
<213> ORGANISM: artificial sequence
<220> FEATURE:
<223> OTHER INFORMATION: synthetic peptide

<400> SEQUENCE: 28

Phe Glu Ile Asp Lys Val Phe Tyr Asp Leu Asp Ala
1               5                   10

<210> SEQ ID NO 29
<211> LENGTH: 13
<212> TYPE: PRT
<213> ORGANISM: artificial sequence
<220> FEATURE:
<223> OTHER INFORMATION: synthetic peptide

<400> SEQUENCE: 29

Gly Phe Glu Ile Asp Lys Ile Phe Tyr Asp Leu Asp Ala
1               5                   10

<210> SEQ ID NO 30
<211> LENGTH: 11
<212> TYPE: PRT
<213> ORGANISM: artificial sequence
<220> FEATURE:
<223> OTHER INFORMATION: synthetic peptide

```
<400> SEQUENCE: 30

Phe Glu Ile Asp Lys Ile Phe Tyr Asp Leu Asp
1               5                   10

<210> SEQ ID NO 31
<211> LENGTH: 12
<212> TYPE: PRT
<213> ORGANISM: artificial sequence
<220> FEATURE:
<223> OTHER INFORMATION: synthetic peptide

<400> SEQUENCE: 31

Gly Phe Glu Ile Asp Lys Ile Phe Tyr Asp Leu Asp
1               5                   10

<210> SEQ ID NO 32
<211> LENGTH: 12
<212> TYPE: PRT
<213> ORGANISM: artificial sequence
<220> FEATURE:
<223> OTHER INFORMATION: synthetic peptide

<400> SEQUENCE: 32

Phe Glu Ile Asp Lys Ile Phe Tyr Asp Leu Asp Ala
1               5                   10

<210> SEQ ID NO 33
<211> LENGTH: 13
<212> TYPE: PRT
<213> ORGANISM: artificial sequence
<220> FEATURE:
<223> OTHER INFORMATION: synthetic peptide

<400> SEQUENCE: 33

Gly Phe Glu Ile Asp Lys Leu Phe Tyr Asp Leu Asp Ala
1               5                   10

<210> SEQ ID NO 34
<211> LENGTH: 11
<212> TYPE: PRT
<213> ORGANISM: artificial sequence
<220> FEATURE:
<223> OTHER INFORMATION: synthetic peptide

<400> SEQUENCE: 34

Phe Glu Ile Asp Lys Leu Phe Tyr Asp Leu Asp
1               5                   10

<210> SEQ ID NO 35
<211> LENGTH: 12
<212> TYPE: PRT
<213> ORGANISM: artificial sequence
<220> FEATURE:
<223> OTHER INFORMATION: synthetic peptide

<400> SEQUENCE: 35

Gly Phe Glu Ile Asp Lys Leu Phe Tyr Asp Leu Asp
1               5                   10

<210> SEQ ID NO 36
<211> LENGTH: 12
<212> TYPE: PRT
<213> ORGANISM: artificial sequence
<220> FEATURE:
<223> OTHER INFORMATION: synthetic peptide

<400> SEQUENCE: 36
```

-continued

```
Phe Glu Ile Asp Lys Leu Phe Tyr Asp Leu Asp Ala
1               5                   10
```

<210> SEQ ID NO 37
<211> LENGTH: 13
<212> TYPE: PRT
<213> ORGANISM: artificial sequence
<220> FEATURE:
<223> OTHER INFORMATION: synthetic peptide

<400> SEQUENCE: 37

```
Gly Phe Glu Ile Asp Lys Phe Phe Tyr Asp Leu Asp Ala
1               5                   10
```

<210> SEQ ID NO 38
<211> LENGTH: 11
<212> TYPE: PRT
<213> ORGANISM: artificial sequence
<220> FEATURE:
<223> OTHER INFORMATION: synthetic peptide

<400> SEQUENCE: 38

```
Phe Glu Ile Asp Lys Phe Phe Tyr Asp Leu Asp
1               5                   10
```

<210> SEQ ID NO 39
<211> LENGTH: 12
<212> TYPE: PRT
<213> ORGANISM: artificial sequence
<220> FEATURE:
<223> OTHER INFORMATION: synthetic peptide

<400> SEQUENCE: 39

```
Gly Phe Glu Ile Asp Lys Phe Phe Tyr Asp Leu Asp
1               5                   10
```

<210> SEQ ID NO 40
<211> LENGTH: 12
<212> TYPE: PRT
<213> ORGANISM: artificial sequence
<220> FEATURE:
<223> OTHER INFORMATION: synthetic peptide

<400> SEQUENCE: 40

```
Phe Glu Ile Asp Lys Phe Phe Tyr Asp Leu Asp Ala
1               5                   10
```

<210> SEQ ID NO 41
<211> LENGTH: 13
<212> TYPE: PRT
<213> ORGANISM: artificial sequence
<220> FEATURE:
<223> OTHER INFORMATION: synthetic peptide

<400> SEQUENCE: 41

```
Gly Phe Glu Ile Asp Lys Ala Phe Tyr Asp Leu Asp Ala
1               5                   10
```

<210> SEQ ID NO 42
<211> LENGTH: 11
<212> TYPE: PRT
<213> ORGANISM: artificial sequence
<220> FEATURE:
<223> OTHER INFORMATION: synthetic peptide

<400> SEQUENCE: 42

```
Phe Glu Ile Asp Lys Ala Phe Tyr Asp Leu Asp
1               5                   10
```

<210> SEQ ID NO 43
<211> LENGTH: 12
<212> TYPE: PRT
<213> ORGANISM: artificial sequence
<220> FEATURE:
<223> OTHER INFORMATION: synthetic peptide

<400> SEQUENCE: 43

Gly Phe Glu Ile Asp Lys Ala Phe Tyr Asp Leu Asp
1               5                   10

<210> SEQ ID NO 44
<211> LENGTH: 12
<212> TYPE: PRT
<213> ORGANISM: artificial sequence
<220> FEATURE:
<223> OTHER INFORMATION: synthetic peptide

<400> SEQUENCE: 44

Phe Glu Ile Asp Lys Ala Phe Tyr Asp Leu Asp Ala
1               5                   10

<210> SEQ ID NO 45
<211> LENGTH: 13
<212> TYPE: PRT
<213> ORGANISM: artificial sequence
<220> FEATURE:
<223> OTHER INFORMATION: synthetic peptide

<400> SEQUENCE: 45

Gly Phe Glu Ile Asp Lys Ser Phe Tyr Asp Leu Asp Ala
1               5                   10

<210> SEQ ID NO 46
<211> LENGTH: 11
<212> TYPE: PRT
<213> ORGANISM: artificial sequence
<220> FEATURE:
<223> OTHER INFORMATION: synthetic peptide

<400> SEQUENCE: 46

Phe Glu Ile Asp Lys Ser Phe Tyr Asp Leu Asp
1               5                   10

<210> SEQ ID NO 47
<211> LENGTH: 12
<212> TYPE: PRT
<213> ORGANISM: artificial sequence
<220> FEATURE:
<223> OTHER INFORMATION: synthetic peptide

<400> SEQUENCE: 47

Gly Phe Glu Ile Asp Lys Ser Phe Tyr Asp Leu Asp
1               5                   10

<210> SEQ ID NO 48
<211> LENGTH: 12
<212> TYPE: PRT
<213> ORGANISM: artificial sequence
<220> FEATURE:
<223> OTHER INFORMATION: synthetic peptide

<400> SEQUENCE: 48

Phe Glu Ile Asp Lys Ser Phe Tyr Asp Leu Asp Ala
1               5                   10

```
<210> SEQ ID NO 49
<211> LENGTH: 13
<212> TYPE: PRT
<213> ORGANISM: artificial sequence
<220> FEATURE:
<223> OTHER INFORMATION: synthetic peptide

<400> SEQUENCE: 49

Gly Phe Glu Ile Asp Lys Val Trp His Asp Leu Asp Ala
1               5                   10

<210> SEQ ID NO 50
<211> LENGTH: 11
<212> TYPE: PRT
<213> ORGANISM: artificial sequence
<220> FEATURE:
<223> OTHER INFORMATION: synthetic peptide

<400> SEQUENCE: 50

Phe Glu Ile Asp Lys Val Trp His Asp Leu Asp
1               5                   10

<210> SEQ ID NO 51
<211> LENGTH: 12
<212> TYPE: PRT
<213> ORGANISM: artificial sequence
<220> FEATURE:
<223> OTHER INFORMATION: synthetic peptide

<400> SEQUENCE: 51

Gly Phe Glu Ile Asp Lys Val Trp His Asp Leu Asp
1               5                   10

<210> SEQ ID NO 52
<211> LENGTH: 12
<212> TYPE: PRT
<213> ORGANISM: artificial sequence
<220> FEATURE:
<223> OTHER INFORMATION: synthetic peptide

<400> SEQUENCE: 52

Phe Glu Ile Asp Lys Val Trp His Asp Leu Asp Ala
1               5                   10

<210> SEQ ID NO 53
<211> LENGTH: 13
<212> TYPE: PRT
<213> ORGANISM: artificial sequence
<220> FEATURE:
<223> OTHER INFORMATION: synthetic peptide

<400> SEQUENCE: 53

Gly Phe Glu Ile Asp Lys Ile Trp His Asp Leu Asp Ala
1               5                   10

<210> SEQ ID NO 54
<211> LENGTH: 11
<212> TYPE: PRT
<213> ORGANISM: artificial sequence
<220> FEATURE:
<223> OTHER INFORMATION: synthetic peptide

<400> SEQUENCE: 54

Phe Glu Ile Asp Lys Ile Trp His Asp Leu Asp
1               5                   10

<210> SEQ ID NO 55
<211> LENGTH: 12
```

```
<212> TYPE: PRT
<213> ORGANISM: artificial sequence
<220> FEATURE:
<223> OTHER INFORMATION: synthetic peptide

<400> SEQUENCE: 55

Gly Phe Glu Ile Asp Lys Ile Trp His Asp Leu Asp
1               5                   10

<210> SEQ ID NO 56
<211> LENGTH: 12
<212> TYPE: PRT
<213> ORGANISM: artificial sequence
<220> FEATURE:
<223> OTHER INFORMATION: synthetic peptide

<400> SEQUENCE: 56

Phe Glu Ile Asp Lys Ile Trp His Asp Leu Asp Ala
1               5                   10

<210> SEQ ID NO 57
<211> LENGTH: 13
<212> TYPE: PRT
<213> ORGANISM: artificial sequence
<220> FEATURE:
<223> OTHER INFORMATION: synthetic peptide

<400> SEQUENCE: 57

Gly Phe Glu Ile Asp Lys Leu Trp His Asp Leu Asp Ala
1               5                   10

<210> SEQ ID NO 58
<211> LENGTH: 11
<212> TYPE: PRT
<213> ORGANISM: artificial sequence
<220> FEATURE:
<223> OTHER INFORMATION: synthetic peptide

<400> SEQUENCE: 58

Phe Glu Ile Asp Lys Leu Trp His Asp Leu Asp
1               5                   10

<210> SEQ ID NO 59
<211> LENGTH: 12
<212> TYPE: PRT
<213> ORGANISM: artificial sequence
<220> FEATURE:
<223> OTHER INFORMATION: synthetic peptide

<400> SEQUENCE: 59

Gly Phe Glu Ile Asp Lys Leu Trp His Asp Leu Asp
1               5                   10

<210> SEQ ID NO 60
<211> LENGTH: 12
<212> TYPE: PRT
<213> ORGANISM: artificial sequence
<220> FEATURE:
<223> OTHER INFORMATION: synthetic peptide

<400> SEQUENCE: 60

Phe Glu Ile Asp Lys Leu Trp His Asp Leu Asp Ala
1               5                   10

<210> SEQ ID NO 61
<211> LENGTH: 13
<212> TYPE: PRT
<213> ORGANISM: artificial sequence
```

<220> FEATURE:
<223> OTHER INFORMATION: synthetic peptide

<400> SEQUENCE: 61

Gly Phe Glu Ile Asp Lys Phe Trp His Asp Leu Asp Ala
1               5                   10

<210> SEQ ID NO 62
<211> LENGTH: 11
<212> TYPE: PRT
<213> ORGANISM: artificial sequence
<220> FEATURE:
<223> OTHER INFORMATION: synthetic peptide

<400> SEQUENCE: 62

Phe Glu Ile Asp Lys Phe Trp His Asp Leu Asp
1               5                   10

<210> SEQ ID NO 63
<211> LENGTH: 12
<212> TYPE: PRT
<213> ORGANISM: artificial sequence
<220> FEATURE:
<223> OTHER INFORMATION: synthetic peptide

<400> SEQUENCE: 63

Gly Phe Glu Ile Asp Lys Phe Trp His Asp Leu Asp
1               5                   10

<210> SEQ ID NO 64
<211> LENGTH: 12
<212> TYPE: PRT
<213> ORGANISM: artificial sequence
<220> FEATURE:
<223> OTHER INFORMATION: synthetic peptide

<400> SEQUENCE: 64

Phe Glu Ile Asp Lys Phe Trp His Asp Leu Asp Ala
1               5                   10

<210> SEQ ID NO 65
<211> LENGTH: 13
<212> TYPE: PRT
<213> ORGANISM: artificial sequence
<220> FEATURE:
<223> OTHER INFORMATION: synthetic peptide

<400> SEQUENCE: 65

Gly Phe Glu Ile Asp Lys Ala Trp His Asp Leu Asp Ala
1               5                   10

<210> SEQ ID NO 66
<211> LENGTH: 11
<212> TYPE: PRT
<213> ORGANISM: artificial sequence
<220> FEATURE:
<223> OTHER INFORMATION: synthetic peptide

<400> SEQUENCE: 66

Phe Glu Ile Asp Lys Ala Trp His Asp Leu Asp
1               5                   10

<210> SEQ ID NO 67
<211> LENGTH: 12
<212> TYPE: PRT
<213> ORGANISM: artificial sequence
<220> FEATURE:
<223> OTHER INFORMATION: synthetic peptide -continued

<400> SEQUENCE: 67

Gly Phe Glu Ile Asp Lys Ala Trp His Asp Leu Asp
1               5                   10

<210> SEQ ID NO 68
<211> LENGTH: 12
<212> TYPE: PRT
<213> ORGANISM: artificial sequence
<220> FEATURE:
<223> OTHER INFORMATION: synthetic peptide

<400> SEQUENCE: 68

Phe Glu Ile Asp Lys Ala Trp His Asp Leu Asp Ala
1               5                   10

<210> SEQ ID NO 69
<211> LENGTH: 13
<212> TYPE: PRT
<213> ORGANISM: artificial sequence
<220> FEATURE:
<223> OTHER INFORMATION: synthetic peptide

<400> SEQUENCE: 69

Gly Phe Glu Ile Asp Lys Ser Trp His Asp Leu Asp Ala
1               5                   10

<210> SEQ ID NO 70
<211> LENGTH: 11
<212> TYPE: PRT
<213> ORGANISM: artificial sequence
<220> FEATURE:
<223> OTHER INFORMATION: synthetic peptide

<400> SEQUENCE: 70

Phe Glu Ile Asp Lys Ser Trp His Asp Leu Asp
1               5                   10

<210> SEQ ID NO 71
<211> LENGTH: 12
<212> TYPE: PRT
<213> ORGANISM: artificial sequence
<220> FEATURE:
<223> OTHER INFORMATION: synthetic peptide

<400> SEQUENCE: 71

Gly Phe Glu Ile Asp Lys Ser Trp His Asp Leu Asp
1               5                   10

<210> SEQ ID NO 72
<211> LENGTH: 12
<212> TYPE: PRT
<213> ORGANISM: artificial sequence
<220> FEATURE:
<223> OTHER INFORMATION: synthetic peptide

<400> SEQUENCE: 72

Phe Glu Ile Asp Lys Ser Trp His Asp Leu Asp Ala
1               5                   10

<210> SEQ ID NO 73
<211> LENGTH: 13
<212> TYPE: PRT
<213> ORGANISM: artificial sequence
<220> FEATURE:
<223> OTHER INFORMATION: synthetic peptide

<400> SEQUENCE: 73

Gly Phe Glu Ile Asp Lys Val Phe His Asp Leu Asp Ala
1               5                   10

<210> SEQ ID NO 74
<211> LENGTH: 11
<212> TYPE: PRT
<213> ORGANISM: artificial sequence
<220> FEATURE:
<223> OTHER INFORMATION: synthetic peptide

<400> SEQUENCE: 74

Phe Glu Ile Asp Lys Val Phe His Asp Leu Asp
1               5                   10

<210> SEQ ID NO 75
<211> LENGTH: 12
<212> TYPE: PRT
<213> ORGANISM: artificial sequence
<220> FEATURE:
<223> OTHER INFORMATION: synthetic peptide

<400> SEQUENCE: 75

Gly Phe Glu Ile Asp Lys Val Phe His Asp Leu Asp
1               5                   10

<210> SEQ ID NO 76
<211> LENGTH: 12
<212> TYPE: PRT
<213> ORGANISM: artificial sequence
<220> FEATURE:
<223> OTHER INFORMATION: synthetic peptide

<400> SEQUENCE: 76

Phe Glu Ile Asp Lys Val Phe His Asp Leu Asp Ala
1               5                   10

<210> SEQ ID NO 77
<211> LENGTH: 13
<212> TYPE: PRT
<213> ORGANISM: artificial sequence
<220> FEATURE:
<223> OTHER INFORMATION: synthetic peptide

<400> SEQUENCE: 77

Gly Phe Glu Ile Asp Lys Ile Phe His Asp Leu Asp Ala
1               5                   10

<210> SEQ ID NO 78
<211> LENGTH: 11
<212> TYPE: PRT
<213> ORGANISM: artificial sequence
<220> FEATURE:
<223> OTHER INFORMATION: synthetic peptide

<400> SEQUENCE: 78

Phe Glu Ile Asp Lys Ile Phe His Asp Leu Asp
1               5                   10

<210> SEQ ID NO 79
<211> LENGTH: 12
<212> TYPE: PRT
<213> ORGANISM: artificial sequence
<220> FEATURE:
<223> OTHER INFORMATION: synthetic peptide

<400> SEQUENCE: 79

Gly Phe Glu Ile Asp Lys Ile Phe His Asp Leu Asp

```
1               5                   10
```

<210> SEQ ID NO 80
<211> LENGTH: 12
<212> TYPE: PRT
<213> ORGANISM: artificial sequence
<220> FEATURE:
<223> OTHER INFORMATION: synthetic peptide

<400> SEQUENCE: 80

```
Phe Glu Ile Asp Lys Ile Phe His Asp Leu Asp Ala
1               5                   10
```

<210> SEQ ID NO 81
<211> LENGTH: 13
<212> TYPE: PRT
<213> ORGANISM: artificial sequence
<220> FEATURE:
<223> OTHER INFORMATION: synthetic peptide

<400> SEQUENCE: 81

```
Gly Phe Glu Ile Asp Lys Leu Phe His Asp Leu Asp Ala
1               5                   10
```

<210> SEQ ID NO 82
<211> LENGTH: 11
<212> TYPE: PRT
<213> ORGANISM: artificial sequence
<220> FEATURE:
<223> OTHER INFORMATION: synthetic peptide

<400> SEQUENCE: 82

```
Phe Glu Ile Asp Lys Leu Phe His Asp Leu Asp
1               5                   10
```

<210> SEQ ID NO 83
<211> LENGTH: 12
<212> TYPE: PRT
<213> ORGANISM: artificial sequence
<220> FEATURE:
<223> OTHER INFORMATION: synthetic peptide

<400> SEQUENCE: 83

```
Gly Phe Glu Ile Asp Lys Leu Phe His Asp Leu Asp
1               5                   10
```

<210> SEQ ID NO 84
<211> LENGTH: 12
<212> TYPE: PRT
<213> ORGANISM: artificial sequence
<220> FEATURE:
<223> OTHER INFORMATION: synthetic peptide

<400> SEQUENCE: 84

```
Phe Glu Ile Asp Lys Leu Phe His Asp Leu Asp Ala
1               5                   10
```

<210> SEQ ID NO 85
<211> LENGTH: 13
<212> TYPE: PRT
<213> ORGANISM: artificial sequence
<220> FEATURE:
<223> OTHER INFORMATION: synthetic peptide

<400> SEQUENCE: 85

```
Gly Phe Glu Ile Asp Lys Phe Phe His Asp Leu Asp Ala
1               5                   10
```

```
<210> SEQ ID NO 86
<211> LENGTH: 11
<212> TYPE: PRT
<213> ORGANISM: artificial sequence
<220> FEATURE:
<223> OTHER INFORMATION: synthetic peptide

<400> SEQUENCE: 86

Phe Glu Ile Asp Lys Phe Phe His Asp Leu Asp
1               5                   10

<210> SEQ ID NO 87
<211> LENGTH: 12
<212> TYPE: PRT
<213> ORGANISM: artificial sequence
<220> FEATURE:
<223> OTHER INFORMATION: synthetic peptide

<400> SEQUENCE: 87

Gly Phe Glu Ile Asp Lys Phe Phe His Asp Leu Asp
1               5                   10

<210> SEQ ID NO 88
<211> LENGTH: 12
<212> TYPE: PRT
<213> ORGANISM: artificial sequence
<220> FEATURE:
<223> OTHER INFORMATION: synthetic peptide

<400> SEQUENCE: 88

Phe Glu Ile Asp Lys Phe Phe His Asp Leu Asp Ala
1               5                   10

<210> SEQ ID NO 89
<211> LENGTH: 13
<212> TYPE: PRT
<213> ORGANISM: artificial sequence
<220> FEATURE:
<223> OTHER INFORMATION: synthetic peptide

<400> SEQUENCE: 89

Gly Phe Glu Ile Asp Lys Ala Phe His Asp Leu Asp Ala
1               5                   10

<210> SEQ ID NO 90
<211> LENGTH: 11
<212> TYPE: PRT
<213> ORGANISM: artificial sequence
<220> FEATURE:
<223> OTHER INFORMATION: synthetic peptide

<400> SEQUENCE: 90

Phe Glu Ile Asp Lys Ala Phe His Asp Leu Asp
1               5                   10

<210> SEQ ID NO 91
<211> LENGTH: 12
<212> TYPE: PRT
<213> ORGANISM: artificial sequence
<220> FEATURE:
<223> OTHER INFORMATION: synthetic peptide

<400> SEQUENCE: 91

Gly Phe Glu Ile Asp Lys Ala Phe His Asp Leu Asp
1               5                   10

<210> SEQ ID NO 92
```

```
<211> LENGTH: 12
<212> TYPE: PRT
<213> ORGANISM: artificial sequence
<220> FEATURE:
<223> OTHER INFORMATION: synthetic peptide

<400> SEQUENCE: 92

Phe Glu Ile Asp Lys Ala Phe His Asp Leu Asp Ala
1               5                   10

<210> SEQ ID NO 93
<211> LENGTH: 13
<212> TYPE: PRT
<213> ORGANISM: artificial sequence
<220> FEATURE:
<223> OTHER INFORMATION: synthetic peptide

<400> SEQUENCE: 93

Gly Phe Glu Ile Asp Lys Ser Phe His Asp Leu Asp Ala
1               5                   10

<210> SEQ ID NO 94
<211> LENGTH: 11
<212> TYPE: PRT
<213> ORGANISM: artificial sequence
<220> FEATURE:
<223> OTHER INFORMATION: synthetic peptide

<400> SEQUENCE: 94

Phe Glu Ile Asp Lys Ser Phe His Asp Leu Asp
1               5                   10

<210> SEQ ID NO 95
<211> LENGTH: 12
<212> TYPE: PRT
<213> ORGANISM: artificial sequence
<220> FEATURE:
<223> OTHER INFORMATION: synthetic peptide

<400> SEQUENCE: 95

Gly Phe Glu Ile Asp Lys Ser Phe His Asp Leu Asp
1               5                   10

<210> SEQ ID NO 96
<211> LENGTH: 12
<212> TYPE: PRT
<213> ORGANISM: artificial sequence
<220> FEATURE:
<223> OTHER INFORMATION: synthetic peptide

<400> SEQUENCE: 96

Phe Glu Ile Asp Lys Ser Phe His Asp Leu Asp Ala
1               5                   10

<210> SEQ ID NO 97
<211> LENGTH: 13
<212> TYPE: PRT
<213> ORGANISM: artificial sequence
<220> FEATURE:
<223> OTHER INFORMATION: synthetic peptide

<400> SEQUENCE: 97

Gly Phe Glu Ile Asp Lys Val Trp Phe Asp Leu Asp Ala
1               5                   10

<210> SEQ ID NO 98
<211> LENGTH: 11
<212> TYPE: PRT
```

```
<213> ORGANISM: artificial sequence
<220> FEATURE:
<223> OTHER INFORMATION: synthetic peptide

<400> SEQUENCE: 98

Phe Glu Ile Asp Lys Val Trp Phe Asp Leu Asp
1               5                   10

<210> SEQ ID NO 99
<211> LENGTH: 12
<212> TYPE: PRT
<213> ORGANISM: artificial sequence
<220> FEATURE:
<223> OTHER INFORMATION: synthetic peptide

<400> SEQUENCE: 99

Gly Phe Glu Ile Asp Lys Val Trp Phe Asp Leu Asp
1               5                   10

<210> SEQ ID NO 100
<211> LENGTH: 12
<212> TYPE: PRT
<213> ORGANISM: artificial sequence
<220> FEATURE:
<223> OTHER INFORMATION: synthetic peptide

<400> SEQUENCE: 100

Phe Glu Ile Asp Lys Val Trp Phe Asp Leu Asp Ala
1               5                   10

<210> SEQ ID NO 101
<211> LENGTH: 13
<212> TYPE: PRT
<213> ORGANISM: artificial sequence
<220> FEATURE:
<223> OTHER INFORMATION: synthetic peptide

<400> SEQUENCE: 101

Gly Phe Glu Ile Asp Lys Ile Trp Phe Asp Leu Asp Ala
1               5                   10

<210> SEQ ID NO 102
<211> LENGTH: 11
<212> TYPE: PRT
<213> ORGANISM: artificial sequence
<220> FEATURE:
<223> OTHER INFORMATION: synthetic peptide

<400> SEQUENCE: 102

Phe Glu Ile Asp Lys Ile Trp Phe Asp Leu Asp
1               5                   10

<210> SEQ ID NO 103
<211> LENGTH: 12
<212> TYPE: PRT
<213> ORGANISM: artificial sequence
<220> FEATURE:
<223> OTHER INFORMATION: synthetic peptide

<400> SEQUENCE: 103

Gly Phe Glu Ile Asp Lys Ile Trp Phe Asp Leu Asp
1               5                   10

<210> SEQ ID NO 104
<211> LENGTH: 12
<212> TYPE: PRT
<213> ORGANISM: artificial sequence
<220> FEATURE:
```

<223> OTHER INFORMATION: synthetic peptide

<400> SEQUENCE: 104

Phe Glu Ile Asp Lys Ile Trp Phe Asp Leu Asp Ala
1               5                   10

<210> SEQ ID NO 105
<211> LENGTH: 13
<212> TYPE: PRT
<213> ORGANISM: artificial sequence
<220> FEATURE:
<223> OTHER INFORMATION: synthetic peptide

<400> SEQUENCE: 105

Gly Phe Glu Ile Asp Lys Leu Trp Phe Asp Leu Asp Ala
1               5                   10

<210> SEQ ID NO 106
<211> LENGTH: 11
<212> TYPE: PRT
<213> ORGANISM: artificial sequence
<220> FEATURE:
<223> OTHER INFORMATION: synthetic peptide

<400> SEQUENCE: 106

Phe Glu Ile Asp Lys Leu Trp Phe Asp Leu Asp
1               5                   10

<210> SEQ ID NO 107
<211> LENGTH: 12
<212> TYPE: PRT
<213> ORGANISM: artificial sequence
<220> FEATURE:
<223> OTHER INFORMATION: synthetic peptide

<400> SEQUENCE: 107

Gly Phe Glu Ile Asp Lys Leu Trp Phe Asp Leu Asp
1               5                   10

<210> SEQ ID NO 108
<211> LENGTH: 12
<212> TYPE: PRT
<213> ORGANISM: artificial sequence
<220> FEATURE:
<223> OTHER INFORMATION: synthetic peptide

<400> SEQUENCE: 108

Phe Glu Ile Asp Lys Leu Trp Phe Asp Leu Asp Ala
1               5                   10

<210> SEQ ID NO 109
<211> LENGTH: 13
<212> TYPE: PRT
<213> ORGANISM: artificial sequence
<220> FEATURE:
<223> OTHER INFORMATION: synthetic peptide

<400> SEQUENCE: 109

Gly Phe Glu Ile Asp Lys Phe Trp Phe Asp Leu Asp Ala
1               5                   10

<210> SEQ ID NO 110
<211> LENGTH: 11
<212> TYPE: PRT
<213> ORGANISM: artificial sequence
<220> FEATURE:
<223> OTHER INFORMATION: synthetic peptide

```
<400> SEQUENCE: 110

Phe Glu Ile Asp Lys Phe Trp Phe Asp Leu Asp
1               5                   10

<210> SEQ ID NO 111
<211> LENGTH: 12
<212> TYPE: PRT
<213> ORGANISM: artificial sequence
<220> FEATURE:
<223> OTHER INFORMATION: synthetic peptide

<400> SEQUENCE: 111

Gly Phe Glu Ile Asp Lys Phe Trp Phe Asp Leu Asp
1               5                   10

<210> SEQ ID NO 112
<211> LENGTH: 12
<212> TYPE: PRT
<213> ORGANISM: artificial sequence
<220> FEATURE:
<223> OTHER INFORMATION: synthetic peptide

<400> SEQUENCE: 112

Phe Glu Ile Asp Lys Phe Trp Phe Asp Leu Asp Ala
1               5                   10

<210> SEQ ID NO 113
<211> LENGTH: 13
<212> TYPE: PRT
<213> ORGANISM: artificial sequence
<220> FEATURE:
<223> OTHER INFORMATION: synthetic peptide

<400> SEQUENCE: 113

Gly Phe Glu Ile Asp Lys Ala Trp Phe Asp Leu Asp Ala
1               5                   10

<210> SEQ ID NO 114
<211> LENGTH: 11
<212> TYPE: PRT
<213> ORGANISM: artificial sequence
<220> FEATURE:
<223> OTHER INFORMATION: synthetic peptide

<400> SEQUENCE: 114

Phe Glu Ile Asp Lys Ala Trp Phe Asp Leu Asp
1               5                   10

<210> SEQ ID NO 115
<211> LENGTH: 12
<212> TYPE: PRT
<213> ORGANISM: artificial sequence
<220> FEATURE:
<223> OTHER INFORMATION: synthetic peptide

<400> SEQUENCE: 115

Gly Phe Glu Ile Asp Lys Ala Trp Phe Asp Leu Asp
1               5                   10

<210> SEQ ID NO 116
<211> LENGTH: 12
<212> TYPE: PRT
<213> ORGANISM: artificial sequence
<220> FEATURE:
<223> OTHER INFORMATION: synthetic peptide

<400> SEQUENCE: 116
```

```
Phe Glu Ile Asp Lys Ala Trp Phe Asp Leu Asp Ala
1               5                   10
```

<210> SEQ ID NO 117
<211> LENGTH: 13
<212> TYPE: PRT
<213> ORGANISM: artificial sequence
<220> FEATURE:
<223> OTHER INFORMATION: synthetic peptide

<400> SEQUENCE: 117

```
Gly Phe Glu Ile Asp Lys Ser Trp Phe Asp Leu Asp Ala
1               5                   10
```

<210> SEQ ID NO 118
<211> LENGTH: 11
<212> TYPE: PRT
<213> ORGANISM: artificial sequence
<220> FEATURE:
<223> OTHER INFORMATION: synthetic peptide

<400> SEQUENCE: 118

```
Phe Glu Ile Asp Lys Ser Trp Phe Asp Leu Asp
1               5                   10
```

<210> SEQ ID NO 119
<211> LENGTH: 12
<212> TYPE: PRT
<213> ORGANISM: artificial sequence
<220> FEATURE:
<223> OTHER INFORMATION: synthetic peptide

<400> SEQUENCE: 119

```
Gly Phe Glu Ile Asp Lys Ser Trp Phe Asp Leu Asp
1               5                   10
```

<210> SEQ ID NO 120
<211> LENGTH: 12
<212> TYPE: PRT
<213> ORGANISM: artificial sequence
<220> FEATURE:
<223> OTHER INFORMATION: synthetic peptide

<400> SEQUENCE: 120

```
Phe Glu Ile Asp Lys Ser Trp Phe Asp Leu Asp Ala
1               5                   10
```

<210> SEQ ID NO 121
<211> LENGTH: 13
<212> TYPE: PRT
<213> ORGANISM: artificial sequence
<220> FEATURE:
<223> OTHER INFORMATION: synthetic peptide

<400> SEQUENCE: 121

```
Gly Phe Glu Ile Asp Lys Val Phe Phe Asp Leu Asp Ala
1               5                   10
```

<210> SEQ ID NO 122
<211> LENGTH: 11
<212> TYPE: PRT
<213> ORGANISM: artificial sequence
<220> FEATURE:
<223> OTHER INFORMATION: synthetic peptide

<400> SEQUENCE: 122

```
Phe Glu Ile Asp Lys Val Phe Phe Asp Leu Asp
1               5                   10
```

```
<210> SEQ ID NO 123
<211> LENGTH: 12
<212> TYPE: PRT
<213> ORGANISM: artificial sequence
<220> FEATURE:
<223> OTHER INFORMATION: synthetic peptide

<400> SEQUENCE: 123

Gly Phe Glu Ile Asp Lys Val Phe Phe Asp Leu Asp
1               5                   10

<210> SEQ ID NO 124
<211> LENGTH: 12
<212> TYPE: PRT
<213> ORGANISM: artificial sequence
<220> FEATURE:
<223> OTHER INFORMATION: synthetic peptide

<400> SEQUENCE: 124

Phe Glu Ile Asp Lys Val Phe Phe Asp Leu Asp Ala
1               5                   10

<210> SEQ ID NO 125
<211> LENGTH: 13
<212> TYPE: PRT
<213> ORGANISM: artificial sequence
<220> FEATURE:
<223> OTHER INFORMATION: synthetic peptide

<400> SEQUENCE: 125

Gly Phe Glu Ile Asp Lys Ile Phe Phe Asp Leu Asp Ala
1               5                   10

<210> SEQ ID NO 126
<211> LENGTH: 11
<212> TYPE: PRT
<213> ORGANISM: artificial sequence
<220> FEATURE:
<223> OTHER INFORMATION: synthetic peptide

<400> SEQUENCE: 126

Phe Glu Ile Asp Lys Ile Phe Phe Asp Leu Asp
1               5                   10

<210> SEQ ID NO 127
<211> LENGTH: 12
<212> TYPE: PRT
<213> ORGANISM: artificial sequence
<220> FEATURE:
<223> OTHER INFORMATION: synthetic peptide

<400> SEQUENCE: 127

Gly Phe Glu Ile Asp Lys Ile Phe Phe Asp Leu Asp
1               5                   10

<210> SEQ ID NO 128
<211> LENGTH: 12
<212> TYPE: PRT
<213> ORGANISM: artificial sequence
<220> FEATURE:
<223> OTHER INFORMATION: synthetic peptide

<400> SEQUENCE: 128

Phe Glu Ile Asp Lys Ile Phe Phe Asp Leu Asp Ala
1               5                   10
```

```
<210> SEQ ID NO 129
<211> LENGTH: 13
<212> TYPE: PRT
<213> ORGANISM: artificial sequence
<220> FEATURE:
<223> OTHER INFORMATION: synthetic peptide

<400> SEQUENCE: 129

Gly Phe Glu Ile Asp Lys Leu Phe Phe Asp Leu Asp Ala
1               5                   10

<210> SEQ ID NO 130
<211> LENGTH: 11
<212> TYPE: PRT
<213> ORGANISM: artificial sequence
<220> FEATURE:
<223> OTHER INFORMATION: synthetic peptide

<400> SEQUENCE: 130

Phe Glu Ile Asp Lys Leu Phe Phe Asp Leu Asp
1               5                   10

<210> SEQ ID NO 131
<211> LENGTH: 12
<212> TYPE: PRT
<213> ORGANISM: artificial sequence
<220> FEATURE:
<223> OTHER INFORMATION: synthetic peptide

<400> SEQUENCE: 131

Gly Phe Glu Ile Asp Lys Leu Phe Phe Asp Leu Asp
1               5                   10

<210> SEQ ID NO 132
<211> LENGTH: 12
<212> TYPE: PRT
<213> ORGANISM: artificial sequence
<220> FEATURE:
<223> OTHER INFORMATION: synthetic peptide

<400> SEQUENCE: 132

Phe Glu Ile Asp Lys Leu Phe Phe Asp Leu Asp Ala
1               5                   10

<210> SEQ ID NO 133
<211> LENGTH: 13
<212> TYPE: PRT
<213> ORGANISM: artificial sequence
<220> FEATURE:
<223> OTHER INFORMATION: synthetic peptide

<400> SEQUENCE: 133

Gly Phe Glu Ile Asp Lys Phe Phe Phe Asp Leu Asp Ala
1               5                   10

<210> SEQ ID NO 134
<211> LENGTH: 11
<212> TYPE: PRT
<213> ORGANISM: artificial sequence
<220> FEATURE:
<223> OTHER INFORMATION: synthetic peptide

<400> SEQUENCE: 134

Phe Glu Ile Asp Lys Phe Phe Phe Asp Leu Asp
1               5                   10

<210> SEQ ID NO 135
<211> LENGTH: 12
```

```
<212> TYPE: PRT
<213> ORGANISM: artificial sequence
<220> FEATURE:
<223> OTHER INFORMATION: synthetic peptide

<400> SEQUENCE: 135

Gly Phe Glu Ile Asp Lys Phe Phe Phe Asp Leu Asp
1               5                   10

<210> SEQ ID NO 136
<211> LENGTH: 12
<212> TYPE: PRT
<213> ORGANISM: artificial sequence
<220> FEATURE:
<223> OTHER INFORMATION: synthetic peptide

<400> SEQUENCE: 136

Phe Glu Ile Asp Lys Phe Phe Phe Asp Leu Asp Ala
1               5                   10

<210> SEQ ID NO 137
<211> LENGTH: 13
<212> TYPE: PRT
<213> ORGANISM: artificial sequence
<220> FEATURE:
<223> OTHER INFORMATION: synthetic peptide

<400> SEQUENCE: 137

Gly Phe Glu Ile Asp Lys Ala Phe Phe Asp Leu Asp Ala
1               5                   10

<210> SEQ ID NO 138
<211> LENGTH: 11
<212> TYPE: PRT
<213> ORGANISM: artificial sequence
<220> FEATURE:
<223> OTHER INFORMATION: synthetic peptide

<400> SEQUENCE: 138

Phe Glu Ile Asp Lys Ala Phe Phe Asp Leu Asp
1               5                   10

<210> SEQ ID NO 139
<211> LENGTH: 12
<212> TYPE: PRT
<213> ORGANISM: artificial sequence
<220> FEATURE:
<223> OTHER INFORMATION: synthetic peptide

<400> SEQUENCE: 139

Gly Phe Glu Ile Asp Lys Ala Phe Phe Asp Leu Asp
1               5                   10

<210> SEQ ID NO 140
<211> LENGTH: 12
<212> TYPE: PRT
<213> ORGANISM: artificial sequence
<220> FEATURE:
<223> OTHER INFORMATION: synthetic peptide

<400> SEQUENCE: 140

Phe Glu Ile Asp Lys Ala Phe Phe Asp Leu Asp Ala
1               5                   10

<210> SEQ ID NO 141
<211> LENGTH: 13
<212> TYPE: PRT
<213> ORGANISM: artificial sequence
```

```
<220> FEATURE:
<223> OTHER INFORMATION: synthetic peptide

<400> SEQUENCE: 141

Gly Phe Glu Ile Asp Lys Ser Phe Phe Asp Leu Asp Ala
1               5                   10

<210> SEQ ID NO 142
<211> LENGTH: 11
<212> TYPE: PRT
<213> ORGANISM: artificial sequence
<220> FEATURE:
<223> OTHER INFORMATION: synthetic peptide

<400> SEQUENCE: 142

Phe Glu Ile Asp Lys Ser Phe Phe Asp Leu Asp
1               5                   10

<210> SEQ ID NO 143
<211> LENGTH: 12
<212> TYPE: PRT
<213> ORGANISM: artificial sequence
<220> FEATURE:
<223> OTHER INFORMATION: synthetic peptide

<400> SEQUENCE: 143

Gly Phe Glu Ile Asp Lys Ser Phe Phe Asp Leu Asp
1               5                   10

<210> SEQ ID NO 144
<211> LENGTH: 12
<212> TYPE: PRT
<213> ORGANISM: artificial sequence
<220> FEATURE:
<223> OTHER INFORMATION: synthetic peptide

<400> SEQUENCE: 144

Phe Glu Ile Asp Lys Ser Phe Phe Asp Leu Asp Ala
1               5                   10

<210> SEQ ID NO 145
<211> LENGTH: 13
<212> TYPE: PRT
<213> ORGANISM: artificial sequence
<220> FEATURE:
<223> OTHER INFORMATION: synthetic peptide

<400> SEQUENCE: 145

Gly Phe Glu Ile Asp Lys Val Trp Ile Asp Leu Asp Ala
1               5                   10

<210> SEQ ID NO 146
<211> LENGTH: 11
<212> TYPE: PRT
<213> ORGANISM: artificial sequence
<220> FEATURE:
<223> OTHER INFORMATION: synthetic peptide

<400> SEQUENCE: 146

Phe Glu Ile Asp Lys Val Trp Ile Asp Leu Asp
1               5                   10

<210> SEQ ID NO 147
<211> LENGTH: 12
<212> TYPE: PRT
<213> ORGANISM: artificial sequence
<220> FEATURE:
<223> OTHER INFORMATION: synthetic peptide
```

<400> SEQUENCE: 147

Gly Phe Glu Ile Asp Lys Val Trp Ile Asp Leu Asp
1               5                   10

<210> SEQ ID NO 148
<211> LENGTH: 12
<212> TYPE: PRT
<213> ORGANISM: artificial sequence
<220> FEATURE:
<223> OTHER INFORMATION: synthetic peptide

<400> SEQUENCE: 148

Phe Glu Ile Asp Lys Val Trp Ile Asp Leu Asp Ala
1               5                   10

<210> SEQ ID NO 149
<211> LENGTH: 13
<212> TYPE: PRT
<213> ORGANISM: artificial sequence
<220> FEATURE:
<223> OTHER INFORMATION: synthetic peptide

<400> SEQUENCE: 149

Gly Phe Glu Ile Asp Lys Val Trp Val Asp Leu Asp Ala
1               5                   10

<210> SEQ ID NO 150
<211> LENGTH: 11
<212> TYPE: PRT
<213> ORGANISM: artificial sequence
<220> FEATURE:
<223> OTHER INFORMATION: synthetic peptide

<400> SEQUENCE: 150

Phe Glu Ile Asp Lys Val Trp Val Asp Leu Asp
1               5                   10

<210> SEQ ID NO 151
<211> LENGTH: 12
<212> TYPE: PRT
<213> ORGANISM: artificial sequence
<220> FEATURE:
<223> OTHER INFORMATION: synthetic peptide

<400> SEQUENCE: 151

Gly Phe Glu Ile Asp Lys Val Trp Val Asp Leu Asp
1               5                   10

<210> SEQ ID NO 152
<211> LENGTH: 12
<212> TYPE: PRT
<213> ORGANISM: artificial sequence
<220> FEATURE:
<223> OTHER INFORMATION: synthetic peptide

<400> SEQUENCE: 152

Phe Glu Ile Asp Lys Val Trp Val Asp Leu Asp Ala
1               5                   10

<210> SEQ ID NO 153
<211> LENGTH: 13
<212> TYPE: PRT
<213> ORGANISM: artificial sequence
<220> FEATURE:
<223> OTHER INFORMATION: synthetic peptide

<400> SEQUENCE: 153

```
Gly Phe Glu Ile Asp Lys Val Trp Leu Asp Leu Asp Ala
1               5                   10
```

<210> SEQ ID NO 154
<211> LENGTH: 11
<212> TYPE: PRT
<213> ORGANISM: artificial sequence
<220> FEATURE:
<223> OTHER INFORMATION: synthetic peptide

<400> SEQUENCE: 154

```
Phe Glu Ile Asp Lys Val Trp Leu Asp Leu Asp
1               5                   10
```

<210> SEQ ID NO 155
<211> LENGTH: 12
<212> TYPE: PRT
<213> ORGANISM: artificial sequence
<220> FEATURE:
<223> OTHER INFORMATION: synthetic peptide

<400> SEQUENCE: 155

```
Gly Phe Glu Ile Asp Lys Val Trp Leu Asp Leu Asp
1               5                   10
```

<210> SEQ ID NO 156
<211> LENGTH: 12
<212> TYPE: PRT
<213> ORGANISM: artificial sequence
<220> FEATURE:
<223> OTHER INFORMATION: synthetic peptide

<400> SEQUENCE: 156

```
Phe Glu Ile Asp Lys Val Trp Leu Asp Leu Asp Ala
1               5                   10
```

<210> SEQ ID NO 157
<211> LENGTH: 13
<212> TYPE: PRT
<213> ORGANISM: artificial sequence
<220> FEATURE:
<223> OTHER INFORMATION: synthetic peptide

<400> SEQUENCE: 157

```
Gly Phe Glu Ile Asp Lys Val Trp Leu Asp Leu Asp Ala
1               5                   10
```

<210> SEQ ID NO 158
<211> LENGTH: 11
<212> TYPE: PRT
<213> ORGANISM: artificial sequence
<220> FEATURE:
<223> OTHER INFORMATION: synthetic peptide

<400> SEQUENCE: 158

```
Phe Glu Ile Asp Lys Val Trp Leu Asp Leu Asp
1               5                   10
```

<210> SEQ ID NO 159
<211> LENGTH: 12
<212> TYPE: PRT
<213> ORGANISM: artificial sequence
<220> FEATURE:
<223> OTHER INFORMATION: synthetic peptide

<400> SEQUENCE: 159

```
Gly Phe Glu Ile Asp Lys Val Trp Leu Asp Leu Asp
```

```
                   1               5                   10

<210> SEQ ID NO 160
<211> LENGTH: 12
<212> TYPE: PRT
<213> ORGANISM: artificial sequence
<220> FEATURE:
<223> OTHER INFORMATION: synthetic peptide

<400> SEQUENCE: 160

Phe Glu Ile Asp Lys Val Trp Leu Asp Leu Asp Ala
 1               5                   10

<210> SEQ ID NO 161
<211> LENGTH: 13
<212> TYPE: PRT
<213> ORGANISM: artificial sequence
<220> FEATURE:
<223> OTHER INFORMATION: synthetic peptide

<400> SEQUENCE: 161

Gly Phe Glu Ile Asp Lys Val Trp Thr Asp Leu Asp Ala
 1               5                   10

<210> SEQ ID NO 162
<211> LENGTH: 11
<212> TYPE: PRT
<213> ORGANISM: artificial sequence
<220> FEATURE:
<223> OTHER INFORMATION: synthetic peptide

<400> SEQUENCE: 162

Phe Glu Ile Asp Lys Val Trp Thr Asp Leu Asp
 1               5                   10

<210> SEQ ID NO 163
<211> LENGTH: 12
<212> TYPE: PRT
<213> ORGANISM: artificial sequence
<220> FEATURE:
<223> OTHER INFORMATION: synthetic peptide

<400> SEQUENCE: 163

Gly Phe Glu Ile Asp Lys Val Trp Thr Asp Leu Asp
 1               5                   10

<210> SEQ ID NO 164
<211> LENGTH: 12
<212> TYPE: PRT
<213> ORGANISM: artificial sequence
<220> FEATURE:
<223> OTHER INFORMATION: synthetic peptide

<400> SEQUENCE: 164

Phe Glu Ile Asp Lys Val Trp Thr Asp Leu Asp Ala
 1               5                   10

<210> SEQ ID NO 165
<211> LENGTH: 13
<212> TYPE: PRT
<213> ORGANISM: artificial sequence
<220> FEATURE:
<223> OTHER INFORMATION: synthetic peptide

<400> SEQUENCE: 165

Gly Phe Glu Ile Asp Lys Val Trp Tyr Glu Leu Asp Ala
 1               5                   10
```

```
<210> SEQ ID NO 166
<211> LENGTH: 11
<212> TYPE: PRT
<213> ORGANISM: artificial sequence
<220> FEATURE:
<223> OTHER INFORMATION: synthetic peptide

<400> SEQUENCE: 166

Phe Glu Ile Asp Lys Val Trp Tyr Glu Leu Asp
1               5                   10

<210> SEQ ID NO 167
<211> LENGTH: 12
<212> TYPE: PRT
<213> ORGANISM: artificial sequence
<220> FEATURE:
<223> OTHER INFORMATION: synthetic peptide

<400> SEQUENCE: 167

Gly Phe Glu Ile Asp Lys Val Trp Tyr Glu Leu Asp
1               5                   10

<210> SEQ ID NO 168
<211> LENGTH: 12
<212> TYPE: PRT
<213> ORGANISM: artificial sequence
<220> FEATURE:
<223> OTHER INFORMATION: synthetic peptide

<400> SEQUENCE: 168

Phe Glu Ile Asp Lys Val Trp Tyr Glu Leu Asp Ala
1               5                   10

<210> SEQ ID NO 169
<211> LENGTH: 13
<212> TYPE: PRT
<213> ORGANISM: artificial sequence
<220> FEATURE:
<223> OTHER INFORMATION: synthetic peptide

<400> SEQUENCE: 169

Gly Phe Glu Ile Asp Lys Ile Trp Tyr Glu Leu Asp Ala
1               5                   10

<210> SEQ ID NO 170
<211> LENGTH: 11
<212> TYPE: PRT
<213> ORGANISM: artificial sequence
<220> FEATURE:
<223> OTHER INFORMATION: synthetic peptide

<400> SEQUENCE: 170

Phe Glu Ile Asp Lys Ile Trp Tyr Glu Leu Asp
1               5                   10

<210> SEQ ID NO 171
<211> LENGTH: 12
<212> TYPE: PRT
<213> ORGANISM: artificial sequence
<220> FEATURE:
<223> OTHER INFORMATION: synthetic peptide

<400> SEQUENCE: 171

Gly Phe Glu Ile Asp Lys Ile Trp Tyr Glu Leu Asp
1               5                   10

<210> SEQ ID NO 172
```

```
<211> LENGTH: 12
<212> TYPE: PRT
<213> ORGANISM: artificial sequence
<220> FEATURE:
<223> OTHER INFORMATION: synthetic peptide

<400> SEQUENCE: 172

Phe Glu Ile Asp Lys Ile Trp Tyr Glu Leu Asp Ala
1               5                   10

<210> SEQ ID NO 173
<211> LENGTH: 13
<212> TYPE: PRT
<213> ORGANISM: artificial sequence
<220> FEATURE:
<223> OTHER INFORMATION: synthetic peptide

<400> SEQUENCE: 173

Gly Phe Glu Ile Asp Lys Leu Trp Tyr Glu Leu Asp Ala
1               5                   10

<210> SEQ ID NO 174
<211> LENGTH: 11
<212> TYPE: PRT
<213> ORGANISM: artificial sequence
<220> FEATURE:
<223> OTHER INFORMATION: synthetic peptide

<400> SEQUENCE: 174

Phe Glu Ile Asp Lys Leu Trp Tyr Glu Leu Asp
1               5                   10

<210> SEQ ID NO 175
<211> LENGTH: 12
<212> TYPE: PRT
<213> ORGANISM: artificial sequence
<220> FEATURE:
<223> OTHER INFORMATION: synthetic peptide

<400> SEQUENCE: 175

Gly Phe Glu Ile Asp Lys Leu Trp Tyr Glu Leu Asp
1               5                   10

<210> SEQ ID NO 176
<211> LENGTH: 12
<212> TYPE: PRT
<213> ORGANISM: artificial sequence
<220> FEATURE:
<223> OTHER INFORMATION: synthetic peptide

<400> SEQUENCE: 176

Phe Glu Ile Asp Lys Leu Trp Tyr Glu Leu Asp Ala
1               5                   10

<210> SEQ ID NO 177
<211> LENGTH: 13
<212> TYPE: PRT
<213> ORGANISM: artificial sequence
<220> FEATURE:
<223> OTHER INFORMATION: synthetic peptide

<400> SEQUENCE: 177

Gly Phe Glu Ile Asp Lys Phe Trp Tyr Glu Leu Asp Ala
1               5                   10

<210> SEQ ID NO 178
<211> LENGTH: 11
<212> TYPE: PRT
```

<213> ORGANISM: artificial sequence
<220> FEATURE:
<223> OTHER INFORMATION: synthetic peptide

<400> SEQUENCE: 178

Phe Glu Ile Asp Lys Phe Trp Tyr Glu Leu Asp
1               5                   10

<210> SEQ ID NO 179
<211> LENGTH: 12
<212> TYPE: PRT
<213> ORGANISM: artificial sequence
<220> FEATURE:
<223> OTHER INFORMATION: synthetic peptide

<400> SEQUENCE: 179

Gly Phe Glu Ile Asp Lys Phe Trp Tyr Glu Leu Asp
1               5                   10

<210> SEQ ID NO 180
<211> LENGTH: 12
<212> TYPE: PRT
<213> ORGANISM: artificial sequence
<220> FEATURE:
<223> OTHER INFORMATION: synthetic peptide

<400> SEQUENCE: 180

Phe Glu Ile Asp Lys Phe Trp Tyr Glu Leu Asp Ala
1               5                   10

<210> SEQ ID NO 181
<211> LENGTH: 13
<212> TYPE: PRT
<213> ORGANISM: artificial sequence
<220> FEATURE:
<223> OTHER INFORMATION: synthetic peptide

<400> SEQUENCE: 181

Gly Phe Glu Ile Asp Lys Ala Trp Tyr Glu Leu Asp Ala
1               5                   10

<210> SEQ ID NO 182
<211> LENGTH: 11
<212> TYPE: PRT
<213> ORGANISM: artificial sequence
<220> FEATURE:
<223> OTHER INFORMATION: synthetic peptide

<400> SEQUENCE: 182

Phe Glu Ile Asp Lys Ala Trp Tyr Glu Leu Asp
1               5                   10

<210> SEQ ID NO 183
<211> LENGTH: 12
<212> TYPE: PRT
<213> ORGANISM: artificial sequence
<220> FEATURE:
<223> OTHER INFORMATION: synthetic peptide

<400> SEQUENCE: 183

Gly Phe Glu Ile Asp Lys Ala Trp Tyr Glu Leu Asp
1               5                   10

<210> SEQ ID NO 184
<211> LENGTH: 12
<212> TYPE: PRT
<213> ORGANISM: artificial sequence
<220> FEATURE:

<223> OTHER INFORMATION: synthetic peptide

<400> SEQUENCE: 184

Phe Glu Ile Asp Lys Ala Trp Tyr Glu Leu Asp Ala
1               5                   10

<210> SEQ ID NO 185
<211> LENGTH: 13
<212> TYPE: PRT
<213> ORGANISM: artificial sequence
<220> FEATURE:
<223> OTHER INFORMATION: synthetic peptide

<400> SEQUENCE: 185

Gly Phe Glu Ile Asp Lys Ser Trp Tyr Glu Leu Asp Ala
1               5                   10

<210> SEQ ID NO 186
<211> LENGTH: 11
<212> TYPE: PRT
<213> ORGANISM: artificial sequence
<220> FEATURE:
<223> OTHER INFORMATION: synthetic peptide

<400> SEQUENCE: 186

Phe Glu Ile Asp Lys Ser Trp Tyr Glu Leu Asp
1               5                   10

<210> SEQ ID NO 187
<211> LENGTH: 12
<212> TYPE: PRT
<213> ORGANISM: artificial sequence
<220> FEATURE:
<223> OTHER INFORMATION: synthetic peptide

<400> SEQUENCE: 187

Gly Phe Glu Ile Asp Lys Ser Trp Tyr Glu Leu Asp
1               5                   10

<210> SEQ ID NO 188
<211> LENGTH: 12
<212> TYPE: PRT
<213> ORGANISM: artificial sequence
<220> FEATURE:
<223> OTHER INFORMATION: synthetic peptide

<400> SEQUENCE: 188

Phe Glu Ile Asp Lys Ser Trp Tyr Glu Leu Asp Ala
1               5                   10

<210> SEQ ID NO 189
<211> LENGTH: 13
<212> TYPE: PRT
<213> ORGANISM: artificial sequence
<220> FEATURE:
<223> OTHER INFORMATION: synthetic peptide

<400> SEQUENCE: 189

Gly Phe Glu Ile Asp Lys Val Trp Tyr Asp Ile Asp Ala
1               5                   10

<210> SEQ ID NO 190
<211> LENGTH: 11
<212> TYPE: PRT
<213> ORGANISM: artificial sequence
<220> FEATURE:
<223> OTHER INFORMATION: synthetic peptide

```
<400> SEQUENCE: 190

Phe Glu Ile Asp Lys Val Trp Tyr Asp Ile Asp
1               5                   10

<210> SEQ ID NO 191
<211> LENGTH: 12
<212> TYPE: PRT
<213> ORGANISM: artificial sequence
<220> FEATURE:
<223> OTHER INFORMATION: synthetic peptide

<400> SEQUENCE: 191

Gly Phe Glu Ile Asp Lys Val Trp Tyr Asp Ile Asp
1               5                   10

<210> SEQ ID NO 192
<211> LENGTH: 12
<212> TYPE: PRT
<213> ORGANISM: artificial sequence
<220> FEATURE:
<223> OTHER INFORMATION: synthetic peptide

<400> SEQUENCE: 192

Phe Glu Ile Asp Lys Val Trp Tyr Asp Ile Asp Ala
1               5                   10

<210> SEQ ID NO 193
<211> LENGTH: 13
<212> TYPE: PRT
<213> ORGANISM: artificial sequence
<220> FEATURE:
<223> OTHER INFORMATION: synthetic peptide

<400> SEQUENCE: 193

Gly Phe Glu Ile Asp Lys Ile Trp Tyr Asp Ile Asp Ala
1               5                   10

<210> SEQ ID NO 194
<211> LENGTH: 11
<212> TYPE: PRT
<213> ORGANISM: artificial sequence
<220> FEATURE:
<223> OTHER INFORMATION: synthetic peptide

<400> SEQUENCE: 194

Phe Glu Ile Asp Lys Ile Trp Tyr Asp Ile Asp
1               5                   10

<210> SEQ ID NO 195
<211> LENGTH: 12
<212> TYPE: PRT
<213> ORGANISM: artificial sequence
<220> FEATURE:
<223> OTHER INFORMATION: synthetic peptide

<400> SEQUENCE: 195

Gly Phe Glu Ile Asp Lys Ile Trp Tyr Asp Ile Asp
1               5                   10

<210> SEQ ID NO 196
<211> LENGTH: 12
<212> TYPE: PRT
<213> ORGANISM: artificial sequence
<220> FEATURE:
<223> OTHER INFORMATION: synthetic peptide

<400> SEQUENCE: 196
```

```
Phe Glu Ile Asp Lys Ile Trp Tyr Asp Ile Asp Ala
1               5                   10
```

<210> SEQ ID NO 197
<211> LENGTH: 13
<212> TYPE: PRT
<213> ORGANISM: artificial sequence
<220> FEATURE:
<223> OTHER INFORMATION: synthetic peptide

<400> SEQUENCE: 197

```
Gly Phe Glu Ile Asp Lys Leu Trp Tyr Asp Ile Asp Ala
1               5                   10
```

<210> SEQ ID NO 198
<211> LENGTH: 11
<212> TYPE: PRT
<213> ORGANISM: artificial sequence
<220> FEATURE:
<223> OTHER INFORMATION: synthetic peptide

<400> SEQUENCE: 198

```
Phe Glu Ile Asp Lys Leu Trp Tyr Asp Ile Asp
1               5                   10
```

<210> SEQ ID NO 199
<211> LENGTH: 12
<212> TYPE: PRT
<213> ORGANISM: artificial sequence
<220> FEATURE:
<223> OTHER INFORMATION: synthetic peptide

<400> SEQUENCE: 199

```
Gly Phe Glu Ile Asp Lys Leu Trp Tyr Asp Ile Asp
1               5                   10
```

<210> SEQ ID NO 200
<211> LENGTH: 12
<212> TYPE: PRT
<213> ORGANISM: artificial sequence
<220> FEATURE:
<223> OTHER INFORMATION: synthetic peptide

<400> SEQUENCE: 200

```
Phe Glu Ile Asp Lys Leu Trp Tyr Asp Ile Asp Ala
1               5                   10
```

<210> SEQ ID NO 201
<211> LENGTH: 13
<212> TYPE: PRT
<213> ORGANISM: artificial sequence
<220> FEATURE:
<223> OTHER INFORMATION: synthetic peptide

<400> SEQUENCE: 201

```
Gly Phe Glu Ile Asp Lys Phe Trp Tyr Asp Ile Asp Ala
1               5                   10
```

<210> SEQ ID NO 202
<211> LENGTH: 11
<212> TYPE: PRT
<213> ORGANISM: artificial sequence
<220> FEATURE:
<223> OTHER INFORMATION: synthetic peptide

<400> SEQUENCE: 202

```
Phe Glu Ile Asp Lys Phe Trp Tyr Asp Ile Asp
1               5                   10
```

<210> SEQ ID NO 203
<211> LENGTH: 12
<212> TYPE: PRT
<213> ORGANISM: artificial sequence
<220> FEATURE:
<223> OTHER INFORMATION: synthetic peptide

<400> SEQUENCE: 203

Gly Phe Glu Ile Asp Lys Phe Trp Tyr Asp Ile Asp
1               5                   10

<210> SEQ ID NO 204
<211> LENGTH: 12
<212> TYPE: PRT
<213> ORGANISM: artificial sequence
<220> FEATURE:
<223> OTHER INFORMATION: synthetic peptide

<400> SEQUENCE: 204

Phe Glu Ile Asp Lys Phe Trp Tyr Asp Ile Asp Ala
1               5                   10

<210> SEQ ID NO 205
<211> LENGTH: 13
<212> TYPE: PRT
<213> ORGANISM: artificial sequence
<220> FEATURE:
<223> OTHER INFORMATION: synthetic peptide

<400> SEQUENCE: 205

Gly Phe Glu Ile Asp Lys Ala Trp Tyr Asp Ile Asp Ala
1               5                   10

<210> SEQ ID NO 206
<211> LENGTH: 11
<212> TYPE: PRT
<213> ORGANISM: artificial sequence
<220> FEATURE:
<223> OTHER INFORMATION: synthetic peptide

<400> SEQUENCE: 206

Phe Glu Ile Asp Lys Ala Trp Tyr Asp Ile Asp
1               5                   10

<210> SEQ ID NO 207
<211> LENGTH: 12
<212> TYPE: PRT
<213> ORGANISM: artificial sequence
<220> FEATURE:
<223> OTHER INFORMATION: synthetic peptide

<400> SEQUENCE: 207

Gly Phe Glu Ile Asp Lys Ala Trp Tyr Asp Ile Asp
1               5                   10

<210> SEQ ID NO 208
<211> LENGTH: 12
<212> TYPE: PRT
<213> ORGANISM: artificial sequence
<220> FEATURE:
<223> OTHER INFORMATION: synthetic peptide

<400> SEQUENCE: 208

Phe Glu Ile Asp Lys Ala Trp Tyr Asp Ile Asp Ala
1               5                   10

```
<210> SEQ ID NO 209
<211> LENGTH: 13
<212> TYPE: PRT
<213> ORGANISM: artificial sequence
<220> FEATURE:
<223> OTHER INFORMATION: synthetic peptide

<400> SEQUENCE: 209

Gly Phe Glu Ile Asp Lys Ser Trp Tyr Asp Ile Asp Ala
1               5                   10

<210> SEQ ID NO 210
<211> LENGTH: 11
<212> TYPE: PRT
<213> ORGANISM: artificial sequence
<220> FEATURE:
<223> OTHER INFORMATION: synthetic peptide

<400> SEQUENCE: 210

Phe Glu Ile Asp Lys Ser Trp Tyr Asp Ile Asp
1               5                   10

<210> SEQ ID NO 211
<211> LENGTH: 12
<212> TYPE: PRT
<213> ORGANISM: artificial sequence
<220> FEATURE:
<223> OTHER INFORMATION: synthetic peptide

<400> SEQUENCE: 211

Gly Phe Glu Ile Asp Lys Ser Trp Tyr Asp Ile Asp
1               5                   10

<210> SEQ ID NO 212
<211> LENGTH: 12
<212> TYPE: PRT
<213> ORGANISM: artificial sequence
<220> FEATURE:
<223> OTHER INFORMATION: synthetic peptide

<400> SEQUENCE: 212

Phe Glu Ile Asp Lys Ser Trp Tyr Asp Ile Asp Ala
1               5                   10

<210> SEQ ID NO 213
<211> LENGTH: 13
<212> TYPE: PRT
<213> ORGANISM: artificial sequence
<220> FEATURE:
<223> OTHER INFORMATION: synthetic peptide

<400> SEQUENCE: 213

Gly Phe Glu Ile Asp Lys Val Trp Tyr Asp Phe Asp Ala
1               5                   10

<210> SEQ ID NO 214
<211> LENGTH: 11
<212> TYPE: PRT
<213> ORGANISM: artificial sequence
<220> FEATURE:
<223> OTHER INFORMATION: synthetic peptide

<400> SEQUENCE: 214

Phe Glu Ile Asp Lys Val Trp Tyr Asp Phe Asp
1               5                   10

<210> SEQ ID NO 215
<211> LENGTH: 12
```

```
<212> TYPE: PRT
<213> ORGANISM: artificial sequence
<220> FEATURE:
<223> OTHER INFORMATION: synthetic peptide

<400> SEQUENCE: 215

Gly Phe Glu Ile Asp Lys Val Trp Tyr Asp Phe Asp
1               5                   10

<210> SEQ ID NO 216
<211> LENGTH: 12
<212> TYPE: PRT
<213> ORGANISM: artificial sequence
<220> FEATURE:
<223> OTHER INFORMATION: synthetic peptide

<400> SEQUENCE: 216

Phe Glu Ile Asp Lys Val Trp Tyr Asp Phe Asp Ala
1               5                   10

<210> SEQ ID NO 217
<211> LENGTH: 13
<212> TYPE: PRT
<213> ORGANISM: artificial sequence
<220> FEATURE:
<223> OTHER INFORMATION: synthetic peptide

<400> SEQUENCE: 217

Gly Phe Glu Ile Asp Lys Ile Trp Tyr Asp Phe Asp Ala
1               5                   10

<210> SEQ ID NO 218
<211> LENGTH: 11
<212> TYPE: PRT
<213> ORGANISM: artificial sequence
<220> FEATURE:
<223> OTHER INFORMATION: synthetic peptide

<400> SEQUENCE: 218

Phe Glu Ile Asp Lys Ile Trp Tyr Asp Phe Asp
1               5                   10

<210> SEQ ID NO 219
<211> LENGTH: 12
<212> TYPE: PRT
<213> ORGANISM: artificial sequence
<220> FEATURE:
<223> OTHER INFORMATION: synthetic peptide

<400> SEQUENCE: 219

Gly Phe Glu Ile Asp Lys Ile Trp Tyr Asp Phe Asp
1               5                   10

<210> SEQ ID NO 220
<211> LENGTH: 12
<212> TYPE: PRT
<213> ORGANISM: artificial sequence
<220> FEATURE:
<223> OTHER INFORMATION: synthetic peptide

<400> SEQUENCE: 220

Phe Glu Ile Asp Lys Ile Trp Tyr Asp Phe Asp Ala
1               5                   10

<210> SEQ ID NO 221
<211> LENGTH: 13
<212> TYPE: PRT
<213> ORGANISM: artificial sequence
```

```
<220> FEATURE:
<223> OTHER INFORMATION: synthetic peptide

<400> SEQUENCE: 221

Gly Phe Glu Ile Asp Lys Leu Trp Tyr Asp Phe Asp Ala
1               5                   10

<210> SEQ ID NO 222
<211> LENGTH: 11
<212> TYPE: PRT
<213> ORGANISM: artificial sequence
<220> FEATURE:
<223> OTHER INFORMATION: synthetic peptide

<400> SEQUENCE: 222

Phe Glu Ile Asp Lys Leu Trp Tyr Asp Phe Asp
1               5                   10

<210> SEQ ID NO 223
<211> LENGTH: 12
<212> TYPE: PRT
<213> ORGANISM: artificial sequence
<220> FEATURE:
<223> OTHER INFORMATION: synthetic peptide

<400> SEQUENCE: 223

Gly Phe Glu Ile Asp Lys Leu Trp Tyr Asp Phe Asp
1               5                   10

<210> SEQ ID NO 224
<211> LENGTH: 12
<212> TYPE: PRT
<213> ORGANISM: artificial sequence
<220> FEATURE:
<223> OTHER INFORMATION: synthetic peptide

<400> SEQUENCE: 224

Phe Glu Ile Asp Lys Leu Trp Tyr Asp Phe Asp Ala
1               5                   10

<210> SEQ ID NO 225
<211> LENGTH: 13
<212> TYPE: PRT
<213> ORGANISM: artificial sequence
<220> FEATURE:
<223> OTHER INFORMATION: synthetic peptide

<400> SEQUENCE: 225

Gly Phe Glu Ile Asp Lys Phe Trp Tyr Asp Phe Asp Ala
1               5                   10

<210> SEQ ID NO 226
<211> LENGTH: 11
<212> TYPE: PRT
<213> ORGANISM: artificial sequence
<220> FEATURE:
<223> OTHER INFORMATION: synthetic peptide

<400> SEQUENCE: 226

Phe Glu Ile Asp Lys Phe Trp Tyr Asp Phe Asp
1               5                   10

<210> SEQ ID NO 227
<211> LENGTH: 12
<212> TYPE: PRT
<213> ORGANISM: artificial sequence
<220> FEATURE:
<223> OTHER INFORMATION: synthetic peptide
```

<400> SEQUENCE: 227

Gly Phe Glu Ile Asp Lys Phe Trp Tyr Asp Phe Asp
1               5                   10

<210> SEQ ID NO 228
<211> LENGTH: 12
<212> TYPE: PRT
<213> ORGANISM: artificial sequence
<220> FEATURE:
<223> OTHER INFORMATION: synthetic peptide

<400> SEQUENCE: 228

Phe Glu Ile Asp Lys Phe Trp Tyr Asp Phe Asp Ala
1               5                   10

<210> SEQ ID NO 229
<211> LENGTH: 13
<212> TYPE: PRT
<213> ORGANISM: artificial sequence
<220> FEATURE:
<223> OTHER INFORMATION: synthetic peptide

<400> SEQUENCE: 229

Gly Phe Glu Ile Asp Lys Ala Trp Tyr Asp Phe Asp Ala
1               5                   10

<210> SEQ ID NO 230
<211> LENGTH: 11
<212> TYPE: PRT
<213> ORGANISM: artificial sequence
<220> FEATURE:
<223> OTHER INFORMATION: synthetic peptide

<400> SEQUENCE: 230

Phe Glu Ile Asp Lys Ala Trp Tyr Asp Phe Asp
1               5                   10

<210> SEQ ID NO 231
<211> LENGTH: 12
<212> TYPE: PRT
<213> ORGANISM: artificial sequence
<220> FEATURE:
<223> OTHER INFORMATION: synthetic peptide

<400> SEQUENCE: 231

Gly Phe Glu Ile Asp Lys Ala Trp Tyr Asp Phe Asp
1               5                   10

<210> SEQ ID NO 232
<211> LENGTH: 12
<212> TYPE: PRT
<213> ORGANISM: artificial sequence
<220> FEATURE:
<223> OTHER INFORMATION: synthetic peptide

<400> SEQUENCE: 232

Phe Glu Ile Asp Lys Ala Trp Tyr Asp Phe Asp Ala
1               5                   10

<210> SEQ ID NO 233
<211> LENGTH: 13
<212> TYPE: PRT
<213> ORGANISM: artificial sequence
<220> FEATURE:
<223> OTHER INFORMATION: synthetic peptide

<400> SEQUENCE: 233

```
Gly Phe Glu Ile Asp Lys Ser Trp Tyr Asp Phe Asp Ala
1               5                   10
```

<210> SEQ ID NO 234
<211> LENGTH: 11
<212> TYPE: PRT
<213> ORGANISM: artificial sequence
<220> FEATURE:
<223> OTHER INFORMATION: synthetic peptide

<400> SEQUENCE: 234

```
Phe Glu Ile Asp Lys Ser Trp Tyr Asp Phe Asp
1               5                   10
```

<210> SEQ ID NO 235
<211> LENGTH: 12
<212> TYPE: PRT
<213> ORGANISM: artificial sequence
<220> FEATURE:
<223> OTHER INFORMATION: synthetic peptide

<400> SEQUENCE: 235

```
Gly Phe Glu Ile Asp Lys Ser Trp Tyr Asp Phe Asp
1               5                   10
```

<210> SEQ ID NO 236
<211> LENGTH: 12
<212> TYPE: PRT
<213> ORGANISM: artificial sequence
<220> FEATURE:
<223> OTHER INFORMATION: synthetic peptide

<400> SEQUENCE: 236

```
Phe Glu Ile Asp Lys Ser Trp Tyr Asp Phe Asp Ala
1               5                   10
```

<210> SEQ ID NO 237
<211> LENGTH: 13
<212> TYPE: PRT
<213> ORGANISM: artificial sequence
<220> FEATURE:
<223> OTHER INFORMATION: synthetic peptide

<400> SEQUENCE: 237

```
Gly Phe Glu Ile Asp Lys Val Trp Tyr Asp Val Asp Ala
1               5                   10
```

<210> SEQ ID NO 238
<211> LENGTH: 11
<212> TYPE: PRT
<213> ORGANISM: artificial sequence
<220> FEATURE:
<223> OTHER INFORMATION: synthetic peptide

<400> SEQUENCE: 238

```
Phe Glu Ile Asp Lys Val Trp Tyr Asp Val Asp
1               5                   10
```

<210> SEQ ID NO 239
<211> LENGTH: 12
<212> TYPE: PRT
<213> ORGANISM: artificial sequence
<220> FEATURE:
<223> OTHER INFORMATION: synthetic peptide

<400> SEQUENCE: 239

```
Gly Phe Glu Ile Asp Lys Val Trp Tyr Asp Val Asp
```

```
1               5                   10
```

<210> SEQ ID NO 240
<211> LENGTH: 12
<212> TYPE: PRT
<213> ORGANISM: artificial sequence
<220> FEATURE:
<223> OTHER INFORMATION: synthetic peptide

<400> SEQUENCE: 240

```
Phe Glu Ile Asp Lys Val Trp Tyr Asp Val Asp Ala
1               5                   10
```

<210> SEQ ID NO 241
<211> LENGTH: 13
<212> TYPE: PRT
<213> ORGANISM: artificial sequence
<220> FEATURE:
<223> OTHER INFORMATION: synthetic peptide

<400> SEQUENCE: 241

```
Gly Phe Glu Ile Asp Lys Ile Trp Tyr Asp Val Asp Ala
1               5                   10
```

<210> SEQ ID NO 242
<211> LENGTH: 11
<212> TYPE: PRT
<213> ORGANISM: artificial sequence
<220> FEATURE:
<223> OTHER INFORMATION: synthetic peptide

<400> SEQUENCE: 242

```
Phe Glu Ile Asp Lys Ile Trp Tyr Asp Val Asp
1               5                   10
```

<210> SEQ ID NO 243
<211> LENGTH: 12
<212> TYPE: PRT
<213> ORGANISM: artificial sequence
<220> FEATURE:
<223> OTHER INFORMATION: synthetic peptide

<400> SEQUENCE: 243

```
Gly Phe Glu Ile Asp Lys Ile Trp Tyr Asp Val Asp
1               5                   10
```

<210> SEQ ID NO 244
<211> LENGTH: 12
<212> TYPE: PRT
<213> ORGANISM: artificial sequence
<220> FEATURE:
<223> OTHER INFORMATION: synthetic peptide

<400> SEQUENCE: 244

```
Phe Glu Ile Asp Lys Ile Trp Tyr Asp Val Asp Ala
1               5                   10
```

<210> SEQ ID NO 245
<211> LENGTH: 13
<212> TYPE: PRT
<213> ORGANISM: artificial sequence
<220> FEATURE:
<223> OTHER INFORMATION: synthetic peptide

<400> SEQUENCE: 245

```
Gly Phe Glu Ile Asp Lys Leu Trp Tyr Asp Val Asp Ala
1               5                   10
```

```
<210> SEQ ID NO 246
<211> LENGTH: 11
<212> TYPE: PRT
<213> ORGANISM: artificial sequence
<220> FEATURE:
<223> OTHER INFORMATION: synthetic peptide

<400> SEQUENCE: 246

Phe Glu Ile Asp Lys Leu Trp Tyr Asp Val Asp
1               5                   10

<210> SEQ ID NO 247
<211> LENGTH: 12
<212> TYPE: PRT
<213> ORGANISM: artificial sequence
<220> FEATURE:
<223> OTHER INFORMATION: synthetic peptide

<400> SEQUENCE: 247

Gly Phe Glu Ile Asp Lys Leu Trp Tyr Asp Val Asp
1               5                   10

<210> SEQ ID NO 248
<211> LENGTH: 12
<212> TYPE: PRT
<213> ORGANISM: artificial sequence
<220> FEATURE:
<223> OTHER INFORMATION: synthetic peptide

<400> SEQUENCE: 248

Phe Glu Ile Asp Lys Leu Trp Tyr Asp Val Asp Ala
1               5                   10

<210> SEQ ID NO 249
<211> LENGTH: 13
<212> TYPE: PRT
<213> ORGANISM: artificial sequence
<220> FEATURE:
<223> OTHER INFORMATION: synthetic peptide

<400> SEQUENCE: 249

Gly Phe Glu Ile Asp Lys Phe Trp Tyr Asp Val Asp Ala
1               5                   10

<210> SEQ ID NO 250
<211> LENGTH: 11
<212> TYPE: PRT
<213> ORGANISM: artificial sequence
<220> FEATURE:
<223> OTHER INFORMATION: synthetic peptide

<400> SEQUENCE: 250

Phe Glu Ile Asp Lys Phe Trp Tyr Asp Val Asp
1               5                   10

<210> SEQ ID NO 251
<211> LENGTH: 12
<212> TYPE: PRT
<213> ORGANISM: artificial sequence
<220> FEATURE:
<223> OTHER INFORMATION: synthetic peptide

<400> SEQUENCE: 251

Gly Phe Glu Ile Asp Lys Phe Trp Tyr Asp Val Asp
1               5                   10

<210> SEQ ID NO 252
```

```
<211> LENGTH: 12
<212> TYPE: PRT
<213> ORGANISM: artificial sequence
<220> FEATURE:
<223> OTHER INFORMATION: synthetic peptide

<400> SEQUENCE: 252

Phe Glu Ile Asp Lys Phe Trp Tyr Asp Val Asp Ala
1               5                   10

<210> SEQ ID NO 253
<211> LENGTH: 13
<212> TYPE: PRT
<213> ORGANISM: artificial sequence
<220> FEATURE:
<223> OTHER INFORMATION: synthetic peptide

<400> SEQUENCE: 253

Gly Phe Glu Ile Asp Lys Ala Trp Tyr Asp Val Asp Ala
1               5                   10

<210> SEQ ID NO 254
<211> LENGTH: 11
<212> TYPE: PRT
<213> ORGANISM: artificial sequence
<220> FEATURE:
<223> OTHER INFORMATION: synthetic peptide

<400> SEQUENCE: 254

Phe Glu Ile Asp Lys Ala Trp Tyr Asp Val Asp
1               5                   10

<210> SEQ ID NO 255
<211> LENGTH: 12
<212> TYPE: PRT
<213> ORGANISM: artificial sequence
<220> FEATURE:
<223> OTHER INFORMATION: synthetic peptide

<400> SEQUENCE: 255

Gly Phe Glu Ile Asp Lys Ala Trp Tyr Asp Val Asp
1               5                   10

<210> SEQ ID NO 256
<211> LENGTH: 12
<212> TYPE: PRT
<213> ORGANISM: artificial sequence
<220> FEATURE:
<223> OTHER INFORMATION: synthetic peptide

<400> SEQUENCE: 256

Phe Glu Ile Asp Lys Ala Trp Tyr Asp Val Asp Ala
1               5                   10

<210> SEQ ID NO 257
<211> LENGTH: 13
<212> TYPE: PRT
<213> ORGANISM: artificial sequence
<220> FEATURE:
<223> OTHER INFORMATION: synthetic peptide

<400> SEQUENCE: 257

Gly Phe Glu Ile Asp Lys Ser Trp Tyr Asp Val Asp Ala
1               5                   10

<210> SEQ ID NO 258
<211> LENGTH: 11
<212> TYPE: PRT
```

-continued

<213> ORGANISM: artificial sequence
<220> FEATURE:
<223> OTHER INFORMATION: synthetic peptide

<400> SEQUENCE: 258

Phe Glu Ile Asp Lys Ser Trp Tyr Asp Val Asp
1               5                   10

<210> SEQ ID NO 259
<211> LENGTH: 12
<212> TYPE: PRT
<213> ORGANISM: artificial sequence
<220> FEATURE:
<223> OTHER INFORMATION: synthetic peptide

<400> SEQUENCE: 259

Gly Phe Glu Ile Asp Lys Ser Trp Tyr Asp Val Asp
1               5                   10

<210> SEQ ID NO 260
<211> LENGTH: 12
<212> TYPE: PRT
<213> ORGANISM: artificial sequence
<220> FEATURE:
<223> OTHER INFORMATION: synthetic peptide

<400> SEQUENCE: 260

Phe Glu Ile Asp Lys Ser Trp Tyr Asp Val Asp Ala
1               5                   10

<210> SEQ ID NO 261
<211> LENGTH: 13
<212> TYPE: PRT
<213> ORGANISM: artificial sequence
<220> FEATURE:
<223> OTHER INFORMATION: synthetic peptide

<400> SEQUENCE: 261

Gly Phe Glu Ile Asp Lys Val Trp Tyr Asp Leu Asp Ser
1               5                   10

<210> SEQ ID NO 262
<211> LENGTH: 12
<212> TYPE: PRT
<213> ORGANISM: artificial sequence
<220> FEATURE:
<223> OTHER INFORMATION: synthetic peptide

<400> SEQUENCE: 262

Phe Glu Ile Asp Lys Val Trp Tyr Asp Leu Asp Ser
1               5                   10

<210> SEQ ID NO 263
<211> LENGTH: 13
<212> TYPE: PRT
<213> ORGANISM: artificial sequence
<220> FEATURE:
<223> OTHER INFORMATION: synthetic peptide

<400> SEQUENCE: 263

Gly Phe Glu Ile Asp Lys Ile Trp Tyr Asp Leu Asp Ser
1               5                   10

<210> SEQ ID NO 264
<211> LENGTH: 12
<212> TYPE: PRT
<213> ORGANISM: artificial sequence
<220> FEATURE:

<223> OTHER INFORMATION: synthetic peptide

<400> SEQUENCE: 264

Phe Glu Ile Asp Lys Ile Trp Tyr Asp Leu Asp Ser
1               5                   10

<210> SEQ ID NO 265
<211> LENGTH: 13
<212> TYPE: PRT
<213> ORGANISM: artificial sequence
<220> FEATURE:
<223> OTHER INFORMATION: synthetic peptide

<400> SEQUENCE: 265

Gly Phe Glu Ile Asp Lys Leu Trp Tyr Asp Leu Asp Ser
1               5                   10

<210> SEQ ID NO 266
<211> LENGTH: 12
<212> TYPE: PRT
<213> ORGANISM: artificial sequence
<220> FEATURE:
<223> OTHER INFORMATION: synthetic peptide

<400> SEQUENCE: 266

Phe Glu Ile Asp Lys Leu Trp Tyr Asp Leu Asp Ser
1               5                   10

<210> SEQ ID NO 267
<211> LENGTH: 13
<212> TYPE: PRT
<213> ORGANISM: artificial sequence
<220> FEATURE:
<223> OTHER INFORMATION: synthetic peptide

<400> SEQUENCE: 267

Gly Phe Glu Ile Asp Lys Phe Trp Tyr Asp Leu Asp Ser
1               5                   10

<210> SEQ ID NO 268
<211> LENGTH: 12
<212> TYPE: PRT
<213> ORGANISM: artificial sequence
<220> FEATURE:
<223> OTHER INFORMATION: synthetic peptide

<400> SEQUENCE: 268

Phe Glu Ile Asp Lys Phe Trp Tyr Asp Leu Asp Ser
1               5                   10

<210> SEQ ID NO 269
<211> LENGTH: 13
<212> TYPE: PRT
<213> ORGANISM: artificial sequence
<220> FEATURE:
<223> OTHER INFORMATION: synthetic peptide

<400> SEQUENCE: 269

Gly Phe Glu Ile Asp Lys Ala Trp Tyr Asp Leu Asp Ser
1               5                   10

<210> SEQ ID NO 270
<211> LENGTH: 12
<212> TYPE: PRT
<213> ORGANISM: artificial sequence
<220> FEATURE:
<223> OTHER INFORMATION: synthetic peptide

```
-continued

<400> SEQUENCE: 270

Phe Glu Ile Asp Lys Ala Trp Tyr Asp Leu Asp Ser
1               5                   10

<210> SEQ ID NO 271
<211> LENGTH: 13
<212> TYPE: PRT
<213> ORGANISM: artificial sequence
<220> FEATURE:
<223> OTHER INFORMATION: synthetic peptide

<400> SEQUENCE: 271

Gly Phe Glu Ile Asp Lys Ser Trp Tyr Asp Leu Asp Ser
1               5                   10

<210> SEQ ID NO 272
<211> LENGTH: 12
<212> TYPE: PRT
<213> ORGANISM: artificial sequence
<220> FEATURE:
<223> OTHER INFORMATION: synthetic peptide

<400> SEQUENCE: 272

Phe Glu Ile Asp Lys Ser Trp Tyr Asp Leu Asp Ser
1               5                   10

<210> SEQ ID NO 273
<211> LENGTH: 13
<212> TYPE: PRT
<213> ORGANISM: artificial sequence
<220> FEATURE:
<223> OTHER INFORMATION: synthetic peptide

<400> SEQUENCE: 273

Gly Phe Glu Ile Asn Lys Val Trp Tyr Asp Leu Asp Ala
1               5                   10

<210> SEQ ID NO 274
<211> LENGTH: 11
<212> TYPE: PRT
<213> ORGANISM: artificial sequence
<220> FEATURE:
<223> OTHER INFORMATION: synthetic peptide

<400> SEQUENCE: 274

Phe Glu Ile Asn Lys Val Trp Tyr Asp Leu Asp
1               5                   10

<210> SEQ ID NO 275
<211> LENGTH: 12
<212> TYPE: PRT
<213> ORGANISM: artificial sequence
<220> FEATURE:
<223> OTHER INFORMATION: synthetic peptide

<400> SEQUENCE: 275

Gly Phe Glu Ile Asn Lys Val Trp Tyr Asp Leu Asp
1               5                   10

<210> SEQ ID NO 276
<211> LENGTH: 12
<212> TYPE: PRT
<213> ORGANISM: artificial sequence
<220> FEATURE:
<223> OTHER INFORMATION: synthetic peptide

<400> SEQUENCE: 276
```

```
Phe Glu Ile Asn Lys Val Trp Tyr Asp Leu Asp Ala
1               5                   10
```

```
<210> SEQ ID NO 277
<211> LENGTH: 13
<212> TYPE: PRT
<213> ORGANISM: artificial sequence
<220> FEATURE:
<223> OTHER INFORMATION: synthetic peptide

<400> SEQUENCE: 277

Gly Phe Glu Ile Asn Lys Ile Trp Tyr Asp Leu Asp Ala
1               5                   10
```

```
<210> SEQ ID NO 278
<211> LENGTH: 11
<212> TYPE: PRT
<213> ORGANISM: artificial sequence
<220> FEATURE:
<223> OTHER INFORMATION: synthetic peptide

<400> SEQUENCE: 278

Phe Glu Ile Asn Lys Ile Trp Tyr Asp Leu Asp
1               5                   10
```

```
<210> SEQ ID NO 279
<211> LENGTH: 12
<212> TYPE: PRT
<213> ORGANISM: artificial sequence
<220> FEATURE:
<223> OTHER INFORMATION: synthetic peptide

<400> SEQUENCE: 279

Gly Phe Glu Ile Asn Lys Ile Trp Tyr Asp Leu Asp
1               5                   10
```

```
<210> SEQ ID NO 280
<211> LENGTH: 12
<212> TYPE: PRT
<213> ORGANISM: artificial sequence
<220> FEATURE:
<223> OTHER INFORMATION: synthetic peptide

<400> SEQUENCE: 280

Phe Glu Ile Asn Lys Ile Trp Tyr Asp Leu Asp Ala
1               5                   10
```

```
<210> SEQ ID NO 281
<211> LENGTH: 13
<212> TYPE: PRT
<213> ORGANISM: artificial sequence
<220> FEATURE:
<223> OTHER INFORMATION: synthetic peptide

<400> SEQUENCE: 281

Gly Phe Glu Ile Asn Lys Leu Trp Tyr Asp Leu Asp Ala
1               5                   10
```

```
<210> SEQ ID NO 282
<211> LENGTH: 11
<212> TYPE: PRT
<213> ORGANISM: artificial sequence
<220> FEATURE:
<223> OTHER INFORMATION: synthetic peptide

<400> SEQUENCE: 282

Phe Glu Ile Asn Lys Leu Trp Tyr Asp Leu Asp
1               5                   10
```

<210> SEQ ID NO 283
<211> LENGTH: 12
<212> TYPE: PRT
<213> ORGANISM: artificial sequence
<220> FEATURE:
<223> OTHER INFORMATION: synthetic peptide

<400> SEQUENCE: 283

Gly Phe Glu Ile Asn Lys Leu Trp Tyr Asp Leu Asp
1               5                   10

<210> SEQ ID NO 284
<211> LENGTH: 12
<212> TYPE: PRT
<213> ORGANISM: artificial sequence
<220> FEATURE:
<223> OTHER INFORMATION: synthetic peptide

<400> SEQUENCE: 284

Phe Glu Ile Asn Lys Leu Trp Tyr Asp Leu Asp Ala
1               5                   10

<210> SEQ ID NO 285
<211> LENGTH: 13
<212> TYPE: PRT
<213> ORGANISM: artificial sequence
<220> FEATURE:
<223> OTHER INFORMATION: synthetic peptide

<400> SEQUENCE: 285

Gly Phe Glu Ile Asn Lys Phe Trp Tyr Asp Leu Asp Ala
1               5                   10

<210> SEQ ID NO 286
<211> LENGTH: 11
<212> TYPE: PRT
<213> ORGANISM: artificial sequence
<220> FEATURE:
<223> OTHER INFORMATION: synthetic peptide

<400> SEQUENCE: 286

Phe Glu Ile Asn Lys Phe Trp Tyr Asp Leu Asp
1               5                   10

<210> SEQ ID NO 287
<211> LENGTH: 12
<212> TYPE: PRT
<213> ORGANISM: artificial sequence
<220> FEATURE:
<223> OTHER INFORMATION: synthetic peptide

<400> SEQUENCE: 287

Gly Phe Glu Ile Asn Lys Phe Trp Tyr Asp Leu Asp
1               5                   10

<210> SEQ ID NO 288
<211> LENGTH: 12
<212> TYPE: PRT
<213> ORGANISM: artificial sequence
<220> FEATURE:
<223> OTHER INFORMATION: synthetic peptide

<400> SEQUENCE: 288

Phe Glu Ile Asn Lys Phe Trp Tyr Asp Leu Asp Ala
1               5                   10

```
<210> SEQ ID NO 289
<211> LENGTH: 13
<212> TYPE: PRT
<213> ORGANISM: artificial sequence
<220> FEATURE:
<223> OTHER INFORMATION: synthetic peptide

<400> SEQUENCE: 289

Gly Phe Glu Ile Asn Lys Ala Trp Tyr Asp Leu Asp Ala
1               5                   10

<210> SEQ ID NO 290
<211> LENGTH: 11
<212> TYPE: PRT
<213> ORGANISM: artificial sequence
<220> FEATURE:
<223> OTHER INFORMATION: synthetic peptide

<400> SEQUENCE: 290

Phe Glu Ile Asn Lys Ala Trp Tyr Asp Leu Asp
1               5                   10

<210> SEQ ID NO 291
<211> LENGTH: 12
<212> TYPE: PRT
<213> ORGANISM: artificial sequence
<220> FEATURE:
<223> OTHER INFORMATION: synthetic peptide

<400> SEQUENCE: 291

Gly Phe Glu Ile Asn Lys Ala Trp Tyr Asp Leu Asp
1               5                   10

<210> SEQ ID NO 292
<211> LENGTH: 12
<212> TYPE: PRT
<213> ORGANISM: artificial sequence
<220> FEATURE:
<223> OTHER INFORMATION: synthetic peptide

<400> SEQUENCE: 292

Phe Glu Ile Asn Lys Ala Trp Tyr Asp Leu Asp Ala
1               5                   10

<210> SEQ ID NO 293
<211> LENGTH: 13
<212> TYPE: PRT
<213> ORGANISM: artificial sequence
<220> FEATURE:
<223> OTHER INFORMATION: synthetic peptide

<400> SEQUENCE: 293

Gly Phe Glu Ile Asn Lys Ser Trp Tyr Asp Leu Asp Ala
1               5                   10

<210> SEQ ID NO 294
<211> LENGTH: 11
<212> TYPE: PRT
<213> ORGANISM: artificial sequence
<220> FEATURE:
<223> OTHER INFORMATION: synthetic peptide

<400> SEQUENCE: 294

Phe Glu Ile Asn Lys Ser Trp Tyr Asp Leu Asp
1               5                   10

<210> SEQ ID NO 295
<211> LENGTH: 12
```

```
<212> TYPE: PRT
<213> ORGANISM: artificial sequence
<220> FEATURE:
<223> OTHER INFORMATION: synthetic peptide

<400> SEQUENCE: 295

Gly Phe Glu Ile Asn Lys Ser Trp Tyr Asp Leu Asp
1               5                   10

<210> SEQ ID NO 296
<211> LENGTH: 12
<212> TYPE: PRT
<213> ORGANISM: artificial sequence
<220> FEATURE:
<223> OTHER INFORMATION: synthetic peptide

<400> SEQUENCE: 296

Phe Glu Ile Asn Lys Ser Trp Tyr Asp Leu Asp Ala
1               5                   10

<210> SEQ ID NO 297
<211> LENGTH: 13
<212> TYPE: PRT
<213> ORGANISM: artificial sequence
<220> FEATURE:
<223> OTHER INFORMATION: synthetic peptide

<400> SEQUENCE: 297

Gly Phe Glu Ile Glu Lys Val Trp Tyr Asp Leu Asp Ala
1               5                   10

<210> SEQ ID NO 298
<211> LENGTH: 11
<212> TYPE: PRT
<213> ORGANISM: artificial sequence
<220> FEATURE:
<223> OTHER INFORMATION: synthetic peptide

<400> SEQUENCE: 298

Phe Glu Ile Glu Lys Val Trp Tyr Asp Leu Asp
1               5                   10

<210> SEQ ID NO 299
<211> LENGTH: 12
<212> TYPE: PRT
<213> ORGANISM: artificial sequence
<220> FEATURE:
<223> OTHER INFORMATION: synthetic peptide

<400> SEQUENCE: 299

Gly Phe Glu Ile Glu Lys Val Trp Tyr Asp Leu Asp
1               5                   10

<210> SEQ ID NO 300
<211> LENGTH: 12
<212> TYPE: PRT
<213> ORGANISM: artificial sequence
<220> FEATURE:
<223> OTHER INFORMATION: synthetic peptide

<400> SEQUENCE: 300

Phe Glu Ile Glu Lys Val Trp Tyr Asp Leu Asp Ala
1               5                   10

<210> SEQ ID NO 301
<211> LENGTH: 13
<212> TYPE: PRT
<213> ORGANISM: artificial sequence
```

<220> FEATURE:
<223> OTHER INFORMATION: synthetic peptide

<400> SEQUENCE: 301

Gly Phe Glu Ile Glu Lys Ile Trp Tyr Asp Leu Asp Ala
1               5                   10

<210> SEQ ID NO 302
<211> LENGTH: 11
<212> TYPE: PRT
<213> ORGANISM: artificial sequence
<220> FEATURE:
<223> OTHER INFORMATION: synthetic peptide

<400> SEQUENCE: 302

Phe Glu Ile Glu Lys Ile Trp Tyr Asp Leu Asp
1               5                   10

<210> SEQ ID NO 303
<211> LENGTH: 12
<212> TYPE: PRT
<213> ORGANISM: artificial sequence
<220> FEATURE:
<223> OTHER INFORMATION: synthetic peptide

<400> SEQUENCE: 303

Gly Phe Glu Ile Glu Lys Ile Trp Tyr Asp Leu Asp
1               5                   10

<210> SEQ ID NO 304
<211> LENGTH: 12
<212> TYPE: PRT
<213> ORGANISM: artificial sequence
<220> FEATURE:
<223> OTHER INFORMATION: synthetic peptide

<400> SEQUENCE: 304

Phe Glu Ile Glu Lys Ile Trp Tyr Asp Leu Asp Ala
1               5                   10

<210> SEQ ID NO 305
<211> LENGTH: 13
<212> TYPE: PRT
<213> ORGANISM: artificial sequence
<220> FEATURE:
<223> OTHER INFORMATION: synthetic peptide

<400> SEQUENCE: 305

Gly Phe Glu Ile Glu Lys Leu Trp Tyr Asp Leu Asp Ala
1               5                   10

<210> SEQ ID NO 306
<211> LENGTH: 11
<212> TYPE: PRT
<213> ORGANISM: artificial sequence
<220> FEATURE:
<223> OTHER INFORMATION: synthetic peptide

<400> SEQUENCE: 306

Phe Glu Ile Glu Lys Leu Trp Tyr Asp Leu Asp
1               5                   10

<210> SEQ ID NO 307
<211> LENGTH: 12
<212> TYPE: PRT
<213> ORGANISM: artificial sequence
<220> FEATURE:
<223> OTHER INFORMATION: synthetic peptide

```
<400> SEQUENCE: 307

Gly Phe Glu Ile Glu Lys Leu Trp Tyr Asp Leu Asp
1               5                   10

<210> SEQ ID NO 308
<211> LENGTH: 12
<212> TYPE: PRT
<213> ORGANISM: artificial sequence
<220> FEATURE:
<223> OTHER INFORMATION: synthetic peptide

<400> SEQUENCE: 308

Phe Glu Ile Glu Lys Leu Trp Tyr Asp Leu Asp Ala
1               5                   10

<210> SEQ ID NO 309
<211> LENGTH: 13
<212> TYPE: PRT
<213> ORGANISM: artificial sequence
<220> FEATURE:
<223> OTHER INFORMATION: synthetic peptide

<400> SEQUENCE: 309

Gly Phe Glu Ile Glu Lys Phe Trp Tyr Asp Leu Asp Ala
1               5                   10

<210> SEQ ID NO 310
<211> LENGTH: 11
<212> TYPE: PRT
<213> ORGANISM: artificial sequence
<220> FEATURE:
<223> OTHER INFORMATION: synthetic peptide

<400> SEQUENCE: 310

Phe Glu Ile Glu Lys Phe Trp Tyr Asp Leu Asp
1               5                   10

<210> SEQ ID NO 311
<211> LENGTH: 12
<212> TYPE: PRT
<213> ORGANISM: artificial sequence
<220> FEATURE:
<223> OTHER INFORMATION: synthetic peptide

<400> SEQUENCE: 311

Gly Phe Glu Ile Glu Lys Phe Trp Tyr Asp Leu Asp
1               5                   10

<210> SEQ ID NO 312
<211> LENGTH: 12
<212> TYPE: PRT
<213> ORGANISM: artificial sequence
<220> FEATURE:
<223> OTHER INFORMATION: synthetic peptide

<400> SEQUENCE: 312

Phe Glu Ile Glu Lys Phe Trp Tyr Asp Leu Asp Ala
1               5                   10

<210> SEQ ID NO 313
<211> LENGTH: 13
<212> TYPE: PRT
<213> ORGANISM: artificial sequence
<220> FEATURE:
<223> OTHER INFORMATION: synthetic peptide

<400> SEQUENCE: 313
```

```
Gly Phe Glu Ile Glu Lys Ala Trp Tyr Asp Leu Asp Ala
1               5                   10
```

<210> SEQ ID NO 314
<211> LENGTH: 11
<212> TYPE: PRT
<213> ORGANISM: artificial sequence
<220> FEATURE:
<223> OTHER INFORMATION: synthetic peptide

<400> SEQUENCE: 314

```
Phe Glu Ile Glu Lys Ala Trp Tyr Asp Leu Asp
1               5                   10
```

<210> SEQ ID NO 315
<211> LENGTH: 12
<212> TYPE: PRT
<213> ORGANISM: artificial sequence
<220> FEATURE:
<223> OTHER INFORMATION: synthetic peptide

<400> SEQUENCE: 315

```
Gly Phe Glu Ile Glu Lys Ala Trp Tyr Asp Leu Asp
1               5                   10
```

<210> SEQ ID NO 316
<211> LENGTH: 12
<212> TYPE: PRT
<213> ORGANISM: artificial sequence
<220> FEATURE:
<223> OTHER INFORMATION: synthetic peptide

<400> SEQUENCE: 316

```
Phe Glu Ile Glu Lys Ala Trp Tyr Asp Leu Asp Ala
1               5                   10
```

<210> SEQ ID NO 317
<211> LENGTH: 13
<212> TYPE: PRT
<213> ORGANISM: artificial sequence
<220> FEATURE:
<223> OTHER INFORMATION: synthetic peptide

<400> SEQUENCE: 317

```
Gly Phe Glu Ile Glu Lys Ser Trp Tyr Asp Leu Asp Ala
1               5                   10
```

<210> SEQ ID NO 318
<211> LENGTH: 11
<212> TYPE: PRT
<213> ORGANISM: artificial sequence
<220> FEATURE:
<223> OTHER INFORMATION: synthetic peptide

<400> SEQUENCE: 318

```
Phe Glu Ile Glu Lys Ser Trp Tyr Asp Leu Asp
1               5                   10
```

<210> SEQ ID NO 319
<211> LENGTH: 12
<212> TYPE: PRT
<213> ORGANISM: artificial sequence
<220> FEATURE:
<223> OTHER INFORMATION: synthetic peptide

<400> SEQUENCE: 319

```
Gly Phe Glu Ile Glu Lys Ser Trp Tyr Asp Leu Asp
```

```
1               5                   10
```

<210> SEQ ID NO 320
<211> LENGTH: 12
<212> TYPE: PRT
<213> ORGANISM: artificial sequence
<220> FEATURE:
<223> OTHER INFORMATION: synthetic peptide

<400> SEQUENCE: 320

```
Phe Glu Ile Glu Lys Ser Trp Tyr Asp Leu Asp Ala
1               5                   10
```

<210> SEQ ID NO 321
<211> LENGTH: 13
<212> TYPE: PRT
<213> ORGANISM: artificial sequence
<220> FEATURE:
<223> OTHER INFORMATION: synthetic peptide

<400> SEQUENCE: 321

```
Gly Phe Glu Ile Tyr Lys Val Trp Tyr Asp Leu Asp Ala
1               5                   10
```

<210> SEQ ID NO 322
<211> LENGTH: 11
<212> TYPE: PRT
<213> ORGANISM: artificial sequence
<220> FEATURE:
<223> OTHER INFORMATION: synthetic peptide

<400> SEQUENCE: 322

```
Phe Glu Ile Tyr Lys Val Trp Tyr Asp Leu Asp
1               5                   10
```

<210> SEQ ID NO 323
<211> LENGTH: 12
<212> TYPE: PRT
<213> ORGANISM: artificial sequence
<220> FEATURE:
<223> OTHER INFORMATION: synthetic peptide

<400> SEQUENCE: 323

```
Gly Phe Glu Ile Tyr Lys Val Trp Tyr Asp Leu Asp
1               5                   10
```

<210> SEQ ID NO 324
<211> LENGTH: 12
<212> TYPE: PRT
<213> ORGANISM: artificial sequence
<220> FEATURE:
<223> OTHER INFORMATION: synthetic peptide

<400> SEQUENCE: 324

```
Phe Glu Ile Tyr Lys Val Trp Tyr Asp Leu Asp Ala
1               5                   10
```

<210> SEQ ID NO 325
<211> LENGTH: 13
<212> TYPE: PRT
<213> ORGANISM: artificial sequence
<220> FEATURE:
<223> OTHER INFORMATION: synthetic peptide

<400> SEQUENCE: 325

```
Gly Phe Glu Ile Tyr Lys Ile Trp Tyr Asp Leu Asp Ala
1               5                   10
```

<210> SEQ ID NO 326
<211> LENGTH: 11
<212> TYPE: PRT
<213> ORGANISM: artificial sequence
<220> FEATURE:
<223> OTHER INFORMATION: synthetic peptide

<400> SEQUENCE: 326

Phe Glu Ile Tyr Lys Ile Trp Tyr Asp Leu Asp
1               5                   10

<210> SEQ ID NO 327
<211> LENGTH: 12
<212> TYPE: PRT
<213> ORGANISM: artificial sequence
<220> FEATURE:
<223> OTHER INFORMATION: synthetic peptide

<400> SEQUENCE: 327

Gly Phe Glu Ile Tyr Lys Ile Trp Tyr Asp Leu Asp
1               5                   10

<210> SEQ ID NO 328
<211> LENGTH: 12
<212> TYPE: PRT
<213> ORGANISM: artificial sequence
<220> FEATURE:
<223> OTHER INFORMATION: synthetic peptide

<400> SEQUENCE: 328

Phe Glu Ile Tyr Lys Ile Trp Tyr Asp Leu Asp Ala
1               5                   10

<210> SEQ ID NO 329
<211> LENGTH: 13
<212> TYPE: PRT
<213> ORGANISM: artificial sequence
<220> FEATURE:
<223> OTHER INFORMATION: synthetic peptide

<400> SEQUENCE: 329

Gly Phe Glu Ile Tyr Lys Leu Trp Tyr Asp Leu Asp Ala
1               5                   10

<210> SEQ ID NO 330
<211> LENGTH: 11
<212> TYPE: PRT
<213> ORGANISM: artificial sequence
<220> FEATURE:
<223> OTHER INFORMATION: synthetic peptide

<400> SEQUENCE: 330

Phe Glu Ile Tyr Lys Leu Trp Tyr Asp Leu Asp
1               5                   10

<210> SEQ ID NO 331
<211> LENGTH: 12
<212> TYPE: PRT
<213> ORGANISM: artificial sequence
<220> FEATURE:
<223> OTHER INFORMATION: synthetic peptide

<400> SEQUENCE: 331

Gly Phe Glu Ile Tyr Lys Leu Trp Tyr Asp Leu Asp
1               5                   10

<210> SEQ ID NO 332

```
<211> LENGTH: 12
<212> TYPE: PRT
<213> ORGANISM: artificial sequence
<220> FEATURE:
<223> OTHER INFORMATION: synthetic peptide

<400> SEQUENCE: 332

Phe Glu Ile Tyr Lys Leu Trp Tyr Asp Leu Asp Ala
1               5                   10

<210> SEQ ID NO 333
<211> LENGTH: 13
<212> TYPE: PRT
<213> ORGANISM: artificial sequence
<220> FEATURE:
<223> OTHER INFORMATION: synthetic peptide

<400> SEQUENCE: 333

Gly Phe Glu Ile Tyr Lys Phe Trp Tyr Asp Leu Asp Ala
1               5                   10

<210> SEQ ID NO 334
<211> LENGTH: 11
<212> TYPE: PRT
<213> ORGANISM: artificial sequence
<220> FEATURE:
<223> OTHER INFORMATION: synthetic peptide

<400> SEQUENCE: 334

Phe Glu Ile Tyr Lys Phe Trp Tyr Asp Leu Asp
1               5                   10

<210> SEQ ID NO 335
<211> LENGTH: 12
<212> TYPE: PRT
<213> ORGANISM: artificial sequence
<220> FEATURE:
<223> OTHER INFORMATION: synthetic peptide

<400> SEQUENCE: 335

Gly Phe Glu Ile Tyr Lys Phe Trp Tyr Asp Leu Asp
1               5                   10

<210> SEQ ID NO 336
<211> LENGTH: 12
<212> TYPE: PRT
<213> ORGANISM: artificial sequence
<220> FEATURE:
<223> OTHER INFORMATION: synthetic peptide

<400> SEQUENCE: 336

Phe Glu Ile Tyr Lys Phe Trp Tyr Asp Leu Asp Ala
1               5                   10

<210> SEQ ID NO 337
<211> LENGTH: 13
<212> TYPE: PRT
<213> ORGANISM: artificial sequence
<220> FEATURE:
<223> OTHER INFORMATION: synthetic peptide

<400> SEQUENCE: 337

Gly Phe Glu Ile Tyr Lys Ala Trp Tyr Asp Leu Asp Ala
1               5                   10

<210> SEQ ID NO 338
<211> LENGTH: 11
<212> TYPE: PRT
```

<213> ORGANISM: artificial sequence
<220> FEATURE:
<223> OTHER INFORMATION: synthetic peptide

<400> SEQUENCE: 338

Phe Glu Ile Tyr Lys Ala Trp Tyr Asp Leu Asp
1               5                   10

<210> SEQ ID NO 339
<211> LENGTH: 12
<212> TYPE: PRT
<213> ORGANISM: artificial sequence
<220> FEATURE:
<223> OTHER INFORMATION: synthetic peptide

<400> SEQUENCE: 339

Gly Phe Glu Ile Tyr Lys Ala Trp Tyr Asp Leu Asp
1               5                   10

<210> SEQ ID NO 340
<211> LENGTH: 12
<212> TYPE: PRT
<213> ORGANISM: artificial sequence
<220> FEATURE:
<223> OTHER INFORMATION: synthetic peptide

<400> SEQUENCE: 340

Phe Glu Ile Tyr Lys Ala Trp Tyr Asp Leu Asp Ala
1               5                   10

<210> SEQ ID NO 341
<211> LENGTH: 13
<212> TYPE: PRT
<213> ORGANISM: artificial sequence
<220> FEATURE:
<223> OTHER INFORMATION: synthetic peptide

<400> SEQUENCE: 341

Gly Phe Glu Ile Tyr Lys Ser Trp Tyr Asp Leu Asp Ala
1               5                   10

<210> SEQ ID NO 342
<211> LENGTH: 11
<212> TYPE: PRT
<213> ORGANISM: artificial sequence
<220> FEATURE:
<223> OTHER INFORMATION: synthetic peptide

<400> SEQUENCE: 342

Phe Glu Ile Tyr Lys Ser Trp Tyr Asp Leu Asp
1               5                   10

<210> SEQ ID NO 343
<211> LENGTH: 12
<212> TYPE: PRT
<213> ORGANISM: artificial sequence
<220> FEATURE:
<223> OTHER INFORMATION: synthetic peptide

<400> SEQUENCE: 343

Gly Phe Glu Ile Tyr Lys Ser Trp Tyr Asp Leu Asp
1               5                   10

<210> SEQ ID NO 344
<211> LENGTH: 12
<212> TYPE: PRT
<213> ORGANISM: artificial sequence
<220> FEATURE:

<223> OTHER INFORMATION: synthetic peptide

<400> SEQUENCE: 344

Phe Glu Ile Tyr Lys Ser Trp Tyr Asp Leu Asp Ala
1               5                   10

<210> SEQ ID NO 345
<211> LENGTH: 13
<212> TYPE: PRT
<213> ORGANISM: artificial sequence
<220> FEATURE:
<223> OTHER INFORMATION: synthetic peptide

<400> SEQUENCE: 345

Gly Phe Glu Ile Ala Lys Val Trp Tyr Asp Leu Asp Ala
1               5                   10

<210> SEQ ID NO 346
<211> LENGTH: 11
<212> TYPE: PRT
<213> ORGANISM: artificial sequence
<220> FEATURE:
<223> OTHER INFORMATION: synthetic peptide

<400> SEQUENCE: 346

Phe Glu Ile Ala Lys Val Trp Tyr Asp Leu Asp
1               5                   10

<210> SEQ ID NO 347
<211> LENGTH: 12
<212> TYPE: PRT
<213> ORGANISM: artificial sequence
<220> FEATURE:
<223> OTHER INFORMATION: synthetic peptide

<400> SEQUENCE: 347

Gly Phe Glu Ile Ala Lys Val Trp Tyr Asp Leu Asp
1               5                   10

<210> SEQ ID NO 348
<211> LENGTH: 12
<212> TYPE: PRT
<213> ORGANISM: artificial sequence
<220> FEATURE:
<223> OTHER INFORMATION: synthetic peptide

<400> SEQUENCE: 348

Phe Glu Ile Ala Lys Val Trp Tyr Asp Leu Asp Ala
1               5                   10

<210> SEQ ID NO 349
<211> LENGTH: 13
<212> TYPE: PRT
<213> ORGANISM: artificial sequence
<220> FEATURE:
<223> OTHER INFORMATION: synthetic peptide

<400> SEQUENCE: 349

Gly Phe Glu Ile Ala Lys Ile Trp Tyr Asp Leu Asp Ala
1               5                   10

<210> SEQ ID NO 350
<211> LENGTH: 11
<212> TYPE: PRT
<213> ORGANISM: artificial sequence
<220> FEATURE:
<223> OTHER INFORMATION: synthetic peptide

```
<400> SEQUENCE: 350

Phe Glu Ile Ala Lys Ile Trp Tyr Asp Leu Asp
1               5                   10

<210> SEQ ID NO 351
<211> LENGTH: 12
<212> TYPE: PRT
<213> ORGANISM: artificial sequence
<220> FEATURE:
<223> OTHER INFORMATION: synthetic peptide

<400> SEQUENCE: 351

Gly Phe Glu Ile Ala Lys Ile Trp Tyr Asp Leu Asp
1               5                   10

<210> SEQ ID NO 352
<211> LENGTH: 12
<212> TYPE: PRT
<213> ORGANISM: artificial sequence
<220> FEATURE:
<223> OTHER INFORMATION: synthetic peptide

<400> SEQUENCE: 352

Phe Glu Ile Ala Lys Ile Trp Tyr Asp Leu Asp Ala
1               5                   10

<210> SEQ ID NO 353
<211> LENGTH: 13
<212> TYPE: PRT
<213> ORGANISM: artificial sequence
<220> FEATURE:
<223> OTHER INFORMATION: synthetic peptide

<400> SEQUENCE: 353

Gly Phe Glu Ile Ala Lys Leu Trp Tyr Asp Leu Asp Ala
1               5                   10

<210> SEQ ID NO 354
<211> LENGTH: 11
<212> TYPE: PRT
<213> ORGANISM: artificial sequence
<220> FEATURE:
<223> OTHER INFORMATION: synthetic peptide

<400> SEQUENCE: 354

Phe Glu Ile Ala Lys Leu Trp Tyr Asp Leu Asp
1               5                   10

<210> SEQ ID NO 355
<211> LENGTH: 12
<212> TYPE: PRT
<213> ORGANISM: artificial sequence
<220> FEATURE:
<223> OTHER INFORMATION: synthetic peptide

<400> SEQUENCE: 355

Gly Phe Glu Ile Ala Lys Leu Trp Tyr Asp Leu Asp
1               5                   10

<210> SEQ ID NO 356
<211> LENGTH: 12
<212> TYPE: PRT
<213> ORGANISM: artificial sequence
<220> FEATURE:
<223> OTHER INFORMATION: synthetic peptide

<400> SEQUENCE: 356
```

```
Phe Glu Ile Ala Lys Leu Trp Tyr Asp Leu Asp Ala
1               5                   10
```

<210> SEQ ID NO 357
<211> LENGTH: 13
<212> TYPE: PRT
<213> ORGANISM: artificial sequence
<220> FEATURE:
<223> OTHER INFORMATION: synthetic peptide

<400> SEQUENCE: 357

```
Gly Phe Glu Ile Ala Lys Phe Trp Tyr Asp Leu Asp Ala
1               5                   10
```

<210> SEQ ID NO 358
<211> LENGTH: 11
<212> TYPE: PRT
<213> ORGANISM: artificial sequence
<220> FEATURE:
<223> OTHER INFORMATION: synthetic peptide

<400> SEQUENCE: 358

```
Phe Glu Ile Ala Lys Phe Trp Tyr Asp Leu Asp
1               5                   10
```

<210> SEQ ID NO 359
<211> LENGTH: 12
<212> TYPE: PRT
<213> ORGANISM: artificial sequence
<220> FEATURE:
<223> OTHER INFORMATION: synthetic peptide

<400> SEQUENCE: 359

```
Gly Phe Glu Ile Ala Lys Phe Trp Tyr Asp Leu Asp
1               5                   10
```

<210> SEQ ID NO 360
<211> LENGTH: 12
<212> TYPE: PRT
<213> ORGANISM: artificial sequence
<220> FEATURE:
<223> OTHER INFORMATION: synthetic peptide

<400> SEQUENCE: 360

```
Phe Glu Ile Ala Lys Phe Trp Tyr Asp Leu Asp Ala
1               5                   10
```

<210> SEQ ID NO 361
<211> LENGTH: 13
<212> TYPE: PRT
<213> ORGANISM: artificial sequence
<220> FEATURE:
<223> OTHER INFORMATION: synthetic peptide

<400> SEQUENCE: 361

```
Gly Phe Glu Ile Ala Lys Ala Trp Tyr Asp Leu Asp Ala
1               5                   10
```

<210> SEQ ID NO 362
<211> LENGTH: 11
<212> TYPE: PRT
<213> ORGANISM: artificial sequence
<220> FEATURE:
<223> OTHER INFORMATION: synthetic peptide

<400> SEQUENCE: 362

```
Phe Glu Ile Ala Lys Ala Trp Tyr Asp Leu Asp
1               5                   10
```

```
<210> SEQ ID NO 363
<211> LENGTH: 12
<212> TYPE: PRT
<213> ORGANISM: artificial sequence
<220> FEATURE:
<223> OTHER INFORMATION: synthetic peptide

<400> SEQUENCE: 363

Gly Phe Glu Ile Ala Lys Ala Trp Tyr Asp Leu Asp
1               5                   10

<210> SEQ ID NO 364
<211> LENGTH: 12
<212> TYPE: PRT
<213> ORGANISM: artificial sequence
<220> FEATURE:
<223> OTHER INFORMATION: synthetic peptide

<400> SEQUENCE: 364

Phe Glu Ile Ala Lys Ala Trp Tyr Asp Leu Asp Ala
1               5                   10

<210> SEQ ID NO 365
<211> LENGTH: 13
<212> TYPE: PRT
<213> ORGANISM: artificial sequence
<220> FEATURE:
<223> OTHER INFORMATION: synthetic peptide

<400> SEQUENCE: 365

Gly Phe Glu Ile Ala Lys Ser Trp Tyr Asp Leu Asp Ala
1               5                   10

<210> SEQ ID NO 366
<211> LENGTH: 11
<212> TYPE: PRT
<213> ORGANISM: artificial sequence
<220> FEATURE:
<223> OTHER INFORMATION: synthetic peptide

<400> SEQUENCE: 366

Phe Glu Ile Ala Lys Ser Trp Tyr Asp Leu Asp
1               5                   10

<210> SEQ ID NO 367
<211> LENGTH: 12
<212> TYPE: PRT
<213> ORGANISM: artificial sequence
<220> FEATURE:
<223> OTHER INFORMATION: synthetic peptide

<400> SEQUENCE: 367

Gly Phe Glu Ile Ala Lys Ser Trp Tyr Asp Leu Asp
1               5                   10

<210> SEQ ID NO 368
<211> LENGTH: 12
<212> TYPE: PRT
<213> ORGANISM: artificial sequence
<220> FEATURE:
<223> OTHER INFORMATION: synthetic peptide

<400> SEQUENCE: 368

Phe Glu Ile Ala Lys Ser Trp Tyr Asp Leu Asp Ala
1               5                   10
```

```
<210> SEQ ID NO 369
<211> LENGTH: 13
<212> TYPE: PRT
<213> ORGANISM: artificial sequence
<220> FEATURE:
<223> OTHER INFORMATION: synthetic peptide

<400> SEQUENCE: 369

Gly Phe Asp Ile Asp Lys Val Trp Tyr Asp Leu Asp Ala
1               5                   10

<210> SEQ ID NO 370
<211> LENGTH: 11
<212> TYPE: PRT
<213> ORGANISM: artificial sequence
<220> FEATURE:
<223> OTHER INFORMATION: synthetic peptide

<400> SEQUENCE: 370

Phe Asp Ile Asp Lys Val Trp Tyr Asp Leu Asp
1               5                   10

<210> SEQ ID NO 371
<211> LENGTH: 12
<212> TYPE: PRT
<213> ORGANISM: artificial sequence
<220> FEATURE:
<223> OTHER INFORMATION: synthetic peptide

<400> SEQUENCE: 371

Gly Phe Asp Ile Asp Lys Val Trp Tyr Asp Leu Asp
1               5                   10

<210> SEQ ID NO 372
<211> LENGTH: 12
<212> TYPE: PRT
<213> ORGANISM: artificial sequence
<220> FEATURE:
<223> OTHER INFORMATION: synthetic peptide

<400> SEQUENCE: 372

Phe Asp Ile Asp Lys Val Trp Tyr Asp Leu Asp Ala
1               5                   10

<210> SEQ ID NO 373
<211> LENGTH: 13
<212> TYPE: PRT
<213> ORGANISM: artificial sequence
<220> FEATURE:
<223> OTHER INFORMATION: synthetic peptide

<400> SEQUENCE: 373

Gly Phe Asp Ile Asp Lys Ile Trp Tyr Asp Leu Asp Ala
1               5                   10

<210> SEQ ID NO 374
<211> LENGTH: 11
<212> TYPE: PRT
<213> ORGANISM: artificial sequence
<220> FEATURE:
<223> OTHER INFORMATION: synthetic peptide

<400> SEQUENCE: 374

Phe Asp Ile Asp Lys Ile Trp Tyr Asp Leu Asp
1               5                   10

<210> SEQ ID NO 375
<211> LENGTH: 12
```

```
<212> TYPE: PRT
<213> ORGANISM: artificial sequence
<220> FEATURE:
<223> OTHER INFORMATION: synthetic peptide

<400> SEQUENCE: 375

Gly Phe Asp Ile Asp Lys Ile Trp Tyr Asp Leu Asp
1               5                   10

<210> SEQ ID NO 376
<211> LENGTH: 12
<212> TYPE: PRT
<213> ORGANISM: artificial sequence
<220> FEATURE:
<223> OTHER INFORMATION: synthetic peptide

<400> SEQUENCE: 376

Phe Asp Ile Asp Lys Ile Trp Tyr Asp Leu Asp Ala
1               5                   10

<210> SEQ ID NO 377
<211> LENGTH: 13
<212> TYPE: PRT
<213> ORGANISM: artificial sequence
<220> FEATURE:
<223> OTHER INFORMATION: synthetic peptide

<400> SEQUENCE: 377

Gly Phe Asp Ile Asp Lys Leu Trp Tyr Asp Leu Asp Ala
1               5                   10

<210> SEQ ID NO 378
<211> LENGTH: 11
<212> TYPE: PRT
<213> ORGANISM: artificial sequence
<220> FEATURE:
<223> OTHER INFORMATION: synthetic peptide

<400> SEQUENCE: 378

Phe Asp Ile Asp Lys Leu Trp Tyr Asp Leu Asp
1               5                   10

<210> SEQ ID NO 379
<211> LENGTH: 12
<212> TYPE: PRT
<213> ORGANISM: artificial sequence
<220> FEATURE:
<223> OTHER INFORMATION: synthetic peptide

<400> SEQUENCE: 379

Gly Phe Asp Ile Asp Lys Leu Trp Tyr Asp Leu Asp
1               5                   10

<210> SEQ ID NO 380
<211> LENGTH: 12
<212> TYPE: PRT
<213> ORGANISM: artificial sequence
<220> FEATURE:
<223> OTHER INFORMATION: synthetic peptide

<400> SEQUENCE: 380

Phe Asp Ile Asp Lys Leu Trp Tyr Asp Leu Asp Ala
1               5                   10

<210> SEQ ID NO 381
<211> LENGTH: 13
<212> TYPE: PRT
<213> ORGANISM: artificial sequence
```

```
<220> FEATURE:
<223> OTHER INFORMATION: synthetic peptide

<400> SEQUENCE: 381

Gly Phe Asp Ile Asp Lys Phe Trp Tyr Asp Leu Asp Ala
1               5                   10

<210> SEQ ID NO 382
<211> LENGTH: 11
<212> TYPE: PRT
<213> ORGANISM: artificial sequence
<220> FEATURE:
<223> OTHER INFORMATION: synthetic peptide

<400> SEQUENCE: 382

Phe Asp Ile Asp Lys Phe Trp Tyr Asp Leu Asp
1               5                   10

<210> SEQ ID NO 383
<211> LENGTH: 12
<212> TYPE: PRT
<213> ORGANISM: artificial sequence
<220> FEATURE:
<223> OTHER INFORMATION: synthetic peptide

<400> SEQUENCE: 383

Gly Phe Asp Ile Asp Lys Phe Trp Tyr Asp Leu Asp
1               5                   10

<210> SEQ ID NO 384
<211> LENGTH: 12
<212> TYPE: PRT
<213> ORGANISM: artificial sequence
<220> FEATURE:
<223> OTHER INFORMATION: synthetic peptide

<400> SEQUENCE: 384

Phe Asp Ile Asp Lys Phe Trp Tyr Asp Leu Asp Ala
1               5                   10

<210> SEQ ID NO 385
<211> LENGTH: 13
<212> TYPE: PRT
<213> ORGANISM: artificial sequence
<220> FEATURE:
<223> OTHER INFORMATION: synthetic peptide

<400> SEQUENCE: 385

Gly Phe Asp Ile Asp Lys Ala Trp Tyr Asp Leu Asp Ala
1               5                   10

<210> SEQ ID NO 386
<211> LENGTH: 11
<212> TYPE: PRT
<213> ORGANISM: artificial sequence
<220> FEATURE:
<223> OTHER INFORMATION: synthetic peptide

<400> SEQUENCE: 386

Phe Asp Ile Asp Lys Ala Trp Tyr Asp Leu Asp
1               5                   10

<210> SEQ ID NO 387
<211> LENGTH: 12
<212> TYPE: PRT
<213> ORGANISM: artificial sequence
<220> FEATURE:
<223> OTHER INFORMATION: synthetic peptide
```

<400> SEQUENCE: 387

Gly Phe Asp Ile Asp Lys Ala Trp Tyr Asp Leu Asp
1               5                   10

<210> SEQ ID NO 388
<211> LENGTH: 12
<212> TYPE: PRT
<213> ORGANISM: artificial sequence
<220> FEATURE:
<223> OTHER INFORMATION: synthetic peptide

<400> SEQUENCE: 388

Phe Asp Ile Asp Lys Ala Trp Tyr Asp Leu Asp Ala
1               5                   10

<210> SEQ ID NO 389
<211> LENGTH: 13
<212> TYPE: PRT
<213> ORGANISM: artificial sequence
<220> FEATURE:
<223> OTHER INFORMATION: synthetic peptide

<400> SEQUENCE: 389

Gly Phe Asp Ile Asp Lys Ser Trp Tyr Asp Leu Asp Ala
1               5                   10

<210> SEQ ID NO 390
<211> LENGTH: 11
<212> TYPE: PRT
<213> ORGANISM: artificial sequence
<220> FEATURE:
<223> OTHER INFORMATION: synthetic peptide

<400> SEQUENCE: 390

Phe Asp Ile Asp Lys Ser Trp Tyr Asp Leu Asp
1               5                   10

<210> SEQ ID NO 391
<211> LENGTH: 12
<212> TYPE: PRT
<213> ORGANISM: artificial sequence
<220> FEATURE:
<223> OTHER INFORMATION: synthetic peptide

<400> SEQUENCE: 391

Gly Phe Asp Ile Asp Lys Ser Trp Tyr Asp Leu Asp
1               5                   10

<210> SEQ ID NO 392
<211> LENGTH: 12
<212> TYPE: PRT
<213> ORGANISM: artificial sequence
<220> FEATURE:
<223> OTHER INFORMATION: synthetic peptide

<400> SEQUENCE: 392

Phe Asp Ile Asp Lys Ser Trp Tyr Asp Leu Asp Ala
1               5                   10

<210> SEQ ID NO 393
<211> LENGTH: 13
<212> TYPE: PRT
<213> ORGANISM: artificial sequence
<220> FEATURE:
<223> OTHER INFORMATION: synthetic peptide

<400> SEQUENCE: 393

```
Gly Ile Glu Ile Asp Lys Val Trp Tyr Asp Leu Asp Ala
1               5                   10
```

<210> SEQ ID NO 394
<211> LENGTH: 11
<212> TYPE: PRT
<213> ORGANISM: artificial sequence
<220> FEATURE:
<223> OTHER INFORMATION: synthetic peptide

<400> SEQUENCE: 394

```
Ile Glu Ile Asp Lys Val Trp Tyr Asp Leu Asp
1               5                   10
```

<210> SEQ ID NO 395
<211> LENGTH: 12
<212> TYPE: PRT
<213> ORGANISM: artificial sequence
<220> FEATURE:
<223> OTHER INFORMATION: synthetic peptide

<400> SEQUENCE: 395

```
Gly Ile Glu Ile Asp Lys Val Trp Tyr Asp Leu Asp
1               5                   10
```

<210> SEQ ID NO 396
<211> LENGTH: 12
<212> TYPE: PRT
<213> ORGANISM: artificial sequence
<220> FEATURE:
<223> OTHER INFORMATION: synthetic peptide

<400> SEQUENCE: 396

```
Ile Glu Ile Asp Lys Val Trp Tyr Asp Leu Asp Ala
1               5                   10
```

<210> SEQ ID NO 397
<211> LENGTH: 13
<212> TYPE: PRT
<213> ORGANISM: artificial sequence
<220> FEATURE:
<223> OTHER INFORMATION: synthetic peptide

<400> SEQUENCE: 397

```
Gly Ile Glu Ile Asp Lys Ile Trp Tyr Asp Leu Asp Ala
1               5                   10
```

<210> SEQ ID NO 398
<211> LENGTH: 11
<212> TYPE: PRT
<213> ORGANISM: artificial sequence
<220> FEATURE:
<223> OTHER INFORMATION: synthetic peptide

<400> SEQUENCE: 398

```
Ile Glu Ile Asp Lys Ile Trp Tyr Asp Leu Asp
1               5                   10
```

<210> SEQ ID NO 399
<211> LENGTH: 12
<212> TYPE: PRT
<213> ORGANISM: artificial sequence
<220> FEATURE:
<223> OTHER INFORMATION: synthetic peptide

<400> SEQUENCE: 399

```
Gly Ile Glu Ile Asp Lys Ile Trp Tyr Asp Leu Asp
```

<210> SEQ ID NO 400
<211> LENGTH: 12
<212> TYPE: PRT
<213> ORGANISM: artificial sequence
<220> FEATURE:
<223> OTHER INFORMATION: synthetic peptide

<400> SEQUENCE: 400

Ile Glu Ile Asp Lys Ile Trp Tyr Asp Leu Asp Ala
1               5                   10

<210> SEQ ID NO 401
<211> LENGTH: 13
<212> TYPE: PRT
<213> ORGANISM: artificial sequence
<220> FEATURE:
<223> OTHER INFORMATION: synthetic peptide

<400> SEQUENCE: 401

Gly Ile Glu Ile Asp Lys Leu Trp Tyr Asp Leu Asp Ala
1               5                   10

<210> SEQ ID NO 402
<211> LENGTH: 11
<212> TYPE: PRT
<213> ORGANISM: artificial sequence
<220> FEATURE:
<223> OTHER INFORMATION: synthetic peptide

<400> SEQUENCE: 402

Ile Glu Ile Asp Lys Leu Trp Tyr Asp Leu Asp
1               5                   10

<210> SEQ ID NO 403
<211> LENGTH: 12
<212> TYPE: PRT
<213> ORGANISM: artificial sequence
<220> FEATURE:
<223> OTHER INFORMATION: synthetic peptide

<400> SEQUENCE: 403

Gly Ile Glu Ile Asp Lys Leu Trp Tyr Asp Leu Asp
1               5                   10

<210> SEQ ID NO 404
<211> LENGTH: 12
<212> TYPE: PRT
<213> ORGANISM: artificial sequence
<220> FEATURE:
<223> OTHER INFORMATION: synthetic peptide

<400> SEQUENCE: 404

Ile Glu Ile Asp Lys Leu Trp Tyr Asp Leu Asp Ala
1               5                   10

<210> SEQ ID NO 405
<211> LENGTH: 13
<212> TYPE: PRT
<213> ORGANISM: artificial sequence
<220> FEATURE:
<223> OTHER INFORMATION: synthetic peptide

<400> SEQUENCE: 405

Gly Ile Glu Ile Asp Lys Phe Trp Tyr Asp Leu Asp Ala
1               5                   10

<210> SEQ ID NO 406
<211> LENGTH: 11
<212> TYPE: PRT
<213> ORGANISM: artificial sequence
<220> FEATURE:
<223> OTHER INFORMATION: synthetic peptide

<400> SEQUENCE: 406

Ile Glu Ile Asp Lys Phe Trp Tyr Asp Leu Asp
1               5                   10

<210> SEQ ID NO 407
<211> LENGTH: 12
<212> TYPE: PRT
<213> ORGANISM: artificial sequence
<220> FEATURE:
<223> OTHER INFORMATION: synthetic peptide

<400> SEQUENCE: 407

Gly Ile Glu Ile Asp Lys Phe Trp Tyr Asp Leu Asp
1               5                   10

<210> SEQ ID NO 408
<211> LENGTH: 12
<212> TYPE: PRT
<213> ORGANISM: artificial sequence
<220> FEATURE:
<223> OTHER INFORMATION: synthetic peptide

<400> SEQUENCE: 408

Ile Glu Ile Asp Lys Phe Trp Tyr Asp Leu Asp Ala
1               5                   10

<210> SEQ ID NO 409
<211> LENGTH: 13
<212> TYPE: PRT
<213> ORGANISM: artificial sequence
<220> FEATURE:
<223> OTHER INFORMATION: synthetic peptide

<400> SEQUENCE: 409

Gly Ile Glu Ile Asp Lys Ala Trp Tyr Asp Leu Asp Ala
1               5                   10

<210> SEQ ID NO 410
<211> LENGTH: 11
<212> TYPE: PRT
<213> ORGANISM: artificial sequence
<220> FEATURE:
<223> OTHER INFORMATION: synthetic peptide

<400> SEQUENCE: 410

Ile Glu Ile Asp Lys Ala Trp Tyr Asp Leu Asp
1               5                   10

<210> SEQ ID NO 411
<211> LENGTH: 12
<212> TYPE: PRT
<213> ORGANISM: artificial sequence
<220> FEATURE:
<223> OTHER INFORMATION: synthetic peptide

<400> SEQUENCE: 411

Gly Ile Glu Ile Asp Lys Ala Trp Tyr Asp Leu Asp
1               5                   10

<210> SEQ ID NO 412

```
<211> LENGTH: 12
<212> TYPE: PRT
<213> ORGANISM: artificial sequence
<220> FEATURE:
<223> OTHER INFORMATION: synthetic peptide

<400> SEQUENCE: 412

Ile Glu Ile Asp Lys Ala Trp Tyr Asp Leu Asp Ala
1               5                   10

<210> SEQ ID NO 413
<211> LENGTH: 13
<212> TYPE: PRT
<213> ORGANISM: artificial sequence
<220> FEATURE:
<223> OTHER INFORMATION: synthetic peptide

<400> SEQUENCE: 413

Gly Ile Glu Ile Asp Lys Ser Trp Tyr Asp Leu Asp Ala
1               5                   10

<210> SEQ ID NO 414
<211> LENGTH: 11
<212> TYPE: PRT
<213> ORGANISM: artificial sequence
<220> FEATURE:
<223> OTHER INFORMATION: synthetic peptide

<400> SEQUENCE: 414

Ile Glu Ile Asp Lys Ser Trp Tyr Asp Leu Asp
1               5                   10

<210> SEQ ID NO 415
<211> LENGTH: 12
<212> TYPE: PRT
<213> ORGANISM: artificial sequence
<220> FEATURE:
<223> OTHER INFORMATION: synthetic peptide

<400> SEQUENCE: 415

Gly Ile Glu Ile Asp Lys Ser Trp Tyr Asp Leu Asp
1               5                   10

<210> SEQ ID NO 416
<211> LENGTH: 12
<212> TYPE: PRT
<213> ORGANISM: artificial sequence
<220> FEATURE:
<223> OTHER INFORMATION: synthetic peptide

<400> SEQUENCE: 416

Ile Glu Ile Asp Lys Ser Trp Tyr Asp Leu Asp Ala
1               5                   10

<210> SEQ ID NO 417
<211> LENGTH: 13
<212> TYPE: PRT
<213> ORGANISM: artificial sequence
<220> FEATURE:
<223> OTHER INFORMATION: synthetic peptide

<400> SEQUENCE: 417

Gly Val Glu Ile Asp Lys Val Trp Tyr Asp Leu Asp Ala
1               5                   10

<210> SEQ ID NO 418
<211> LENGTH: 11
<212> TYPE: PRT
```

<213> ORGANISM: artificial sequence
<220> FEATURE:
<223> OTHER INFORMATION: synthetic peptide

<400> SEQUENCE: 418

Val Glu Ile Asp Lys Val Trp Tyr Asp Leu Asp
1               5                   10

<210> SEQ ID NO 419
<211> LENGTH: 12
<212> TYPE: PRT
<213> ORGANISM: artificial sequence
<220> FEATURE:
<223> OTHER INFORMATION: synthetic peptide

<400> SEQUENCE: 419

Gly Val Glu Ile Asp Lys Val Trp Tyr Asp Leu Asp
1               5                   10

<210> SEQ ID NO 420
<211> LENGTH: 12
<212> TYPE: PRT
<213> ORGANISM: artificial sequence
<220> FEATURE:
<223> OTHER INFORMATION: synthetic peptide

<400> SEQUENCE: 420

Val Glu Ile Asp Lys Val Trp Tyr Asp Leu Asp Ala
1               5                   10

<210> SEQ ID NO 421
<211> LENGTH: 13
<212> TYPE: PRT
<213> ORGANISM: artificial sequence
<220> FEATURE:
<223> OTHER INFORMATION: synthetic peptide

<400> SEQUENCE: 421

Gly Val Glu Ile Asp Lys Ile Trp Tyr Asp Leu Asp Ala
1               5                   10

<210> SEQ ID NO 422
<211> LENGTH: 11
<212> TYPE: PRT
<213> ORGANISM: artificial sequence
<220> FEATURE:
<223> OTHER INFORMATION: synthetic peptide

<400> SEQUENCE: 422

Val Glu Ile Asp Lys Ile Trp Tyr Asp Leu Asp
1               5                   10

<210> SEQ ID NO 423
<211> LENGTH: 12
<212> TYPE: PRT
<213> ORGANISM: artificial sequence
<220> FEATURE:
<223> OTHER INFORMATION: synthetic peptide

<400> SEQUENCE: 423

Gly Val Glu Ile Asp Lys Ile Trp Tyr Asp Leu Asp
1               5                   10

<210> SEQ ID NO 424
<211> LENGTH: 12
<212> TYPE: PRT
<213> ORGANISM: artificial sequence
<220> FEATURE:

<223> OTHER INFORMATION: synthetic peptide

<400> SEQUENCE: 424

Val Glu Ile Asp Lys Ile Trp Tyr Asp Leu Asp Ala
1               5                   10

<210> SEQ ID NO 425
<211> LENGTH: 13
<212> TYPE: PRT
<213> ORGANISM: artificial sequence
<220> FEATURE:
<223> OTHER INFORMATION: synthetic peptide

<400> SEQUENCE: 425

Gly Val Glu Ile Asp Lys Leu Trp Tyr Asp Leu Asp Ala
1               5                   10

<210> SEQ ID NO 426
<211> LENGTH: 11
<212> TYPE: PRT
<213> ORGANISM: artificial sequence
<220> FEATURE:
<223> OTHER INFORMATION: synthetic peptide

<400> SEQUENCE: 426

Val Glu Ile Asp Lys Leu Trp Tyr Asp Leu Asp
1               5                   10

<210> SEQ ID NO 427
<211> LENGTH: 12
<212> TYPE: PRT
<213> ORGANISM: artificial sequence
<220> FEATURE:
<223> OTHER INFORMATION: synthetic peptide

<400> SEQUENCE: 427

Gly Val Glu Ile Asp Lys Leu Trp Tyr Asp Leu Asp
1               5                   10

<210> SEQ ID NO 428
<211> LENGTH: 12
<212> TYPE: PRT
<213> ORGANISM: artificial sequence
<220> FEATURE:
<223> OTHER INFORMATION: synthetic peptide

<400> SEQUENCE: 428

Val Glu Ile Asp Lys Leu Trp Tyr Asp Leu Asp Ala
1               5                   10

<210> SEQ ID NO 429
<211> LENGTH: 13
<212> TYPE: PRT
<213> ORGANISM: artificial sequence
<220> FEATURE:
<223> OTHER INFORMATION: synthetic peptide

<400> SEQUENCE: 429

Gly Val Glu Ile Asp Lys Phe Trp Tyr Asp Leu Asp Ala
1               5                   10

<210> SEQ ID NO 430
<211> LENGTH: 11
<212> TYPE: PRT
<213> ORGANISM: artificial sequence
<220> FEATURE:
<223> OTHER INFORMATION: synthetic peptide

```
<400> SEQUENCE: 430

Val Glu Ile Asp Lys Phe Trp Tyr Asp Leu Asp
1               5                   10

<210> SEQ ID NO 431
<211> LENGTH: 12
<212> TYPE: PRT
<213> ORGANISM: artificial sequence
<220> FEATURE:
<223> OTHER INFORMATION: synthetic peptide

<400> SEQUENCE: 431

Gly Val Glu Ile Asp Lys Phe Trp Tyr Asp Leu Asp
1               5                   10

<210> SEQ ID NO 432
<211> LENGTH: 12
<212> TYPE: PRT
<213> ORGANISM: artificial sequence
<220> FEATURE:
<223> OTHER INFORMATION: synthetic peptide

<400> SEQUENCE: 432

Val Glu Ile Asp Lys Phe Trp Tyr Asp Leu Asp Ala
1               5                   10

<210> SEQ ID NO 433
<211> LENGTH: 13
<212> TYPE: PRT
<213> ORGANISM: artificial sequence
<220> FEATURE:
<223> OTHER INFORMATION: synthetic peptide

<400> SEQUENCE: 433

Gly Val Glu Ile Asp Lys Ala Trp Tyr Asp Leu Asp Ala
1               5                   10

<210> SEQ ID NO 434
<211> LENGTH: 11
<212> TYPE: PRT
<213> ORGANISM: artificial sequence
<220> FEATURE:
<223> OTHER INFORMATION: synthetic peptide

<400> SEQUENCE: 434

Val Glu Ile Asp Lys Ala Trp Tyr Asp Leu Asp
1               5                   10

<210> SEQ ID NO 435
<211> LENGTH: 12
<212> TYPE: PRT
<213> ORGANISM: artificial sequence
<220> FEATURE:
<223> OTHER INFORMATION: synthetic peptide

<400> SEQUENCE: 435

Gly Val Glu Ile Asp Lys Ala Trp Tyr Asp Leu Asp
1               5                   10

<210> SEQ ID NO 436
<211> LENGTH: 12
<212> TYPE: PRT
<213> ORGANISM: artificial sequence
<220> FEATURE:
<223> OTHER INFORMATION: synthetic peptide

<400> SEQUENCE: 436
```

-continued

Val Glu Ile Asp Lys Ala Trp Tyr Asp Leu Asp Ala
1               5                   10

<210> SEQ ID NO 437
<211> LENGTH: 13
<212> TYPE: PRT
<213> ORGANISM: artificial sequence
<220> FEATURE:
<223> OTHER INFORMATION: synthetic peptide

<400> SEQUENCE: 437

Gly Val Glu Ile Asp Lys Ser Trp Tyr Asp Leu Asp Ala
1               5                   10

<210> SEQ ID NO 438
<211> LENGTH: 11
<212> TYPE: PRT
<213> ORGANISM: artificial sequence
<220> FEATURE:
<223> OTHER INFORMATION: synthetic peptide

<400> SEQUENCE: 438

Val Glu Ile Asp Lys Ser Trp Tyr Asp Leu Asp
1               5                   10

<210> SEQ ID NO 439
<211> LENGTH: 12
<212> TYPE: PRT
<213> ORGANISM: artificial sequence
<220> FEATURE:
<223> OTHER INFORMATION: synthetic peptide

<400> SEQUENCE: 439

Gly Val Glu Ile Asp Lys Ser Trp Tyr Asp Leu Asp
1               5                   10

<210> SEQ ID NO 440
<211> LENGTH: 12
<212> TYPE: PRT
<213> ORGANISM: artificial sequence
<220> FEATURE:
<223> OTHER INFORMATION: synthetic peptide

<400> SEQUENCE: 440

Val Glu Ile Asp Lys Ser Trp Tyr Asp Leu Asp Ala
1               5                   10

<210> SEQ ID NO 441
<211> LENGTH: 13
<212> TYPE: PRT
<213> ORGANISM: artificial sequence
<220> FEATURE:
<223> OTHER INFORMATION: synthetic peptide

<400> SEQUENCE: 441

Gly Leu Glu Ile Asp Lys Val Trp Tyr Asp Leu Asp Ala
1               5                   10

<210> SEQ ID NO 442
<211> LENGTH: 11
<212> TYPE: PRT
<213> ORGANISM: artificial sequence
<220> FEATURE:
<223> OTHER INFORMATION: synthetic peptide

<400> SEQUENCE: 442

Leu Glu Ile Asp Lys Val Trp Tyr Asp Leu Asp
1               5                   10

```
<210> SEQ ID NO 443
<211> LENGTH: 12
<212> TYPE: PRT
<213> ORGANISM: artificial sequence
<220> FEATURE:
<223> OTHER INFORMATION: synthetic peptide

<400> SEQUENCE: 443

Gly Leu Glu Ile Asp Lys Val Trp Tyr Asp Leu Asp
1               5                   10

<210> SEQ ID NO 444
<211> LENGTH: 12
<212> TYPE: PRT
<213> ORGANISM: artificial sequence
<220> FEATURE:
<223> OTHER INFORMATION: synthetic peptide

<400> SEQUENCE: 444

Leu Glu Ile Asp Lys Val Trp Tyr Asp Leu Asp Ala
1               5                   10

<210> SEQ ID NO 445
<211> LENGTH: 13
<212> TYPE: PRT
<213> ORGANISM: artificial sequence
<220> FEATURE:
<223> OTHER INFORMATION: synthetic peptide

<400> SEQUENCE: 445

Gly Leu Glu Ile Asp Lys Ile Trp Tyr Asp Leu Asp Ala
1               5                   10

<210> SEQ ID NO 446
<211> LENGTH: 11
<212> TYPE: PRT
<213> ORGANISM: artificial sequence
<220> FEATURE:
<223> OTHER INFORMATION: synthetic peptide

<400> SEQUENCE: 446

Leu Glu Ile Asp Lys Ile Trp Tyr Asp Leu Asp
1               5                   10

<210> SEQ ID NO 447
<211> LENGTH: 12
<212> TYPE: PRT
<213> ORGANISM: artificial sequence
<220> FEATURE:
<223> OTHER INFORMATION: synthetic peptide

<400> SEQUENCE: 447

Gly Leu Glu Ile Asp Lys Ile Trp Tyr Asp Leu Asp
1               5                   10

<210> SEQ ID NO 448
<211> LENGTH: 12
<212> TYPE: PRT
<213> ORGANISM: artificial sequence
<220> FEATURE:
<223> OTHER INFORMATION: synthetic peptide

<400> SEQUENCE: 448

Leu Glu Ile Asp Lys Ile Trp Tyr Asp Leu Asp Ala
1               5                   10
```

```
<210> SEQ ID NO 449
<211> LENGTH: 13
<212> TYPE: PRT
<213> ORGANISM: artificial sequence
<220> FEATURE:
<223> OTHER INFORMATION: synthetic peptide

<400> SEQUENCE: 449

Gly Leu Glu Ile Asp Lys Leu Trp Tyr Asp Leu Asp Ala
1               5                   10

<210> SEQ ID NO 450
<211> LENGTH: 11
<212> TYPE: PRT
<213> ORGANISM: artificial sequence
<220> FEATURE:
<223> OTHER INFORMATION: synthetic peptide

<400> SEQUENCE: 450

Leu Glu Ile Asp Lys Leu Trp Tyr Asp Leu Asp
1               5                   10

<210> SEQ ID NO 451
<211> LENGTH: 12
<212> TYPE: PRT
<213> ORGANISM: artificial sequence
<220> FEATURE:
<223> OTHER INFORMATION: synthetic peptide

<400> SEQUENCE: 451

Gly Leu Glu Ile Asp Lys Leu Trp Tyr Asp Leu Asp
1               5                   10

<210> SEQ ID NO 452
<211> LENGTH: 12
<212> TYPE: PRT
<213> ORGANISM: artificial sequence
<220> FEATURE:
<223> OTHER INFORMATION: synthetic peptide

<400> SEQUENCE: 452

Leu Glu Ile Asp Lys Leu Trp Tyr Asp Leu Asp Ala
1               5                   10

<210> SEQ ID NO 453
<211> LENGTH: 13
<212> TYPE: PRT
<213> ORGANISM: artificial sequence
<220> FEATURE:
<223> OTHER INFORMATION: synthetic peptide

<400> SEQUENCE: 453

Gly Leu Glu Ile Asp Lys Phe Trp Tyr Asp Leu Asp Ala
1               5                   10

<210> SEQ ID NO 454
<211> LENGTH: 11
<212> TYPE: PRT
<213> ORGANISM: artificial sequence
<220> FEATURE:
<223> OTHER INFORMATION: synthetic peptide

<400> SEQUENCE: 454

Leu Glu Ile Asp Lys Phe Trp Tyr Asp Leu Asp
1               5                   10

<210> SEQ ID NO 455
<211> LENGTH: 12
```

<212> TYPE: PRT
<213> ORGANISM: artificial sequence
<220> FEATURE:
<223> OTHER INFORMATION: synthetic peptide

<400> SEQUENCE: 455

Gly Leu Glu Ile Asp Lys Phe Trp Tyr Asp Leu Asp
1               5                   10

<210> SEQ ID NO 456
<211> LENGTH: 12
<212> TYPE: PRT
<213> ORGANISM: artificial sequence
<220> FEATURE:
<223> OTHER INFORMATION: synthetic peptide

<400> SEQUENCE: 456

Leu Glu Ile Asp Lys Phe Trp Tyr Asp Leu Asp Ala
1               5                   10

<210> SEQ ID NO 457
<211> LENGTH: 13
<212> TYPE: PRT
<213> ORGANISM: artificial sequence
<220> FEATURE:
<223> OTHER INFORMATION: synthetic peptide

<400> SEQUENCE: 457

Gly Leu Glu Ile Asp Lys Ala Trp Tyr Asp Leu Asp Ala
1               5                   10

<210> SEQ ID NO 458
<211> LENGTH: 11
<212> TYPE: PRT
<213> ORGANISM: artificial sequence
<220> FEATURE:
<223> OTHER INFORMATION: synthetic peptide

<400> SEQUENCE: 458

Leu Glu Ile Asp Lys Ala Trp Tyr Asp Leu Asp
1               5                   10

<210> SEQ ID NO 459
<211> LENGTH: 12
<212> TYPE: PRT
<213> ORGANISM: artificial sequence
<220> FEATURE:
<223> OTHER INFORMATION: synthetic peptide

<400> SEQUENCE: 459

Gly Leu Glu Ile Asp Lys Ala Trp Tyr Asp Leu Asp
1               5                   10

<210> SEQ ID NO 460
<211> LENGTH: 12
<212> TYPE: PRT
<213> ORGANISM: artificial sequence
<220> FEATURE:
<223> OTHER INFORMATION: synthetic peptide

<400> SEQUENCE: 460

Leu Glu Ile Asp Lys Ala Trp Tyr Asp Leu Asp Ala
1               5                   10

<210> SEQ ID NO 461
<211> LENGTH: 13
<212> TYPE: PRT
<213> ORGANISM: artificial sequence
<220> FEATURE:
<223> OTHER INFORMATION: synthetic peptide

<400> SEQUENCE: 461

Gly Leu Glu Ile Asp Lys Ser Trp Tyr Asp Leu Asp Ala
1               5                   10

<210> SEQ ID NO 462
<211> LENGTH: 11
<212> TYPE: PRT
<213> ORGANISM: artificial sequence
<220> FEATURE:
<223> OTHER INFORMATION: synthetic peptide

<400> SEQUENCE: 462

Leu Glu Ile Asp Lys Ser Trp Tyr Asp Leu Asp
1               5                   10

<210> SEQ ID NO 463
<211> LENGTH: 12
<212> TYPE: PRT
<213> ORGANISM: artificial sequence
<220> FEATURE:
<223> OTHER INFORMATION: synthetic peptide

<400> SEQUENCE: 463

Gly Leu Glu Ile Asp Lys Ser Trp Tyr Asp Leu Asp
1               5                   10

<210> SEQ ID NO 464
<211> LENGTH: 12
<212> TYPE: PRT
<213> ORGANISM: artificial sequence
<220> FEATURE:
<223> OTHER INFORMATION: synthetic peptide

<400> SEQUENCE: 464

Leu Glu Ile Asp Lys Ser Trp Tyr Asp Leu Asp Ala
1               5                   10

<210> SEQ ID NO 465
<211> LENGTH: 9
<212> TYPE: PRT
<213> ORGANISM: artificial sequence
<220> FEATURE:
<223> OTHER INFORMATION: synthetic peptide

<400> SEQUENCE: 465

Phe Glu Ile Asp Lys Val Trp Tyr Asp
1               5

<210> SEQ ID NO 466
<211> LENGTH: 9
<212> TYPE: PRT
<213> ORGANISM: artificial sequence
<220> FEATURE:
<223> OTHER INFORMATION: synthetic peptide

<400> SEQUENCE: 466

Phe Glu Ile Asp Lys Ile Trp Tyr Asp
1               5

<210> SEQ ID NO 467
<211> LENGTH: 9
<212> TYPE: PRT
<213> ORGANISM: artificial sequence
<220> FEATURE:
<223> OTHER INFORMATION: synthetic peptide

<400> SEQUENCE: 467

Phe Glu Ile Asp Lys Leu Trp Tyr Asp
1               5

<210> SEQ ID NO 468
<211> LENGTH: 9
<212> TYPE: PRT
<213> ORGANISM: artificial sequence
<220> FEATURE:
<223> OTHER INFORMATION: synthetic peptide

<400> SEQUENCE: 468

Phe Glu Ile Asp Lys Phe Trp Tyr Asp
1               5

<210> SEQ ID NO 469
<211> LENGTH: 9
<212> TYPE: PRT
<213> ORGANISM: artificial sequence
<220> FEATURE:
<223> OTHER INFORMATION: synthetic peptide

<400> SEQUENCE: 469

Phe Glu Ile Asp Lys Ala Trp Tyr Asp
1               5

<210> SEQ ID NO 470
<211> LENGTH: 9
<212> TYPE: PRT
<213> ORGANISM: artificial sequence
<220> FEATURE:
<223> OTHER INFORMATION: synthetic peptide

<400> SEQUENCE: 470

Phe Glu Ile Asp Lys Ser Trp Tyr Asp
1               5

<210> SEQ ID NO 471
<211> LENGTH: 9
<212> TYPE: PRT
<213> ORGANISM: artificial sequence
<220> FEATURE:
<223> OTHER INFORMATION: synthetic peptide

<400> SEQUENCE: 471

Phe Glu Ile Asp Lys Val Phe Tyr Asp
1               5

<210> SEQ ID NO 472
<211> LENGTH: 9
<212> TYPE: PRT
<213> ORGANISM: artificial sequence
<220> FEATURE:
<223> OTHER INFORMATION: synthetic peptide

<400> SEQUENCE: 472

Phe Glu Ile Asp Lys Ile Phe Tyr Asp
1               5

<210> SEQ ID NO 473
<211> LENGTH: 9
<212> TYPE: PRT
<213> ORGANISM: artificial sequence
<220> FEATURE:
<223> OTHER INFORMATION: synthetic peptide

<400> SEQUENCE: 473

```
Phe Glu Ile Asp Lys Leu Phe Tyr Asp
1               5

<210> SEQ ID NO 474
<211> LENGTH: 9
<212> TYPE: PRT
<213> ORGANISM: artificial sequence
<220> FEATURE:
<223> OTHER INFORMATION: synthetic peptide

<400> SEQUENCE: 474

Phe Glu Ile Asp Lys Phe Phe Tyr Asp
1               5

<210> SEQ ID NO 475
<211> LENGTH: 9
<212> TYPE: PRT
<213> ORGANISM: artificial sequence
<220> FEATURE:
<223> OTHER INFORMATION: synthetic peptide

<400> SEQUENCE: 475

Phe Glu Ile Asp Lys Ala Phe Tyr Asp
1               5

<210> SEQ ID NO 476
<211> LENGTH: 9
<212> TYPE: PRT
<213> ORGANISM: artificial sequence
<220> FEATURE:
<223> OTHER INFORMATION: synthetic peptide

<400> SEQUENCE: 476

Phe Glu Ile Asp Lys Ser Phe Tyr Asp
1               5

<210> SEQ ID NO 477
<211> LENGTH: 9
<212> TYPE: PRT
<213> ORGANISM: artificial sequence
<220> FEATURE:
<223> OTHER INFORMATION: synthetic peptide

<400> SEQUENCE: 477

Phe Glu Ile Asp Lys Val Trp His Asp
1               5

<210> SEQ ID NO 478
<211> LENGTH: 9
<212> TYPE: PRT
<213> ORGANISM: artificial sequence
<220> FEATURE:
<223> OTHER INFORMATION: synthetic peptide

<400> SEQUENCE: 478

Phe Glu Ile Asp Lys Ile Trp His Asp
1               5

<210> SEQ ID NO 479
<211> LENGTH: 9
<212> TYPE: PRT
<213> ORGANISM: artificial sequence
<220> FEATURE:
<223> OTHER INFORMATION: synthetic peptide

<400> SEQUENCE: 479

Phe Glu Ile Asp Lys Leu Trp His Asp
```

```
1               5

<210> SEQ ID NO 480
<211> LENGTH: 9
<212> TYPE: PRT
<213> ORGANISM: artificial sequence
<220> FEATURE:
<223> OTHER INFORMATION: synthetic peptide

<400> SEQUENCE: 480

Phe Glu Ile Asp Lys Phe Trp His Asp
1               5

<210> SEQ ID NO 481
<211> LENGTH: 9
<212> TYPE: PRT
<213> ORGANISM: artificial sequence
<220> FEATURE:
<223> OTHER INFORMATION: synthetic peptide

<400> SEQUENCE: 481

Phe Glu Ile Asp Lys Ala Trp His Asp
1               5

<210> SEQ ID NO 482
<211> LENGTH: 9
<212> TYPE: PRT
<213> ORGANISM: artificial sequence
<220> FEATURE:
<223> OTHER INFORMATION: synthetic peptide

<400> SEQUENCE: 482

Phe Glu Ile Asp Lys Ser Trp His Asp
1               5

<210> SEQ ID NO 483
<211> LENGTH: 9
<212> TYPE: PRT
<213> ORGANISM: artificial sequence
<220> FEATURE:
<223> OTHER INFORMATION: synthetic peptide

<400> SEQUENCE: 483

Phe Glu Ile Asp Lys Val Phe His Asp
1               5

<210> SEQ ID NO 484
<211> LENGTH: 9
<212> TYPE: PRT
<213> ORGANISM: artificial sequence
<220> FEATURE:
<223> OTHER INFORMATION: synthetic peptide

<400> SEQUENCE: 484

Phe Glu Ile Asp Lys Ile Phe His Asp
1               5

<210> SEQ ID NO 485
<211> LENGTH: 9
<212> TYPE: PRT
<213> ORGANISM: artificial sequence
<220> FEATURE:
<223> OTHER INFORMATION: synthetic peptide

<400> SEQUENCE: 485

Phe Glu Ile Asp Lys Leu Phe His Asp
1               5
```

<210> SEQ ID NO 486
<211> LENGTH: 9
<212> TYPE: PRT
<213> ORGANISM: artificial sequence
<220> FEATURE:
<223> OTHER INFORMATION: synthetic peptide

<400> SEQUENCE: 486

Phe Glu Ile Asp Lys Phe Phe His Asp
1               5

<210> SEQ ID NO 487
<211> LENGTH: 9
<212> TYPE: PRT
<213> ORGANISM: artificial sequence
<220> FEATURE:
<223> OTHER INFORMATION: synthetic peptide

<400> SEQUENCE: 487

Phe Glu Ile Asp Lys Ala Phe His Asp
1               5

<210> SEQ ID NO 488
<211> LENGTH: 9
<212> TYPE: PRT
<213> ORGANISM: artificial sequence
<220> FEATURE:
<223> OTHER INFORMATION: synthetic peptide

<400> SEQUENCE: 488

Phe Glu Ile Asp Lys Ser Phe His Asp
1               5

<210> SEQ ID NO 489
<211> LENGTH: 9
<212> TYPE: PRT
<213> ORGANISM: artificial sequence
<220> FEATURE:
<223> OTHER INFORMATION: synthetic peptide

<400> SEQUENCE: 489

Phe Glu Ile Asp Lys Val Trp Phe Asp
1               5

<210> SEQ ID NO 490
<211> LENGTH: 9
<212> TYPE: PRT
<213> ORGANISM: artificial sequence
<220> FEATURE:
<223> OTHER INFORMATION: synthetic peptide

<400> SEQUENCE: 490

Phe Glu Ile Asp Lys Ile Trp Phe Asp
1               5

<210> SEQ ID NO 491
<211> LENGTH: 9
<212> TYPE: PRT
<213> ORGANISM: artificial sequence
<220> FEATURE:
<223> OTHER INFORMATION: synthetic peptide

<400> SEQUENCE: 491

Phe Glu Ile Asp Lys Leu Trp Phe Asp
1               5

<210> SEQ ID NO 492

```
<211> LENGTH: 9
<212> TYPE: PRT
<213> ORGANISM: artificial sequence
<220> FEATURE:
<223> OTHER INFORMATION: synthetic peptide

<400> SEQUENCE: 492

Phe Glu Ile Asp Lys Phe Trp Phe Asp
1               5

<210> SEQ ID NO 493
<211> LENGTH: 9
<212> TYPE: PRT
<213> ORGANISM: artificial sequence
<220> FEATURE:
<223> OTHER INFORMATION: synthetic peptide

<400> SEQUENCE: 493

Phe Glu Ile Asp Lys Ala Trp Phe Asp
1               5

<210> SEQ ID NO 494
<211> LENGTH: 9
<212> TYPE: PRT
<213> ORGANISM: artificial sequence
<220> FEATURE:
<223> OTHER INFORMATION: synthetic peptide

<400> SEQUENCE: 494

Phe Glu Ile Asp Lys Ser Trp Phe Asp
1               5

<210> SEQ ID NO 495
<211> LENGTH: 9
<212> TYPE: PRT
<213> ORGANISM: artificial sequence
<220> FEATURE:
<223> OTHER INFORMATION: synthetic peptide

<400> SEQUENCE: 495

Phe Glu Ile Asp Lys Val Phe Phe Asp
1               5

<210> SEQ ID NO 496
<211> LENGTH: 9
<212> TYPE: PRT
<213> ORGANISM: artificial sequence
<220> FEATURE:
<223> OTHER INFORMATION: synthetic peptide

<400> SEQUENCE: 496

Phe Glu Ile Asp Lys Ile Phe Phe Asp
1               5

<210> SEQ ID NO 497
<211> LENGTH: 9
<212> TYPE: PRT
<213> ORGANISM: artificial sequence
<220> FEATURE:
<223> OTHER INFORMATION: synthetic peptide

<400> SEQUENCE: 497

Phe Glu Ile Asp Lys Leu Phe Phe Asp
1               5

<210> SEQ ID NO 498
<211> LENGTH: 9
<212> TYPE: PRT
```

<213> ORGANISM: artificial sequence
<220> FEATURE:
<223> OTHER INFORMATION: synthetic peptide

<400> SEQUENCE: 498

Phe Glu Ile Asp Lys Phe Phe Phe Asp
1               5

<210> SEQ ID NO 499
<211> LENGTH: 9
<212> TYPE: PRT
<213> ORGANISM: artificial sequence
<220> FEATURE:
<223> OTHER INFORMATION: synthetic peptide

<400> SEQUENCE: 499

Phe Glu Ile Asp Lys Ala Phe Phe Asp
1               5

<210> SEQ ID NO 500
<211> LENGTH: 9
<212> TYPE: PRT
<213> ORGANISM: artificial sequence
<220> FEATURE:
<223> OTHER INFORMATION: synthetic peptide

<400> SEQUENCE: 500

Phe Glu Ile Asp Lys Ser Phe Phe Asp
1               5

<210> SEQ ID NO 501
<211> LENGTH: 9
<212> TYPE: PRT
<213> ORGANISM: artificial sequence
<220> FEATURE:
<223> OTHER INFORMATION: synthetic peptide

<400> SEQUENCE: 501

Phe Glu Ile Asp Lys Val Trp Leu Asp
1               5

<210> SEQ ID NO 502
<211> LENGTH: 9
<212> TYPE: PRT
<213> ORGANISM: artificial sequence
<220> FEATURE:
<223> OTHER INFORMATION: synthetic peptide

<400> SEQUENCE: 502

Phe Glu Ile Asp Lys Ile Trp Leu Asp
1               5

<210> SEQ ID NO 503
<211> LENGTH: 9
<212> TYPE: PRT
<213> ORGANISM: artificial sequence
<220> FEATURE:
<223> OTHER INFORMATION: synthetic peptide

<400> SEQUENCE: 503

Phe Glu Ile Asp Lys Leu Trp Leu Asp
1               5

<210> SEQ ID NO 504
<211> LENGTH: 9
<212> TYPE: PRT
<213> ORGANISM: artificial sequence
<220> FEATURE:

<223> OTHER INFORMATION: synthetic peptide

<400> SEQUENCE: 504

Phe Glu Ile Asp Lys Phe Trp Leu Asp
1               5

<210> SEQ ID NO 505
<211> LENGTH: 9
<212> TYPE: PRT
<213> ORGANISM: artificial sequence
<220> FEATURE:
<223> OTHER INFORMATION: synthetic peptide

<400> SEQUENCE: 505

Phe Glu Ile Asp Lys Ala Trp Leu Asp
1               5

<210> SEQ ID NO 506
<211> LENGTH: 9
<212> TYPE: PRT
<213> ORGANISM: artificial sequence
<220> FEATURE:
<223> OTHER INFORMATION: synthetic peptide

<400> SEQUENCE: 506

Phe Glu Ile Asp Lys Ser Trp Leu Asp
1               5

<210> SEQ ID NO 507
<211> LENGTH: 9
<212> TYPE: PRT
<213> ORGANISM: artificial sequence
<220> FEATURE:
<223> OTHER INFORMATION: synthetic peptide

<400> SEQUENCE: 507

Phe Glu Ile Asp Lys Val Phe Leu Asp
1               5

<210> SEQ ID NO 508
<211> LENGTH: 9
<212> TYPE: PRT
<213> ORGANISM: artificial sequence
<220> FEATURE:
<223> OTHER INFORMATION: synthetic peptide

<400> SEQUENCE: 508

Phe Glu Ile Asp Lys Ile Phe Leu Asp
1               5

<210> SEQ ID NO 509
<211> LENGTH: 9
<212> TYPE: PRT
<213> ORGANISM: artificial sequence
<220> FEATURE:
<223> OTHER INFORMATION: synthetic peptide

<400> SEQUENCE: 509

Phe Glu Ile Asp Lys Leu Phe Leu Asp
1               5

<210> SEQ ID NO 510
<211> LENGTH: 9
<212> TYPE: PRT
<213> ORGANISM: artificial sequence
<220> FEATURE:
<223> OTHER INFORMATION: synthetic peptide

```
<400> SEQUENCE: 510

Phe Glu Ile Asp Lys Phe Phe Leu Asp
1               5

<210> SEQ ID NO 511
<211> LENGTH: 9
<212> TYPE: PRT
<213> ORGANISM: artificial sequence
<220> FEATURE:
<223> OTHER INFORMATION: synthetic peptide

<400> SEQUENCE: 511

Phe Glu Ile Asp Lys Ala Phe Leu Asp
1               5

<210> SEQ ID NO 512
<211> LENGTH: 9
<212> TYPE: PRT
<213> ORGANISM: artificial sequence
<220> FEATURE:
<223> OTHER INFORMATION: synthetic peptide

<400> SEQUENCE: 512

Phe Glu Ile Asp Lys Ser Phe Leu Asp
1               5

<210> SEQ ID NO 513
<211> LENGTH: 9
<212> TYPE: PRT
<213> ORGANISM: artificial sequence
<220> FEATURE:
<223> OTHER INFORMATION: synthetic peptide

<400> SEQUENCE: 513

Phe Glu Ile Asp Lys Val Trp Ile Asp
1               5

<210> SEQ ID NO 514
<211> LENGTH: 9
<212> TYPE: PRT
<213> ORGANISM: artificial sequence
<220> FEATURE:
<223> OTHER INFORMATION: synthetic peptide

<400> SEQUENCE: 514

Phe Glu Ile Asp Lys Ile Trp Ile Asp
1               5

<210> SEQ ID NO 515
<211> LENGTH: 9
<212> TYPE: PRT
<213> ORGANISM: artificial sequence
<220> FEATURE:
<223> OTHER INFORMATION: synthetic peptide

<400> SEQUENCE: 515

Phe Glu Ile Asp Lys Leu Trp Ile Asp
1               5

<210> SEQ ID NO 516
<211> LENGTH: 9
<212> TYPE: PRT
<213> ORGANISM: artificial sequence
<220> FEATURE:
<223> OTHER INFORMATION: synthetic peptide

<400> SEQUENCE: 516
```

```
Phe Glu Ile Asp Lys Phe Trp Ile Asp
1               5

<210> SEQ ID NO 517
<211> LENGTH: 9
<212> TYPE: PRT
<213> ORGANISM: artificial sequence
<220> FEATURE:
<223> OTHER INFORMATION: synthetic peptide

<400> SEQUENCE: 517

Phe Glu Ile Asp Lys Ala Trp Ile Asp
1               5

<210> SEQ ID NO 518
<211> LENGTH: 9
<212> TYPE: PRT
<213> ORGANISM: artificial sequence
<220> FEATURE:
<223> OTHER INFORMATION: synthetic peptide

<400> SEQUENCE: 518

Phe Glu Ile Asp Lys Ser Trp Ile Asp
1               5

<210> SEQ ID NO 519
<211> LENGTH: 9
<212> TYPE: PRT
<213> ORGANISM: artificial sequence
<220> FEATURE:
<223> OTHER INFORMATION: synthetic peptide

<400> SEQUENCE: 519

Phe Glu Ile Asp Lys Val Phe Ile Asp
1               5

<210> SEQ ID NO 520
<211> LENGTH: 9
<212> TYPE: PRT
<213> ORGANISM: artificial sequence
<220> FEATURE:
<223> OTHER INFORMATION: synthetic peptide

<400> SEQUENCE: 520

Phe Glu Ile Asp Lys Ile Phe Ile Asp
1               5

<210> SEQ ID NO 521
<211> LENGTH: 9
<212> TYPE: PRT
<213> ORGANISM: artificial sequence
<220> FEATURE:
<223> OTHER INFORMATION: synthetic peptide

<400> SEQUENCE: 521

Phe Glu Ile Asp Lys Leu Phe Ile Asp
1               5

<210> SEQ ID NO 522
<211> LENGTH: 9
<212> TYPE: PRT
<213> ORGANISM: artificial sequence
<220> FEATURE:
<223> OTHER INFORMATION: synthetic peptide

<400> SEQUENCE: 522

Phe Glu Ile Asp Lys Phe Phe Ile Asp
1               5
```

```
<210> SEQ ID NO 523
<211> LENGTH: 9
<212> TYPE: PRT
<213> ORGANISM: artificial sequence
<220> FEATURE:
<223> OTHER INFORMATION: synthetic peptide

<400> SEQUENCE: 523

Phe Glu Ile Asp Lys Ala Phe Ile Asp
1               5

<210> SEQ ID NO 524
<211> LENGTH: 9
<212> TYPE: PRT
<213> ORGANISM: artificial sequence
<220> FEATURE:
<223> OTHER INFORMATION: synthetic peptide

<400> SEQUENCE: 524

Phe Glu Ile Asp Lys Ser Phe Ile Asp
1               5

<210> SEQ ID NO 525
<211> LENGTH: 9
<212> TYPE: PRT
<213> ORGANISM: artificial sequence
<220> FEATURE:
<223> OTHER INFORMATION: synthetic peptide

<400> SEQUENCE: 525

Phe Glu Ile Asp Lys Val Trp Val Asp
1               5

<210> SEQ ID NO 526
<211> LENGTH: 9
<212> TYPE: PRT
<213> ORGANISM: artificial sequence
<220> FEATURE:
<223> OTHER INFORMATION: synthetic peptide

<400> SEQUENCE: 526

Phe Glu Ile Asp Lys Ile Trp Val Asp
1               5

<210> SEQ ID NO 527
<211> LENGTH: 9
<212> TYPE: PRT
<213> ORGANISM: artificial sequence
<220> FEATURE:
<223> OTHER INFORMATION: synthetic peptide

<400> SEQUENCE: 527

Phe Glu Ile Asp Lys Leu Trp Val Asp
1               5

<210> SEQ ID NO 528
<211> LENGTH: 9
<212> TYPE: PRT
<213> ORGANISM: artificial sequence
<220> FEATURE:
<223> OTHER INFORMATION: synthetic peptide

<400> SEQUENCE: 528

Phe Glu Ile Asp Lys Phe Trp Val Asp
1               5
```

```
<210> SEQ ID NO 529
<211> LENGTH: 9
<212> TYPE: PRT
<213> ORGANISM: artificial sequence
<220> FEATURE:
<223> OTHER INFORMATION: synthetic peptide

<400> SEQUENCE: 529

Phe Glu Ile Asp Lys Ala Trp Val Asp
1               5

<210> SEQ ID NO 530
<211> LENGTH: 9
<212> TYPE: PRT
<213> ORGANISM: artificial sequence
<220> FEATURE:
<223> OTHER INFORMATION: synthetic peptide

<400> SEQUENCE: 530

Phe Glu Ile Asp Lys Ser Trp Val Asp
1               5

<210> SEQ ID NO 531
<211> LENGTH: 9
<212> TYPE: PRT
<213> ORGANISM: artificial sequence
<220> FEATURE:
<223> OTHER INFORMATION: synthetic peptide

<400> SEQUENCE: 531

Phe Glu Ile Asp Lys Val Phe Val Asp
1               5

<210> SEQ ID NO 532
<211> LENGTH: 9
<212> TYPE: PRT
<213> ORGANISM: artificial sequence
<220> FEATURE:
<223> OTHER INFORMATION: synthetic peptide

<400> SEQUENCE: 532

Phe Glu Ile Asp Lys Ile Phe Val Asp
1               5

<210> SEQ ID NO 533
<211> LENGTH: 9
<212> TYPE: PRT
<213> ORGANISM: artificial sequence
<220> FEATURE:
<223> OTHER INFORMATION: synthetic peptide

<400> SEQUENCE: 533

Phe Glu Ile Asp Lys Leu Phe Val Asp
1               5

<210> SEQ ID NO 534
<211> LENGTH: 9
<212> TYPE: PRT
<213> ORGANISM: artificial sequence
<220> FEATURE:
<223> OTHER INFORMATION: synthetic peptide

<400> SEQUENCE: 534

Phe Glu Ile Asp Lys Phe Phe Val Asp
1               5

<210> SEQ ID NO 535
<211> LENGTH: 9
```

```
<212> TYPE: PRT
<213> ORGANISM: artificial sequence
<220> FEATURE:
<223> OTHER INFORMATION: synthetic peptide

<400> SEQUENCE: 535

Phe Glu Ile Asp Lys Ala Phe Val Asp
1               5

<210> SEQ ID NO 536
<211> LENGTH: 9
<212> TYPE: PRT
<213> ORGANISM: artificial sequence
<220> FEATURE:
<223> OTHER INFORMATION: synthetic peptide

<400> SEQUENCE: 536

Phe Glu Ile Asp Lys Ser Phe Val Asp
1               5

<210> SEQ ID NO 537
<211> LENGTH: 9
<212> TYPE: PRT
<213> ORGANISM: artificial sequence
<220> FEATURE:
<223> OTHER INFORMATION: synthetic peptide

<400> SEQUENCE: 537

Phe Glu Ile Asp Lys Val Trp Thr Asp
1               5

<210> SEQ ID NO 538
<211> LENGTH: 9
<212> TYPE: PRT
<213> ORGANISM: artificial sequence
<220> FEATURE:
<223> OTHER INFORMATION: synthetic peptide

<400> SEQUENCE: 538

Phe Glu Ile Asp Lys Ile Trp Thr Asp
1               5

<210> SEQ ID NO 539
<211> LENGTH: 9
<212> TYPE: PRT
<213> ORGANISM: artificial sequence
<220> FEATURE:
<223> OTHER INFORMATION: synthetic peptide

<400> SEQUENCE: 539

Phe Glu Ile Asp Lys Leu Trp Thr Asp
1               5

<210> SEQ ID NO 540
<211> LENGTH: 9
<212> TYPE: PRT
<213> ORGANISM: artificial sequence
<220> FEATURE:
<223> OTHER INFORMATION: synthetic peptide

<400> SEQUENCE: 540

Phe Glu Ile Asp Lys Phe Trp Thr Asp
1               5

<210> SEQ ID NO 541
<211> LENGTH: 9
<212> TYPE: PRT
<213> ORGANISM: artificial sequence
```

```
<220> FEATURE:
<223> OTHER INFORMATION: synthetic peptide

<400> SEQUENCE: 541

Phe Glu Ile Asp Lys Ala Trp Thr Asp
1               5

<210> SEQ ID NO 542
<211> LENGTH: 9
<212> TYPE: PRT
<213> ORGANISM: artificial sequence
<220> FEATURE:
<223> OTHER INFORMATION: synthetic peptide

<400> SEQUENCE: 542

Phe Glu Ile Asp Lys Ser Trp Thr Asp
1               5

<210> SEQ ID NO 543
<211> LENGTH: 9
<212> TYPE: PRT
<213> ORGANISM: artificial sequence
<220> FEATURE:
<223> OTHER INFORMATION: synthetic peptide

<400> SEQUENCE: 543

Phe Glu Ile Asp Lys Val Phe Thr Asp
1               5

<210> SEQ ID NO 544
<211> LENGTH: 9
<212> TYPE: PRT
<213> ORGANISM: artificial sequence
<220> FEATURE:
<223> OTHER INFORMATION: synthetic peptide

<400> SEQUENCE: 544

Phe Glu Ile Asp Lys Ile Phe Thr Asp
1               5

<210> SEQ ID NO 545
<211> LENGTH: 9
<212> TYPE: PRT
<213> ORGANISM: artificial sequence
<220> FEATURE:
<223> OTHER INFORMATION: synthetic peptide

<400> SEQUENCE: 545

Phe Glu Ile Asp Lys Leu Phe Thr Asp
1               5

<210> SEQ ID NO 546
<211> LENGTH: 9
<212> TYPE: PRT
<213> ORGANISM: artificial sequence
<220> FEATURE:
<223> OTHER INFORMATION: synthetic peptide

<400> SEQUENCE: 546

Phe Glu Ile Asp Lys Phe Phe Thr Asp
1               5

<210> SEQ ID NO 547
<211> LENGTH: 9
<212> TYPE: PRT
<213> ORGANISM: artificial sequence
<220> FEATURE:
<223> OTHER INFORMATION: synthetic peptide
```

```
<400> SEQUENCE: 547

Phe Glu Ile Asp Lys Ala Phe Thr Asp
1               5

<210> SEQ ID NO 548
<211> LENGTH: 9
<212> TYPE: PRT
<213> ORGANISM: artificial sequence
<220> FEATURE:
<223> OTHER INFORMATION: synthetic peptide

<400> SEQUENCE: 548

Phe Glu Ile Asp Lys Ser Phe Thr Asp
1               5

<210> SEQ ID NO 549
<211> LENGTH: 9
<212> TYPE: PRT
<213> ORGANISM: artificial sequence
<220> FEATURE:
<223> OTHER INFORMATION: synthetic peptide

<400> SEQUENCE: 549

Phe Glu Ile Asp Lys Val Trp Tyr Glu
1               5

<210> SEQ ID NO 550
<211> LENGTH: 9
<212> TYPE: PRT
<213> ORGANISM: artificial sequence
<220> FEATURE:
<223> OTHER INFORMATION: synthetic peptide

<400> SEQUENCE: 550

Phe Glu Ile Asp Lys Ile Trp Tyr Glu
1               5

<210> SEQ ID NO 551
<211> LENGTH: 9
<212> TYPE: PRT
<213> ORGANISM: artificial sequence
<220> FEATURE:
<223> OTHER INFORMATION: synthetic peptide

<400> SEQUENCE: 551

Phe Glu Ile Asp Lys Leu Trp Tyr Glu
1               5

<210> SEQ ID NO 552
<211> LENGTH: 9
<212> TYPE: PRT
<213> ORGANISM: artificial sequence
<220> FEATURE:
<223> OTHER INFORMATION: synthetic peptide

<400> SEQUENCE: 552

Phe Glu Ile Asp Lys Phe Trp Tyr Glu
1               5

<210> SEQ ID NO 553
<211> LENGTH: 9
<212> TYPE: PRT
<213> ORGANISM: artificial sequence
<220> FEATURE:
<223> OTHER INFORMATION: synthetic peptide

<400> SEQUENCE: 553
```

```
Phe Glu Ile Asp Lys Ala Trp Tyr Glu
1               5

<210> SEQ ID NO 554
<211> LENGTH: 9
<212> TYPE: PRT
<213> ORGANISM: artificial sequence
<220> FEATURE:
<223> OTHER INFORMATION: synthetic peptide

<400> SEQUENCE: 554

Phe Glu Ile Asp Lys Ser Trp Tyr Glu
1               5

<210> SEQ ID NO 555
<211> LENGTH: 9
<212> TYPE: PRT
<213> ORGANISM: artificial sequence
<220> FEATURE:
<223> OTHER INFORMATION: synthetic peptide

<400> SEQUENCE: 555

Phe Glu Ile Asp Lys Val Phe Tyr Glu
1               5

<210> SEQ ID NO 556
<211> LENGTH: 9
<212> TYPE: PRT
<213> ORGANISM: artificial sequence
<220> FEATURE:
<223> OTHER INFORMATION: synthetic peptide

<400> SEQUENCE: 556

Phe Glu Ile Asp Lys Ile Phe Tyr Glu
1               5

<210> SEQ ID NO 557
<211> LENGTH: 9
<212> TYPE: PRT
<213> ORGANISM: artificial sequence
<220> FEATURE:
<223> OTHER INFORMATION: synthetic peptide

<400> SEQUENCE: 557

Phe Glu Ile Asp Lys Leu Phe Tyr Glu
1               5

<210> SEQ ID NO 558
<211> LENGTH: 9
<212> TYPE: PRT
<213> ORGANISM: artificial sequence
<220> FEATURE:
<223> OTHER INFORMATION: synthetic peptide

<400> SEQUENCE: 558

Phe Glu Ile Asp Lys Phe Phe Tyr Glu
1               5

<210> SEQ ID NO 559
<211> LENGTH: 9
<212> TYPE: PRT
<213> ORGANISM: artificial sequence
<220> FEATURE:
<223> OTHER INFORMATION: synthetic peptide

<400> SEQUENCE: 559

Phe Glu Ile Asp Lys Ala Phe Tyr Glu
```

```
1               5

<210> SEQ ID NO 560
<211> LENGTH: 9
<212> TYPE: PRT
<213> ORGANISM: artificial sequence
<220> FEATURE:
<223> OTHER INFORMATION: synthetic peptide

<400> SEQUENCE: 560

Phe Glu Ile Asp Lys Ser Phe Tyr Glu
1               5

<210> SEQ ID NO 561
<211> LENGTH: 9
<212> TYPE: PRT
<213> ORGANISM: artificial sequence
<220> FEATURE:
<223> OTHER INFORMATION: synthetic peptide

<400> SEQUENCE: 561

Phe Glu Ile Asp Lys Val Trp His Glu
1               5

<210> SEQ ID NO 562
<211> LENGTH: 9
<212> TYPE: PRT
<213> ORGANISM: artificial sequence
<220> FEATURE:
<223> OTHER INFORMATION: synthetic peptide

<400> SEQUENCE: 562

Phe Glu Ile Asp Lys Ile Trp His Glu
1               5

<210> SEQ ID NO 563
<211> LENGTH: 9
<212> TYPE: PRT
<213> ORGANISM: artificial sequence
<220> FEATURE:
<223> OTHER INFORMATION: synthetic peptide

<400> SEQUENCE: 563

Phe Glu Ile Asp Lys Leu Trp His Glu
1               5

<210> SEQ ID NO 564
<211> LENGTH: 9
<212> TYPE: PRT
<213> ORGANISM: artificial sequence
<220> FEATURE:
<223> OTHER INFORMATION: synthetic peptide

<400> SEQUENCE: 564

Phe Glu Ile Asp Lys Phe Trp His Glu
1               5

<210> SEQ ID NO 565
<211> LENGTH: 9
<212> TYPE: PRT
<213> ORGANISM: artificial sequence
<220> FEATURE:
<223> OTHER INFORMATION: synthetic peptide

<400> SEQUENCE: 565

Phe Glu Ile Asp Lys Ala Trp His Glu
1               5
```

```
<210> SEQ ID NO 566
<211> LENGTH: 9
<212> TYPE: PRT
<213> ORGANISM: artificial sequence
<220> FEATURE:
<223> OTHER INFORMATION: synthetic peptide

<400> SEQUENCE: 566

Phe Glu Ile Asp Lys Ser Trp His Glu
1               5

<210> SEQ ID NO 567
<211> LENGTH: 9
<212> TYPE: PRT
<213> ORGANISM: artificial sequence
<220> FEATURE:
<223> OTHER INFORMATION: synthetic peptide

<400> SEQUENCE: 567

Phe Glu Ile Asp Lys Val Phe His Glu
1               5

<210> SEQ ID NO 568
<211> LENGTH: 9
<212> TYPE: PRT
<213> ORGANISM: artificial sequence
<220> FEATURE:
<223> OTHER INFORMATION: synthetic peptide

<400> SEQUENCE: 568

Phe Glu Ile Asp Lys Ile Phe His Glu
1               5

<210> SEQ ID NO 569
<211> LENGTH: 9
<212> TYPE: PRT
<213> ORGANISM: artificial sequence
<220> FEATURE:
<223> OTHER INFORMATION: synthetic peptide

<400> SEQUENCE: 569

Phe Glu Ile Asp Lys Leu Phe His Glu
1               5

<210> SEQ ID NO 570
<211> LENGTH: 9
<212> TYPE: PRT
<213> ORGANISM: artificial sequence
<220> FEATURE:
<223> OTHER INFORMATION: synthetic peptide

<400> SEQUENCE: 570

Phe Glu Ile Asp Lys Phe Phe His Glu
1               5

<210> SEQ ID NO 571
<211> LENGTH: 9
<212> TYPE: PRT
<213> ORGANISM: artificial sequence
<220> FEATURE:
<223> OTHER INFORMATION: synthetic peptide

<400> SEQUENCE: 571

Phe Glu Ile Asp Lys Ala Phe His Glu
1               5

<210> SEQ ID NO 572
```

```
<211> LENGTH: 9
<212> TYPE: PRT
<213> ORGANISM: artificial sequence
<220> FEATURE:
<223> OTHER INFORMATION: synthetic peptide

<400> SEQUENCE: 572

Phe Glu Ile Asp Lys Ser Phe His Glu
1               5

<210> SEQ ID NO 573
<211> LENGTH: 9
<212> TYPE: PRT
<213> ORGANISM: artificial sequence
<220> FEATURE:
<223> OTHER INFORMATION: synthetic peptide

<400> SEQUENCE: 573

Phe Glu Ile Asp Lys Val Trp Phe Glu
1               5

<210> SEQ ID NO 574
<211> LENGTH: 9
<212> TYPE: PRT
<213> ORGANISM: artificial sequence
<220> FEATURE:
<223> OTHER INFORMATION: synthetic peptide

<400> SEQUENCE: 574

Phe Glu Ile Asp Lys Ile Trp Phe Glu
1               5

<210> SEQ ID NO 575
<211> LENGTH: 9
<212> TYPE: PRT
<213> ORGANISM: artificial sequence
<220> FEATURE:
<223> OTHER INFORMATION: synthetic peptide

<400> SEQUENCE: 575

Phe Glu Ile Asp Lys Leu Trp Phe Glu
1               5

<210> SEQ ID NO 576
<211> LENGTH: 9
<212> TYPE: PRT
<213> ORGANISM: artificial sequence
<220> FEATURE:
<223> OTHER INFORMATION: synthetic peptide

<400> SEQUENCE: 576

Phe Glu Ile Asp Lys Phe Trp Phe Glu
1               5

<210> SEQ ID NO 577
<211> LENGTH: 9
<212> TYPE: PRT
<213> ORGANISM: artificial sequence
<220> FEATURE:
<223> OTHER INFORMATION: synthetic peptide

<400> SEQUENCE: 577

Phe Glu Ile Asp Lys Ala Trp Phe Glu
1               5

<210> SEQ ID NO 578
<211> LENGTH: 9
<212> TYPE: PRT
```

```
<213> ORGANISM: artificial sequence
<220> FEATURE:
<223> OTHER INFORMATION: synthetic peptide

<400> SEQUENCE: 578

Phe Glu Ile Asp Lys Ser Trp Phe Glu
1               5

<210> SEQ ID NO 579
<211> LENGTH: 9
<212> TYPE: PRT
<213> ORGANISM: artificial sequence
<220> FEATURE:
<223> OTHER INFORMATION: synthetic peptide

<400> SEQUENCE: 579

Phe Glu Ile Asp Lys Val Phe Phe Glu
1               5

<210> SEQ ID NO 580
<211> LENGTH: 9
<212> TYPE: PRT
<213> ORGANISM: artificial sequence
<220> FEATURE:
<223> OTHER INFORMATION: synthetic peptide

<400> SEQUENCE: 580

Phe Glu Ile Asp Lys Ile Phe Phe Glu
1               5

<210> SEQ ID NO 581
<211> LENGTH: 9
<212> TYPE: PRT
<213> ORGANISM: artificial sequence
<220> FEATURE:
<223> OTHER INFORMATION: synthetic peptide

<400> SEQUENCE: 581

Phe Glu Ile Asp Lys Leu Phe Phe Glu
1               5

<210> SEQ ID NO 582
<211> LENGTH: 9
<212> TYPE: PRT
<213> ORGANISM: artificial sequence
<220> FEATURE:
<223> OTHER INFORMATION: synthetic peptide

<400> SEQUENCE: 582

Phe Glu Ile Asp Lys Phe Phe Phe Glu
1               5

<210> SEQ ID NO 583
<211> LENGTH: 9
<212> TYPE: PRT
<213> ORGANISM: artificial sequence
<220> FEATURE:
<223> OTHER INFORMATION: synthetic peptide

<400> SEQUENCE: 583

Phe Glu Ile Asp Lys Ala Phe Phe Glu
1               5

<210> SEQ ID NO 584
<211> LENGTH: 9
<212> TYPE: PRT
<213> ORGANISM: artificial sequence
<220> FEATURE:
```

<223> OTHER INFORMATION: synthetic peptide

<400> SEQUENCE: 584

Phe Glu Ile Asp Lys Ser Phe Phe Glu
1               5

<210> SEQ ID NO 585
<211> LENGTH: 9
<212> TYPE: PRT
<213> ORGANISM: artificial sequence
<220> FEATURE:
<223> OTHER INFORMATION: synthetic peptide

<400> SEQUENCE: 585

Phe Glu Ile Asp Lys Val Trp Leu Glu
1               5

<210> SEQ ID NO 586
<211> LENGTH: 9
<212> TYPE: PRT
<213> ORGANISM: artificial sequence
<220> FEATURE:
<223> OTHER INFORMATION: synthetic peptide

<400> SEQUENCE: 586

Phe Glu Ile Asp Lys Ile Trp Leu Glu
1               5

<210> SEQ ID NO 587
<211> LENGTH: 9
<212> TYPE: PRT
<213> ORGANISM: artificial sequence
<220> FEATURE:
<223> OTHER INFORMATION: synthetic peptide

<400> SEQUENCE: 587

Phe Glu Ile Asp Lys Leu Trp Leu Glu
1               5

<210> SEQ ID NO 588
<211> LENGTH: 9
<212> TYPE: PRT
<213> ORGANISM: artificial sequence
<220> FEATURE:
<223> OTHER INFORMATION: synthetic peptide

<400> SEQUENCE: 588

Phe Glu Ile Asp Lys Phe Trp Leu Glu
1               5

<210> SEQ ID NO 589
<211> LENGTH: 9
<212> TYPE: PRT
<213> ORGANISM: artificial sequence
<220> FEATURE:
<223> OTHER INFORMATION: synthetic peptide

<400> SEQUENCE: 589

Phe Glu Ile Asp Lys Ala Trp Leu Glu
1               5

<210> SEQ ID NO 590
<211> LENGTH: 9
<212> TYPE: PRT
<213> ORGANISM: artificial sequence
<220> FEATURE:
<223> OTHER INFORMATION: synthetic peptide

```
<400> SEQUENCE: 590

Phe Glu Ile Asp Lys Ser Trp Leu Glu
1               5

<210> SEQ ID NO 591
<211> LENGTH: 9
<212> TYPE: PRT
<213> ORGANISM: artificial sequence
<220> FEATURE:
<223> OTHER INFORMATION: synthetic peptide

<400> SEQUENCE: 591

Phe Glu Ile Asp Lys Val Phe Leu Glu
1               5

<210> SEQ ID NO 592
<211> LENGTH: 9
<212> TYPE: PRT
<213> ORGANISM: artificial sequence
<220> FEATURE:
<223> OTHER INFORMATION: synthetic peptide

<400> SEQUENCE: 592

Phe Glu Ile Asp Lys Ile Phe Leu Glu
1               5

<210> SEQ ID NO 593
<211> LENGTH: 9
<212> TYPE: PRT
<213> ORGANISM: artificial sequence
<220> FEATURE:
<223> OTHER INFORMATION: synthetic peptide

<400> SEQUENCE: 593

Phe Glu Ile Asp Lys Leu Phe Leu Glu
1               5

<210> SEQ ID NO 594
<211> LENGTH: 9
<212> TYPE: PRT
<213> ORGANISM: artificial sequence
<220> FEATURE:
<223> OTHER INFORMATION: synthetic peptide

<400> SEQUENCE: 594

Phe Glu Ile Asp Lys Phe Phe Leu Glu
1               5

<210> SEQ ID NO 595
<211> LENGTH: 9
<212> TYPE: PRT
<213> ORGANISM: artificial sequence
<220> FEATURE:
<223> OTHER INFORMATION: synthetic peptide

<400> SEQUENCE: 595

Phe Glu Ile Asp Lys Ala Phe Leu Glu
1               5

<210> SEQ ID NO 596
<211> LENGTH: 9
<212> TYPE: PRT
<213> ORGANISM: artificial sequence
<220> FEATURE:
<223> OTHER INFORMATION: synthetic peptide

<400> SEQUENCE: 596
```

```
Phe Glu Ile Asp Lys Ser Phe Leu Glu
1               5

<210> SEQ ID NO 597
<211> LENGTH: 9
<212> TYPE: PRT
<213> ORGANISM: artificial sequence
<220> FEATURE:
<223> OTHER INFORMATION: synthetic peptide

<400> SEQUENCE: 597

Phe Glu Ile Asp Lys Val Trp Ile Glu
1               5

<210> SEQ ID NO 598
<211> LENGTH: 9
<212> TYPE: PRT
<213> ORGANISM: artificial sequence
<220> FEATURE:
<223> OTHER INFORMATION: synthetic peptide

<400> SEQUENCE: 598

Phe Glu Ile Asp Lys Ile Trp Ile Glu
1               5

<210> SEQ ID NO 599
<211> LENGTH: 9
<212> TYPE: PRT
<213> ORGANISM: artificial sequence
<220> FEATURE:
<223> OTHER INFORMATION: synthetic peptide

<400> SEQUENCE: 599

Phe Glu Ile Asp Lys Leu Trp Ile Glu
1               5

<210> SEQ ID NO 600
<211> LENGTH: 9
<212> TYPE: PRT
<213> ORGANISM: artificial sequence
<220> FEATURE:
<223> OTHER INFORMATION: synthetic peptide

<400> SEQUENCE: 600

Phe Glu Ile Asp Lys Phe Trp Ile Glu
1               5

<210> SEQ ID NO 601
<211> LENGTH: 9
<212> TYPE: PRT
<213> ORGANISM: artificial sequence
<220> FEATURE:
<223> OTHER INFORMATION: synthetic peptide

<400> SEQUENCE: 601

Phe Glu Ile Asp Lys Ala Trp Ile Glu
1               5

<210> SEQ ID NO 602
<211> LENGTH: 9
<212> TYPE: PRT
<213> ORGANISM: artificial sequence
<220> FEATURE:
<223> OTHER INFORMATION: synthetic peptide

<400> SEQUENCE: 602

Phe Glu Ile Asp Lys Ser Trp Ile Glu
1               5
```

```
<210> SEQ ID NO 603
<211> LENGTH: 9
<212> TYPE: PRT
<213> ORGANISM: artificial sequence
<220> FEATURE:
<223> OTHER INFORMATION: synthetic peptide

<400> SEQUENCE: 603

Phe Glu Ile Asp Lys Val Phe Ile Glu
1               5

<210> SEQ ID NO 604
<211> LENGTH: 9
<212> TYPE: PRT
<213> ORGANISM: artificial sequence
<220> FEATURE:
<223> OTHER INFORMATION: synthetic peptide

<400> SEQUENCE: 604

Phe Glu Ile Asp Lys Ile Phe Ile Glu
1               5

<210> SEQ ID NO 605
<211> LENGTH: 9
<212> TYPE: PRT
<213> ORGANISM: artificial sequence
<220> FEATURE:
<223> OTHER INFORMATION: synthetic peptide

<400> SEQUENCE: 605

Phe Glu Ile Asp Lys Leu Phe Ile Glu
1               5

<210> SEQ ID NO 606
<211> LENGTH: 9
<212> TYPE: PRT
<213> ORGANISM: artificial sequence
<220> FEATURE:
<223> OTHER INFORMATION: synthetic peptide

<400> SEQUENCE: 606

Phe Glu Ile Asp Lys Phe Phe Ile Glu
1               5

<210> SEQ ID NO 607
<211> LENGTH: 9
<212> TYPE: PRT
<213> ORGANISM: artificial sequence
<220> FEATURE:
<223> OTHER INFORMATION: synthetic peptide

<400> SEQUENCE: 607

Phe Glu Ile Asp Lys Ala Phe Ile Glu
1               5

<210> SEQ ID NO 608
<211> LENGTH: 9
<212> TYPE: PRT
<213> ORGANISM: artificial sequence
<220> FEATURE:
<223> OTHER INFORMATION: synthetic peptide

<400> SEQUENCE: 608

Phe Glu Ile Asp Lys Ser Phe Ile Glu
1               5
```

```
<210> SEQ ID NO 609
<211> LENGTH: 9
<212> TYPE: PRT
<213> ORGANISM: artificial sequence
<220> FEATURE:
<223> OTHER INFORMATION: synthetic peptide

<400> SEQUENCE: 609

Phe Glu Ile Asp Lys Val Trp Val Glu
1               5

<210> SEQ ID NO 610
<211> LENGTH: 9
<212> TYPE: PRT
<213> ORGANISM: artificial sequence
<220> FEATURE:
<223> OTHER INFORMATION: synthetic peptide

<400> SEQUENCE: 610

Phe Glu Ile Asp Lys Ile Trp Val Glu
1               5

<210> SEQ ID NO 611
<211> LENGTH: 9
<212> TYPE: PRT
<213> ORGANISM: artificial sequence
<220> FEATURE:
<223> OTHER INFORMATION: synthetic peptide

<400> SEQUENCE: 611

Phe Glu Ile Asp Lys Leu Trp Val Glu
1               5

<210> SEQ ID NO 612
<211> LENGTH: 9
<212> TYPE: PRT
<213> ORGANISM: artificial sequence
<220> FEATURE:
<223> OTHER INFORMATION: synthetic peptide

<400> SEQUENCE: 612

Phe Glu Ile Asp Lys Phe Trp Val Glu
1               5

<210> SEQ ID NO 613
<211> LENGTH: 9
<212> TYPE: PRT
<213> ORGANISM: artificial sequence
<220> FEATURE:
<223> OTHER INFORMATION: synthetic peptide

<400> SEQUENCE: 613

Phe Glu Ile Asp Lys Ala Trp Val Glu
1               5

<210> SEQ ID NO 614
<211> LENGTH: 9
<212> TYPE: PRT
<213> ORGANISM: artificial sequence
<220> FEATURE:
<223> OTHER INFORMATION: synthetic peptide

<400> SEQUENCE: 614

Phe Glu Ile Asp Lys Ser Trp Val Glu
1               5

<210> SEQ ID NO 615
<211> LENGTH: 9
```

```
<212> TYPE: PRT
<213> ORGANISM: artificial sequence
<220> FEATURE:
<223> OTHER INFORMATION: synthetic peptide

<400> SEQUENCE: 615

Phe Glu Ile Asp Lys Val Phe Val Glu
1               5

<210> SEQ ID NO 616
<211> LENGTH: 9
<212> TYPE: PRT
<213> ORGANISM: artificial sequence
<220> FEATURE:
<223> OTHER INFORMATION: synthetic peptide

<400> SEQUENCE: 616

Phe Glu Ile Asp Lys Ile Phe Val Glu
1               5

<210> SEQ ID NO 617
<211> LENGTH: 9
<212> TYPE: PRT
<213> ORGANISM: artificial sequence
<220> FEATURE:
<223> OTHER INFORMATION: synthetic peptide

<400> SEQUENCE: 617

Phe Glu Ile Asp Lys Leu Phe Val Glu
1               5

<210> SEQ ID NO 618
<211> LENGTH: 9
<212> TYPE: PRT
<213> ORGANISM: artificial sequence
<220> FEATURE:
<223> OTHER INFORMATION: synthetic peptide

<400> SEQUENCE: 618

Phe Glu Ile Asp Lys Phe Phe Val Glu
1               5

<210> SEQ ID NO 619
<211> LENGTH: 9
<212> TYPE: PRT
<213> ORGANISM: artificial sequence
<220> FEATURE:
<223> OTHER INFORMATION: synthetic peptide

<400> SEQUENCE: 619

Phe Glu Ile Asp Lys Ala Phe Val Glu
1               5

<210> SEQ ID NO 620
<211> LENGTH: 9
<212> TYPE: PRT
<213> ORGANISM: artificial sequence
<220> FEATURE:
<223> OTHER INFORMATION: synthetic peptide

<400> SEQUENCE: 620

Phe Glu Ile Asp Lys Ser Phe Val Glu
1               5

<210> SEQ ID NO 621
<211> LENGTH: 9
<212> TYPE: PRT
<213> ORGANISM: artificial sequence
```

-continued

```
<220> FEATURE:
<223> OTHER INFORMATION: synthetic peptide

<400> SEQUENCE: 621

Phe Glu Ile Asp Lys Val Trp Thr Glu
1               5

<210> SEQ ID NO 622
<211> LENGTH: 9
<212> TYPE: PRT
<213> ORGANISM: artificial sequence
<220> FEATURE:
<223> OTHER INFORMATION: synthetic peptide

<400> SEQUENCE: 622

Phe Glu Ile Asp Lys Ile Trp Thr Glu
1               5

<210> SEQ ID NO 623
<211> LENGTH: 9
<212> TYPE: PRT
<213> ORGANISM: artificial sequence
<220> FEATURE:
<223> OTHER INFORMATION: synthetic peptide

<400> SEQUENCE: 623

Phe Glu Ile Asp Lys Leu Trp Thr Glu
1               5

<210> SEQ ID NO 624
<211> LENGTH: 9
<212> TYPE: PRT
<213> ORGANISM: artificial sequence
<220> FEATURE:
<223> OTHER INFORMATION: synthetic peptide

<400> SEQUENCE: 624

Phe Glu Ile Asp Lys Phe Trp Thr Glu
1               5

<210> SEQ ID NO 625
<211> LENGTH: 9
<212> TYPE: PRT
<213> ORGANISM: artificial sequence
<220> FEATURE:
<223> OTHER INFORMATION: synthetic peptide

<400> SEQUENCE: 625

Phe Glu Ile Asp Lys Ala Trp Thr Glu
1               5

<210> SEQ ID NO 626
<211> LENGTH: 9
<212> TYPE: PRT
<213> ORGANISM: artificial sequence
<220> FEATURE:
<223> OTHER INFORMATION: synthetic peptide

<400> SEQUENCE: 626

Phe Glu Ile Asp Lys Ser Trp Thr Glu
1               5

<210> SEQ ID NO 627
<211> LENGTH: 9
<212> TYPE: PRT
<213> ORGANISM: artificial sequence
<220> FEATURE:
<223> OTHER INFORMATION: synthetic peptide
```

<400> SEQUENCE: 627

Phe Glu Ile Asp Lys Val Phe Thr Glu
1               5

<210> SEQ ID NO 628
<211> LENGTH: 9
<212> TYPE: PRT
<213> ORGANISM: artificial sequence
<220> FEATURE:
<223> OTHER INFORMATION: synthetic peptide

<400> SEQUENCE: 628

Phe Glu Ile Asp Lys Ile Phe Thr Glu
1               5

<210> SEQ ID NO 629
<211> LENGTH: 9
<212> TYPE: PRT
<213> ORGANISM: artificial sequence
<220> FEATURE:
<223> OTHER INFORMATION: synthetic peptide

<400> SEQUENCE: 629

Phe Glu Ile Asp Lys Leu Phe Thr Glu
1               5

<210> SEQ ID NO 630
<211> LENGTH: 9
<212> TYPE: PRT
<213> ORGANISM: artificial sequence
<220> FEATURE:
<223> OTHER INFORMATION: synthetic peptide

<400> SEQUENCE: 630

Phe Glu Ile Asp Lys Phe Phe Thr Glu
1               5

<210> SEQ ID NO 631
<211> LENGTH: 9
<212> TYPE: PRT
<213> ORGANISM: artificial sequence
<220> FEATURE:
<223> OTHER INFORMATION: synthetic peptide

<400> SEQUENCE: 631

Phe Glu Ile Asp Lys Ala Phe Thr Glu
1               5

<210> SEQ ID NO 632
<211> LENGTH: 9
<212> TYPE: PRT
<213> ORGANISM: artificial sequence
<220> FEATURE:
<223> OTHER INFORMATION: synthetic peptide

<400> SEQUENCE: 632

Phe Glu Ile Asp Lys Ser Phe Thr Glu
1               5

<210> SEQ ID NO 633
<211> LENGTH: 9
<212> TYPE: PRT
<213> ORGANISM: artificial sequence
<220> FEATURE:
<223> OTHER INFORMATION: synthetic peptide

<400> SEQUENCE: 633

Phe Glu Ile Asn Lys Val Trp Tyr Asp
1               5

<210> SEQ ID NO 634
<211> LENGTH: 9
<212> TYPE: PRT
<213> ORGANISM: artificial sequence
<220> FEATURE:
<223> OTHER INFORMATION: synthetic peptide

<400> SEQUENCE: 634

Phe Glu Ile Glu Lys Val Trp Tyr Asp
1               5

<210> SEQ ID NO 635
<211> LENGTH: 9
<212> TYPE: PRT
<213> ORGANISM: artificial sequence
<220> FEATURE:
<223> OTHER INFORMATION: synthetic peptide

<400> SEQUENCE: 635

Phe Glu Ile Tyr Lys Val Trp Tyr Asp
1               5

<210> SEQ ID NO 636
<211> LENGTH: 9
<212> TYPE: PRT
<213> ORGANISM: artificial sequence
<220> FEATURE:
<223> OTHER INFORMATION: synthetic peptide

<400> SEQUENCE: 636

Phe Glu His Asp Lys Val Trp Tyr Asp
1               5

<210> SEQ ID NO 637
<211> LENGTH: 9
<212> TYPE: PRT
<213> ORGANISM: artificial sequence
<220> FEATURE:
<223> OTHER INFORMATION: synthetic peptide

<400> SEQUENCE: 637

Phe Glu Leu Asp Lys Val Trp Tyr Asp
1               5

<210> SEQ ID NO 638
<211> LENGTH: 9
<212> TYPE: PRT
<213> ORGANISM: artificial sequence
<220> FEATURE:
<223> OTHER INFORMATION: synthetic peptide

<400> SEQUENCE: 638

Phe Glu Arg Asp Lys Val Trp Tyr Asp
1               5

<210> SEQ ID NO 639
<211> LENGTH: 9
<212> TYPE: PRT
<213> ORGANISM: artificial sequence
<220> FEATURE:
<223> OTHER INFORMATION: synthetic peptide

<400> SEQUENCE: 639

Phe Glu Glu Asp Lys Val Trp Tyr Asp

```
1               5

<210> SEQ ID NO 640
<211> LENGTH: 9
<212> TYPE: PRT
<213> ORGANISM: artificial sequence
<220> FEATURE:
<223> OTHER INFORMATION: synthetic peptide

<400> SEQUENCE: 640

Phe Asp Ile Asp Lys Val Trp Tyr Asp
1               5

<210> SEQ ID NO 641
<211> LENGTH: 9
<212> TYPE: PRT
<213> ORGANISM: artificial sequence
<220> FEATURE:
<223> OTHER INFORMATION: synthetic peptide

<400> SEQUENCE: 641

Leu Glu Ile Asp Lys Val Trp Tyr Asp
1               5

<210> SEQ ID NO 642
<211> LENGTH: 9
<212> TYPE: PRT
<213> ORGANISM: artificial sequence
<220> FEATURE:
<223> OTHER INFORMATION: synthetic peptide

<400> SEQUENCE: 642

Ile Glu Ile Asp Lys Val Trp Tyr Asp
1               5

<210> SEQ ID NO 643
<211> LENGTH: 9
<212> TYPE: PRT
<213> ORGANISM: artificial sequence
<220> FEATURE:
<223> OTHER INFORMATION: synthetic peptide

<400> SEQUENCE: 643

Val Glu Ile Asp Lys Val Trp Tyr Asp
1               5

<210> SEQ ID NO 644
<211> LENGTH: 9
<212> TYPE: PRT
<213> ORGANISM: artificial sequence
<220> FEATURE:
<223> OTHER INFORMATION: synthetic peptide

<400> SEQUENCE: 644

Phe Glu Arg Asp Lys Val Trp His Asp
1               5

<210> SEQ ID NO 645
<211> LENGTH: 9
<212> TYPE: PRT
<213> ORGANISM: artificial sequence
<220> FEATURE:
<223> OTHER INFORMATION: synthetic peptide

<400> SEQUENCE: 645

Phe Glu Arg Asp Lys Ala Trp Tyr Asp
1               5
```

<210> SEQ ID NO 646
<211> LENGTH: 9
<212> TYPE: PRT
<213> ORGANISM: artificial sequence
<220> FEATURE:
<223> OTHER INFORMATION: synthetic peptide

<400> SEQUENCE: 646

Phe Glu Arg Asp Lys Ala Trp His Asp
1               5

<210> SEQ ID NO 647
<211> LENGTH: 13
<212> TYPE: PRT
<213> ORGANISM: artificial sequence
<220> FEATURE:
<223> OTHER INFORMATION: synthetic peptide

<400> SEQUENCE: 647

Gly Phe Glu Arg Asp Lys Val Trp His Asp Leu Asp Ser
1               5                   10

<210> SEQ ID NO 648
<211> LENGTH: 13
<212> TYPE: PRT
<213> ORGANISM: artificial sequence
<220> FEATURE:
<223> OTHER INFORMATION: synthetic peptide

<400> SEQUENCE: 648

Gly Phe Glu Arg Asp Lys Ala Trp His Asp Leu Asp Ser
1               5                   10

<210> SEQ ID NO 649
<211> LENGTH: 13
<212> TYPE: PRT
<213> ORGANISM: artificial sequence
<220> FEATURE:
<223> OTHER INFORMATION: synthetic peptide

<400> SEQUENCE: 649

Gly Phe Glu His Asp Lys Val Trp His Asp Leu Asp Ser
1               5                   10

<210> SEQ ID NO 650
<211> LENGTH: 13
<212> TYPE: PRT
<213> ORGANISM: artificial sequence
<220> FEATURE:
<223> OTHER INFORMATION: synthetic peptide

<400> SEQUENCE: 650

Gly Phe Glu Arg Asp Lys Val Trp Tyr Asp Leu Asp Ala
1               5                   10

<210> SEQ ID NO 651
<211> LENGTH: 8
<212> TYPE: PRT
<213> ORGANISM: artificial sequence
<220> FEATURE:
<223> OTHER INFORMATION: synthetic peptide

<400> SEQUENCE: 651

Glu Ile Asp Lys Val Trp Tyr Asp
1               5

<210> SEQ ID NO 652

```
<211> LENGTH: 8
<212> TYPE: PRT
<213> ORGANISM: artificial sequence
<220> FEATURE:
<223> OTHER INFORMATION: synthetic peptide

<400> SEQUENCE: 652

Asp Ile Asp Lys Val Trp Tyr Asp
1               5

<210> SEQ ID NO 653
<211> LENGTH: 8
<212> TYPE: PRT
<213> ORGANISM: artificial sequence
<220> FEATURE:
<223> OTHER INFORMATION: synthetic peptide

<400> SEQUENCE: 653

Glu His Asp Lys Val Trp Tyr Asp
1               5

<210> SEQ ID NO 654
<211> LENGTH: 8
<212> TYPE: PRT
<213> ORGANISM: artificial sequence
<220> FEATURE:
<223> OTHER INFORMATION: synthetic peptide

<400> SEQUENCE: 654

Asp His Asp Lys Val Trp Tyr Asp
1               5

<210> SEQ ID NO 655
<211> LENGTH: 8
<212> TYPE: PRT
<213> ORGANISM: artificial sequence
<220> FEATURE:
<223> OTHER INFORMATION: synthetic peptide

<400> SEQUENCE: 655

Glu Leu Asp Lys Val Trp Tyr Asp
1               5

<210> SEQ ID NO 656
<211> LENGTH: 8
<212> TYPE: PRT
<213> ORGANISM: artificial sequence
<220> FEATURE:
<223> OTHER INFORMATION: synthetic peptide

<400> SEQUENCE: 656

Asp Leu Asp Lys Val Trp Tyr Asp
1               5

<210> SEQ ID NO 657
<211> LENGTH: 8
<212> TYPE: PRT
<213> ORGANISM: artificial sequence
<220> FEATURE:
<223> OTHER INFORMATION: synthetic peptide

<400> SEQUENCE: 657

Glu Arg Asp Lys Val Trp Tyr Asp
1               5

<210> SEQ ID NO 658
<211> LENGTH: 8
<212> TYPE: PRT
```

```
<213> ORGANISM: artificial sequence
<220> FEATURE:
<223> OTHER INFORMATION: synthetic peptide

<400> SEQUENCE: 658

Asp Arg Asp Lys Val Trp Tyr Asp
1               5

<210> SEQ ID NO 659
<211> LENGTH: 8
<212> TYPE: PRT
<213> ORGANISM: artificial sequence
<220> FEATURE:
<223> OTHER INFORMATION: synthetic peptide

<400> SEQUENCE: 659

Glu Glu Asp Lys Val Trp Tyr Asp
1               5

<210> SEQ ID NO 660
<211> LENGTH: 8
<212> TYPE: PRT
<213> ORGANISM: artificial sequence
<220> FEATURE:
<223> OTHER INFORMATION: synthetic peptide

<400> SEQUENCE: 660

Asp Glu Asp Lys Val Trp Tyr Asp
1               5

<210> SEQ ID NO 661
<211> LENGTH: 8
<212> TYPE: PRT
<213> ORGANISM: artificial sequence
<220> FEATURE:
<223> OTHER INFORMATION: synthetic peptide

<400> SEQUENCE: 661

Glu Ile Asn Lys Val Trp Tyr Asp
1               5

<210> SEQ ID NO 662
<211> LENGTH: 8
<212> TYPE: PRT
<213> ORGANISM: artificial sequence
<220> FEATURE:
<223> OTHER INFORMATION: synthetic peptide

<400> SEQUENCE: 662

Glu His Asn Lys Val Trp Tyr Asp
1               5

<210> SEQ ID NO 663
<211> LENGTH: 8
<212> TYPE: PRT
<213> ORGANISM: artificial sequence
<220> FEATURE:
<223> OTHER INFORMATION: synthetic peptide

<400> SEQUENCE: 663

Glu Leu Asn Lys Val Trp Tyr Asp
1               5

<210> SEQ ID NO 664
<211> LENGTH: 8
<212> TYPE: PRT
<213> ORGANISM: artificial sequence
<220> FEATURE:
```

<223> OTHER INFORMATION: synthetic peptide

<400> SEQUENCE: 664

Glu Arg Asn Lys Val Trp Tyr Asp
1               5

<210> SEQ ID NO 665
<211> LENGTH: 8
<212> TYPE: PRT
<213> ORGANISM: artificial sequence
<220> FEATURE:
<223> OTHER INFORMATION: synthetic peptide

<400> SEQUENCE: 665

Asp Ile Asn Lys Val Trp Tyr Asp
1               5

<210> SEQ ID NO 666
<211> LENGTH: 8
<212> TYPE: PRT
<213> ORGANISM: artificial sequence
<220> FEATURE:
<223> OTHER INFORMATION: synthetic peptide

<400> SEQUENCE: 666

Asp His Asn Lys Val Trp Tyr Asp
1               5

<210> SEQ ID NO 667
<211> LENGTH: 8
<212> TYPE: PRT
<213> ORGANISM: artificial sequence
<220> FEATURE:
<223> OTHER INFORMATION: synthetic peptide

<400> SEQUENCE: 667

Asp Leu Asn Lys Val Trp Tyr Asp
1               5

<210> SEQ ID NO 668
<211> LENGTH: 8
<212> TYPE: PRT
<213> ORGANISM: artificial sequence
<220> FEATURE:
<223> OTHER INFORMATION: synthetic peptide

<400> SEQUENCE: 668

Asp Arg Asn Lys Val Trp Tyr Asp
1               5

<210> SEQ ID NO 669
<211> LENGTH: 8
<212> TYPE: PRT
<213> ORGANISM: artificial sequence
<220> FEATURE:
<223> OTHER INFORMATION: synthetic peptide

<400> SEQUENCE: 669

Asp Glu Asn Lys Val Trp Tyr Asp
1               5

<210> SEQ ID NO 670
<211> LENGTH: 8
<212> TYPE: PRT
<213> ORGANISM: artificial sequence
<220> FEATURE:
<223> OTHER INFORMATION: synthetic peptide

```
<400> SEQUENCE: 670

Glu Ile Glu Lys Val Trp Tyr Asp
1               5

<210> SEQ ID NO 671
<211> LENGTH: 8
<212> TYPE: PRT
<213> ORGANISM: artificial sequence
<220> FEATURE:
<223> OTHER INFORMATION: synthetic peptide

<400> SEQUENCE: 671

Glu His Glu Lys Val Trp Tyr Asp
1               5

<210> SEQ ID NO 672
<211> LENGTH: 8
<212> TYPE: PRT
<213> ORGANISM: artificial sequence
<220> FEATURE:
<223> OTHER INFORMATION: synthetic peptide

<400> SEQUENCE: 672

Glu Leu Glu Lys Val Trp Tyr Asp
1               5

<210> SEQ ID NO 673
<211> LENGTH: 8
<212> TYPE: PRT
<213> ORGANISM: artificial sequence
<220> FEATURE:
<223> OTHER INFORMATION: synthetic peptide

<400> SEQUENCE: 673

Glu Arg Glu Lys Val Trp Tyr Asp
1               5

<210> SEQ ID NO 674
<211> LENGTH: 8
<212> TYPE: PRT
<213> ORGANISM: artificial sequence
<220> FEATURE:
<223> OTHER INFORMATION: synthetic peptide

<400> SEQUENCE: 674

Glu Glu Glu Lys Val Trp Tyr Asp
1               5

<210> SEQ ID NO 675
<211> LENGTH: 8
<212> TYPE: PRT
<213> ORGANISM: artificial sequence
<220> FEATURE:
<223> OTHER INFORMATION: synthetic peptide

<400> SEQUENCE: 675

Asp Ile Glu Lys Val Trp Tyr Asp
1               5

<210> SEQ ID NO 676
<211> LENGTH: 8
<212> TYPE: PRT
<213> ORGANISM: artificial sequence
<220> FEATURE:
<223> OTHER INFORMATION: synthetic peptide

<400> SEQUENCE: 676
```

```
Asp His Glu Lys Val Trp Tyr Asp
1               5
```

```
<210> SEQ ID NO 677
<211> LENGTH: 8
<212> TYPE: PRT
<213> ORGANISM: artificial sequence
<220> FEATURE:
<223> OTHER INFORMATION: synthetic peptide

<400> SEQUENCE: 677

Asp Leu Glu Lys Val Trp Tyr Asp
1               5
```

```
<210> SEQ ID NO 678
<211> LENGTH: 8
<212> TYPE: PRT
<213> ORGANISM: artificial sequence
<220> FEATURE:
<223> OTHER INFORMATION: synthetic peptide

<400> SEQUENCE: 678

Asp Arg Glu Lys Val Trp Tyr Asp
1               5
```

```
<210> SEQ ID NO 679
<211> LENGTH: 8
<212> TYPE: PRT
<213> ORGANISM: artificial sequence
<220> FEATURE:
<223> OTHER INFORMATION: synthetic peptide

<400> SEQUENCE: 679

Asp Glu Glu Lys Val Trp Tyr Asp
1               5
```

```
<210> SEQ ID NO 680
<211> LENGTH: 8
<212> TYPE: PRT
<213> ORGANISM: artificial sequence
<220> FEATURE:
<223> OTHER INFORMATION: synthetic peptide

<400> SEQUENCE: 680

Glu Ile Tyr Lys Val Trp Tyr Asp
1               5
```

```
<210> SEQ ID NO 681
<211> LENGTH: 8
<212> TYPE: PRT
<213> ORGANISM: artificial sequence
<220> FEATURE:
<223> OTHER INFORMATION: synthetic peptide

<400> SEQUENCE: 681

Glu His Tyr Lys Val Trp Tyr Asp
1               5
```

```
<210> SEQ ID NO 682
<211> LENGTH: 8
<212> TYPE: PRT
<213> ORGANISM: artificial sequence
<220> FEATURE:
<223> OTHER INFORMATION: synthetic peptide

<400> SEQUENCE: 682

Glu Leu Tyr Lys Val Trp Tyr Asp
1               5
```

<210> SEQ ID NO 683
<211> LENGTH: 8
<212> TYPE: PRT
<213> ORGANISM: artificial sequence
<220> FEATURE:
<223> OTHER INFORMATION: synthetic peptide

<400> SEQUENCE: 683

Glu Arg Tyr Lys Val Trp Tyr Asp
1               5

<210> SEQ ID NO 684
<211> LENGTH: 8
<212> TYPE: PRT
<213> ORGANISM: artificial sequence
<220> FEATURE:
<223> OTHER INFORMATION: synthetic peptide

<400> SEQUENCE: 684

Glu Glu Tyr Lys Val Trp Tyr Asp
1               5

<210> SEQ ID NO 685
<211> LENGTH: 8
<212> TYPE: PRT
<213> ORGANISM: artificial sequence
<220> FEATURE:
<223> OTHER INFORMATION: synthetic peptide

<400> SEQUENCE: 685

Asp Ile Tyr Lys Val Trp Tyr Asp
1               5

<210> SEQ ID NO 686
<211> LENGTH: 8
<212> TYPE: PRT
<213> ORGANISM: artificial sequence
<220> FEATURE:
<223> OTHER INFORMATION: synthetic peptide

<400> SEQUENCE: 686

Asp His Tyr Lys Val Trp Tyr Asp
1               5

<210> SEQ ID NO 687
<211> LENGTH: 8
<212> TYPE: PRT
<213> ORGANISM: artificial sequence
<220> FEATURE:
<223> OTHER INFORMATION: synthetic peptide

<400> SEQUENCE: 687

Asp Leu Tyr Lys Val Trp Tyr Asp
1               5

<210> SEQ ID NO 688
<211> LENGTH: 8
<212> TYPE: PRT
<213> ORGANISM: artificial sequence
<220> FEATURE:
<223> OTHER INFORMATION: synthetic peptide

<400> SEQUENCE: 688

Asp Arg Tyr Lys Val Trp Tyr Asp
1               5

```
<210> SEQ ID NO 689
<211> LENGTH: 8
<212> TYPE: PRT
<213> ORGANISM: artificial sequence
<220> FEATURE:
<223> OTHER INFORMATION: synthetic peptide

<400> SEQUENCE: 689

Asp Glu Tyr Lys Val Trp Tyr Asp
1               5

<210> SEQ ID NO 690
<211> LENGTH: 8
<212> TYPE: PRT
<213> ORGANISM: artificial sequence
<220> FEATURE:
<223> OTHER INFORMATION: synthetic peptide

<400> SEQUENCE: 690

Glu Ile Asp Lys Ile Trp Tyr Asp
1               5

<210> SEQ ID NO 691
<211> LENGTH: 8
<212> TYPE: PRT
<213> ORGANISM: artificial sequence
<220> FEATURE:
<223> OTHER INFORMATION: synthetic peptide

<400> SEQUENCE: 691

Asp Ile Asp Lys Ile Trp Tyr Asp
1               5

<210> SEQ ID NO 692
<211> LENGTH: 8
<212> TYPE: PRT
<213> ORGANISM: artificial sequence
<220> FEATURE:
<223> OTHER INFORMATION: synthetic peptide

<400> SEQUENCE: 692

Glu His Asp Lys Ile Trp Tyr Asp
1               5

<210> SEQ ID NO 693
<211> LENGTH: 8
<212> TYPE: PRT
<213> ORGANISM: artificial sequence
<220> FEATURE:
<223> OTHER INFORMATION: synthetic peptide

<400> SEQUENCE: 693

Asp His Asp Lys Ile Trp Tyr Asp
1               5

<210> SEQ ID NO 694
<211> LENGTH: 8
<212> TYPE: PRT
<213> ORGANISM: artificial sequence
<220> FEATURE:
<223> OTHER INFORMATION: synthetic peptide

<400> SEQUENCE: 694

Glu Leu Asp Lys Ile Trp Tyr Asp
1               5

<210> SEQ ID NO 695
<211> LENGTH: 8
```

```
<212> TYPE: PRT
<213> ORGANISM: artificial sequence
<220> FEATURE:
<223> OTHER INFORMATION: synthetic peptide

<400> SEQUENCE: 695

Asp Leu Asp Lys Ile Trp Tyr Asp
1               5

<210> SEQ ID NO 696
<211> LENGTH: 8
<212> TYPE: PRT
<213> ORGANISM: artificial sequence
<220> FEATURE:
<223> OTHER INFORMATION: synthetic peptide

<400> SEQUENCE: 696

Glu Arg Asp Lys Ile Trp Tyr Asp
1               5

<210> SEQ ID NO 697
<211> LENGTH: 8
<212> TYPE: PRT
<213> ORGANISM: artificial sequence
<220> FEATURE:
<223> OTHER INFORMATION: synthetic peptide

<400> SEQUENCE: 697

Asp Arg Asp Lys Ile Trp Tyr Asp
1               5

<210> SEQ ID NO 698
<211> LENGTH: 8
<212> TYPE: PRT
<213> ORGANISM: artificial sequence
<220> FEATURE:
<223> OTHER INFORMATION: synthetic peptide

<400> SEQUENCE: 698

Glu Glu Asp Lys Ile Trp Tyr Asp
1               5

<210> SEQ ID NO 699
<211> LENGTH: 8
<212> TYPE: PRT
<213> ORGANISM: artificial sequence
<220> FEATURE:
<223> OTHER INFORMATION: synthetic peptide

<400> SEQUENCE: 699

Asp Glu Asp Lys Ile Trp Tyr Asp
1               5

<210> SEQ ID NO 700
<211> LENGTH: 8
<212> TYPE: PRT
<213> ORGANISM: artificial sequence
<220> FEATURE:
<223> OTHER INFORMATION: synthetic peptide

<400> SEQUENCE: 700

Glu Ile Asn Lys Ile Trp Tyr Asp
1               5

<210> SEQ ID NO 701
<211> LENGTH: 8
<212> TYPE: PRT
<213> ORGANISM: artificial sequence
```

```
<220> FEATURE:
<223> OTHER INFORMATION: synthetic peptide

<400> SEQUENCE: 701

Glu His Asn Lys Ile Trp Tyr Asp
1               5

<210> SEQ ID NO 702
<211> LENGTH: 8
<212> TYPE: PRT
<213> ORGANISM: artificial sequence
<220> FEATURE:
<223> OTHER INFORMATION: synthetic peptide

<400> SEQUENCE: 702

Glu Leu Asn Lys Ile Trp Tyr Asp
1               5

<210> SEQ ID NO 703
<211> LENGTH: 8
<212> TYPE: PRT
<213> ORGANISM: artificial sequence
<220> FEATURE:
<223> OTHER INFORMATION: synthetic peptide

<400> SEQUENCE: 703

Glu Arg Asn Lys Ile Trp Tyr Asp
1               5

<210> SEQ ID NO 704
<211> LENGTH: 8
<212> TYPE: PRT
<213> ORGANISM: artificial sequence
<220> FEATURE:
<223> OTHER INFORMATION: synthetic peptide

<400> SEQUENCE: 704

Asp Ile Asn Lys Ile Trp Tyr Asp
1               5

<210> SEQ ID NO 705
<211> LENGTH: 8
<212> TYPE: PRT
<213> ORGANISM: artificial sequence
<220> FEATURE:
<223> OTHER INFORMATION: synthetic peptide

<400> SEQUENCE: 705

Asp His Asn Lys Ile Trp Tyr Asp
1               5

<210> SEQ ID NO 706
<211> LENGTH: 8
<212> TYPE: PRT
<213> ORGANISM: artificial sequence
<220> FEATURE:
<223> OTHER INFORMATION: synthetic peptide

<400> SEQUENCE: 706

Asp Leu Asn Lys Ile Trp Tyr Asp
1               5

<210> SEQ ID NO 707
<211> LENGTH: 8
<212> TYPE: PRT
<213> ORGANISM: artificial sequence
<220> FEATURE:
<223> OTHER INFORMATION: synthetic peptide
```

```
<400> SEQUENCE: 707

Asp Arg Asn Lys Ile Trp Tyr Asp
1               5

<210> SEQ ID NO 708
<211> LENGTH: 8
<212> TYPE: PRT
<213> ORGANISM: artificial sequence
<220> FEATURE:
<223> OTHER INFORMATION: synthetic peptide

<400> SEQUENCE: 708

Asp Glu Asn Lys Ile Trp Tyr Asp
1               5

<210> SEQ ID NO 709
<211> LENGTH: 8
<212> TYPE: PRT
<213> ORGANISM: artificial sequence
<220> FEATURE:
<223> OTHER INFORMATION: synthetic peptide

<400> SEQUENCE: 709

Glu Ile Glu Lys Ile Trp Tyr Asp
1               5

<210> SEQ ID NO 710
<211> LENGTH: 8
<212> TYPE: PRT
<213> ORGANISM: artificial sequence
<220> FEATURE:
<223> OTHER INFORMATION: synthetic peptide

<400> SEQUENCE: 710

Glu His Glu Lys Ile Trp Tyr Asp
1               5

<210> SEQ ID NO 711
<211> LENGTH: 8
<212> TYPE: PRT
<213> ORGANISM: artificial sequence
<220> FEATURE:
<223> OTHER INFORMATION: synthetic peptide

<400> SEQUENCE: 711

Glu Leu Glu Lys Ile Trp Tyr Asp
1               5

<210> SEQ ID NO 712
<211> LENGTH: 8
<212> TYPE: PRT
<213> ORGANISM: artificial sequence
<220> FEATURE:
<223> OTHER INFORMATION: synthetic peptide

<400> SEQUENCE: 712

Glu Arg Glu Lys Ile Trp Tyr Asp
1               5

<210> SEQ ID NO 713
<211> LENGTH: 8
<212> TYPE: PRT
<213> ORGANISM: artificial sequence
<220> FEATURE:
<223> OTHER INFORMATION: synthetic peptide

<400> SEQUENCE: 713
```

```
Glu Glu Glu Lys Ile Trp Tyr Asp
1               5

<210> SEQ ID NO 714
<211> LENGTH: 8
<212> TYPE: PRT
<213> ORGANISM: artificial sequence
<220> FEATURE:
<223> OTHER INFORMATION: synthetic peptide

<400> SEQUENCE: 714

Asp Ile Glu Lys Ile Trp Tyr Asp
1               5

<210> SEQ ID NO 715
<211> LENGTH: 8
<212> TYPE: PRT
<213> ORGANISM: artificial sequence
<220> FEATURE:
<223> OTHER INFORMATION: synthetic peptide

<400> SEQUENCE: 715

Asp His Glu Lys Ile Trp Tyr Asp
1               5

<210> SEQ ID NO 716
<211> LENGTH: 8
<212> TYPE: PRT
<213> ORGANISM: artificial sequence
<220> FEATURE:
<223> OTHER INFORMATION: synthetic peptide

<400> SEQUENCE: 716

Asp Leu Glu Lys Ile Trp Tyr Asp
1               5

<210> SEQ ID NO 717
<211> LENGTH: 8
<212> TYPE: PRT
<213> ORGANISM: artificial sequence
<220> FEATURE:
<223> OTHER INFORMATION: synthetic peptide

<400> SEQUENCE: 717

Asp Arg Glu Lys Ile Trp Tyr Asp
1               5

<210> SEQ ID NO 718
<211> LENGTH: 8
<212> TYPE: PRT
<213> ORGANISM: artificial sequence
<220> FEATURE:
<223> OTHER INFORMATION: synthetic peptide

<400> SEQUENCE: 718

Asp Glu Glu Lys Ile Trp Tyr Asp
1               5

<210> SEQ ID NO 719
<211> LENGTH: 8
<212> TYPE: PRT
<213> ORGANISM: artificial sequence
<220> FEATURE:
<223> OTHER INFORMATION: synthetic peptide

<400> SEQUENCE: 719

Glu Ile Tyr Lys Ile Trp Tyr Asp
```

```
<210> SEQ ID NO 720
<211> LENGTH: 8
<212> TYPE: PRT
<213> ORGANISM: artificial sequence
<220> FEATURE:
<223> OTHER INFORMATION: synthetic peptide

<400> SEQUENCE: 720

Glu His Tyr Lys Ile Trp Tyr Asp
1               5

<210> SEQ ID NO 721
<211> LENGTH: 8
<212> TYPE: PRT
<213> ORGANISM: artificial sequence
<220> FEATURE:
<223> OTHER INFORMATION: synthetic peptide

<400> SEQUENCE: 721

Glu Leu Tyr Lys Ile Trp Tyr Asp
1               5

<210> SEQ ID NO 722
<211> LENGTH: 8
<212> TYPE: PRT
<213> ORGANISM: artificial sequence
<220> FEATURE:
<223> OTHER INFORMATION: synthetic peptide

<400> SEQUENCE: 722

Glu Arg Tyr Lys Ile Trp Tyr Asp
1               5

<210> SEQ ID NO 723
<211> LENGTH: 8
<212> TYPE: PRT
<213> ORGANISM: artificial sequence
<220> FEATURE:
<223> OTHER INFORMATION: synthetic peptide

<400> SEQUENCE: 723

Glu Glu Tyr Lys Ile Trp Tyr Asp
1               5

<210> SEQ ID NO 724
<211> LENGTH: 8
<212> TYPE: PRT
<213> ORGANISM: artificial sequence
<220> FEATURE:
<223> OTHER INFORMATION: synthetic peptide

<400> SEQUENCE: 724

Asp Ile Tyr Lys Ile Trp Tyr Asp
1               5

<210> SEQ ID NO 725
<211> LENGTH: 8
<212> TYPE: PRT
<213> ORGANISM: artificial sequence
<220> FEATURE:
<223> OTHER INFORMATION: synthetic peptide

<400> SEQUENCE: 725

Asp His Tyr Lys Ile Trp Tyr Asp
1               5
```

<210> SEQ ID NO 726
<211> LENGTH: 8
<212> TYPE: PRT
<213> ORGANISM: artificial sequence
<220> FEATURE:
<223> OTHER INFORMATION: synthetic peptide

<400> SEQUENCE: 726

Asp Leu Tyr Lys Ile Trp Tyr Asp
1               5

<210> SEQ ID NO 727
<211> LENGTH: 8
<212> TYPE: PRT
<213> ORGANISM: artificial sequence
<220> FEATURE:
<223> OTHER INFORMATION: synthetic peptide

<400> SEQUENCE: 727

Asp Arg Tyr Lys Ile Trp Tyr Asp
1               5

<210> SEQ ID NO 728
<211> LENGTH: 8
<212> TYPE: PRT
<213> ORGANISM: artificial sequence
<220> FEATURE:
<223> OTHER INFORMATION: synthetic peptide

<400> SEQUENCE: 728

Asp Glu Tyr Lys Ile Trp Tyr Asp
1               5

<210> SEQ ID NO 729
<211> LENGTH: 8
<212> TYPE: PRT
<213> ORGANISM: artificial sequence
<220> FEATURE:
<223> OTHER INFORMATION: synthetic peptide

<400> SEQUENCE: 729

Glu Ile Asp Lys Leu Trp Tyr Asp
1               5

<210> SEQ ID NO 730
<211> LENGTH: 8
<212> TYPE: PRT
<213> ORGANISM: artificial sequence
<220> FEATURE:
<223> OTHER INFORMATION: synthetic peptide

<400> SEQUENCE: 730

Asp Ile Asp Lys Leu Trp Tyr Asp
1               5

<210> SEQ ID NO 731
<211> LENGTH: 8
<212> TYPE: PRT
<213> ORGANISM: artificial sequence
<220> FEATURE:
<223> OTHER INFORMATION: synthetic peptide

<400> SEQUENCE: 731

Glu His Asp Lys Leu Trp Tyr Asp
1               5

<210> SEQ ID NO 732

<211> LENGTH: 8
<212> TYPE: PRT
<213> ORGANISM: artificial sequence
<220> FEATURE:
<223> OTHER INFORMATION: synthetic peptide

<400> SEQUENCE: 732

Asp His Asp Lys Leu Trp Tyr Asp
1               5

<210> SEQ ID NO 733
<211> LENGTH: 8
<212> TYPE: PRT
<213> ORGANISM: artificial sequence
<220> FEATURE:
<223> OTHER INFORMATION: synthetic peptide

<400> SEQUENCE: 733

Glu Leu Asp Lys Leu Trp Tyr Asp
1               5

<210> SEQ ID NO 734
<211> LENGTH: 8
<212> TYPE: PRT
<213> ORGANISM: artificial sequence
<220> FEATURE:
<223> OTHER INFORMATION: synthetic peptide

<400> SEQUENCE: 734

Asp Leu Asp Lys Leu Trp Tyr Asp
1               5

<210> SEQ ID NO 735
<211> LENGTH: 8
<212> TYPE: PRT
<213> ORGANISM: artificial sequence
<220> FEATURE:
<223> OTHER INFORMATION: synthetic peptide

<400> SEQUENCE: 735

Glu Arg Asp Lys Leu Trp Tyr Asp
1               5

<210> SEQ ID NO 736
<211> LENGTH: 8
<212> TYPE: PRT
<213> ORGANISM: artificial sequence
<220> FEATURE:
<223> OTHER INFORMATION: synthetic peptide

<400> SEQUENCE: 736

Asp Arg Asp Lys Leu Trp Tyr Asp
1               5

<210> SEQ ID NO 737
<211> LENGTH: 8
<212> TYPE: PRT
<213> ORGANISM: artificial sequence
<220> FEATURE:
<223> OTHER INFORMATION: synthetic peptide

<400> SEQUENCE: 737

Glu Glu Asp Lys Leu Trp Tyr Asp
1               5

<210> SEQ ID NO 738
<211> LENGTH: 8
<212> TYPE: PRT

<213> ORGANISM: artificial sequence
<220> FEATURE:
<223> OTHER INFORMATION: synthetic peptide

<400> SEQUENCE: 738

Asp Glu Asp Lys Leu Trp Tyr Asp
1               5

<210> SEQ ID NO 739
<211> LENGTH: 8
<212> TYPE: PRT
<213> ORGANISM: artificial sequence
<220> FEATURE:
<223> OTHER INFORMATION: synthetic peptide

<400> SEQUENCE: 739

Glu Ile Asn Lys Leu Trp Tyr Asp
1               5

<210> SEQ ID NO 740
<211> LENGTH: 8
<212> TYPE: PRT
<213> ORGANISM: artificial sequence
<220> FEATURE:
<223> OTHER INFORMATION: synthetic peptide

<400> SEQUENCE: 740

Glu His Asn Lys Leu Trp Tyr Asp
1               5

<210> SEQ ID NO 741
<211> LENGTH: 8
<212> TYPE: PRT
<213> ORGANISM: artificial sequence
<220> FEATURE:
<223> OTHER INFORMATION: synthetic peptide

<400> SEQUENCE: 741

Glu Leu Asn Lys Leu Trp Tyr Asp
1               5

<210> SEQ ID NO 742
<211> LENGTH: 8
<212> TYPE: PRT
<213> ORGANISM: artificial sequence
<220> FEATURE:
<223> OTHER INFORMATION: synthetic peptide

<400> SEQUENCE: 742

Glu Arg Asn Lys Leu Trp Tyr Asp
1               5

<210> SEQ ID NO 743
<211> LENGTH: 8
<212> TYPE: PRT
<213> ORGANISM: artificial sequence
<220> FEATURE:
<223> OTHER INFORMATION: synthetic peptide

<400> SEQUENCE: 743

Asp Ile Asn Lys Leu Trp Tyr Asp
1               5

<210> SEQ ID NO 744
<211> LENGTH: 8
<212> TYPE: PRT
<213> ORGANISM: artificial sequence
<220> FEATURE:

<223> OTHER INFORMATION: synthetic peptide

<400> SEQUENCE: 744

Asp His Asn Lys Leu Trp Tyr Asp
1               5

<210> SEQ ID NO 745
<211> LENGTH: 8
<212> TYPE: PRT
<213> ORGANISM: artificial sequence
<220> FEATURE:
<223> OTHER INFORMATION: synthetic peptide

<400> SEQUENCE: 745

Asp Leu Asn Lys Leu Trp Tyr Asp
1               5

<210> SEQ ID NO 746
<211> LENGTH: 8
<212> TYPE: PRT
<213> ORGANISM: artificial sequence
<220> FEATURE:
<223> OTHER INFORMATION: synthetic peptide

<400> SEQUENCE: 746

Asp Arg Asn Lys Leu Trp Tyr Asp
1               5

<210> SEQ ID NO 747
<211> LENGTH: 8
<212> TYPE: PRT
<213> ORGANISM: artificial sequence
<220> FEATURE:
<223> OTHER INFORMATION: synthetic peptide

<400> SEQUENCE: 747

Asp Glu Asn Lys Leu Trp Tyr Asp
1               5

<210> SEQ ID NO 748
<211> LENGTH: 8
<212> TYPE: PRT
<213> ORGANISM: artificial sequence
<220> FEATURE:
<223> OTHER INFORMATION: synthetic peptide

<400> SEQUENCE: 748

Glu Ile Glu Lys Leu Trp Tyr Asp
1               5

<210> SEQ ID NO 749
<211> LENGTH: 8
<212> TYPE: PRT
<213> ORGANISM: artificial sequence
<220> FEATURE:
<223> OTHER INFORMATION: synthetic peptide

<400> SEQUENCE: 749

Glu His Glu Lys Leu Trp Tyr Asp
1               5

<210> SEQ ID NO 750
<211> LENGTH: 8
<212> TYPE: PRT
<213> ORGANISM: artificial sequence
<220> FEATURE:
<223> OTHER INFORMATION: synthetic peptide

```
<400> SEQUENCE: 750

Glu Leu Glu Lys Leu Trp Tyr Asp
1               5

<210> SEQ ID NO 751
<211> LENGTH: 8
<212> TYPE: PRT
<213> ORGANISM: artificial sequence
<220> FEATURE:
<223> OTHER INFORMATION: synthetic peptide

<400> SEQUENCE: 751

Glu Arg Glu Lys Leu Trp Tyr Asp
1               5

<210> SEQ ID NO 752
<211> LENGTH: 8
<212> TYPE: PRT
<213> ORGANISM: artificial sequence
<220> FEATURE:
<223> OTHER INFORMATION: synthetic peptide

<400> SEQUENCE: 752

Glu Glu Glu Lys Leu Trp Tyr Asp
1               5

<210> SEQ ID NO 753
<211> LENGTH: 8
<212> TYPE: PRT
<213> ORGANISM: artificial sequence
<220> FEATURE:
<223> OTHER INFORMATION: synthetic peptide

<400> SEQUENCE: 753

Asp Ile Glu Lys Leu Trp Tyr Asp
1               5

<210> SEQ ID NO 754
<211> LENGTH: 8
<212> TYPE: PRT
<213> ORGANISM: artificial sequence
<220> FEATURE:
<223> OTHER INFORMATION: synthetic peptide

<400> SEQUENCE: 754

Asp His Glu Lys Leu Trp Tyr Asp
1               5

<210> SEQ ID NO 755
<211> LENGTH: 8
<212> TYPE: PRT
<213> ORGANISM: artificial sequence
<220> FEATURE:
<223> OTHER INFORMATION: synthetic peptide

<400> SEQUENCE: 755

Asp Leu Glu Lys Leu Trp Tyr Asp
1               5

<210> SEQ ID NO 756
<211> LENGTH: 8
<212> TYPE: PRT
<213> ORGANISM: artificial sequence
<220> FEATURE:
<223> OTHER INFORMATION: synthetic peptide

<400> SEQUENCE: 756
```

```
Asp Arg Glu Lys Leu Trp Tyr Asp
1               5
```

<210> SEQ ID NO 757
<211> LENGTH: 8
<212> TYPE: PRT
<213> ORGANISM: artificial sequence
<220> FEATURE:
<223> OTHER INFORMATION: synthetic peptide

<400> SEQUENCE: 757

```
Asp Glu Glu Lys Leu Trp Tyr Asp
1               5
```

<210> SEQ ID NO 758
<211> LENGTH: 8
<212> TYPE: PRT
<213> ORGANISM: artificial sequence
<220> FEATURE:
<223> OTHER INFORMATION: synthetic peptide

<400> SEQUENCE: 758

```
Glu Ile Tyr Lys Leu Trp Tyr Asp
1               5
```

<210> SEQ ID NO 759
<211> LENGTH: 8
<212> TYPE: PRT
<213> ORGANISM: artificial sequence
<220> FEATURE:
<223> OTHER INFORMATION: synthetic peptide

<400> SEQUENCE: 759

```
Glu His Tyr Lys Leu Trp Tyr Asp
1               5
```

<210> SEQ ID NO 760
<211> LENGTH: 8
<212> TYPE: PRT
<213> ORGANISM: artificial sequence
<220> FEATURE:
<223> OTHER INFORMATION: synthetic peptide

<400> SEQUENCE: 760

```
Glu Leu Tyr Lys Leu Trp Tyr Asp
1               5
```

<210> SEQ ID NO 761
<211> LENGTH: 8
<212> TYPE: PRT
<213> ORGANISM: artificial sequence
<220> FEATURE:
<223> OTHER INFORMATION: synthetic peptide

<400> SEQUENCE: 761

```
Glu Arg Tyr Lys Leu Trp Tyr Asp
1               5
```

<210> SEQ ID NO 762
<211> LENGTH: 8
<212> TYPE: PRT
<213> ORGANISM: artificial sequence
<220> FEATURE:
<223> OTHER INFORMATION: synthetic peptide

<400> SEQUENCE: 762

```
Glu Glu Tyr Lys Leu Trp Tyr Asp
1               5
```

```
<210> SEQ ID NO 763
<211> LENGTH: 8
<212> TYPE: PRT
<213> ORGANISM: artificial sequence
<220> FEATURE:
<223> OTHER INFORMATION: synthetic peptide

<400> SEQUENCE: 763

Asp Ile Tyr Lys Leu Trp Tyr Asp
1               5

<210> SEQ ID NO 764
<211> LENGTH: 8
<212> TYPE: PRT
<213> ORGANISM: artificial sequence
<220> FEATURE:
<223> OTHER INFORMATION: synthetic peptide

<400> SEQUENCE: 764

Asp His Tyr Lys Leu Trp Tyr Asp
1               5

<210> SEQ ID NO 765
<211> LENGTH: 8
<212> TYPE: PRT
<213> ORGANISM: artificial sequence
<220> FEATURE:
<223> OTHER INFORMATION: synthetic peptide

<400> SEQUENCE: 765

Asp Leu Tyr Lys Leu Trp Tyr Asp
1               5

<210> SEQ ID NO 766
<211> LENGTH: 8
<212> TYPE: PRT
<213> ORGANISM: artificial sequence
<220> FEATURE:
<223> OTHER INFORMATION: synthetic peptide

<400> SEQUENCE: 766

Asp Arg Tyr Lys Leu Trp Tyr Asp
1               5

<210> SEQ ID NO 767
<211> LENGTH: 8
<212> TYPE: PRT
<213> ORGANISM: artificial sequence
<220> FEATURE:
<223> OTHER INFORMATION: synthetic peptide

<400> SEQUENCE: 767

Asp Glu Tyr Lys Leu Trp Tyr Asp
1               5

<210> SEQ ID NO 768
<211> LENGTH: 8
<212> TYPE: PRT
<213> ORGANISM: artificial sequence
<220> FEATURE:
<223> OTHER INFORMATION: synthetic peptide

<400> SEQUENCE: 768

Glu Ile Asp Lys Phe Trp Tyr Asp
1               5
```

```
<210> SEQ ID NO 769
<211> LENGTH: 8
<212> TYPE: PRT
<213> ORGANISM: artificial sequence
<220> FEATURE:
<223> OTHER INFORMATION: synthetic peptide

<400> SEQUENCE: 769

Asp Ile Asp Lys Phe Trp Tyr Asp
1               5

<210> SEQ ID NO 770
<211> LENGTH: 8
<212> TYPE: PRT
<213> ORGANISM: artificial sequence
<220> FEATURE:
<223> OTHER INFORMATION: synthetic peptide

<400> SEQUENCE: 770

Glu His Asp Lys Phe Trp Tyr Asp
1               5

<210> SEQ ID NO 771
<211> LENGTH: 8
<212> TYPE: PRT
<213> ORGANISM: artificial sequence
<220> FEATURE:
<223> OTHER INFORMATION: synthetic peptide

<400> SEQUENCE: 771

Asp His Asp Lys Phe Trp Tyr Asp
1               5

<210> SEQ ID NO 772
<211> LENGTH: 8
<212> TYPE: PRT
<213> ORGANISM: artificial sequence
<220> FEATURE:
<223> OTHER INFORMATION: synthetic peptide

<400> SEQUENCE: 772

Glu Leu Asp Lys Phe Trp Tyr Asp
1               5

<210> SEQ ID NO 773
<211> LENGTH: 8
<212> TYPE: PRT
<213> ORGANISM: artificial sequence
<220> FEATURE:
<223> OTHER INFORMATION: synthetic peptide

<400> SEQUENCE: 773

Asp Leu Asp Lys Phe Trp Tyr Asp
1               5

<210> SEQ ID NO 774
<211> LENGTH: 8
<212> TYPE: PRT
<213> ORGANISM: artificial sequence
<220> FEATURE:
<223> OTHER INFORMATION: synthetic peptide

<400> SEQUENCE: 774

Glu Arg Asp Lys Phe Trp Tyr Asp
1               5

<210> SEQ ID NO 775
<211> LENGTH: 8
```

```
<212> TYPE: PRT
<213> ORGANISM: artificial sequence
<220> FEATURE:
<223> OTHER INFORMATION: synthetic peptide

<400> SEQUENCE: 775

Asp Arg Asp Lys Phe Trp Tyr Asp
1               5

<210> SEQ ID NO 776
<211> LENGTH: 8
<212> TYPE: PRT
<213> ORGANISM: artificial sequence
<220> FEATURE:
<223> OTHER INFORMATION: synthetic peptide

<400> SEQUENCE: 776

Glu Glu Asp Lys Phe Trp Tyr Asp
1               5

<210> SEQ ID NO 777
<211> LENGTH: 8
<212> TYPE: PRT
<213> ORGANISM: artificial sequence
<220> FEATURE:
<223> OTHER INFORMATION: synthetic peptide

<400> SEQUENCE: 777

Asp Glu Asp Lys Phe Trp Tyr Asp
1               5

<210> SEQ ID NO 778
<211> LENGTH: 8
<212> TYPE: PRT
<213> ORGANISM: artificial sequence
<220> FEATURE:
<223> OTHER INFORMATION: synthetic peptide

<400> SEQUENCE: 778

Glu Ile Asn Lys Phe Trp Tyr Asp
1               5

<210> SEQ ID NO 779
<211> LENGTH: 8
<212> TYPE: PRT
<213> ORGANISM: artificial sequence
<220> FEATURE:
<223> OTHER INFORMATION: synthetic peptide

<400> SEQUENCE: 779

Glu His Asn Lys Phe Trp Tyr Asp
1               5

<210> SEQ ID NO 780
<211> LENGTH: 8
<212> TYPE: PRT
<213> ORGANISM: artificial sequence
<220> FEATURE:
<223> OTHER INFORMATION: synthetic peptide

<400> SEQUENCE: 780

Glu Leu Asn Lys Phe Trp Tyr Asp
1               5

<210> SEQ ID NO 781
<211> LENGTH: 8
<212> TYPE: PRT
<213> ORGANISM: artificial sequence
```

```
<220> FEATURE:
<223> OTHER INFORMATION: synthetic peptide

<400> SEQUENCE: 781

Glu Arg Asn Lys Phe Trp Tyr Asp
1               5

<210> SEQ ID NO 782
<211> LENGTH: 8
<212> TYPE: PRT
<213> ORGANISM: artificial sequence
<220> FEATURE:
<223> OTHER INFORMATION: synthetic peptide

<400> SEQUENCE: 782

Asp Ile Asn Lys Phe Trp Tyr Asp
1               5

<210> SEQ ID NO 783
<211> LENGTH: 8
<212> TYPE: PRT
<213> ORGANISM: artificial sequence
<220> FEATURE:
<223> OTHER INFORMATION: synthetic peptide

<400> SEQUENCE: 783

Asp His Asn Lys Phe Trp Tyr Asp
1               5

<210> SEQ ID NO 784
<211> LENGTH: 8
<212> TYPE: PRT
<213> ORGANISM: artificial sequence
<220> FEATURE:
<223> OTHER INFORMATION: synthetic peptide

<400> SEQUENCE: 784

Asp Leu Asn Lys Phe Trp Tyr Asp
1               5

<210> SEQ ID NO 785
<211> LENGTH: 8
<212> TYPE: PRT
<213> ORGANISM: artificial sequence
<220> FEATURE:
<223> OTHER INFORMATION: synthetic peptide

<400> SEQUENCE: 785

Asp Arg Asn Lys Phe Trp Tyr Asp
1               5

<210> SEQ ID NO 786
<211> LENGTH: 8
<212> TYPE: PRT
<213> ORGANISM: artificial sequence
<220> FEATURE:
<223> OTHER INFORMATION: synthetic peptide

<400> SEQUENCE: 786

Asp Glu Asn Lys Phe Trp Tyr Asp
1               5

<210> SEQ ID NO 787
<211> LENGTH: 8
<212> TYPE: PRT
<213> ORGANISM: artificial sequence
<220> FEATURE:
<223> OTHER INFORMATION: synthetic peptide
```

```
<400> SEQUENCE: 787

Glu Ile Glu Lys Phe Trp Tyr Asp
1               5

<210> SEQ ID NO 788
<211> LENGTH: 8
<212> TYPE: PRT
<213> ORGANISM: artificial sequence
<220> FEATURE:
<223> OTHER INFORMATION: synthetic peptide

<400> SEQUENCE: 788

Glu His Glu Lys Phe Trp Tyr Asp
1               5

<210> SEQ ID NO 789
<211> LENGTH: 8
<212> TYPE: PRT
<213> ORGANISM: artificial sequence
<220> FEATURE:
<223> OTHER INFORMATION: synthetic peptide

<400> SEQUENCE: 789

Glu Leu Glu Lys Phe Trp Tyr Asp
1               5

<210> SEQ ID NO 790
<211> LENGTH: 8
<212> TYPE: PRT
<213> ORGANISM: artificial sequence
<220> FEATURE:
<223> OTHER INFORMATION: synthetic peptide

<400> SEQUENCE: 790

Glu Arg Glu Lys Phe Trp Tyr Asp
1               5

<210> SEQ ID NO 791
<211> LENGTH: 8
<212> TYPE: PRT
<213> ORGANISM: artificial sequence
<220> FEATURE:
<223> OTHER INFORMATION: synthetic peptide

<400> SEQUENCE: 791

Glu Glu Glu Lys Phe Trp Tyr Asp
1               5

<210> SEQ ID NO 792
<211> LENGTH: 8
<212> TYPE: PRT
<213> ORGANISM: artificial sequence
<220> FEATURE:
<223> OTHER INFORMATION: synthetic peptide

<400> SEQUENCE: 792

Asp Ile Glu Lys Phe Trp Tyr Asp
1               5

<210> SEQ ID NO 793
<211> LENGTH: 8
<212> TYPE: PRT
<213> ORGANISM: artificial sequence
<220> FEATURE:
<223> OTHER INFORMATION: synthetic peptide

<400> SEQUENCE: 793
```

Asp His Glu Lys Phe Trp Tyr Asp
1               5

<210> SEQ ID NO 794
<211> LENGTH: 8
<212> TYPE: PRT
<213> ORGANISM: artificial sequence
<220> FEATURE:
<223> OTHER INFORMATION: synthetic peptide

<400> SEQUENCE: 794

Asp Leu Glu Lys Phe Trp Tyr Asp
1               5

<210> SEQ ID NO 795
<211> LENGTH: 8
<212> TYPE: PRT
<213> ORGANISM: artificial sequence
<220> FEATURE:
<223> OTHER INFORMATION: synthetic peptide

<400> SEQUENCE: 795

Asp Arg Glu Lys Phe Trp Tyr Asp
1               5

<210> SEQ ID NO 796
<211> LENGTH: 8
<212> TYPE: PRT
<213> ORGANISM: artificial sequence
<220> FEATURE:
<223> OTHER INFORMATION: synthetic peptide

<400> SEQUENCE: 796

Asp Glu Glu Lys Phe Trp Tyr Asp
1               5

<210> SEQ ID NO 797
<211> LENGTH: 8
<212> TYPE: PRT
<213> ORGANISM: artificial sequence
<220> FEATURE:
<223> OTHER INFORMATION: synthetic peptide

<400> SEQUENCE: 797

Glu Ile Tyr Lys Phe Trp Tyr Asp
1               5

<210> SEQ ID NO 798
<211> LENGTH: 8
<212> TYPE: PRT
<213> ORGANISM: artificial sequence
<220> FEATURE:
<223> OTHER INFORMATION: synthetic peptide

<400> SEQUENCE: 798

Glu His Tyr Lys Phe Trp Tyr Asp
1               5

<210> SEQ ID NO 799
<211> LENGTH: 8
<212> TYPE: PRT
<213> ORGANISM: artificial sequence
<220> FEATURE:
<223> OTHER INFORMATION: synthetic peptide

<400> SEQUENCE: 799

Glu Leu Tyr Lys Phe Trp Tyr Asp

```
<210> SEQ ID NO 800
<211> LENGTH: 8
<212> TYPE: PRT
<213> ORGANISM: artificial sequence
<220> FEATURE:
<223> OTHER INFORMATION: synthetic peptide

<400> SEQUENCE: 800

Glu Arg Tyr Lys Phe Trp Tyr Asp
1               5

<210> SEQ ID NO 801
<211> LENGTH: 8
<212> TYPE: PRT
<213> ORGANISM: artificial sequence
<220> FEATURE:
<223> OTHER INFORMATION: synthetic peptide

<400> SEQUENCE: 801

Glu Glu Tyr Lys Phe Trp Tyr Asp
1               5

<210> SEQ ID NO 802
<211> LENGTH: 8
<212> TYPE: PRT
<213> ORGANISM: artificial sequence
<220> FEATURE:
<223> OTHER INFORMATION: synthetic peptide

<400> SEQUENCE: 802

Asp Ile Tyr Lys Phe Trp Tyr Asp
1               5

<210> SEQ ID NO 803
<211> LENGTH: 8
<212> TYPE: PRT
<213> ORGANISM: artificial sequence
<220> FEATURE:
<223> OTHER INFORMATION: synthetic peptide

<400> SEQUENCE: 803

Asp His Tyr Lys Phe Trp Tyr Asp
1               5

<210> SEQ ID NO 804
<211> LENGTH: 8
<212> TYPE: PRT
<213> ORGANISM: artificial sequence
<220> FEATURE:
<223> OTHER INFORMATION: synthetic peptide

<400> SEQUENCE: 804

Asp Leu Tyr Lys Phe Trp Tyr Asp
1               5

<210> SEQ ID NO 805
<211> LENGTH: 8
<212> TYPE: PRT
<213> ORGANISM: artificial sequence
<220> FEATURE:
<223> OTHER INFORMATION: synthetic peptide

<400> SEQUENCE: 805

Asp Arg Tyr Lys Phe Trp Tyr Asp
1               5
```

```
<210> SEQ ID NO 806
<211> LENGTH: 8
<212> TYPE: PRT
<213> ORGANISM: artificial sequence
<220> FEATURE:
<223> OTHER INFORMATION: synthetic peptide

<400> SEQUENCE: 806

Asp Glu Tyr Lys Phe Trp Tyr Asp
1               5

<210> SEQ ID NO 807
<211> LENGTH: 8
<212> TYPE: PRT
<213> ORGANISM: artificial sequence
<220> FEATURE:
<223> OTHER INFORMATION: synthetic peptide

<400> SEQUENCE: 807

Glu Ile Asp Lys Ala Trp Tyr Asp
1               5

<210> SEQ ID NO 808
<211> LENGTH: 8
<212> TYPE: PRT
<213> ORGANISM: artificial sequence
<220> FEATURE:
<223> OTHER INFORMATION: synthetic peptide

<400> SEQUENCE: 808

Asp Ile Asp Lys Ala Trp Tyr Asp
1               5

<210> SEQ ID NO 809
<211> LENGTH: 8
<212> TYPE: PRT
<213> ORGANISM: artificial sequence
<220> FEATURE:
<223> OTHER INFORMATION: synthetic peptide

<400> SEQUENCE: 809

Glu His Asp Lys Ala Trp Tyr Asp
1               5

<210> SEQ ID NO 810
<211> LENGTH: 8
<212> TYPE: PRT
<213> ORGANISM: artificial sequence
<220> FEATURE:
<223> OTHER INFORMATION: synthetic peptide

<400> SEQUENCE: 810

Asp His Asp Lys Ala Trp Tyr Asp
1               5

<210> SEQ ID NO 811
<211> LENGTH: 8
<212> TYPE: PRT
<213> ORGANISM: artificial sequence
<220> FEATURE:
<223> OTHER INFORMATION: synthetic peptide

<400> SEQUENCE: 811

Glu Leu Asp Lys Ala Trp Tyr Asp
1               5

<210> SEQ ID NO 812
```

```
<211> LENGTH: 8
<212> TYPE: PRT
<213> ORGANISM: artificial sequence
<220> FEATURE:
<223> OTHER INFORMATION: synthetic peptide

<400> SEQUENCE: 812

Asp Leu Asp Lys Ala Trp Tyr Asp
1               5

<210> SEQ ID NO 813
<211> LENGTH: 8
<212> TYPE: PRT
<213> ORGANISM: artificial sequence
<220> FEATURE:
<223> OTHER INFORMATION: synthetic peptide

<400> SEQUENCE: 813

Glu Arg Asp Lys Ala Trp Tyr Asp
1               5

<210> SEQ ID NO 814
<211> LENGTH: 8
<212> TYPE: PRT
<213> ORGANISM: artificial sequence
<220> FEATURE:
<223> OTHER INFORMATION: synthetic peptide

<400> SEQUENCE: 814

Asp Arg Asp Lys Ala Trp Tyr Asp
1               5

<210> SEQ ID NO 815
<211> LENGTH: 8
<212> TYPE: PRT
<213> ORGANISM: artificial sequence
<220> FEATURE:
<223> OTHER INFORMATION: synthetic peptide

<400> SEQUENCE: 815

Glu Glu Asp Lys Ala Trp Tyr Asp
1               5

<210> SEQ ID NO 816
<211> LENGTH: 8
<212> TYPE: PRT
<213> ORGANISM: artificial sequence
<220> FEATURE:
<223> OTHER INFORMATION: synthetic peptide

<400> SEQUENCE: 816

Asp Glu Asp Lys Ala Trp Tyr Asp
1               5

<210> SEQ ID NO 817
<211> LENGTH: 8
<212> TYPE: PRT
<213> ORGANISM: artificial sequence
<220> FEATURE:
<223> OTHER INFORMATION: synthetic peptide

<400> SEQUENCE: 817

Glu Ile Asn Lys Ala Trp Tyr Asp
1               5

<210> SEQ ID NO 818
<211> LENGTH: 8
<212> TYPE: PRT
```

<213> ORGANISM: artificial sequence
<220> FEATURE:
<223> OTHER INFORMATION: synthetic peptide

<400> SEQUENCE: 818

Glu His Asn Lys Ala Trp Tyr Asp
1               5

<210> SEQ ID NO 819
<211> LENGTH: 8
<212> TYPE: PRT
<213> ORGANISM: artificial sequence
<220> FEATURE:
<223> OTHER INFORMATION: synthetic peptide

<400> SEQUENCE: 819

Glu Leu Asn Lys Ala Trp Tyr Asp
1               5

<210> SEQ ID NO 820
<211> LENGTH: 8
<212> TYPE: PRT
<213> ORGANISM: artificial sequence
<220> FEATURE:
<223> OTHER INFORMATION: synthetic peptide

<400> SEQUENCE: 820

Glu Arg Asn Lys Ala Trp Tyr Asp
1               5

<210> SEQ ID NO 821
<211> LENGTH: 8
<212> TYPE: PRT
<213> ORGANISM: artificial sequence
<220> FEATURE:
<223> OTHER INFORMATION: synthetic peptide

<400> SEQUENCE: 821

Asp Ile Asn Lys Ala Trp Tyr Asp
1               5

<210> SEQ ID NO 822
<211> LENGTH: 8
<212> TYPE: PRT
<213> ORGANISM: artificial sequence
<220> FEATURE:
<223> OTHER INFORMATION: synthetic peptide

<400> SEQUENCE: 822

Asp His Asn Lys Ala Trp Tyr Asp
1               5

<210> SEQ ID NO 823
<211> LENGTH: 8
<212> TYPE: PRT
<213> ORGANISM: artificial sequence
<220> FEATURE:
<223> OTHER INFORMATION: synthetic peptide

<400> SEQUENCE: 823

Asp Leu Asn Lys Ala Trp Tyr Asp
1               5

<210> SEQ ID NO 824
<211> LENGTH: 8
<212> TYPE: PRT
<213> ORGANISM: artificial sequence
<220> FEATURE:

<223> OTHER INFORMATION: synthetic peptide

<400> SEQUENCE: 824

Asp Arg Asn Lys Ala Trp Tyr Asp
1               5

<210> SEQ ID NO 825
<211> LENGTH: 8
<212> TYPE: PRT
<213> ORGANISM: artificial sequence
<220> FEATURE:
<223> OTHER INFORMATION: synthetic peptide

<400> SEQUENCE: 825

Asp Glu Asn Lys Ala Trp Tyr Asp
1               5

<210> SEQ ID NO 826
<211> LENGTH: 8
<212> TYPE: PRT
<213> ORGANISM: artificial sequence
<220> FEATURE:
<223> OTHER INFORMATION: synthetic peptide

<400> SEQUENCE: 826

Glu Ile Glu Lys Ala Trp Tyr Asp
1               5

<210> SEQ ID NO 827
<211> LENGTH: 8
<212> TYPE: PRT
<213> ORGANISM: artificial sequence
<220> FEATURE:
<223> OTHER INFORMATION: synthetic peptide

<400> SEQUENCE: 827

Glu His Glu Lys Ala Trp Tyr Asp
1               5

<210> SEQ ID NO 828
<211> LENGTH: 8
<212> TYPE: PRT
<213> ORGANISM: artificial sequence
<220> FEATURE:
<223> OTHER INFORMATION: synthetic peptide

<400> SEQUENCE: 828

Glu Leu Glu Lys Ala Trp Tyr Asp
1               5

<210> SEQ ID NO 829
<211> LENGTH: 8
<212> TYPE: PRT
<213> ORGANISM: artificial sequence
<220> FEATURE:
<223> OTHER INFORMATION: synthetic peptide

<400> SEQUENCE: 829

Glu Arg Glu Lys Ala Trp Tyr Asp
1               5

<210> SEQ ID NO 830
<211> LENGTH: 8
<212> TYPE: PRT
<213> ORGANISM: artificial sequence
<220> FEATURE:
<223> OTHER INFORMATION: synthetic peptide

```
<400> SEQUENCE: 830

Glu Glu Glu Lys Ala Trp Tyr Asp
1               5

<210> SEQ ID NO 831
<211> LENGTH: 8
<212> TYPE: PRT
<213> ORGANISM: artificial sequence
<220> FEATURE:
<223> OTHER INFORMATION: synthetic peptide

<400> SEQUENCE: 831

Asp Ile Glu Lys Ala Trp Tyr Asp
1               5

<210> SEQ ID NO 832
<211> LENGTH: 8
<212> TYPE: PRT
<213> ORGANISM: artificial sequence
<220> FEATURE:
<223> OTHER INFORMATION: synthetic peptide

<400> SEQUENCE: 832

Asp His Glu Lys Ala Trp Tyr Asp
1               5

<210> SEQ ID NO 833
<211> LENGTH: 8
<212> TYPE: PRT
<213> ORGANISM: artificial sequence
<220> FEATURE:
<223> OTHER INFORMATION: synthetic peptide

<400> SEQUENCE: 833

Asp Leu Glu Lys Ala Trp Tyr Asp
1               5

<210> SEQ ID NO 834
<211> LENGTH: 8
<212> TYPE: PRT
<213> ORGANISM: artificial sequence
<220> FEATURE:
<223> OTHER INFORMATION: synthetic peptide

<400> SEQUENCE: 834

Asp Arg Glu Lys Ala Trp Tyr Asp
1               5

<210> SEQ ID NO 835
<211> LENGTH: 8
<212> TYPE: PRT
<213> ORGANISM: artificial sequence
<220> FEATURE:
<223> OTHER INFORMATION: synthetic peptide

<400> SEQUENCE: 835

Asp Glu Glu Lys Ala Trp Tyr Asp
1               5

<210> SEQ ID NO 836
<211> LENGTH: 8
<212> TYPE: PRT
<213> ORGANISM: artificial sequence
<220> FEATURE:
<223> OTHER INFORMATION: synthetic peptide

<400> SEQUENCE: 836
```

```
Glu Ile Tyr Lys Ala Trp Tyr Asp
1               5

<210> SEQ ID NO 837
<211> LENGTH: 8
<212> TYPE: PRT
<213> ORGANISM: artificial sequence
<220> FEATURE:
<223> OTHER INFORMATION: synthetic peptide

<400> SEQUENCE: 837

Glu His Tyr Lys Ala Trp Tyr Asp
1               5

<210> SEQ ID NO 838
<211> LENGTH: 8
<212> TYPE: PRT
<213> ORGANISM: artificial sequence
<220> FEATURE:
<223> OTHER INFORMATION: synthetic peptide

<400> SEQUENCE: 838

Glu Leu Tyr Lys Ala Trp Tyr Asp
1               5

<210> SEQ ID NO 839
<211> LENGTH: 8
<212> TYPE: PRT
<213> ORGANISM: artificial sequence
<220> FEATURE:
<223> OTHER INFORMATION: synthetic peptide

<400> SEQUENCE: 839

Glu Arg Tyr Lys Ala Trp Tyr Asp
1               5

<210> SEQ ID NO 840
<211> LENGTH: 8
<212> TYPE: PRT
<213> ORGANISM: artificial sequence
<220> FEATURE:
<223> OTHER INFORMATION: synthetic peptide

<400> SEQUENCE: 840

Glu Glu Tyr Lys Ala Trp Tyr Asp
1               5

<210> SEQ ID NO 841
<211> LENGTH: 8
<212> TYPE: PRT
<213> ORGANISM: artificial sequence
<220> FEATURE:
<223> OTHER INFORMATION: synthetic peptide

<400> SEQUENCE: 841

Asp Ile Tyr Lys Ala Trp Tyr Asp
1               5

<210> SEQ ID NO 842
<211> LENGTH: 8
<212> TYPE: PRT
<213> ORGANISM: artificial sequence
<220> FEATURE:
<223> OTHER INFORMATION: synthetic peptide

<400> SEQUENCE: 842

Asp His Tyr Lys Ala Trp Tyr Asp
1               5
```

```
<210> SEQ ID NO 843
<211> LENGTH: 8
<212> TYPE: PRT
<213> ORGANISM: artificial sequence
<220> FEATURE:
<223> OTHER INFORMATION: synthetic peptide

<400> SEQUENCE: 843

Asp Leu Tyr Lys Ala Trp Tyr Asp
1               5

<210> SEQ ID NO 844
<211> LENGTH: 8
<212> TYPE: PRT
<213> ORGANISM: artificial sequence
<220> FEATURE:
<223> OTHER INFORMATION: synthetic peptide

<400> SEQUENCE: 844

Asp Arg Tyr Lys Ala Trp Tyr Asp
1               5

<210> SEQ ID NO 845
<211> LENGTH: 8
<212> TYPE: PRT
<213> ORGANISM: artificial sequence
<220> FEATURE:
<223> OTHER INFORMATION: synthetic peptide

<400> SEQUENCE: 845

Asp Glu Tyr Lys Ala Trp Tyr Asp
1               5

<210> SEQ ID NO 846
<211> LENGTH: 8
<212> TYPE: PRT
<213> ORGANISM: artificial sequence
<220> FEATURE:
<223> OTHER INFORMATION: synthetic peptide

<400> SEQUENCE: 846

Glu Ile Asp Lys Ser Trp Tyr Asp
1               5

<210> SEQ ID NO 847
<211> LENGTH: 8
<212> TYPE: PRT
<213> ORGANISM: artificial sequence
<220> FEATURE:
<223> OTHER INFORMATION: synthetic peptide

<400> SEQUENCE: 847

Asp Ile Asp Lys Ser Trp Tyr Asp
1               5

<210> SEQ ID NO 848
<211> LENGTH: 8
<212> TYPE: PRT
<213> ORGANISM: artificial sequence
<220> FEATURE:
<223> OTHER INFORMATION: synthetic peptide

<400> SEQUENCE: 848

Glu His Asp Lys Ser Trp Tyr Asp
1               5
```

```
<210> SEQ ID NO 849
<211> LENGTH: 8
<212> TYPE: PRT
<213> ORGANISM: artificial sequence
<220> FEATURE:
<223> OTHER INFORMATION: synthetic peptide

<400> SEQUENCE: 849

Asp His Asp Lys Ser Trp Tyr Asp
1               5

<210> SEQ ID NO 850
<211> LENGTH: 8
<212> TYPE: PRT
<213> ORGANISM: artificial sequence
<220> FEATURE:
<223> OTHER INFORMATION: synthetic peptide

<400> SEQUENCE: 850

Glu Leu Asp Lys Ser Trp Tyr Asp
1               5

<210> SEQ ID NO 851
<211> LENGTH: 8
<212> TYPE: PRT
<213> ORGANISM: artificial sequence
<220> FEATURE:
<223> OTHER INFORMATION: synthetic peptide

<400> SEQUENCE: 851

Asp Leu Asp Lys Ser Trp Tyr Asp
1               5

<210> SEQ ID NO 852
<211> LENGTH: 8
<212> TYPE: PRT
<213> ORGANISM: artificial sequence
<220> FEATURE:
<223> OTHER INFORMATION: synthetic peptide

<400> SEQUENCE: 852

Glu Arg Asp Lys Ser Trp Tyr Asp
1               5

<210> SEQ ID NO 853
<211> LENGTH: 8
<212> TYPE: PRT
<213> ORGANISM: artificial sequence
<220> FEATURE:
<223> OTHER INFORMATION: synthetic peptide

<400> SEQUENCE: 853

Asp Arg Asp Lys Ser Trp Tyr Asp
1               5

<210> SEQ ID NO 854
<211> LENGTH: 8
<212> TYPE: PRT
<213> ORGANISM: artificial sequence
<220> FEATURE:
<223> OTHER INFORMATION: synthetic peptide

<400> SEQUENCE: 854

Glu Glu Asp Lys Ser Trp Tyr Asp
1               5

<210> SEQ ID NO 855
<211> LENGTH: 8
```

```
<212> TYPE: PRT
<213> ORGANISM: artificial sequence
<220> FEATURE:
<223> OTHER INFORMATION: synthetic peptide

<400> SEQUENCE: 855

Asp Glu Asp Lys Ser Trp Tyr Asp
1               5

<210> SEQ ID NO 856
<211> LENGTH: 8
<212> TYPE: PRT
<213> ORGANISM: artificial sequence
<220> FEATURE:
<223> OTHER INFORMATION: synthetic peptide

<400> SEQUENCE: 856

Glu Ile Asn Lys Ser Trp Tyr Asp
1               5

<210> SEQ ID NO 857
<211> LENGTH: 8
<212> TYPE: PRT
<213> ORGANISM: artificial sequence
<220> FEATURE:
<223> OTHER INFORMATION: synthetic peptide

<400> SEQUENCE: 857

Glu His Asn Lys Ser Trp Tyr Asp
1               5

<210> SEQ ID NO 858
<211> LENGTH: 8
<212> TYPE: PRT
<213> ORGANISM: artificial sequence
<220> FEATURE:
<223> OTHER INFORMATION: synthetic peptide

<400> SEQUENCE: 858

Glu Leu Asn Lys Ser Trp Tyr Asp
1               5

<210> SEQ ID NO 859
<211> LENGTH: 8
<212> TYPE: PRT
<213> ORGANISM: artificial sequence
<220> FEATURE:
<223> OTHER INFORMATION: synthetic peptide

<400> SEQUENCE: 859

Glu Arg Asn Lys Ser Trp Tyr Asp
1               5

<210> SEQ ID NO 860
<211> LENGTH: 8
<212> TYPE: PRT
<213> ORGANISM: artificial sequence
<220> FEATURE:
<223> OTHER INFORMATION: synthetic peptide

<400> SEQUENCE: 860

Asp Ile Asn Lys Ser Trp Tyr Asp
1               5

<210> SEQ ID NO 861
<211> LENGTH: 8
<212> TYPE: PRT
<213> ORGANISM: artificial sequence
```

<220> FEATURE:
<223> OTHER INFORMATION: synthetic peptide

<400> SEQUENCE: 861

Asp His Asn Lys Ser Trp Tyr Asp
1               5

<210> SEQ ID NO 862
<211> LENGTH: 8
<212> TYPE: PRT
<213> ORGANISM: artificial sequence
<220> FEATURE:
<223> OTHER INFORMATION: synthetic peptide

<400> SEQUENCE: 862

Asp Leu Asn Lys Ser Trp Tyr Asp
1               5

<210> SEQ ID NO 863
<211> LENGTH: 8
<212> TYPE: PRT
<213> ORGANISM: artificial sequence
<220> FEATURE:
<223> OTHER INFORMATION: synthetic peptide

<400> SEQUENCE: 863

Asp Arg Asn Lys Ser Trp Tyr Asp
1               5

<210> SEQ ID NO 864
<211> LENGTH: 8
<212> TYPE: PRT
<213> ORGANISM: artificial sequence
<220> FEATURE:
<223> OTHER INFORMATION: synthetic peptide

<400> SEQUENCE: 864

Asp Glu Asn Lys Ser Trp Tyr Asp
1               5

<210> SEQ ID NO 865
<211> LENGTH: 8
<212> TYPE: PRT
<213> ORGANISM: artificial sequence
<220> FEATURE:
<223> OTHER INFORMATION: synthetic peptide

<400> SEQUENCE: 865

Glu Ile Glu Lys Ser Trp Tyr Asp
1               5

<210> SEQ ID NO 866
<211> LENGTH: 8
<212> TYPE: PRT
<213> ORGANISM: artificial sequence
<220> FEATURE:
<223> OTHER INFORMATION: synthetic peptide

<400> SEQUENCE: 866

Glu His Glu Lys Ser Trp Tyr Asp
1               5

<210> SEQ ID NO 867
<211> LENGTH: 8
<212> TYPE: PRT
<213> ORGANISM: artificial sequence
<220> FEATURE:
<223> OTHER INFORMATION: synthetic peptide

```
<400> SEQUENCE: 867

Glu Leu Glu Lys Ser Trp Tyr Asp
1               5

<210> SEQ ID NO 868
<211> LENGTH: 8
<212> TYPE: PRT
<213> ORGANISM: artificial sequence
<220> FEATURE:
<223> OTHER INFORMATION: synthetic peptide

<400> SEQUENCE: 868

Glu Arg Glu Lys Ser Trp Tyr Asp
1               5

<210> SEQ ID NO 869
<211> LENGTH: 8
<212> TYPE: PRT
<213> ORGANISM: artificial sequence
<220> FEATURE:
<223> OTHER INFORMATION: synthetic peptide

<400> SEQUENCE: 869

Glu Glu Glu Lys Ser Trp Tyr Asp
1               5

<210> SEQ ID NO 870
<211> LENGTH: 8
<212> TYPE: PRT
<213> ORGANISM: artificial sequence
<220> FEATURE:
<223> OTHER INFORMATION: synthetic peptide

<400> SEQUENCE: 870

Asp Ile Glu Lys Ser Trp Tyr Asp
1               5

<210> SEQ ID NO 871
<211> LENGTH: 8
<212> TYPE: PRT
<213> ORGANISM: artificial sequence
<220> FEATURE:
<223> OTHER INFORMATION: synthetic peptide

<400> SEQUENCE: 871

Asp His Glu Lys Ser Trp Tyr Asp
1               5

<210> SEQ ID NO 872
<211> LENGTH: 8
<212> TYPE: PRT
<213> ORGANISM: artificial sequence
<220> FEATURE:
<223> OTHER INFORMATION: synthetic peptide

<400> SEQUENCE: 872

Asp Leu Glu Lys Ser Trp Tyr Asp
1               5

<210> SEQ ID NO 873
<211> LENGTH: 8
<212> TYPE: PRT
<213> ORGANISM: artificial sequence
<220> FEATURE:
<223> OTHER INFORMATION: synthetic peptide

<400> SEQUENCE: 873
```

```
Asp Arg Glu Lys Ser Trp Tyr Asp
1               5

<210> SEQ ID NO 874
<211> LENGTH: 8
<212> TYPE: PRT
<213> ORGANISM: artificial sequence
<220> FEATURE:
<223> OTHER INFORMATION: synthetic peptide

<400> SEQUENCE: 874

Asp Glu Glu Lys Ser Trp Tyr Asp
1               5

<210> SEQ ID NO 875
<211> LENGTH: 8
<212> TYPE: PRT
<213> ORGANISM: artificial sequence
<220> FEATURE:
<223> OTHER INFORMATION: synthetic peptide

<400> SEQUENCE: 875

Glu Ile Tyr Lys Ser Trp Tyr Asp
1               5

<210> SEQ ID NO 876
<211> LENGTH: 8
<212> TYPE: PRT
<213> ORGANISM: artificial sequence
<220> FEATURE:
<223> OTHER INFORMATION: synthetic peptide

<400> SEQUENCE: 876

Glu His Tyr Lys Ser Trp Tyr Asp
1               5

<210> SEQ ID NO 877
<211> LENGTH: 8
<212> TYPE: PRT
<213> ORGANISM: artificial sequence
<220> FEATURE:
<223> OTHER INFORMATION: synthetic peptide

<400> SEQUENCE: 877

Glu Leu Tyr Lys Ser Trp Tyr Asp
1               5

<210> SEQ ID NO 878
<211> LENGTH: 8
<212> TYPE: PRT
<213> ORGANISM: artificial sequence
<220> FEATURE:
<223> OTHER INFORMATION: synthetic peptide

<400> SEQUENCE: 878

Glu Arg Tyr Lys Ser Trp Tyr Asp
1               5

<210> SEQ ID NO 879
<211> LENGTH: 8
<212> TYPE: PRT
<213> ORGANISM: artificial sequence
<220> FEATURE:
<223> OTHER INFORMATION: synthetic peptide

<400> SEQUENCE: 879

Glu Glu Tyr Lys Ser Trp Tyr Asp
```

```
<210> SEQ ID NO 880
<211> LENGTH: 8
<212> TYPE: PRT
<213> ORGANISM: artificial sequence
<220> FEATURE:
<223> OTHER INFORMATION: synthetic peptide

<400> SEQUENCE: 880

Asp Ile Tyr Lys Ser Trp Tyr Asp
1               5

<210> SEQ ID NO 881
<211> LENGTH: 8
<212> TYPE: PRT
<213> ORGANISM: artificial sequence
<220> FEATURE:
<223> OTHER INFORMATION: synthetic peptide

<400> SEQUENCE: 881

Asp His Tyr Lys Ser Trp Tyr Asp
1               5

<210> SEQ ID NO 882
<211> LENGTH: 8
<212> TYPE: PRT
<213> ORGANISM: artificial sequence
<220> FEATURE:
<223> OTHER INFORMATION: synthetic peptide

<400> SEQUENCE: 882

Asp Leu Tyr Lys Ser Trp Tyr Asp
1               5

<210> SEQ ID NO 883
<211> LENGTH: 8
<212> TYPE: PRT
<213> ORGANISM: artificial sequence
<220> FEATURE:
<223> OTHER INFORMATION: synthetic peptide

<400> SEQUENCE: 883

Asp Arg Tyr Lys Ser Trp Tyr Asp
1               5

<210> SEQ ID NO 884
<211> LENGTH: 8
<212> TYPE: PRT
<213> ORGANISM: artificial sequence
<220> FEATURE:
<223> OTHER INFORMATION: synthetic peptide

<400> SEQUENCE: 884

Asp Glu Tyr Lys Ser Trp Tyr Asp
1               5

<210> SEQ ID NO 885
<211> LENGTH: 8
<212> TYPE: PRT
<213> ORGANISM: artificial sequence
<220> FEATURE:
<223> OTHER INFORMATION: synthetic peptide

<400> SEQUENCE: 885

Glu Ile Asp Lys Ser Phe Tyr Asp
1               5
```

```
<210> SEQ ID NO 886
<211> LENGTH: 8
<212> TYPE: PRT
<213> ORGANISM: artificial sequence
<220> FEATURE:
<223> OTHER INFORMATION: synthetic peptide

<400> SEQUENCE: 886

Asp Ile Asp Lys Ser Phe Tyr Asp
1               5

<210> SEQ ID NO 887
<211> LENGTH: 8
<212> TYPE: PRT
<213> ORGANISM: artificial sequence
<220> FEATURE:
<223> OTHER INFORMATION: synthetic peptide

<400> SEQUENCE: 887

Glu His Asp Lys Ser Phe Tyr Asp
1               5

<210> SEQ ID NO 888
<211> LENGTH: 8
<212> TYPE: PRT
<213> ORGANISM: artificial sequence
<220> FEATURE:
<223> OTHER INFORMATION: synthetic peptide

<400> SEQUENCE: 888

Asp His Asp Lys Ser Phe Tyr Asp
1               5

<210> SEQ ID NO 889
<211> LENGTH: 8
<212> TYPE: PRT
<213> ORGANISM: artificial sequence
<220> FEATURE:
<223> OTHER INFORMATION: synthetic peptide

<400> SEQUENCE: 889

Glu Leu Asp Lys Ser Phe Tyr Asp
1               5

<210> SEQ ID NO 890
<211> LENGTH: 8
<212> TYPE: PRT
<213> ORGANISM: artificial sequence
<220> FEATURE:
<223> OTHER INFORMATION: synthetic peptide

<400> SEQUENCE: 890

Asp Leu Asp Lys Ser Phe Tyr Asp
1               5

<210> SEQ ID NO 891
<211> LENGTH: 8
<212> TYPE: PRT
<213> ORGANISM: artificial sequence
<220> FEATURE:
<223> OTHER INFORMATION: synthetic peptide

<400> SEQUENCE: 891

Glu Arg Asp Lys Ser Phe Tyr Asp
1               5

<210> SEQ ID NO 892
```

```
<211> LENGTH: 8
<212> TYPE: PRT
<213> ORGANISM: artificial sequence
<220> FEATURE:
<223> OTHER INFORMATION: synthetic peptide

<400> SEQUENCE: 892

Asp Arg Asp Lys Ser Phe Tyr Asp
1               5

<210> SEQ ID NO 893
<211> LENGTH: 8
<212> TYPE: PRT
<213> ORGANISM: artificial sequence
<220> FEATURE:
<223> OTHER INFORMATION: synthetic peptide

<400> SEQUENCE: 893

Glu Glu Asp Lys Ser Phe Tyr Asp
1               5

<210> SEQ ID NO 894
<211> LENGTH: 8
<212> TYPE: PRT
<213> ORGANISM: artificial sequence
<220> FEATURE:
<223> OTHER INFORMATION: synthetic peptide

<400> SEQUENCE: 894

Asp Glu Asp Lys Ser Phe Tyr Asp
1               5

<210> SEQ ID NO 895
<211> LENGTH: 8
<212> TYPE: PRT
<213> ORGANISM: artificial sequence
<220> FEATURE:
<223> OTHER INFORMATION: synthetic peptide

<400> SEQUENCE: 895

Glu Ile Asn Lys Ser Phe Tyr Asp
1               5

<210> SEQ ID NO 896
<211> LENGTH: 8
<212> TYPE: PRT
<213> ORGANISM: artificial sequence
<220> FEATURE:
<223> OTHER INFORMATION: synthetic peptide

<400> SEQUENCE: 896

Glu His Asn Lys Ser Phe Tyr Asp
1               5

<210> SEQ ID NO 897
<211> LENGTH: 8
<212> TYPE: PRT
<213> ORGANISM: artificial sequence
<220> FEATURE:
<223> OTHER INFORMATION: synthetic peptide

<400> SEQUENCE: 897

Glu Leu Asn Lys Ser Phe Tyr Asp
1               5

<210> SEQ ID NO 898
<211> LENGTH: 8
<212> TYPE: PRT
```

<213> ORGANISM: artificial sequence
<220> FEATURE:
<223> OTHER INFORMATION: synthetic peptide

<400> SEQUENCE: 898

Glu Arg Asn Lys Ser Phe Tyr Asp
1               5

<210> SEQ ID NO 899
<211> LENGTH: 8
<212> TYPE: PRT
<213> ORGANISM: artificial sequence
<220> FEATURE:
<223> OTHER INFORMATION: synthetic peptide

<400> SEQUENCE: 899

Asp Ile Asn Lys Ser Phe Tyr Asp
1               5

<210> SEQ ID NO 900
<211> LENGTH: 8
<212> TYPE: PRT
<213> ORGANISM: artificial sequence
<220> FEATURE:
<223> OTHER INFORMATION: synthetic peptide

<400> SEQUENCE: 900

Asp His Asn Lys Ser Phe Tyr Asp
1               5

<210> SEQ ID NO 901
<211> LENGTH: 8
<212> TYPE: PRT
<213> ORGANISM: artificial sequence
<220> FEATURE:
<223> OTHER INFORMATION: synthetic peptide

<400> SEQUENCE: 901

Asp Leu Asn Lys Ser Phe Tyr Asp
1               5

<210> SEQ ID NO 902
<211> LENGTH: 8
<212> TYPE: PRT
<213> ORGANISM: artificial sequence
<220> FEATURE:
<223> OTHER INFORMATION: synthetic peptide

<400> SEQUENCE: 902

Asp Arg Asn Lys Ser Phe Tyr Asp
1               5

<210> SEQ ID NO 903
<211> LENGTH: 8
<212> TYPE: PRT
<213> ORGANISM: artificial sequence
<220> FEATURE:
<223> OTHER INFORMATION: synthetic peptide

<400> SEQUENCE: 903

Asp Glu Asn Lys Ser Phe Tyr Asp
1               5

<210> SEQ ID NO 904
<211> LENGTH: 8
<212> TYPE: PRT
<213> ORGANISM: artificial sequence
<220> FEATURE:

```
<223> OTHER INFORMATION: synthetic peptide

<400> SEQUENCE: 904

Glu Ile Glu Lys Ser Phe Tyr Asp
1               5

<210> SEQ ID NO 905
<211> LENGTH: 8
<212> TYPE: PRT
<213> ORGANISM: artificial sequence
<220> FEATURE:
<223> OTHER INFORMATION: synthetic peptide

<400> SEQUENCE: 905

Glu His Glu Lys Ser Phe Tyr Asp
1               5

<210> SEQ ID NO 906
<211> LENGTH: 8
<212> TYPE: PRT
<213> ORGANISM: artificial sequence
<220> FEATURE:
<223> OTHER INFORMATION: synthetic peptide

<400> SEQUENCE: 906

Glu Leu Glu Lys Ser Phe Tyr Asp
1               5

<210> SEQ ID NO 907
<211> LENGTH: 8
<212> TYPE: PRT
<213> ORGANISM: artificial sequence
<220> FEATURE:
<223> OTHER INFORMATION: synthetic peptide

<400> SEQUENCE: 907

Glu Arg Glu Lys Ser Phe Tyr Asp
1               5

<210> SEQ ID NO 908
<211> LENGTH: 8
<212> TYPE: PRT
<213> ORGANISM: artificial sequence
<220> FEATURE:
<223> OTHER INFORMATION: synthetic peptide

<400> SEQUENCE: 908

Glu Glu Glu Lys Ser Phe Tyr Asp
1               5

<210> SEQ ID NO 909
<211> LENGTH: 8
<212> TYPE: PRT
<213> ORGANISM: artificial sequence
<220> FEATURE:
<223> OTHER INFORMATION: synthetic peptide

<400> SEQUENCE: 909

Asp Ile Glu Lys Ser Phe Tyr Asp
1               5

<210> SEQ ID NO 910
<211> LENGTH: 8
<212> TYPE: PRT
<213> ORGANISM: artificial sequence
<220> FEATURE:
<223> OTHER INFORMATION: synthetic peptide
```

<400> SEQUENCE: 910

Asp His Glu Lys Ser Phe Tyr Asp
1               5

<210> SEQ ID NO 911
<211> LENGTH: 8
<212> TYPE: PRT
<213> ORGANISM: artificial sequence
<220> FEATURE:
<223> OTHER INFORMATION: synthetic peptide

<400> SEQUENCE: 911

Asp Leu Glu Lys Ser Phe Tyr Asp
1               5

<210> SEQ ID NO 912
<211> LENGTH: 8
<212> TYPE: PRT
<213> ORGANISM: artificial sequence
<220> FEATURE:
<223> OTHER INFORMATION: synthetic peptide

<400> SEQUENCE: 912

Asp Arg Glu Lys Ser Phe Tyr Asp
1               5

<210> SEQ ID NO 913
<211> LENGTH: 8
<212> TYPE: PRT
<213> ORGANISM: artificial sequence
<220> FEATURE:
<223> OTHER INFORMATION: synthetic peptide

<400> SEQUENCE: 913

Asp Glu Glu Lys Ser Phe Tyr Asp
1               5

<210> SEQ ID NO 914
<211> LENGTH: 8
<212> TYPE: PRT
<213> ORGANISM: artificial sequence
<220> FEATURE:
<223> OTHER INFORMATION: synthetic peptide

<400> SEQUENCE: 914

Glu Ile Tyr Lys Ser Phe Tyr Asp
1               5

<210> SEQ ID NO 915
<211> LENGTH: 8
<212> TYPE: PRT
<213> ORGANISM: artificial sequence
<220> FEATURE:
<223> OTHER INFORMATION: synthetic peptide

<400> SEQUENCE: 915

Glu His Tyr Lys Ser Phe Tyr Asp
1               5

<210> SEQ ID NO 916
<211> LENGTH: 8
<212> TYPE: PRT
<213> ORGANISM: artificial sequence
<220> FEATURE:
<223> OTHER INFORMATION: synthetic peptide

<400> SEQUENCE: 916

```
Glu Leu Tyr Lys Ser Phe Tyr Asp
1               5

<210> SEQ ID NO 917
<211> LENGTH: 8
<212> TYPE: PRT
<213> ORGANISM: artificial sequence
<220> FEATURE:
<223> OTHER INFORMATION: synthetic peptide

<400> SEQUENCE: 917

Glu Arg Tyr Lys Ser Phe Tyr Asp
1               5

<210> SEQ ID NO 918
<211> LENGTH: 8
<212> TYPE: PRT
<213> ORGANISM: artificial sequence
<220> FEATURE:
<223> OTHER INFORMATION: synthetic peptide

<400> SEQUENCE: 918

Glu Glu Tyr Lys Ser Phe Tyr Asp
1               5

<210> SEQ ID NO 919
<211> LENGTH: 8
<212> TYPE: PRT
<213> ORGANISM: artificial sequence
<220> FEATURE:
<223> OTHER INFORMATION: synthetic peptide

<400> SEQUENCE: 919

Asp Ile Tyr Lys Ser Phe Tyr Asp
1               5

<210> SEQ ID NO 920
<211> LENGTH: 8
<212> TYPE: PRT
<213> ORGANISM: artificial sequence
<220> FEATURE:
<223> OTHER INFORMATION: synthetic peptide

<400> SEQUENCE: 920

Asp His Tyr Lys Ser Phe Tyr Asp
1               5

<210> SEQ ID NO 921
<211> LENGTH: 8
<212> TYPE: PRT
<213> ORGANISM: artificial sequence
<220> FEATURE:
<223> OTHER INFORMATION: synthetic peptide

<400> SEQUENCE: 921

Asp Leu Tyr Lys Ser Phe Tyr Asp
1               5

<210> SEQ ID NO 922
<211> LENGTH: 8
<212> TYPE: PRT
<213> ORGANISM: artificial sequence
<220> FEATURE:
<223> OTHER INFORMATION: synthetic peptide

<400> SEQUENCE: 922

Asp Arg Tyr Lys Ser Phe Tyr Asp
1               5
```

<210> SEQ ID NO 923
<211> LENGTH: 8
<212> TYPE: PRT
<213> ORGANISM: artificial sequence
<220> FEATURE:
<223> OTHER INFORMATION: synthetic peptide

<400> SEQUENCE: 923

Asp Glu Tyr Lys Ser Phe Tyr Asp
1               5

<210> SEQ ID NO 924
<211> LENGTH: 8
<212> TYPE: PRT
<213> ORGANISM: artificial sequence
<220> FEATURE:
<223> OTHER INFORMATION: synthetic peptide

<400> SEQUENCE: 924

Glu Ile Asp Lys Ser Phe His Asp
1               5

<210> SEQ ID NO 925
<211> LENGTH: 8
<212> TYPE: PRT
<213> ORGANISM: artificial sequence
<220> FEATURE:
<223> OTHER INFORMATION: synthetic peptide

<400> SEQUENCE: 925

Asp Ile Asp Lys Ser Phe His Asp
1               5

<210> SEQ ID NO 926
<211> LENGTH: 8
<212> TYPE: PRT
<213> ORGANISM: artificial sequence
<220> FEATURE:
<223> OTHER INFORMATION: synthetic peptide

<400> SEQUENCE: 926

Glu His Asp Lys Ser Phe His Asp
1               5

<210> SEQ ID NO 927
<211> LENGTH: 8
<212> TYPE: PRT
<213> ORGANISM: artificial sequence
<220> FEATURE:
<223> OTHER INFORMATION: synthetic peptide

<400> SEQUENCE: 927

Asp His Asp Lys Ser Phe His Asp
1               5

<210> SEQ ID NO 928
<211> LENGTH: 8
<212> TYPE: PRT
<213> ORGANISM: artificial sequence
<220> FEATURE:
<223> OTHER INFORMATION: synthetic peptide

<400> SEQUENCE: 928

Glu Leu Asp Lys Ser Phe His Asp
1               5

```
<210> SEQ ID NO 929
<211> LENGTH: 8
<212> TYPE: PRT
<213> ORGANISM: artificial sequence
<220> FEATURE:
<223> OTHER INFORMATION: synthetic peptide

<400> SEQUENCE: 929

Asp Leu Asp Lys Ser Phe His Asp
1               5

<210> SEQ ID NO 930
<211> LENGTH: 8
<212> TYPE: PRT
<213> ORGANISM: artificial sequence
<220> FEATURE:
<223> OTHER INFORMATION: synthetic peptide

<400> SEQUENCE: 930

Glu Arg Asp Lys Ser Phe His Asp
1               5

<210> SEQ ID NO 931
<211> LENGTH: 8
<212> TYPE: PRT
<213> ORGANISM: artificial sequence
<220> FEATURE:
<223> OTHER INFORMATION: synthetic peptide

<400> SEQUENCE: 931

Asp Arg Asp Lys Ser Phe His Asp
1               5

<210> SEQ ID NO 932
<211> LENGTH: 8
<212> TYPE: PRT
<213> ORGANISM: artificial sequence
<220> FEATURE:
<223> OTHER INFORMATION: synthetic peptide

<400> SEQUENCE: 932

Glu Glu Asp Lys Ser Phe His Asp
1               5

<210> SEQ ID NO 933
<211> LENGTH: 8
<212> TYPE: PRT
<213> ORGANISM: artificial sequence
<220> FEATURE:
<223> OTHER INFORMATION: synthetic peptide

<400> SEQUENCE: 933

Asp Glu Asp Lys Ser Phe His Asp
1               5

<210> SEQ ID NO 934
<211> LENGTH: 8
<212> TYPE: PRT
<213> ORGANISM: artificial sequence
<220> FEATURE:
<223> OTHER INFORMATION: synthetic peptide

<400> SEQUENCE: 934

Glu Ile Asn Lys Ser Phe His Asp
1               5

<210> SEQ ID NO 935
<211> LENGTH: 8
```

```
<212> TYPE: PRT
<213> ORGANISM: artificial sequence
<220> FEATURE:
<223> OTHER INFORMATION: synthetic peptide

<400> SEQUENCE: 935

Glu His Asn Lys Ser Phe His Asp
1               5

<210> SEQ ID NO 936
<211> LENGTH: 8
<212> TYPE: PRT
<213> ORGANISM: artificial sequence
<220> FEATURE:
<223> OTHER INFORMATION: synthetic peptide

<400> SEQUENCE: 936

Glu Leu Asn Lys Ser Phe His Asp
1               5

<210> SEQ ID NO 937
<211> LENGTH: 8
<212> TYPE: PRT
<213> ORGANISM: artificial sequence
<220> FEATURE:
<223> OTHER INFORMATION: synthetic peptide

<400> SEQUENCE: 937

Glu Arg Asn Lys Ser Phe His Asp
1               5

<210> SEQ ID NO 938
<211> LENGTH: 8
<212> TYPE: PRT
<213> ORGANISM: artificial sequence
<220> FEATURE:
<223> OTHER INFORMATION: synthetic peptide

<400> SEQUENCE: 938

Asp Ile Asn Lys Ser Phe His Asp
1               5

<210> SEQ ID NO 939
<211> LENGTH: 8
<212> TYPE: PRT
<213> ORGANISM: artificial sequence
<220> FEATURE:
<223> OTHER INFORMATION: synthetic peptide

<400> SEQUENCE: 939

Asp His Asn Lys Ser Phe His Asp
1               5

<210> SEQ ID NO 940
<211> LENGTH: 8
<212> TYPE: PRT
<213> ORGANISM: artificial sequence
<220> FEATURE:
<223> OTHER INFORMATION: synthetic peptide

<400> SEQUENCE: 940

Asp Leu Asn Lys Ser Phe His Asp
1               5

<210> SEQ ID NO 941
<211> LENGTH: 8
<212> TYPE: PRT
<213> ORGANISM: artificial sequence
```

```
<220> FEATURE:
<223> OTHER INFORMATION: synthetic peptide

<400> SEQUENCE: 941

Asp Arg Asn Lys Ser Phe His Asp
1               5

<210> SEQ ID NO 942
<211> LENGTH: 8
<212> TYPE: PRT
<213> ORGANISM: artificial sequence
<220> FEATURE:
<223> OTHER INFORMATION: synthetic peptide

<400> SEQUENCE: 942

Asp Glu Asn Lys Ser Phe His Asp
1               5

<210> SEQ ID NO 943
<211> LENGTH: 8
<212> TYPE: PRT
<213> ORGANISM: artificial sequence
<220> FEATURE:
<223> OTHER INFORMATION: synthetic peptide

<400> SEQUENCE: 943

Glu Ile Glu Lys Ser Phe His Asp
1               5

<210> SEQ ID NO 944
<211> LENGTH: 8
<212> TYPE: PRT
<213> ORGANISM: artificial sequence
<220> FEATURE:
<223> OTHER INFORMATION: synthetic peptide

<400> SEQUENCE: 944

Glu His Glu Lys Ser Phe His Asp
1               5

<210> SEQ ID NO 945
<211> LENGTH: 8
<212> TYPE: PRT
<213> ORGANISM: artificial sequence
<220> FEATURE:
<223> OTHER INFORMATION: synthetic peptide

<400> SEQUENCE: 945

Glu Leu Glu Lys Ser Phe His Asp
1               5

<210> SEQ ID NO 946
<211> LENGTH: 8
<212> TYPE: PRT
<213> ORGANISM: artificial sequence
<220> FEATURE:
<223> OTHER INFORMATION: synthetic peptide

<400> SEQUENCE: 946

Glu Arg Glu Lys Ser Phe His Asp
1               5

<210> SEQ ID NO 947
<211> LENGTH: 8
<212> TYPE: PRT
<213> ORGANISM: artificial sequence
<220> FEATURE:
<223> OTHER INFORMATION: synthetic peptide
```

```
<400> SEQUENCE: 947

Glu Glu Glu Lys Ser Phe His Asp
1               5

<210> SEQ ID NO 948
<211> LENGTH: 8
<212> TYPE: PRT
<213> ORGANISM: artificial sequence
<220> FEATURE:
<223> OTHER INFORMATION: synthetic peptide

<400> SEQUENCE: 948

Asp Ile Glu Lys Ser Phe His Asp
1               5

<210> SEQ ID NO 949
<211> LENGTH: 8
<212> TYPE: PRT
<213> ORGANISM: artificial sequence
<220> FEATURE:
<223> OTHER INFORMATION: synthetic peptide

<400> SEQUENCE: 949

Asp His Glu Lys Ser Phe His Asp
1               5

<210> SEQ ID NO 950
<211> LENGTH: 8
<212> TYPE: PRT
<213> ORGANISM: artificial sequence
<220> FEATURE:
<223> OTHER INFORMATION: synthetic peptide

<400> SEQUENCE: 950

Asp Leu Glu Lys Ser Phe His Asp
1               5

<210> SEQ ID NO 951
<211> LENGTH: 8
<212> TYPE: PRT
<213> ORGANISM: artificial sequence
<220> FEATURE:
<223> OTHER INFORMATION: synthetic peptide

<400> SEQUENCE: 951

Asp Arg Glu Lys Ser Phe His Asp
1               5

<210> SEQ ID NO 952
<211> LENGTH: 8
<212> TYPE: PRT
<213> ORGANISM: artificial sequence
<220> FEATURE:
<223> OTHER INFORMATION: synthetic peptide

<400> SEQUENCE: 952

Asp Glu Glu Lys Ser Phe His Asp
1               5

<210> SEQ ID NO 953
<211> LENGTH: 8
<212> TYPE: PRT
<213> ORGANISM: artificial sequence
<220> FEATURE:
<223> OTHER INFORMATION: synthetic peptide

<400> SEQUENCE: 953
```

Glu Ile Tyr Lys Ser Phe His Asp
1               5

<210> SEQ ID NO 954
<211> LENGTH: 8
<212> TYPE: PRT
<213> ORGANISM: artificial sequence
<220> FEATURE:
<223> OTHER INFORMATION: synthetic peptide

<400> SEQUENCE: 954

Glu His Tyr Lys Ser Phe His Asp
1               5

<210> SEQ ID NO 955
<211> LENGTH: 8
<212> TYPE: PRT
<213> ORGANISM: artificial sequence
<220> FEATURE:
<223> OTHER INFORMATION: synthetic peptide

<400> SEQUENCE: 955

Glu Leu Tyr Lys Ser Phe His Asp
1               5

<210> SEQ ID NO 956
<211> LENGTH: 8
<212> TYPE: PRT
<213> ORGANISM: artificial sequence
<220> FEATURE:
<223> OTHER INFORMATION: synthetic peptide

<400> SEQUENCE: 956

Glu Arg Tyr Lys Ser Phe His Asp
1               5

<210> SEQ ID NO 957
<211> LENGTH: 8
<212> TYPE: PRT
<213> ORGANISM: artificial sequence
<220> FEATURE:
<223> OTHER INFORMATION: synthetic peptide

<400> SEQUENCE: 957

Glu Glu Tyr Lys Ser Phe His Asp
1               5

<210> SEQ ID NO 958
<211> LENGTH: 8
<212> TYPE: PRT
<213> ORGANISM: artificial sequence
<220> FEATURE:
<223> OTHER INFORMATION: synthetic peptide

<400> SEQUENCE: 958

Asp Ile Tyr Lys Ser Phe His Asp
1               5

<210> SEQ ID NO 959
<211> LENGTH: 8
<212> TYPE: PRT
<213> ORGANISM: artificial sequence
<220> FEATURE:
<223> OTHER INFORMATION: synthetic peptide

<400> SEQUENCE: 959

Asp His Tyr Lys Ser Phe His Asp

```
<210> SEQ ID NO 960
<211> LENGTH: 8
<212> TYPE: PRT
<213> ORGANISM: artificial sequence
<220> FEATURE:
<223> OTHER INFORMATION: synthetic peptide

<400> SEQUENCE: 960

Asp Leu Tyr Lys Ser Phe His Asp
1               5

<210> SEQ ID NO 961
<211> LENGTH: 8
<212> TYPE: PRT
<213> ORGANISM: artificial sequence
<220> FEATURE:
<223> OTHER INFORMATION: synthetic peptide

<400> SEQUENCE: 961

Asp Arg Tyr Lys Ser Phe His Asp
1               5

<210> SEQ ID NO 962
<211> LENGTH: 8
<212> TYPE: PRT
<213> ORGANISM: artificial sequence
<220> FEATURE:
<223> OTHER INFORMATION: synthetic peptide

<400> SEQUENCE: 962

Asp Glu Tyr Lys Ser Phe His Asp
1               5

<210> SEQ ID NO 963
<211> LENGTH: 8
<212> TYPE: PRT
<213> ORGANISM: artificial sequence
<220> FEATURE:
<223> OTHER INFORMATION: synthetic peptide

<400> SEQUENCE: 963

Glu Ile Asp Lys Ser Phe Phe Asp
1               5

<210> SEQ ID NO 964
<211> LENGTH: 8
<212> TYPE: PRT
<213> ORGANISM: artificial sequence
<220> FEATURE:
<223> OTHER INFORMATION: synthetic peptide

<400> SEQUENCE: 964

Asp Ile Asp Lys Ser Phe Phe Asp
1               5

<210> SEQ ID NO 965
<211> LENGTH: 8
<212> TYPE: PRT
<213> ORGANISM: artificial sequence
<220> FEATURE:
<223> OTHER INFORMATION: synthetic peptide

<400> SEQUENCE: 965

Glu His Asp Lys Ser Phe Phe Asp
1               5
```

<210> SEQ ID NO 966
<211> LENGTH: 8
<212> TYPE: PRT
<213> ORGANISM: artificial sequence
<220> FEATURE:
<223> OTHER INFORMATION: synthetic peptide

<400> SEQUENCE: 966

Asp His Asp Lys Ser Phe Phe Asp
1               5

<210> SEQ ID NO 967
<211> LENGTH: 8
<212> TYPE: PRT
<213> ORGANISM: artificial sequence
<220> FEATURE:
<223> OTHER INFORMATION: synthetic peptide

<400> SEQUENCE: 967

Glu Leu Asp Lys Ser Phe Phe Asp
1               5

<210> SEQ ID NO 968
<211> LENGTH: 8
<212> TYPE: PRT
<213> ORGANISM: artificial sequence
<220> FEATURE:
<223> OTHER INFORMATION: synthetic peptide

<400> SEQUENCE: 968

Asp Leu Asp Lys Ser Phe Phe Asp
1               5

<210> SEQ ID NO 969
<211> LENGTH: 8
<212> TYPE: PRT
<213> ORGANISM: artificial sequence
<220> FEATURE:
<223> OTHER INFORMATION: synthetic peptide

<400> SEQUENCE: 969

Glu Arg Asp Lys Ser Phe Phe Asp
1               5

<210> SEQ ID NO 970
<211> LENGTH: 8
<212> TYPE: PRT
<213> ORGANISM: artificial sequence
<220> FEATURE:
<223> OTHER INFORMATION: synthetic peptide

<400> SEQUENCE: 970

Asp Arg Asp Lys Ser Phe Phe Asp
1               5

<210> SEQ ID NO 971
<211> LENGTH: 8
<212> TYPE: PRT
<213> ORGANISM: artificial sequence
<220> FEATURE:
<223> OTHER INFORMATION: synthetic peptide

<400> SEQUENCE: 971

Glu Glu Asp Lys Ser Phe Phe Asp
1               5

<210> SEQ ID NO 972

```
<211> LENGTH: 8
<212> TYPE: PRT
<213> ORGANISM: artificial sequence
<220> FEATURE:
<223> OTHER INFORMATION: synthetic peptide

<400> SEQUENCE: 972

Asp Glu Asp Lys Ser Phe Phe Asp
1               5

<210> SEQ ID NO 973
<211> LENGTH: 8
<212> TYPE: PRT
<213> ORGANISM: artificial sequence
<220> FEATURE:
<223> OTHER INFORMATION: synthetic peptide

<400> SEQUENCE: 973

Glu Ile Asn Lys Ser Phe Phe Asp
1               5

<210> SEQ ID NO 974
<211> LENGTH: 8
<212> TYPE: PRT
<213> ORGANISM: artificial sequence
<220> FEATURE:
<223> OTHER INFORMATION: synthetic peptide

<400> SEQUENCE: 974

Glu His Asn Lys Ser Phe Phe Asp
1               5

<210> SEQ ID NO 975
<211> LENGTH: 8
<212> TYPE: PRT
<213> ORGANISM: artificial sequence
<220> FEATURE:
<223> OTHER INFORMATION: synthetic peptide

<400> SEQUENCE: 975

Glu Leu Asn Lys Ser Phe Phe Asp
1               5

<210> SEQ ID NO 976
<211> LENGTH: 8
<212> TYPE: PRT
<213> ORGANISM: artificial sequence
<220> FEATURE:
<223> OTHER INFORMATION: synthetic peptide

<400> SEQUENCE: 976

Glu Arg Asn Lys Ser Phe Phe Asp
1               5

<210> SEQ ID NO 977
<211> LENGTH: 8
<212> TYPE: PRT
<213> ORGANISM: artificial sequence
<220> FEATURE:
<223> OTHER INFORMATION: synthetic peptide

<400> SEQUENCE: 977

Asp Ile Asn Lys Ser Phe Phe Asp
1               5

<210> SEQ ID NO 978
<211> LENGTH: 8
<212> TYPE: PRT
```

```
<213> ORGANISM: artificial sequence
<220> FEATURE:
<223> OTHER INFORMATION: synthetic peptide

<400> SEQUENCE: 978

Asp His Asn Lys Ser Phe Phe Asp
1               5

<210> SEQ ID NO 979
<211> LENGTH: 8
<212> TYPE: PRT
<213> ORGANISM: artificial sequence
<220> FEATURE:
<223> OTHER INFORMATION: synthetic peptide

<400> SEQUENCE: 979

Asp Leu Asn Lys Ser Phe Phe Asp
1               5

<210> SEQ ID NO 980
<211> LENGTH: 8
<212> TYPE: PRT
<213> ORGANISM: artificial sequence
<220> FEATURE:
<223> OTHER INFORMATION: synthetic peptide

<400> SEQUENCE: 980

Asp Arg Asn Lys Ser Phe Phe Asp
1               5

<210> SEQ ID NO 981
<211> LENGTH: 8
<212> TYPE: PRT
<213> ORGANISM: artificial sequence
<220> FEATURE:
<223> OTHER INFORMATION: synthetic peptide

<400> SEQUENCE: 981

Asp Glu Asn Lys Ser Phe Phe Asp
1               5

<210> SEQ ID NO 982
<211> LENGTH: 8
<212> TYPE: PRT
<213> ORGANISM: artificial sequence
<220> FEATURE:
<223> OTHER INFORMATION: synthetic peptide

<400> SEQUENCE: 982

Glu Ile Glu Lys Ser Phe Phe Asp
1               5

<210> SEQ ID NO 983
<211> LENGTH: 8
<212> TYPE: PRT
<213> ORGANISM: artificial sequence
<220> FEATURE:
<223> OTHER INFORMATION: synthetic peptide

<400> SEQUENCE: 983

Glu His Glu Lys Ser Phe Phe Asp
1               5

<210> SEQ ID NO 984
<211> LENGTH: 8
<212> TYPE: PRT
<213> ORGANISM: artificial sequence
<220> FEATURE:
```

<223> OTHER INFORMATION: synthetic peptide

<400> SEQUENCE: 984

Glu Leu Glu Lys Ser Phe Phe Asp
1               5

<210> SEQ ID NO 985
<211> LENGTH: 8
<212> TYPE: PRT
<213> ORGANISM: artificial sequence
<220> FEATURE:
<223> OTHER INFORMATION: synthetic peptide

<400> SEQUENCE: 985

Glu Arg Glu Lys Ser Phe Phe Asp
1               5

<210> SEQ ID NO 986
<211> LENGTH: 8
<212> TYPE: PRT
<213> ORGANISM: artificial sequence
<220> FEATURE:
<223> OTHER INFORMATION: synthetic peptide

<400> SEQUENCE: 986

Glu Glu Glu Lys Ser Phe Phe Asp
1               5

<210> SEQ ID NO 987
<211> LENGTH: 8
<212> TYPE: PRT
<213> ORGANISM: artificial sequence
<220> FEATURE:
<223> OTHER INFORMATION: synthetic peptide

<400> SEQUENCE: 987

Asp Ile Glu Lys Ser Phe Phe Asp
1               5

<210> SEQ ID NO 988
<211> LENGTH: 8
<212> TYPE: PRT
<213> ORGANISM: artificial sequence
<220> FEATURE:
<223> OTHER INFORMATION: synthetic peptide

<400> SEQUENCE: 988

Asp His Glu Lys Ser Phe Phe Asp
1               5

<210> SEQ ID NO 989
<211> LENGTH: 8
<212> TYPE: PRT
<213> ORGANISM: artificial sequence
<220> FEATURE:
<223> OTHER INFORMATION: synthetic peptide

<400> SEQUENCE: 989

Asp Leu Glu Lys Ser Phe Phe Asp
1               5

<210> SEQ ID NO 990
<211> LENGTH: 8
<212> TYPE: PRT
<213> ORGANISM: artificial sequence
<220> FEATURE:
<223> OTHER INFORMATION: synthetic peptide

```
<400> SEQUENCE: 990

Asp Arg Glu Lys Ser Phe Phe Asp
1               5

<210> SEQ ID NO 991
<211> LENGTH: 8
<212> TYPE: PRT
<213> ORGANISM: artificial sequence
<220> FEATURE:
<223> OTHER INFORMATION: synthetic peptide

<400> SEQUENCE: 991

Asp Glu Glu Lys Ser Phe Phe Asp
1               5

<210> SEQ ID NO 992
<211> LENGTH: 8
<212> TYPE: PRT
<213> ORGANISM: artificial sequence
<220> FEATURE:
<223> OTHER INFORMATION: synthetic peptide

<400> SEQUENCE: 992

Glu Ile Tyr Lys Ser Phe Phe Asp
1               5

<210> SEQ ID NO 993
<211> LENGTH: 8
<212> TYPE: PRT
<213> ORGANISM: artificial sequence
<220> FEATURE:
<223> OTHER INFORMATION: synthetic peptide

<400> SEQUENCE: 993

Glu His Tyr Lys Ser Phe Phe Asp
1               5

<210> SEQ ID NO 994
<211> LENGTH: 8
<212> TYPE: PRT
<213> ORGANISM: artificial sequence
<220> FEATURE:
<223> OTHER INFORMATION: synthetic peptide

<400> SEQUENCE: 994

Glu Leu Tyr Lys Ser Phe Phe Asp
1               5

<210> SEQ ID NO 995
<211> LENGTH: 8
<212> TYPE: PRT
<213> ORGANISM: artificial sequence
<220> FEATURE:
<223> OTHER INFORMATION: synthetic peptide

<400> SEQUENCE: 995

Glu Arg Tyr Lys Ser Phe Phe Asp
1               5

<210> SEQ ID NO 996
<211> LENGTH: 8
<212> TYPE: PRT
<213> ORGANISM: artificial sequence
<220> FEATURE:
<223> OTHER INFORMATION: synthetic peptide

<400> SEQUENCE: 996
```

```
Glu Glu Tyr Lys Ser Phe Phe Asp
1               5

<210> SEQ ID NO 997
<211> LENGTH: 8
<212> TYPE: PRT
<213> ORGANISM: artificial sequence
<220> FEATURE:
<223> OTHER INFORMATION: synthetic peptide

<400> SEQUENCE: 997

Asp Ile Tyr Lys Ser Phe Phe Asp
1               5

<210> SEQ ID NO 998
<211> LENGTH: 8
<212> TYPE: PRT
<213> ORGANISM: artificial sequence
<220> FEATURE:
<223> OTHER INFORMATION: synthetic peptide

<400> SEQUENCE: 998

Asp His Tyr Lys Ser Phe Phe Asp
1               5

<210> SEQ ID NO 999
<211> LENGTH: 8
<212> TYPE: PRT
<213> ORGANISM: artificial sequence
<220> FEATURE:
<223> OTHER INFORMATION: synthetic peptide

<400> SEQUENCE: 999

Asp Leu Tyr Lys Ser Phe Phe Asp
1               5

<210> SEQ ID NO 1000
<211> LENGTH: 8
<212> TYPE: PRT
<213> ORGANISM: artificial sequence
<220> FEATURE:
<223> OTHER INFORMATION: synthetic peptide

<400> SEQUENCE: 1000

Asp Arg Tyr Lys Ser Phe Phe Asp
1               5

<210> SEQ ID NO 1001
<211> LENGTH: 8
<212> TYPE: PRT
<213> ORGANISM: artificial sequence
<220> FEATURE:
<223> OTHER INFORMATION: synthetic peptide

<400> SEQUENCE: 1001

Asp Glu Tyr Lys Ser Phe Phe Asp
1               5

<210> SEQ ID NO 1002
<211> LENGTH: 8
<212> TYPE: PRT
<213> ORGANISM: artificial sequence
<220> FEATURE:
<223> OTHER INFORMATION: synthetic peptide

<400> SEQUENCE: 1002

Glu Ile Asp Lys Ser Phe Leu Asp
1               5
```

```
<210> SEQ ID NO 1003
<211> LENGTH: 8
<212> TYPE: PRT
<213> ORGANISM: artificial sequence
<220> FEATURE:
<223> OTHER INFORMATION: synthetic peptide

<400> SEQUENCE: 1003

Asp Ile Asp Lys Ser Phe Leu Asp
1               5

<210> SEQ ID NO 1004
<211> LENGTH: 8
<212> TYPE: PRT
<213> ORGANISM: artificial sequence
<220> FEATURE:
<223> OTHER INFORMATION: synthetic peptide

<400> SEQUENCE: 1004

Glu His Asp Lys Ser Phe Leu Asp
1               5

<210> SEQ ID NO 1005
<211> LENGTH: 8
<212> TYPE: PRT
<213> ORGANISM: artificial sequence
<220> FEATURE:
<223> OTHER INFORMATION: synthetic peptide

<400> SEQUENCE: 1005

Asp His Asp Lys Ser Phe Leu Asp
1               5

<210> SEQ ID NO 1006
<211> LENGTH: 8
<212> TYPE: PRT
<213> ORGANISM: artificial sequence
<220> FEATURE:
<223> OTHER INFORMATION: synthetic peptide

<400> SEQUENCE: 1006

Glu Leu Asp Lys Ser Phe Leu Asp
1               5

<210> SEQ ID NO 1007
<211> LENGTH: 8
<212> TYPE: PRT
<213> ORGANISM: artificial sequence
<220> FEATURE:
<223> OTHER INFORMATION: synthetic peptide

<400> SEQUENCE: 1007

Asp Leu Asp Lys Ser Phe Leu Asp
1               5

<210> SEQ ID NO 1008
<211> LENGTH: 8
<212> TYPE: PRT
<213> ORGANISM: artificial sequence
<220> FEATURE:
<223> OTHER INFORMATION: synthetic peptide

<400> SEQUENCE: 1008

Glu Arg Asp Lys Ser Phe Leu Asp
1               5
```

<210> SEQ ID NO 1009
<211> LENGTH: 8
<212> TYPE: PRT
<213> ORGANISM: artificial sequence
<220> FEATURE:
<223> OTHER INFORMATION: synthetic peptide

<400> SEQUENCE: 1009

Asp Arg Asp Lys Ser Phe Leu Asp
1               5

<210> SEQ ID NO 1010
<211> LENGTH: 8
<212> TYPE: PRT
<213> ORGANISM: artificial sequence
<220> FEATURE:
<223> OTHER INFORMATION: synthetic peptide

<400> SEQUENCE: 1010

Glu Glu Asp Lys Ser Phe Leu Asp
1               5

<210> SEQ ID NO 1011
<211> LENGTH: 8
<212> TYPE: PRT
<213> ORGANISM: artificial sequence
<220> FEATURE:
<223> OTHER INFORMATION: synthetic peptide

<400> SEQUENCE: 1011

Asp Glu Asp Lys Ser Phe Leu Asp
1               5

<210> SEQ ID NO 1012
<211> LENGTH: 8
<212> TYPE: PRT
<213> ORGANISM: artificial sequence
<220> FEATURE:
<223> OTHER INFORMATION: synthetic peptide

<400> SEQUENCE: 1012

Glu Ile Asn Lys Ser Phe Leu Asp
1               5

<210> SEQ ID NO 1013
<211> LENGTH: 8
<212> TYPE: PRT
<213> ORGANISM: artificial sequence
<220> FEATURE:
<223> OTHER INFORMATION: synthetic peptide

<400> SEQUENCE: 1013

Glu His Asn Lys Ser Phe Leu Asp
1               5

<210> SEQ ID NO 1014
<211> LENGTH: 8
<212> TYPE: PRT
<213> ORGANISM: artificial sequence
<220> FEATURE:
<223> OTHER INFORMATION: synthetic peptide

<400> SEQUENCE: 1014

Glu Leu Asn Lys Ser Phe Leu Asp
1               5

<210> SEQ ID NO 1015
<211> LENGTH: 8

```
<212> TYPE: PRT
<213> ORGANISM: artificial sequence
<220> FEATURE:
<223> OTHER INFORMATION: synthetic peptide

<400> SEQUENCE: 1015

Glu Arg Asn Lys Ser Phe Leu Asp
1               5

<210> SEQ ID NO 1016
<211> LENGTH: 8
<212> TYPE: PRT
<213> ORGANISM: artificial sequence
<220> FEATURE:
<223> OTHER INFORMATION: synthetic peptide

<400> SEQUENCE: 1016

Asp Ile Asn Lys Ser Phe Leu Asp
1               5

<210> SEQ ID NO 1017
<211> LENGTH: 8
<212> TYPE: PRT
<213> ORGANISM: artificial sequence
<220> FEATURE:
<223> OTHER INFORMATION: synthetic peptide

<400> SEQUENCE: 1017

Asp His Asn Lys Ser Phe Leu Asp
1               5

<210> SEQ ID NO 1018
<211> LENGTH: 8
<212> TYPE: PRT
<213> ORGANISM: artificial sequence
<220> FEATURE:
<223> OTHER INFORMATION: synthetic peptide

<400> SEQUENCE: 1018

Asp Leu Asn Lys Ser Phe Leu Asp
1               5

<210> SEQ ID NO 1019
<211> LENGTH: 8
<212> TYPE: PRT
<213> ORGANISM: artificial sequence
<220> FEATURE:
<223> OTHER INFORMATION: synthetic peptide

<400> SEQUENCE: 1019

Asp Arg Asn Lys Ser Phe Leu Asp
1               5

<210> SEQ ID NO 1020
<211> LENGTH: 8
<212> TYPE: PRT
<213> ORGANISM: artificial sequence
<220> FEATURE:
<223> OTHER INFORMATION: synthetic peptide

<400> SEQUENCE: 1020

Asp Glu Asn Lys Ser Phe Leu Asp
1               5

<210> SEQ ID NO 1021
<211> LENGTH: 8
<212> TYPE: PRT
<213> ORGANISM: artificial sequence
```

```
<220> FEATURE:
<223> OTHER INFORMATION: synthetic peptide

<400> SEQUENCE: 1021

Glu Ile Glu Lys Ser Phe Leu Asp
1               5

<210> SEQ ID NO 1022
<211> LENGTH: 8
<212> TYPE: PRT
<213> ORGANISM: artificial sequence
<220> FEATURE:
<223> OTHER INFORMATION: synthetic peptide

<400> SEQUENCE: 1022

Glu His Glu Lys Ser Phe Leu Asp
1               5

<210> SEQ ID NO 1023
<211> LENGTH: 8
<212> TYPE: PRT
<213> ORGANISM: artificial sequence
<220> FEATURE:
<223> OTHER INFORMATION: synthetic peptide

<400> SEQUENCE: 1023

Glu Leu Glu Lys Ser Phe Leu Asp
1               5

<210> SEQ ID NO 1024
<211> LENGTH: 8
<212> TYPE: PRT
<213> ORGANISM: artificial sequence
<220> FEATURE:
<223> OTHER INFORMATION: synthetic peptide

<400> SEQUENCE: 1024

Glu Arg Glu Lys Ser Phe Leu Asp
1               5

<210> SEQ ID NO 1025
<211> LENGTH: 8
<212> TYPE: PRT
<213> ORGANISM: artificial sequence
<220> FEATURE:
<223> OTHER INFORMATION: synthetic peptide

<400> SEQUENCE: 1025

Glu Glu Glu Lys Ser Phe Leu Asp
1               5

<210> SEQ ID NO 1026
<211> LENGTH: 8
<212> TYPE: PRT
<213> ORGANISM: artificial sequence
<220> FEATURE:
<223> OTHER INFORMATION: synthetic peptide

<400> SEQUENCE: 1026

Asp Ile Glu Lys Ser Phe Leu Asp
1               5

<210> SEQ ID NO 1027
<211> LENGTH: 8
<212> TYPE: PRT
<213> ORGANISM: artificial sequence
<220> FEATURE:
<223> OTHER INFORMATION: synthetic peptide
```

```
<400> SEQUENCE: 1027

Asp His Glu Lys Ser Phe Leu Asp
1               5

<210> SEQ ID NO 1028
<211> LENGTH: 8
<212> TYPE: PRT
<213> ORGANISM: artificial sequence
<220> FEATURE:
<223> OTHER INFORMATION: synthetic peptide

<400> SEQUENCE: 1028

Asp Leu Glu Lys Ser Phe Leu Asp
1               5

<210> SEQ ID NO 1029
<211> LENGTH: 8
<212> TYPE: PRT
<213> ORGANISM: artificial sequence
<220> FEATURE:
<223> OTHER INFORMATION: synthetic peptide

<400> SEQUENCE: 1029

Asp Arg Glu Lys Ser Phe Leu Asp
1               5

<210> SEQ ID NO 1030
<211> LENGTH: 8
<212> TYPE: PRT
<213> ORGANISM: artificial sequence
<220> FEATURE:
<223> OTHER INFORMATION: synthetic peptide

<400> SEQUENCE: 1030

Asp Glu Glu Lys Ser Phe Leu Asp
1               5

<210> SEQ ID NO 1031
<211> LENGTH: 8
<212> TYPE: PRT
<213> ORGANISM: artificial sequence
<220> FEATURE:
<223> OTHER INFORMATION: synthetic peptide

<400> SEQUENCE: 1031

Glu Ile Tyr Lys Ser Phe Leu Asp
1               5

<210> SEQ ID NO 1032
<211> LENGTH: 8
<212> TYPE: PRT
<213> ORGANISM: artificial sequence
<220> FEATURE:
<223> OTHER INFORMATION: synthetic peptide

<400> SEQUENCE: 1032

Glu His Tyr Lys Ser Phe Leu Asp
1               5

<210> SEQ ID NO 1033
<211> LENGTH: 8
<212> TYPE: PRT
<213> ORGANISM: artificial sequence
<220> FEATURE:
<223> OTHER INFORMATION: synthetic peptide

<400> SEQUENCE: 1033
```

Glu Leu Tyr Lys Ser Phe Leu Asp
1               5

<210> SEQ ID NO 1034
<211> LENGTH: 8
<212> TYPE: PRT
<213> ORGANISM: artificial sequence
<220> FEATURE:
<223> OTHER INFORMATION: synthetic peptide

<400> SEQUENCE: 1034

Glu Arg Tyr Lys Ser Phe Leu Asp
1               5

<210> SEQ ID NO 1035
<211> LENGTH: 8
<212> TYPE: PRT
<213> ORGANISM: artificial sequence
<220> FEATURE:
<223> OTHER INFORMATION: synthetic peptide

<400> SEQUENCE: 1035

Glu Glu Tyr Lys Ser Phe Leu Asp
1               5

<210> SEQ ID NO 1036
<211> LENGTH: 8
<212> TYPE: PRT
<213> ORGANISM: artificial sequence
<220> FEATURE:
<223> OTHER INFORMATION: synthetic peptide

<400> SEQUENCE: 1036

Asp Ile Tyr Lys Ser Phe Leu Asp
1               5

<210> SEQ ID NO 1037
<211> LENGTH: 8
<212> TYPE: PRT
<213> ORGANISM: artificial sequence
<220> FEATURE:
<223> OTHER INFORMATION: synthetic peptide

<400> SEQUENCE: 1037

Asp His Tyr Lys Ser Phe Leu Asp
1               5

<210> SEQ ID NO 1038
<211> LENGTH: 8
<212> TYPE: PRT
<213> ORGANISM: artificial sequence
<220> FEATURE:
<223> OTHER INFORMATION: synthetic peptide

<400> SEQUENCE: 1038

Asp Leu Tyr Lys Ser Phe Leu Asp
1               5

<210> SEQ ID NO 1039
<211> LENGTH: 8
<212> TYPE: PRT
<213> ORGANISM: artificial sequence
<220> FEATURE:
<223> OTHER INFORMATION: synthetic peptide

<400> SEQUENCE: 1039

Asp Arg Tyr Lys Ser Phe Leu Asp

<210> SEQ ID NO 1040
<211> LENGTH: 8
<212> TYPE: PRT
<213> ORGANISM: artificial sequence
<220> FEATURE:
<223> OTHER INFORMATION: synthetic peptide

<400> SEQUENCE: 1040

Asp Glu Tyr Lys Ser Phe Leu Asp
1               5

<210> SEQ ID NO 1041
<211> LENGTH: 8
<212> TYPE: PRT
<213> ORGANISM: artificial sequence
<220> FEATURE:
<223> OTHER INFORMATION: synthetic peptide

<400> SEQUENCE: 1041

Glu Ile Asp Lys Ser Phe Leu Glu
1               5

<210> SEQ ID NO 1042
<211> LENGTH: 8
<212> TYPE: PRT
<213> ORGANISM: artificial sequence
<220> FEATURE:
<223> OTHER INFORMATION: synthetic peptide

<400> SEQUENCE: 1042

Asp Ile Asp Lys Ser Phe Leu Glu
1               5

<210> SEQ ID NO 1043
<211> LENGTH: 8
<212> TYPE: PRT
<213> ORGANISM: artificial sequence
<220> FEATURE:
<223> OTHER INFORMATION: synthetic peptide

<400> SEQUENCE: 1043

Glu His Asp Lys Ser Phe Leu Glu
1               5

<210> SEQ ID NO 1044
<211> LENGTH: 8
<212> TYPE: PRT
<213> ORGANISM: artificial sequence
<220> FEATURE:
<223> OTHER INFORMATION: synthetic peptide

<400> SEQUENCE: 1044

Asp His Asp Lys Ser Phe Leu Glu
1               5

<210> SEQ ID NO 1045
<211> LENGTH: 8
<212> TYPE: PRT
<213> ORGANISM: artificial sequence
<220> FEATURE:
<223> OTHER INFORMATION: synthetic peptide

<400> SEQUENCE: 1045

Glu Leu Asp Lys Ser Phe Leu Glu
1               5

```
<210> SEQ ID NO 1046
<211> LENGTH: 8
<212> TYPE: PRT
<213> ORGANISM: artificial sequence
<220> FEATURE:
<223> OTHER INFORMATION: synthetic peptide

<400> SEQUENCE: 1046

Asp Leu Asp Lys Ser Phe Leu Glu
1               5

<210> SEQ ID NO 1047
<211> LENGTH: 8
<212> TYPE: PRT
<213> ORGANISM: artificial sequence
<220> FEATURE:
<223> OTHER INFORMATION: synthetic peptide

<400> SEQUENCE: 1047

Glu Arg Asp Lys Ser Phe Leu Glu
1               5

<210> SEQ ID NO 1048
<211> LENGTH: 8
<212> TYPE: PRT
<213> ORGANISM: artificial sequence
<220> FEATURE:
<223> OTHER INFORMATION: synthetic peptide

<400> SEQUENCE: 1048

Asp Arg Asp Lys Ser Phe Leu Glu
1               5

<210> SEQ ID NO 1049
<211> LENGTH: 8
<212> TYPE: PRT
<213> ORGANISM: artificial sequence
<220> FEATURE:
<223> OTHER INFORMATION: synthetic peptide

<400> SEQUENCE: 1049

Glu Glu Asp Lys Ser Phe Leu Glu
1               5

<210> SEQ ID NO 1050
<211> LENGTH: 8
<212> TYPE: PRT
<213> ORGANISM: artificial sequence
<220> FEATURE:
<223> OTHER INFORMATION: synthetic peptide

<400> SEQUENCE: 1050

Asp Glu Asp Lys Ser Phe Leu Glu
1               5

<210> SEQ ID NO 1051
<211> LENGTH: 8
<212> TYPE: PRT
<213> ORGANISM: artificial sequence
<220> FEATURE:
<223> OTHER INFORMATION: synthetic peptide

<400> SEQUENCE: 1051

Glu Ile Asn Lys Ser Phe Leu Glu
1               5

<210> SEQ ID NO 1052
```

```
<211> LENGTH: 8
<212> TYPE: PRT
<213> ORGANISM: artificial sequence
<220> FEATURE:
<223> OTHER INFORMATION: synthetic peptide

<400> SEQUENCE: 1052

Glu His Asn Lys Ser Phe Leu Glu
1               5

<210> SEQ ID NO 1053
<211> LENGTH: 8
<212> TYPE: PRT
<213> ORGANISM: artificial sequence
<220> FEATURE:
<223> OTHER INFORMATION: synthetic peptide

<400> SEQUENCE: 1053

Glu Leu Asn Lys Ser Phe Leu Glu
1               5

<210> SEQ ID NO 1054
<211> LENGTH: 8
<212> TYPE: PRT
<213> ORGANISM: artificial sequence
<220> FEATURE:
<223> OTHER INFORMATION: synthetic peptide

<400> SEQUENCE: 1054

Glu Arg Asn Lys Ser Phe Leu Glu
1               5

<210> SEQ ID NO 1055
<211> LENGTH: 8
<212> TYPE: PRT
<213> ORGANISM: artificial sequence
<220> FEATURE:
<223> OTHER INFORMATION: synthetic peptide

<400> SEQUENCE: 1055

Asp Ile Asn Lys Ser Phe Leu Glu
1               5

<210> SEQ ID NO 1056
<211> LENGTH: 8
<212> TYPE: PRT
<213> ORGANISM: artificial sequence
<220> FEATURE:
<223> OTHER INFORMATION: synthetic peptide

<400> SEQUENCE: 1056

Asp His Asn Lys Ser Phe Leu Glu
1               5

<210> SEQ ID NO 1057
<211> LENGTH: 8
<212> TYPE: PRT
<213> ORGANISM: artificial sequence
<220> FEATURE:
<223> OTHER INFORMATION: synthetic peptide

<400> SEQUENCE: 1057

Asp Leu Asn Lys Ser Phe Leu Glu
1               5

<210> SEQ ID NO 1058
<211> LENGTH: 8
<212> TYPE: PRT
```

```
<213> ORGANISM: artificial sequence
<220> FEATURE:
<223> OTHER INFORMATION: synthetic peptide

<400> SEQUENCE: 1058

Asp Arg Asn Lys Ser Phe Leu Glu
1               5

<210> SEQ ID NO 1059
<211> LENGTH: 8
<212> TYPE: PRT
<213> ORGANISM: artificial sequence
<220> FEATURE:
<223> OTHER INFORMATION: synthetic peptide

<400> SEQUENCE: 1059

Asp Glu Asn Lys Ser Phe Leu Glu
1               5

<210> SEQ ID NO 1060
<211> LENGTH: 8
<212> TYPE: PRT
<213> ORGANISM: artificial sequence
<220> FEATURE:
<223> OTHER INFORMATION: synthetic peptide

<400> SEQUENCE: 1060

Glu Ile Glu Lys Ser Phe Leu Glu
1               5

<210> SEQ ID NO 1061
<211> LENGTH: 8
<212> TYPE: PRT
<213> ORGANISM: artificial sequence
<220> FEATURE:
<223> OTHER INFORMATION: synthetic peptide

<400> SEQUENCE: 1061

Glu His Glu Lys Ser Phe Leu Glu
1               5

<210> SEQ ID NO 1062
<211> LENGTH: 8
<212> TYPE: PRT
<213> ORGANISM: artificial sequence
<220> FEATURE:
<223> OTHER INFORMATION: synthetic peptide

<400> SEQUENCE: 1062

Glu Leu Glu Lys Ser Phe Leu Glu
1               5

<210> SEQ ID NO 1063
<211> LENGTH: 8
<212> TYPE: PRT
<213> ORGANISM: artificial sequence
<220> FEATURE:
<223> OTHER INFORMATION: synthetic peptide

<400> SEQUENCE: 1063

Glu Arg Glu Lys Ser Phe Leu Glu
1               5

<210> SEQ ID NO 1064
<211> LENGTH: 8
<212> TYPE: PRT
<213> ORGANISM: artificial sequence
<220> FEATURE:
```

<223> OTHER INFORMATION: synthetic peptide

<400> SEQUENCE: 1064

Glu Glu Glu Lys Ser Phe Leu Glu
1               5

<210> SEQ ID NO 1065
<211> LENGTH: 8
<212> TYPE: PRT
<213> ORGANISM: artificial sequence
<220> FEATURE:
<223> OTHER INFORMATION: synthetic peptide

<400> SEQUENCE: 1065

Asp Ile Glu Lys Ser Phe Leu Glu
1               5

<210> SEQ ID NO 1066
<211> LENGTH: 8
<212> TYPE: PRT
<213> ORGANISM: artificial sequence
<220> FEATURE:
<223> OTHER INFORMATION: synthetic peptide

<400> SEQUENCE: 1066

Asp His Glu Lys Ser Phe Leu Glu
1               5

<210> SEQ ID NO 1067
<211> LENGTH: 8
<212> TYPE: PRT
<213> ORGANISM: artificial sequence
<220> FEATURE:
<223> OTHER INFORMATION: synthetic peptide

<400> SEQUENCE: 1067

Asp Leu Glu Lys Ser Phe Leu Glu
1               5

<210> SEQ ID NO 1068
<211> LENGTH: 8
<212> TYPE: PRT
<213> ORGANISM: artificial sequence
<220> FEATURE:
<223> OTHER INFORMATION: synthetic peptide

<400> SEQUENCE: 1068

Asp Arg Glu Lys Ser Phe Leu Glu
1               5

<210> SEQ ID NO 1069
<211> LENGTH: 8
<212> TYPE: PRT
<213> ORGANISM: artificial sequence
<220> FEATURE:
<223> OTHER INFORMATION: synthetic peptide

<400> SEQUENCE: 1069

Asp Glu Glu Lys Ser Phe Leu Glu
1               5

<210> SEQ ID NO 1070
<211> LENGTH: 8
<212> TYPE: PRT
<213> ORGANISM: artificial sequence
<220> FEATURE:
<223> OTHER INFORMATION: synthetic peptide

```
<400> SEQUENCE: 1070

Glu Ile Tyr Lys Ser Phe Leu Glu
1               5

<210> SEQ ID NO 1071
<211> LENGTH: 8
<212> TYPE: PRT
<213> ORGANISM: artificial sequence
<220> FEATURE:
<223> OTHER INFORMATION: synthetic peptide

<400> SEQUENCE: 1071

Glu His Tyr Lys Ser Phe Leu Glu
1               5

<210> SEQ ID NO 1072
<211> LENGTH: 8
<212> TYPE: PRT
<213> ORGANISM: artificial sequence
<220> FEATURE:
<223> OTHER INFORMATION: synthetic peptide

<400> SEQUENCE: 1072

Glu Leu Tyr Lys Ser Phe Leu Glu
1               5

<210> SEQ ID NO 1073
<211> LENGTH: 8
<212> TYPE: PRT
<213> ORGANISM: artificial sequence
<220> FEATURE:
<223> OTHER INFORMATION: synthetic peptide

<400> SEQUENCE: 1073

Glu Arg Tyr Lys Ser Phe Leu Glu
1               5

<210> SEQ ID NO 1074
<211> LENGTH: 8
<212> TYPE: PRT
<213> ORGANISM: artificial sequence
<220> FEATURE:
<223> OTHER INFORMATION: synthetic peptide

<400> SEQUENCE: 1074

Glu Glu Tyr Lys Ser Phe Leu Glu
1               5

<210> SEQ ID NO 1075
<211> LENGTH: 8
<212> TYPE: PRT
<213> ORGANISM: artificial sequence
<220> FEATURE:
<223> OTHER INFORMATION: synthetic peptide

<400> SEQUENCE: 1075

Asp Ile Tyr Lys Ser Phe Leu Glu
1               5

<210> SEQ ID NO 1076
<211> LENGTH: 8
<212> TYPE: PRT
<213> ORGANISM: artificial sequence
<220> FEATURE:
<223> OTHER INFORMATION: synthetic peptide

<400> SEQUENCE: 1076
```

Asp His Tyr Lys Ser Phe Leu Glu
1               5

<210> SEQ ID NO 1077
<211> LENGTH: 8
<212> TYPE: PRT
<213> ORGANISM: artificial sequence
<220> FEATURE:
<223> OTHER INFORMATION: synthetic peptide

<400> SEQUENCE: 1077

Asp Leu Tyr Lys Ser Phe Leu Glu
1               5

<210> SEQ ID NO 1078
<211> LENGTH: 8
<212> TYPE: PRT
<213> ORGANISM: artificial sequence
<220> FEATURE:
<223> OTHER INFORMATION: synthetic peptide

<400> SEQUENCE: 1078

Asp Arg Tyr Lys Ser Phe Leu Glu
1               5

<210> SEQ ID NO 1079
<211> LENGTH: 8
<212> TYPE: PRT
<213> ORGANISM: artificial sequence
<220> FEATURE:
<223> OTHER INFORMATION: synthetic peptide

<400> SEQUENCE: 1079

Asp Glu Tyr Lys Ser Phe Leu Glu
1               5

<210> SEQ ID NO 1080
<211> LENGTH: 45
<212> TYPE: DNA
<213> ORGANISM: artificial sequence
<220> FEATURE:
<223> OTHER INFORMATION: synthetic oligonucleotide

<400> SEQUENCE: 1080
ctagcggatt tgaacttgat aaagtatggt ttgatgtcga ttcac          45

<210> SEQ ID NO 1081
<211> LENGTH: 45
<212> TYPE: DNA
<213> ORGANISM: artificial sequence
<220> FEATURE:
<223> OTHER INFORMATION: synthetic oligonucleotide

<400> SEQUENCE: 1081
ctagcggatt cgagattgat aaagtatggc atgatttccc tgcac          45

<210> SEQ ID NO 1082
<211> LENGTH: 45
<212> TYPE: DNA
<213> ORGANISM: artificial sequence
<220> FEATURE:
<223> OTHER INFORMATION: synthetic oligonucleotide

<400> SEQUENCE: 1082
ctagcggatt tgagcatgag aaagtttggt atgatctcga tgcgc          45

<210> SEQ ID NO 1083

```
<211> LENGTH: 45
<212> TYPE: DNA
<213> ORGANISM: artificial sequence
<220> FEATURE:
<223> OTHER INFORMATION: synthetic oligonucleotide

<400> SEQUENCE: 1083
ctagcggctt cgagatcgac aaggtgtggt acgacctgga cgccc            45

<210> SEQ ID NO 1084
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 1084
ctagcggctt cgagatcgac aaggtgtggt acgacctgga cgcctaagag       50

<210> SEQ ID NO 1085
<211> LENGTH: 45
<212> TYPE: DNA
<213> ORGANISM: artificial sequence
<220> FEATURE:
<223> OTHER INFORMATION: synthetic oligonucleotide

<400> SEQUENCE: 1085
aattgtgaat cgacatcaaa ccatacttta tcaagttcaa atccg             45

<210> SEQ ID NO 1086
<211> LENGTH: 45
<212> TYPE: DNA
<213> ORGANISM: artificial sequence
<220> FEATURE:
<223> OTHER INFORMATION: synthetic oligonucleotide

<400> SEQUENCE: 1086
aattgtgcag ggaaatcatg ccatacttta tcaatctcga atccg             45

<210> SEQ ID NO 1087
<211> LENGTH: 45
<212> TYPE: DNA
<213> ORGANISM: artificial sequence
<220> FEATURE:
<223> OTHER INFORMATION: synthetic oligonucleotide

<400> SEQUENCE: 1087
aattgcgcat cgagatcata ccaaactttc tcatgctcaa atccg             45

<210> SEQ ID NO 1088
<211> LENGTH: 45
<212> TYPE: DNA
<213> ORGANISM: artificial sequence
<220> FEATURE:
<223> OTHER INFORMATION: synthetic oligonucleotide

<400> SEQUENCE: 1088
aattgggcgt ccaggtcgta ccacaccttg tcgatctcga agccg             45

<210> SEQ ID NO 1089
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 1089
```

```
gatcctctta ggcgtccagg tcgtaccaca ccttgtcgat ctcgaagccg          50
```

<210> SEQ ID NO 1090
<211> LENGTH: 36
<212> TYPE: DNA
<213> ORGANISM: artificial sequence
<220> FEATURE:
<223> OTHER INFORMATION: synthetic oligonucleotide

<400> SEQUENCE: 1090

```
gcatcgctag catggctatc gaaatcaaag taccgg                         36
```

<210> SEQ ID NO 1091
<211> LENGTH: 28
<212> TYPE: DNA
<213> ORGANISM: artificial sequence
<220> FEATURE:
<223> OTHER INFORMATION: synthetic oligonucleotide

<400> SEQUENCE: 1091

```
ggtgaggatc ccgcaggagc tgccgcag                                  28
```

<210> SEQ ID NO 1092
<211> LENGTH: 72
<212> TYPE: DNA
<213> ORGANISM: artificial sequence
<220> FEATURE:
<223> OTHER INFORMATION: synthetic oligonucleotide

<400> SEQUENCE: 1092

```
ctagcgacga agtactggtt gaaatcgaaa ccgacaaagc agttctggaa gtaccgggcg    60
gtgaggagga gg                                                       72
```

<210> SEQ ID NO 1093
<211> LENGTH: 72
<212> TYPE: DNA
<213> ORGANISM: artificial sequence
<220> FEATURE:
<223> OTHER INFORMATION: synthetic oligonucleotide

<400> SEQUENCE: 1093

```
gatccctcct cctcaccgcc cggtacttcc agaactgctt tgtcggtttc gatttcaacc    60
agtacttcgt cg                                                       72
```

<210> SEQ ID NO 1094
<211> LENGTH: 22
<212> TYPE: PRT
<213> ORGANISM: artificial sequence
<220> FEATURE:
<223> OTHER INFORMATION: synthetic peptide

<400> SEQUENCE: 1094

Asp Glu Val Leu Val Glu Ile Glu Thr Asp Lys Ala Val Leu Glu Val
1               5                   10                  15

Pro Gly Gly Glu Glu Glu
            20

<210> SEQ ID NO 1095
<211> LENGTH: 42
<212> TYPE: DNA
<213> ORGANISM: artificial sequence
<220> FEATURE:
<223> OTHER INFORMATION: synthetic oligonucleotide

<400> SEQUENCE: 1095
gatcaccgta gaaggcgacg ctgcttctat ggaagttccg gc    42

<210> SEQ ID NO 1096
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 1096
gcggttctca cccctcaaca ac    22

<210> SEQ ID NO 1097
<211> LENGTH: 26
<212> TYPE: DNA
<213> ORGANISM: artificial sequence
<220> FEATURE:
<223> OTHER INFORMATION: synthetic oligonucleotide

<400> SEQUENCE: 1097
gtatgtgtaa agttggtaac ggaacg    26

<210> SEQ ID NO 1098
<211> LENGTH: 76
<212> TYPE: DNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (23)..(23)
<223> OTHER INFORMATION: n is a, c, g or t
<220> FEATURE:
<221> NAME/KEY: misc_feature
<222> LOCATION: (25)..(26)
<223> OTHER INFORMATION: m is a or c
<220> FEATURE:
<221> NAME/KEY: misc_feature
<222> LOCATION: (27)..(29)
<223> OTHER INFORMATION: n is a, c, g or t
<220> FEATURE:
<221> NAME/KEY: misc_feature
<222> LOCATION: (31)..(32)
<223> OTHER INFORMATION: n is a, c, g or t
<220> FEATURE:
<221> NAME/KEY: misc_feature
<222> LOCATION: (35)..(35)
<223> OTHER INFORMATION: m is a or c
<220> FEATURE:
<221> NAME/KEY: misc_feature
<222> LOCATION: (36)..(37)
<223> OTHER INFORMATION: n is a, c, g or t
<220> FEATURE:
<221> NAME/KEY: misc_feature
<222> LOCATION: (38)..(38)
<223> OTHER INFORMATION: m is a or c
<220> FEATURE:
<221> NAME/KEY: misc_feature
<222> LOCATION: (39)..(40)
<223> OTHER INFORMATION: n is a, c, g or t
<220> FEATURE:
<221> NAME/KEY: misc_feature
<222> LOCATION: (50)..(50)
<223> OTHER INFORMATION: m is a or c
<220> FEATURE:
<221> NAME/KEY: misc_feature
<222> LOCATION: (51)..(53)
<223> OTHER INFORMATION: n is a, c, g or t
<220> FEATURE:
<221> NAME/KEY: misc_feature
<222> LOCATION: (56)..(56)
<223> OTHER INFORMATION: n is a, c, g or t
<220> FEATURE:
<221> NAME/KEY: misc_feature
<222> LOCATION: (58)..(58)

<223> OTHER INFORMATION: n is a, c, g or t

<400> SEQUENCE: 1098
aaataagctt ttgttcggat ccngmmnnna nntsmnnmnn aactttatcm nnntsnantc    60
cgctagccga ccctcc    76

<210> SEQ ID NO 1099
<211> LENGTH: 59
<212> TYPE: DNA
<213> ORGANISM: artificial sequence
<220> FEATURE:
<223> OTHER INFORMATION: synthetic oligonucleotide

<400> SEQUENCE: 1099
ctagtggtgg aggaggctct ggtggaggcg gtagcggagg cggagggtcg gctagcgga    59

<210> SEQ ID NO 1100
<211> LENGTH: 56
<212> TYPE: DNA
<213> ORGANISM: artificial sequence
<220> FEATURE:
<223> OTHER INFORMATION: synthetic oligonucleotide

<400> SEQUENCE: 1100
tatcagatct cgagctatta caagtcctct tcagaaataa gctttgttc ggatcc    56

<210> SEQ ID NO 1101
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 1101
ggcagcccca taaacacac    19

<210> SEQ ID NO 1102
<211> LENGTH: 47
<212> TYPE: DNA
<213> ORGANISM: artificial sequence
<220> FEATURE:
<223> OTHER INFORMATION: synthetic oligonucleotide

<400> SEQUENCE: 1102
aagcagttct ggaagtaccg caattgggcg gtgaggagga gtacgcc    47

<210> SEQ ID NO 1103
<211> LENGTH: 46
<212> TYPE: DNA
<213> ORGANISM: artificial sequence
<220> FEATURE:
<223> OTHER INFORMATION: synthetic oligonucleotide

<400> SEQUENCE: 1103
gaagtaccat cagcagacgg ccaattgact gtgagcaagg gcgagg    46

<210> SEQ ID NO 1104
<211> LENGTH: 44
<212> TYPE: DNA
<213> ORGANISM: artificial sequence
<220> FEATURE:
<223> OTHER INFORMATION: synthetic oligonucleotide

<400> SEQUENCE: 1104
gcacctcggt tctatcgata acgcgtacca tggggccctg gggc    44

```
<210> SEQ ID NO 1105
<211> LENGTH: 47
<212> TYPE: DNA
<213> ORGANISM: artificial sequence
<220> FEATURE:
<223> OTHER INFORMATION: synthetic oligonucleotide

<400> SEQUENCE: 1105
ctgcagttgg cgacagaagt gctagcgacg aagtactggt tgaaatc        47

<210> SEQ ID NO 1106
<211> LENGTH: 46
<212> TYPE: DNA
<213> ORGANISM: artificial sequence
<220> FEATURE:
<223> OTHER INFORMATION: synthetic oligonucleotide

<400> SEQUENCE: 1106
gatctggctt cgagatcgac aaggtgtggt acgacctgga cgccgg           46

<210> SEQ ID NO 1107
<211> LENGTH: 46
<212> TYPE: DNA
<213> ORGANISM: artificial sequence
<220> FEATURE:
<223> OTHER INFORMATION: synthetic oligonucleotide

<400> SEQUENCE: 1107
cgcgccggcg tccaggtcgt accacacctt gtcgatctcg aagcca           46

<210> SEQ ID NO 1108
<211> LENGTH: 49
<212> TYPE: DNA
<213> ORGANISM: artificial sequence
<220> FEATURE:
<223> OTHER INFORMATION: synthetic oligonucleotide

<400> SEQUENCE: 1108
ggagggtcgg ctagcggagt ggaacttgat aaagtatggt ttgatgtcg         49

<210> SEQ ID NO 1109
<211> LENGTH: 8
<212> TYPE: PRT
<213> ORGANISM: artificial sequence
<220> FEATURE:
<223> OTHER INFORMATION: synthetic peptide

<400> SEQUENCE: 1109

Phe Glu Ile Asp Lys Val Trp Tyr
 1               5

<210> SEQ ID NO 1110
<211> LENGTH: 12
<212> TYPE: PRT
<213> ORGANISM: artificial sequence
<220> FEATURE:
<223> OTHER INFORMATION: synthetic peptide

<400> SEQUENCE: 1110

Val Gln Asn Asp Lys Leu Met Gln Glu Ile Leu Ser
 1               5                  10

<210> SEQ ID NO 1111
<211> LENGTH: 12
<212> TYPE: PRT
<213> ORGANISM: artificial sequence
<220> FEATURE:
```

-continued

<223> OTHER INFORMATION: synthetic peptide

<400> SEQUENCE: 1111

Val Gln Asn Asp Lys Ala Val Val Glu Ile Pro Ser
1               5                   10

<210> SEQ ID NO 1112
<211> LENGTH: 12
<212> TYPE: PRT
<213> ORGANISM: artificial sequence
<220> FEATURE:
<223> OTHER INFORMATION: synthetic peptide

<400> SEQUENCE: 1112

Ile Glu Ser Asp Lys Leu Asn Val Asp Val Arg Ala
1               5                   10

<210> SEQ ID NO 1113
<211> LENGTH: 12
<212> TYPE: PRT
<213> ORGANISM: artificial sequence
<220> FEATURE:
<223> OTHER INFORMATION: synthetic peptide

<400> SEQUENCE: 1113

Val Glu Gly Asp Lys Ala Ser Met Glu Ile Pro Ser
1               5                   10

<210> SEQ ID NO 1114
<211> LENGTH: 12
<212> TYPE: PRT
<213> ORGANISM: artificial sequence
<220> FEATURE:
<223> OTHER INFORMATION: synthetic peptide

<400> SEQUENCE: 1114

Leu Glu Gly Asp Lys Ala Ser Met Asp Val Pro Ala
1               5                   10

<210> SEQ ID NO 1115
<211> LENGTH: 12
<212> TYPE: PRT
<213> ORGANISM: artificial sequence
<220> FEATURE:
<223> OTHER INFORMATION: synthetic peptide

<400> SEQUENCE: 1115

Val Glu Gly Asp Lys Ala Ser Met Glu Ile Pro Ser
1               5                   10

<210> SEQ ID NO 1116
<211> LENGTH: 12
<212> TYPE: PRT
<213> ORGANISM: artificial sequence
<220> FEATURE:
<223> OTHER INFORMATION: synthetic peptide

<400> SEQUENCE: 1116

Ile Glu Thr Asp Lys Val Val Leu Glu Val Pro Ala
1               5                   10

<210> SEQ ID NO 1117
<211> LENGTH: 12
<212> TYPE: PRT
<213> ORGANISM: artificial sequence
<220> FEATURE:
<223> OTHER INFORMATION: synthetic peptide

```
<400> SEQUENCE: 1117

Ile Glu Ser Val Lys Ala Ala Ala Asp Val Tyr Ala
1               5                   10

<210> SEQ ID NO 1118
<211> LENGTH: 12
<212> TYPE: PRT
<213> ORGANISM: artificial sequence
<220> FEATURE:
<223> OTHER INFORMATION: synthetic peptide

<400> SEQUENCE: 1118

Ile Glu Thr Asp Lys Ala Val Leu Glu Val Pro Gly
1               5                   10

<210> SEQ ID NO 1119
<211> LENGTH: 12
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: x is any amino acid
<220> FEATURE:
<221> NAME/KEY: MISC_FEATURE
<222> LOCATION: (7)..(8)
<223> OTHER INFORMATION: x is any amino acid
<220> FEATURE:
<221> NAME/KEY: MISC_FEATURE
<222> LOCATION: (11)..(11)
<223> OTHER INFORMATION: x is any amino acid

<400> SEQUENCE: 1119

Val Glu Xaa Asp Lys Val Xaa Xaa Glu Val Xaa Ala
1               5                   10

<210> SEQ ID NO 1120
<211> LENGTH: 18
<212> TYPE: PRT
<213> ORGANISM: artificial sequence
<220> FEATURE:
<223> OTHER INFORMATION: synthetic peptide

<400> SEQUENCE: 1120

Gly Asp Glu Val Leu Val Glu Ile Glu Thr Asp Lys Ala Val Leu Glu
1               5                   10                  15

Val Pro

<210> SEQ ID NO 1121
<211> LENGTH: 13
<212> TYPE: PRT
<213> ORGANISM: artificial sequence
<220> FEATURE:
<223> OTHER INFORMATION: synthetic peptide

<400> SEQUENCE: 1121

Gly Phe Glu Leu Asp Lys Val Trp Phe Asp Val Asp Ser
1               5                   10

<210> SEQ ID NO 1122
<211> LENGTH: 13
<212> TYPE: PRT
<213> ORGANISM: artificial sequence
<220> FEATURE:
<223> OTHER INFORMATION: synthetic peptide

<400> SEQUENCE: 1122
```

Gly Phe Glu Ile Asp Lys Val Trp His Asp Phe Pro Ala
1               5                   10

<210> SEQ ID NO 1123
<211> LENGTH: 13
<212> TYPE: PRT
<213> ORGANISM: artificial sequence
<220> FEATURE:
<223> OTHER INFORMATION: synthetic peptide

<400> SEQUENCE: 1123

Gly Phe Glu His Glu Lys Val Trp Tyr Asp Leu Asp Ala
1               5                   10

<210> SEQ ID NO 1124
<211> LENGTH: 19
<212> TYPE: PRT
<213> ORGANISM: artificial sequence
<220> FEATURE:
<223> OTHER INFORMATION: synthetic peptide

<400> SEQUENCE: 1124

Glu Gln Ser Leu Ile Thr Val Glu Gly Asp Lys Ala Ser Met Glu Val
1               5                   10                  15

Pro Ala Pro

<210> SEQ ID NO 1125
<211> LENGTH: 12
<212> TYPE: PRT
<213> ORGANISM: artificial sequence
<220> FEATURE:
<223> OTHER INFORMATION: synthetic peptide

<400> SEQUENCE: 1125

Met Glu Met Asn Lys Val Trp Arg Asp Leu Ala Ala
1               5                   10

<210> SEQ ID NO 1126
<211> LENGTH: 12
<212> TYPE: PRT
<213> ORGANISM: artificial sequence
<220> FEATURE:
<223> OTHER INFORMATION: synthetic peptide

<400> SEQUENCE: 1126

Ile Asp Gln Asp Lys Phe Trp Arg Glu Leu Gly Ser
1               5                   10

<210> SEQ ID NO 1127
<211> LENGTH: 12
<212> TYPE: PRT
<213> ORGANISM: artificial sequence
<220> FEATURE:
<223> OTHER INFORMATION: synthetic peptide

<400> SEQUENCE: 1127

Leu Glu Gly Asp Lys Val Trp Leu Glu Val Arg Ser
1               5                   10

<210> SEQ ID NO 1128
<211> LENGTH: 12
<212> TYPE: PRT
<213> ORGANISM: artificial sequence
<220> FEATURE:
<223> OTHER INFORMATION: synthetic peptide

<400> SEQUENCE: 1128

Ile Glu Val Asp Lys Val Gln His Asp Leu Leu Ser
1               5                   10

<210> SEQ ID NO 1129
<211> LENGTH: 12
<212> TYPE: PRT
<213> ORGANISM: artificial sequence
<220> FEATURE:
<223> OTHER INFORMATION: synthetic peptide

<400> SEQUENCE: 1129

Phe Asp Glu His Lys Leu Trp Tyr Glu Leu Ala Ala
1               5                   10

<210> SEQ ID NO 1130
<211> LENGTH: 12
<212> TYPE: PRT
<213> ORGANISM: artificial sequence
<220> FEATURE:
<223> OTHER INFORMATION: synthetic peptide

<400> SEQUENCE: 1130

Leu Asp Val Asp Lys Phe Arg Glu Glu Val Ala Ser
1               5                   10

<210> SEQ ID NO 1131
<211> LENGTH: 12
<212> TYPE: PRT
<213> ORGANISM: artificial sequence
<220> FEATURE:
<223> OTHER INFORMATION: synthetic peptide

<400> SEQUENCE: 1131

Leu Glu Arg Asn Lys Val Trp Tyr Glu Ile Lys Ala
1               5                   10

<210> SEQ ID NO 1132
<211> LENGTH: 12
<212> TYPE: PRT
<213> ORGANISM: artificial sequence
<220> FEATURE:
<223> OTHER INFORMATION: synthetic peptide

<400> SEQUENCE: 1132

Ile Glu Val Asp Lys Ser Trp Leu Glu Leu Arg Ser
1               5                   10

<210> SEQ ID NO 1133
<211> LENGTH: 12
<212> TYPE: PRT
<213> ORGANISM: artificial sequence
<220> FEATURE:
<223> OTHER INFORMATION: synthetic peptide

<400> SEQUENCE: 1133

Met Glu Leu Asp Lys Ala Trp Val Glu Val Trp Ser
1               5                   10

<210> SEQ ID NO 1134
<211> LENGTH: 12
<212> TYPE: PRT
<213> ORGANISM: artificial sequence
<220> FEATURE:
<223> OTHER INFORMATION: synthetic peptide

<400> SEQUENCE: 1134

Ile Asp Ile Asp Lys Ile Trp Tyr Glu Phe Gly Ser

```
1               5                  10
```

<210> SEQ ID NO 1135
<211> LENGTH: 12
<212> TYPE: PRT
<213> ORGANISM: artificial sequence
<220> FEATURE:
<223> OTHER INFORMATION: synthetic peptide

<400> SEQUENCE: 1135

```
Phe Glu Asn Asp Lys Ile Trp His Asp Ile Trp Ala
1               5                  10
```

<210> SEQ ID NO 1136
<211> LENGTH: 12
<212> TYPE: PRT
<213> ORGANISM: artificial sequence
<220> FEATURE:
<223> OTHER INFORMATION: synthetic peptide

<400> SEQUENCE: 1136

```
Ile Gln Gly Asp Lys Ile Trp Thr Glu Leu Asp Ser
1               5                  10
```

<210> SEQ ID NO 1137
<211> LENGTH: 12
<212> TYPE: PRT
<213> ORGANISM: artificial sequence
<220> FEATURE:
<223> OTHER INFORMATION: synthetic peptide

<400> SEQUENCE: 1137

```
Phe Glu Tyr Asp Lys Val Trp Val Asp Leu Pro Ala
1               5                  10
```

<210> SEQ ID NO 1138
<211> LENGTH: 12
<212> TYPE: PRT
<213> ORGANISM: artificial sequence
<220> FEATURE:
<223> OTHER INFORMATION: synthetic peptide

<400> SEQUENCE: 1138

```
Phe Glu Leu Asp Lys Val Trp Phe Asp Val Asp Ser
1               5                  10
```

<210> SEQ ID NO 1139
<211> LENGTH: 12
<212> TYPE: PRT
<213> ORGANISM: artificial sequence
<220> FEATURE:
<223> OTHER INFORMATION: synthetic peptide

<400> SEQUENCE: 1139

```
Phe Glu Ile Asp Lys Val Trp His Asp Phe Pro Ala
1               5                  10
```

<210> SEQ ID NO 1140
<211> LENGTH: 12
<212> TYPE: PRT
<213> ORGANISM: artificial sequence
<220> FEATURE:
<223> OTHER INFORMATION: synthetic peptide

<400> SEQUENCE: 1140

```
Phe Glu His Glu Lys Val Trp Tyr Asp Leu Cys Ala
1               5                  10
```

```
<210> SEQ ID NO 1141
<211> LENGTH: 12
<212> TYPE: PRT
<213> ORGANISM: artificial sequence
<220> FEATURE:
<223> OTHER INFORMATION: synthetic peptide

<400> SEQUENCE: 1141

Phe Glu Ile Asn Lys Val Trp Phe Glu Leu Leu Ala
1               5                   10

<210> SEQ ID NO 1142
<211> LENGTH: 12
<212> TYPE: PRT
<213> ORGANISM: artificial sequence
<220> FEATURE:
<223> OTHER INFORMATION: synthetic peptide

<400> SEQUENCE: 1142

Val Glu His Asp Lys Val Phe Tyr Glu Phe Asp Ser
1               5                   10

<210> SEQ ID NO 1143
<211> LENGTH: 12
<212> TYPE: PRT
<213> ORGANISM: artificial sequence
<220> FEATURE:
<223> OTHER INFORMATION: synthetic peptide

<400> SEQUENCE: 1143

Ile Glu Ile Asp Lys Val Trp His Asp Leu Tyr Ser
1               5                   10

<210> SEQ ID NO 1144
<211> LENGTH: 12
<212> TYPE: PRT
<213> ORGANISM: artificial sequence
<220> FEATURE:
<223> OTHER INFORMATION: synthetic peptide

<400> SEQUENCE: 1144

Leu Glu Ile Asp Lys Val Trp His Glu Leu Asp Ser
1               5                   10

<210> SEQ ID NO 1145
<211> LENGTH: 12
<212> TYPE: PRT
<213> ORGANISM: artificial sequence
<220> FEATURE:
<223> OTHER INFORMATION: synthetic peptide

<400> SEQUENCE: 1145

Ile Glu Leu Tyr Lys Val Trp Tyr Glu Ile Asp Ala
1               5                   10

<210> SEQ ID NO 1146
<211> LENGTH: 12
<212> TYPE: PRT
<213> ORGANISM: artificial sequence
<220> FEATURE:
<223> OTHER INFORMATION: synthetic peptide

<400> SEQUENCE: 1146

Leu Glu Glu Asp Lys Ile Trp Tyr Glu Phe Glu Ala
1               5                   10

<210> SEQ ID NO 1147
```

```
<211> LENGTH: 12
<212> TYPE: PRT
<213> ORGANISM: artificial sequence
<220> FEATURE:
<223> OTHER INFORMATION: synthetic peptide

<400> SEQUENCE: 1147

Val Glu Arg Asp Lys Val Trp Tyr Asp Ile Ser Ser
1               5                   10

<210> SEQ ID NO 1148
<211> LENGTH: 12
<212> TYPE: PRT
<213> ORGANISM: artificial sequence
<220> FEATURE:
<223> OTHER INFORMATION: synthetic peptide

<400> SEQUENCE: 1148

Met Glu Arg Ala Lys Val Trp Tyr Glu Leu Glu Ala
1               5                   10

<210> SEQ ID NO 1149
<211> LENGTH: 4
<212> TYPE: PRT
<213> ORGANISM: artificial sequence
<220> FEATURE:
<223> OTHER INFORMATION: synthetic peptide

<400> SEQUENCE: 1149

Leu Asp His Asn
1

<210> SEQ ID NO 1150
<211> LENGTH: 7
<212> TYPE: PRT
<213> ORGANISM: artificial sequence
<220> FEATURE:
<223> OTHER INFORMATION: synthetic peptide

<400> SEQUENCE: 1150

Ile Phe His Glu Ile Glu Ser
1               5

<210> SEQ ID NO 1151
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (3)..(3)
<223> OTHER INFORMATION: Any amino acid
<220> FEATURE:
<221> NAME/KEY: MISC_FEATURE
<222> LOCATION: (4)..(4)
<223> OTHER INFORMATION: Any amino acid
<220> FEATURE:
<221> NAME/KEY: MISC_FEATURE
<222> LOCATION: (8)..(8)
<223> OTHER INFORMATION: Any amino acid
<220> FEATURE:
<221> NAME/KEY: MISC_FEATURE
<222> LOCATION: (9)..(9)
<223> OTHER INFORMATION: Glutamic acid or aspartic acid
<220> FEATURE:
<221> NAME/KEY: MISC_FEATURE
<222> LOCATION: (10)..(10)
<223> OTHER INFORMATION: Hydrophobic Residue

<400> SEQUENCE: 1151
```

-continued

Phe Glu Xaa Xaa Lys Val Trp Xaa Xaa Xaa
1               5                   10

<210> SEQ ID NO 1152
<211> LENGTH: 9
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (3)..(3)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (8)..(8)
<223> OTHER INFORMATION: Glutamic acid or aspartic acid
<220> FEATURE:
<221> NAME/KEY: MISC_FEATURE
<222> LOCATION: (9)..(9)
<223> OTHER INFORMATION: Hydrophobic Residue

<400> SEQUENCE: 1152

Glu Xaa Xaa Lys Val Trp Xaa Xaa Xaa
1               5

<210> SEQ ID NO 1153
<211> LENGTH: 9
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (3)..(3)
<223> OTHER INFORMATION: Any amino acid
<220> FEATURE:
<221> NAME/KEY: MISC_FEATURE
<222> LOCATION: (4)..(4)
<223> OTHER INFORMATION: Any amino acid
<220> FEATURE:
<221> NAME/KEY: MISC_FEATURE
<222> LOCATION: (8)..(8)
<223> OTHER INFORMATION: Any amino acid
<220> FEATURE:
<221> NAME/KEY: MISC_FEATURE
<222> LOCATION: (9)..(9)
<223> OTHER INFORMATION: Glutamic acid or aspartic acid

<400> SEQUENCE: 1153

Phe Glu Xaa Xaa Lys Val Trp Xaa Xaa
1               5

<210> SEQ ID NO 1154
<211> LENGTH: 8
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (3)..(3)
<223> OTHER INFORMATION: Any amino acid

```
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (8)..(8)
<223> OTHER INFORMATION: Glutamic acid or aspartic acid

<400> SEQUENCE: 1154

Glu Xaa Xaa Lys Val Trp Xaa Xaa
1               5

<210> SEQ ID NO 1155
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: hydrophobic or aromatic residue
<220> FEATURE:
<221> NAME/KEY: MISC_FEATURE
<222> LOCATION: (2)..(2)
<223> OTHER INFORMATION: glutamic acid or aspartic acid residue
<220> FEATURE:
<221> NAME/KEY: MISC_FEATURE
<222> LOCATION: (3)..(3)
<223> OTHER INFORMATION: Any amino acid
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: hydrophobic or serine residue
<220> FEATURE:
<221> NAME/KEY: MISC_FEATURE
<222> LOCATION: (7)..(7)
<223> OTHER INFORMATION: aromatic residue
<220> FEATURE:
<221> NAME/KEY: MISC_FEATURE
<222> LOCATION: (8)..(8)
<223> OTHER INFORMATION: an aromatic, aliphatic hydrophobic, histidine
      or theronine residue
<220> FEATURE:
<221> NAME/KEY: MISC_FEATURE
<222> LOCATION: (9)..(9)
<223> OTHER INFORMATION: a glutamic acid or aspartic acid residue
<220> FEATURE:
<221> NAME/KEY: MISC_FEATURE
<222> LOCATION: (10)..(10)
<223> OTHER INFORMATION: an aliphatic hydrophobic residue

<400> SEQUENCE: 1155

Xaa Xaa Xaa Xaa Lys Xaa Xaa Xaa Xaa Xaa
1               5                   10

<210> SEQ ID NO 1156
<211> LENGTH: 9
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: glutamic acid or aspartic acid residue
<220> FEATURE:
<221> NAME/KEY: MISC_FEATURE
<222> LOCATION: (2)..(2)
<223> OTHER INFORMATION: Any Amino Acid
```

```
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (5)..(5)
<223> OTHER INFORMATION: hydrophobic and serine residue
<220> FEATURE:
<221> NAME/KEY: MISC_FEATURE
<222> LOCATION: (6)..(6)
<223> OTHER INFORMATION: aromatic residue
<220> FEATURE:
<221> NAME/KEY: MISC_FEATURE
<222> LOCATION: (7)..(7)
<223> OTHER INFORMATION: aromatic, aliphatic hydrophobic, histidine,
      theronine residue
<220> FEATURE:
<221> NAME/KEY: MISC_FEATURE
<222> LOCATION: (8)..(8)
<223> OTHER INFORMATION: glutamic acid or aspartic acid residue
<220> FEATURE:
<221> NAME/KEY: MISC_FEATURE
<222> LOCATION: (9)..(9)
<223> OTHER INFORMATION: aliphatic hydrophobic residue

<400> SEQUENCE: 1156

Xaa Xaa Xaa Lys Xaa Xaa Xaa Xaa Xaa
1               5

<210> SEQ ID NO 1157
<211> LENGTH: 9
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: hydrophobic or aromatic residue
<220> FEATURE:
<221> NAME/KEY: MISC_FEATURE
<222> LOCATION: (2)..(2)
<223> OTHER INFORMATION: glutamic acid or aspartic acid residue
<220> FEATURE:
<221> NAME/KEY: MISC_FEATURE
<222> LOCATION: (3)..(3)
<223> OTHER INFORMATION: Any Amino Acid
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: hydrophobic or serine residue
<220> FEATURE:
<221> NAME/KEY: MISC_FEATURE
<222> LOCATION: (7)..(7)
<223> OTHER INFORMATION: aromatic residue
<220> FEATURE:
<221> NAME/KEY: MISC_FEATURE
<222> LOCATION: (8)..(8)
<223> OTHER INFORMATION: aromatic, aliphatic hydrophobic, histidine,
      theronine residue
<220> FEATURE:
<221> NAME/KEY: MISC_FEATURE
<222> LOCATION: (9)..(9)
<223> OTHER INFORMATION: glutamic acid or aspartic acid residue

<400> SEQUENCE: 1157

Xaa Xaa Xaa Xaa Lys Xaa Xaa Xaa Xaa
1               5
```

```
<210> SEQ ID NO 1158
<211> LENGTH: 8
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: glutamic acid or aspartic acid residue
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (5)..(5)
<223> OTHER INFORMATION: hydrophobic or serine residue
<220> FEATURE:
<221> NAME/KEY: MISC_FEATURE
<222> LOCATION: (6)..(6)
<223> OTHER INFORMATION: aromatic residue
<220> FEATURE:
<221> NAME/KEY: MISC_FEATURE
<222> LOCATION: (7)..(7)
<223> OTHER INFORMATION: aromatic, aliphatic hydrophobic, histidine,
      theronine residue
<220> FEATURE:
<221> NAME/KEY: MISC_FEATURE
<222> LOCATION: (8)..(8)
<223> OTHER INFORMATION: a glutamic acid or aspartic acid residue

<400> SEQUENCE: 1158

Xaa Xaa Xaa Lys Xaa Xaa Xaa Xaa
1               5

<210> SEQ ID NO 1159
<211> LENGTH: 13
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (3)..(3)
<223> OTHER INFORMATION: Any amino acid
<220> FEATURE:
<221> NAME/KEY: MISC_FEATURE
<222> LOCATION: (4)..(4)
<223> OTHER INFORMATION: Any amino acid
<220> FEATURE:
<221> NAME/KEY: MISC_FEATURE
<222> LOCATION: (5)..(5)
<223> OTHER INFORMATION: Any amino acid
<220> FEATURE:
<221> NAME/KEY: MISC_FEATURE
<222> LOCATION: (6)..(6)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (8)..(8)
<223> OTHER INFORMATION: Any amino acid
<220> FEATURE:
<221> NAME/KEY: MISC_FEATURE
<222> LOCATION: (9)..(9)
```

```
<223> OTHER INFORMATION: Any amino acid
<220> FEATURE:
<221> NAME/KEY: MISC_FEATURE
<222> LOCATION: (10)..(10)
<223> OTHER INFORMATION: Any amino acid
<220> FEATURE:
<221> NAME/KEY: MISC_FEATURE
<222> LOCATION: (11)..(11)
<223> OTHER INFORMATION: Any amino acid
<220> FEATURE:
<221> NAME/KEY: MISC_FEATURE
<222> LOCATION: (12)..(12)
<223> OTHER INFORMATION: Any amino acid
<220> FEATURE:
<221> NAME/KEY: MISC_FEATURE
<222> LOCATION: (13)..(13)
<223> OTHER INFORMATION: a serine residue or an alanine residue

<400> SEQUENCE: 1159

Gly Xaa Xaa Xaa Xaa Xaa Xaa Xaa Xaa Xaa Xaa Xaa Xaa
1               5                   10

<210> SEQ ID NO 1160
<211> LENGTH: 12
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any Amino Acid
<220> FEATURE:
<221> NAME/KEY: MISC_FEATURE
<222> LOCATION: (2)..(2)
<223> OTHER INFORMATION: Any Amino Acid
<220> FEATURE:
<221> NAME/KEY: MISC_FEATURE
<222> LOCATION: (3)..(3)
<223> OTHER INFORMATION: Any Amino Acid
<220> FEATURE:
<221> NAME/KEY: MISC_FEATURE
<222> LOCATION: (4)..(4)
<223> OTHER INFORMATION: Any Amino Acid
<220> FEATURE:
<221> NAME/KEY: MISC_FEATURE
<222> LOCATION: (5)..(5)
<223> OTHER INFORMATION: Any Amino Acid
<220> FEATURE:
<221> NAME/KEY: MISC_FEATURE
<222> LOCATION: (6)..(6)
<223> OTHER INFORMATION: Any Amino Acid
<220> FEATURE:
<221> NAME/KEY: MISC_FEATURE
<222> LOCATION: (7)..(7)
<223> OTHER INFORMATION: Any Amino Acid
<220> FEATURE:
<221> NAME/KEY: MISC_FEATURE
<222> LOCATION: (8)..(8)
<223> OTHER INFORMATION: Any Amino Acid
<220> FEATURE:
<221> NAME/KEY: MISC_FEATURE
<222> LOCATION: (9)..(9)
<223> OTHER INFORMATION: Any Amino Acid
<220> FEATURE:
<221> NAME/KEY: MISC_FEATURE
<222> LOCATION: (10)..(10)
<223> OTHER INFORMATION: Any Amino Acid
<220> FEATURE:
<221> NAME/KEY: MISC_FEATURE
<222> LOCATION: (11)..(11)
<223> OTHER INFORMATION: Any Amino Acid
<220> FEATURE:
<221> NAME/KEY: MISC_FEATURE
<222> LOCATION: (12)..(12)
<223> OTHER INFORMATION: a serine residue or an alanine residue

<400> SEQUENCE: 1160
```

Xaa Xaa Xaa Xaa Xaa Xaa Xaa Xaa Xaa Xaa Xaa
1               5                   10

<210> SEQ ID NO 1161
<211> LENGTH: 12
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (3)..(3)
<223> OTHER INFORMATION: Any amino acid
<220> FEATURE:
<221> NAME/KEY: MISC_FEATURE
<222> LOCATION: (4)..(4)
<223> OTHER INFORMATION: Any amino acid
<220> FEATURE:
<221> NAME/KEY: MISC_FEATURE
<222> LOCATION: (5)..(5)
<223> OTHER INFORMATION: Any amino acid
<220> FEATURE:
<221> NAME/KEY: MISC_FEATURE
<222> LOCATION: (6)..(6)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (8)..(8)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid
<220> FEATURE:
<221> NAME/KEY: MISC_FEATURE
<222> LOCATION: (10)..(10)
<223> OTHER INFORMATION: Any amino acid
<220> FEATURE:
<221> NAME/KEY: MISC_FEATURE
<222> LOCATION: (11)..(11)
<223> OTHER INFORMATION: Any amino acid
<220> FEATURE:
<221> NAME/KEY: MISC_FEATURE
<222> LOCATION: (12)..(12)
<223> OTHER INFORMATION: Any amino acid

<400> SEQUENCE: 1161

Gly Xaa Xaa Xaa Xaa Xaa Xaa Xaa Xaa Xaa Xaa Xaa
1               5                   10

<210> SEQ ID NO 1162
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any amino acid
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (3)..(3)
<223> OTHER INFORMATION: Any amino acid

```
<220> FEATURE:
<221> NAME/KEY: MISC_FEATURE
<222> LOCATION: (4)..(4)
<223> OTHER INFORMATION: Any amino acid
<220> FEATURE:
<221> NAME/KEY: MISC_FEATURE
<222> LOCATION: (5)..(5)
<223> OTHER INFORMATION: Any amino acid
<220> FEATURE:
<221> NAME/KEY: MISC_FEATURE
<222> LOCATION: (6)..(6)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (8)..(8)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid
<220> FEATURE:
<221> NAME/KEY: MISC_FEATURE
<222> LOCATION: (10)..(10)
<223> OTHER INFORMATION: Any amino acid
<220> FEATURE:
<221> NAME/KEY: MISC_FEATURE
<222> LOCATION: (11)..(11)
<223> OTHER INFORMATION: Any amino acid

<400> SEQUENCE: 1162

Xaa Xaa Xaa Xaa Xaa Xaa Xaa Xaa Xaa Xaa Xaa
1               5                   10

<210> SEQ ID NO 1163
<211> LENGTH: 13
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any amino acid or glycine
<220> FEATURE:
<221> NAME/KEY: MISC_FEATURE
<222> LOCATION: (2)..(2)
<223> OTHER INFORMATION: a hydrophobic residue such as phenylalanine,
      isoleucine, valine or leucine or an aromatic residue
<220> FEATURE:
<221> NAME/KEY: MISC_FEATURE
<222> LOCATION: (3)..(3)
<223> OTHER INFORMATION: a negatively charged residue such as glutamic
      acid or aspartic acid
<220> FEATURE:
<221> NAME/KEY: MISC_FEATURE
<222> LOCATION: (4)..(4)
<223> OTHER INFORMATION: any amino acid or an isoleucine, histidine,
      leucine or arginine residue
<220> FEATURE:
<221> NAME/KEY: MISC_FEATURE
<222> LOCATION: (5)..(5)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (7)..(7)
<223> OTHER INFORMATION: hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (8)..(8)
<223> OTHER INFORMATION: an aromatic residue such as a tryptophan or
      phenylalanine residue
```

-continued

```
<220> FEATURE:
<221> NAME/KEY: MISC_FEATURE
<222> LOCATION: (9)..(9)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (10)..(10)
<223> OTHER INFORMATION: a negatively charged residue such as aspartic
      acid or glutamic acid
<220> FEATURE:
<221> NAME/KEY: MISC_FEATURE
<222> LOCATION: (11)..(11)
<223> OTHER INFORMATION: an aliphatic hydrophobic residue such as
      leucine, isoleucine or phenylalanineor a small residue such as
      valine
<220> FEATURE:
<221> NAME/KEY: MISC_FEATURE
<222> LOCATION: (12)..(12)
<223> OTHER INFORMATION: any residue or a negatively charged residue
      such as glutamic acid or aspartic acid, or a hydroxyl/thiol
      containing residue such as serine, threonine, cysteine or
      tyrosine, or a proline residue
<220> FEATURE:
<221> NAME/KEY: MISC_FEATURE
<222> LOCATION: (13)..(13)
<223> OTHER INFORMATION: a serine or alanine residue

<400> SEQUENCE: 1163

Xaa Xaa Xaa Xaa Xaa Lys Xaa Xaa Xaa Xaa Xaa Xaa Xaa
1               5                   10

<210> SEQ ID NO 1164
<211> LENGTH: 12
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any amino acid or a glycine residue
<220> FEATURE:
<221> NAME/KEY: MISC_FEATURE
<222> LOCATION: (2)..(2)
<223> OTHER INFORMATION: a hydrophobic residue such as phenylalanine,
      isoleucine, valine or leucine or an aromatic residue
<220> FEATURE:
<221> NAME/KEY: MISC_FEATURE
<222> LOCATION: (3)..(3)
<223> OTHER INFORMATION: a negatively charged residue such as glutamic
      acid or aspartic acid
<220> FEATURE:
<221> NAME/KEY: MISC_FEATURE
<222> LOCATION: (4)..(4)
<223> OTHER INFORMATION: any amino acid or an isoleucine, histidine,
      leucine or arginine residue
<220> FEATURE:
<221> NAME/KEY: MISC_FEATURE
<222> LOCATION: (5)..(5)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (7)..(7)
<223> OTHER INFORMATION: hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (8)..(8)
<223> OTHER INFORMATION: an aromatic residue such as a tryptophan or
      phenylalanine residue
<220> FEATURE:
<221> NAME/KEY: MISC_FEATURE
<222> LOCATION: (9)..(9)
<223> OTHER INFORMATION: an aliphatic hydrophobic residue such as an
```

-continued isoleucine, valine, leucine or a threonine residue or an aromatic
    residue such as tyrosine, histidine or phenylalanine
<220> FEATURE:
<221> NAME/KEY: MISC_FEATURE
<222> LOCATION: (10)..(10)
<223> OTHER INFORMATION: a negatively charged residue such as aspartic
    acid or glutamic acid
<220> FEATURE:
<221> NAME/KEY: MISC_FEATURE
<222> LOCATION: (11)..(11)
<223> OTHER INFORMATION: an aliphatic hydrophobic residue such as
    leucine, isoleucine or phenylalanineor a small residue such as
    valine
<220> FEATURE:
<221> NAME/KEY: MISC_FEATURE
<222> LOCATION: (12)..(12)
<223> OTHER INFORMATION: any residue or a negatively charged residue
    such as glutamic acid or aspartic acid, or a hydroxyl/thiol
    containing residue such as serine, threonine, cysteine or
    tyrosine, or a proline residue

<400> SEQUENCE: 1164

Xaa Xaa Xaa Xaa Xaa Lys Xaa Xaa Xaa Xaa Xaa Xaa
1               5                   10

<210> SEQ ID NO 1165
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any amino acid or a glycine residue
<220> FEATURE:
<221> NAME/KEY: MISC_FEATURE
<222> LOCATION: (2)..(2)
<223> OTHER INFORMATION: a hydrophobic residue such as phenylalanine,
    isoleucine, valine or leucine or an aromatic residue
<220> FEATURE:
<221> NAME/KEY: MISC_FEATURE
<222> LOCATION: (3)..(3)
<223> OTHER INFORMATION: a negatively charged residue such as glutamic
    acid or aspartic acid
<220> FEATURE:
<221> NAME/KEY: MISC_FEATURE
<222> LOCATION: (4)..(4)
<223> OTHER INFORMATION: any amino acid or an isoleucine, histidine,
    leucine or arginine residue
<220> FEATURE:
<221> NAME/KEY: MISC_FEATURE
<222> LOCATION: (5)..(5)
<223> OTHER INFORMATION: an aspartic acid, asparagine, glutamic acid,
    tyrosine or alanine residue
<220> FEATURE:
<221> NAME/KEY: MISC_FEATURE
<222> LOCATION: (7)..(7)
<223> OTHER INFORMATION: a hydrophobic residue or valine, isoleucine,
    leucine or phenylalanine or a small residue such as alanine or
    serine, or a non-charged residue
<220> FEATURE:
<221> NAME/KEY: MISC_FEATURE
<222> LOCATION: (8)..(8)
<223> OTHER INFORMATION: an aromatic residue such as a tryptophan or
    phenylalanine residue
<220> FEATURE:
<221> NAME/KEY: MISC_FEATURE
<222> LOCATION: (9)..(9)
<223> OTHER INFORMATION: an aliphatic hydrophobic residue such as an
    isoleucine, valine, leucine or a threonine residue or an aromatic
    residue such as tyrosine, histidine or phenylalanine
<220> FEATURE:
<221> NAME/KEY: MISC_FEATURE
<222> LOCATION: (10)..(10)
<223> OTHER INFORMATION: a negatively charged residue such as aspartic
    acid or glutamic acid
<220> FEATURE:

```
<221> NAME/KEY: MISC_FEATURE
<222> LOCATION: (11)..(11)
<223> OTHER INFORMATION: an aliphatic hydrophobic residue such as
      leucine, isoleucine or phenylalanineor a small residue such as
      valine

<400> SEQUENCE: 1165

Xaa Xaa Xaa Xaa Xaa Lys Xaa Xaa Xaa Xaa Xaa
1               5                   10

<210> SEQ ID NO 1166
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any amino acid or a glycine residue
<220> FEATURE:
<221> NAME/KEY: MISC_FEATURE
<222> LOCATION: (2)..(2)
<223> OTHER INFORMATION: a hydrophobic residue such as phenylalanine,
      isoleucine, valine or leucine or an aromatic residue
<220> FEATURE:
<221> NAME/KEY: MISC_FEATURE
<222> LOCATION: (3)..(3)
<223> OTHER INFORMATION: a negatively charged residue such as glutamic
      acid or aspartic acid
<220> FEATURE:
<221> NAME/KEY: MISC_FEATURE
<222> LOCATION: (4)..(4)
<223> OTHER INFORMATION: any amino acid or an isoleucine, histidine,
      leucine or arginine residue
<220> FEATURE:
<221> NAME/KEY: MISC_FEATURE
<222> LOCATION: (5)..(5)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (7)..(7)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (8)..(8)
<223> OTHER INFORMATION: an aromatic residue such as a tryptophan or
      phenylalanine residue
<220> FEATURE:
<221> NAME/KEY: MISC_FEATURE
<222> LOCATION: (9)..(9)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (10)..(10)
<223> OTHER INFORMATION: a negatively charged residue such as aspartic
      acid or glutamic acid

<400> SEQUENCE: 1166

Xaa Xaa Xaa Xaa Xaa Lys Xaa Xaa Xaa Xaa
1               5                   10

<210> SEQ ID NO 1167
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
```

-continued

```
<223> OTHER INFORMATION: Any amino acid or a glycine residue
<220> FEATURE:
<221> NAME/KEY: MISC_FEATURE
<222> LOCATION: (2)..(2)
<223> OTHER INFORMATION: a hydrophobic residue such as phenylalanine,
      isoleucine, valine or leucine or an aromatic residue
<220> FEATURE:
<221> NAME/KEY: MISC_FEATURE
<222> LOCATION: (3)..(3)
<223> OTHER INFORMATION: a negatively charged residue such as glutamic
      acid or aspartic acid
<220> FEATURE:
<221> NAME/KEY: MISC_FEATURE
<222> LOCATION: (4)..(4)
<223> OTHER INFORMATION: any amino acid or an isoleucine, histidine,
      leucine or arginine residue
<220> FEATURE:
<221> NAME/KEY: MISC_FEATURE
<222> LOCATION: (5)..(5)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (7)..(7)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (8)..(8)
<223> OTHER INFORMATION: an aromatic residue such as a tryptophan or
      phenylalanine residue
<220> FEATURE:
<221> NAME/KEY: MISC_FEATURE
<222> LOCATION: (9)..(9)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (10)..(10)
<223> OTHER INFORMATION: a negatively charged residue such as aspartic
      acid or glutamic acid
<220> FEATURE:
<221> NAME/KEY: MISC_FEATURE
<222> LOCATION: (11)..(11)
<223> OTHER INFORMATION: a serine or alanine residue

<400> SEQUENCE: 1167

Xaa Xaa Xaa Xaa Xaa Lys Xaa Xaa Xaa Xaa Xaa
1               5                   10

<210> SEQ ID NO 1168
<211> LENGTH: 12
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any amino acid or a glycine residue
<220> FEATURE:
<221> NAME/KEY: MISC_FEATURE
<222> LOCATION: (2)..(2)
<223> OTHER INFORMATION: a hydrophobic residue such as phenylalanine,
      isoleucine, valine or leucine or an aromatic residue
<220> FEATURE:
<221> NAME/KEY: MISC_FEATURE
<222> LOCATION: (3)..(3)
<223> OTHER INFORMATION: a negatively charged residue such as glutamic
      acid or aspartic acid
<220> FEATURE:
<221> NAME/KEY: MISC_FEATURE
<222> LOCATION: (4)..(4)
<223> OTHER INFORMATION: any amino acid or an isoleucine, histidine,
      leucine or arginine residue
<220> FEATURE:
```

```
<221> NAME/KEY: MISC_FEATURE
<222> LOCATION: (5)..(5)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (7)..(7)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (8)..(8)
<223> OTHER INFORMATION: an aromatic residue such as a tryptophan or
      phenylalanine residue
<220> FEATURE:
<221> NAME/KEY: MISC_FEATURE
<222> LOCATION: (9)..(9)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (10)..(10)
<223> OTHER INFORMATION: a negatively charged residue such as aspartic
      acid or glutamic acid
<220> FEATURE:
<221> NAME/KEY: MISC_FEATURE
<222> LOCATION: (11)..(11)
<223> OTHER INFORMATION: any residue or a negatively charged residue
      such as glutamic acid or aspartic acid, or a hydroxyl/thiol
      containing residue such as serine, threonine, cysteine or
      tyrosine, or a proline residue
<220> FEATURE:
<221> NAME/KEY: MISC_FEATURE
<222> LOCATION: (12)..(12)
<223> OTHER INFORMATION: a serine or alanine residue

<400> SEQUENCE: 1168

Xaa Xaa Xaa Xaa Xaa Lys Xaa Xaa Xaa Xaa Xaa Xaa
1               5                   10

<210> SEQ ID NO 1169
<211> LENGTH: 12
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any amino acid or a glycine residue
<220> FEATURE:
<221> NAME/KEY: MISC_FEATURE
<222> LOCATION: (2)..(2)
<223> OTHER INFORMATION: a hydrophobic residue such as phenylalanine,
      isoleucine, valine or leucine or an aromatic residue
<220> FEATURE:
<221> NAME/KEY: MISC_FEATURE
<222> LOCATION: (3)..(3)
<223> OTHER INFORMATION: a negatively charged residue such as glutamic
      acid or aspartic acid
<220> FEATURE:
<221> NAME/KEY: MISC_FEATURE
<222> LOCATION: (4)..(4)
<223> OTHER INFORMATION: any amino acid or an isoleucine, histidine,
      leucine or arginine residue
<220> FEATURE:
<221> NAME/KEY: MISC_FEATURE
<222> LOCATION: (5)..(5)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (7)..(7)
<223> OTHER INFORMATION: a hydrophobic residue or valine, isoleucine,
      leucine or phenylalanine or a small residue such as alanine or
      serine, or a non-charged residue
```

```
<220> FEATURE:
<221> NAME/KEY: MISC_FEATURE
<222> LOCATION: (8)..(8)
<223> OTHER INFORMATION: an aromatic residue such as a tryptophan or
      phenylalanine residue
<220> FEATURE:
<221> NAME/KEY: MISC_FEATURE
<222> LOCATION: (9)..(9)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (10)..(10)
<223> OTHER INFORMATION: a negatively charged residue such as aspartic
      acid or glutamic acid
<220> FEATURE:
<221> NAME/KEY: MISC_FEATURE
<222> LOCATION: (11)..(11)
<223> OTHER INFORMATION: an aliphatic hydrophobic residue such as
      leucine, isoleucine or phenylalanineor a small residue such as
      valine
<220> FEATURE:
<221> NAME/KEY: MISC_FEATURE
<222> LOCATION: (12)..(12)
<223> OTHER INFORMATION: a serine or alanine residue

<400> SEQUENCE: 1169

Xaa Xaa Xaa Xaa Xaa Lys Xaa Xaa Xaa Xaa Xaa Xaa
1               5                   10

<210> SEQ ID NO 1170
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any amino acid or a glycine residue
<220> FEATURE:
<221> NAME/KEY: MISC_FEATURE
<222> LOCATION: (2)..(2)
<223> OTHER INFORMATION: a hydrophobic residue such as phenylalanine,
      isoleucine, valine or leucine or an aromatic residue
<220> FEATURE:
<221> NAME/KEY: MISC_FEATURE
<222> LOCATION: (3)..(3)
<223> OTHER INFORMATION: a negatively charged residue such as glutamic
      acid or aspartic acid
<220> FEATURE:
<221> NAME/KEY: MISC_FEATURE
<222> LOCATION: (4)..(4)
<223> OTHER INFORMATION: any amino acid or an isoleucine, histidine,
      leucine or arginine residue
<220> FEATURE:
<221> NAME/KEY: MISC_FEATURE
<222> LOCATION: (5)..(5)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (7)..(7)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (8)..(8)
<223> OTHER INFORMATION: an aromatic residue such as a tryptophan or
      phenylalanine residue
<220> FEATURE:
<221> NAME/KEY: MISC_FEATURE
<222> LOCATION: (9)..(9)
<223> OTHER INFORMATION: an aliphatic hydrophobic residue such as an
      isoleucine, valine, leucine or a threonine residue or an aromatic
      residue such as tyrosine, histidine or phenylalanine
```

```
<220> FEATURE:
<221> NAME/KEY: MISC_FEATURE
<222> LOCATION: (10)..(10)
<223> OTHER INFORMATION: a negatively charged residue such as aspartic
      acid or glutamic acid
<220> FEATURE:
<221> NAME/KEY: MISC_FEATURE
<222> LOCATION: (11)..(11)
<223> OTHER INFORMATION: any residue or a negatively charged residue
      such as glutamic acid or aspartic acid, or a hydroxyl/thiol
      containing residue such as serine, threonine, cysteine or
      tyrosine, or a proline residue

<400> SEQUENCE: 1170

Xaa Xaa Xaa Xaa Xaa Lys Xaa Xaa Xaa Xaa Xaa
1               5                   10

<210> SEQ ID NO 1171
<211> LENGTH: 12
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a hydrophobic residue such as phenylalanine,
      isoleucine, valine or leucine or an aromatic residue
<220> FEATURE:
<221> NAME/KEY: MISC_FEATURE
<222> LOCATION: (2)..(2)
<223> OTHER INFORMATION: a negatively charged residue such as glutamic
      acid or aspartic acid
<220> FEATURE:
<221> NAME/KEY: MISC_FEATURE
<222> LOCATION: (3)..(3)
<223> OTHER INFORMATION: any amino acid or an isoleucine, histidine,
      leucine or arginine residue
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (7)..(7)
<223> OTHER INFORMATION: an aromatic residue such as a tryptophan or
      phenylalanine residue
<220> FEATURE:
<221> NAME/KEY: MISC_FEATURE
<222> LOCATION: (8)..(8)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (9)..(9)
<223> OTHER INFORMATION: a negatively charged residue such as aspartic
      acid or glutamic acid
<220> FEATURE:
<221> NAME/KEY: MISC_FEATURE
<222> LOCATION: (10)..(10)
<223> OTHER INFORMATION: an aliphatic hydrophobic residue such as
      leucine, isoleucine or phenylalanineor a small residue such as
      valine
<220> FEATURE:
<221> NAME/KEY: MISC_FEATURE
<222> LOCATION: (11)..(11)
<223> OTHER INFORMATION: any residue or a negatively charged residue
      such as glutamic acid or aspartic acid, or a hydroxyl/thiol
      containing residue such as serine, threonine, cysteine or
      tyrosine, or a proline residue
```

```
<220> FEATURE:
<221> NAME/KEY: MISC_FEATURE
<222> LOCATION: (12)..(12)
<223> OTHER INFORMATION: a serine or alanine residue

<400> SEQUENCE: 1171

Xaa Xaa Xaa Xaa Lys Xaa Xaa Xaa Xaa Xaa Xaa Xaa
1               5                   10

<210> SEQ ID NO 1172
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a hydrophobic residue such as phenylalanine,
      isoleucine, valine or leucine or an aromatic residue
<220> FEATURE:
<221> NAME/KEY: MISC_FEATURE
<222> LOCATION: (2)..(2)
<223> OTHER INFORMATION: a negatively charged residue such as glutamic
      acid or aspartic acid
<220> FEATURE:
<221> NAME/KEY: MISC_FEATURE
<222> LOCATION: (3)..(3)
<223> OTHER INFORMATION: any amino acid or an isoleucine, histidine,
      leucine or arginine residue
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (7)..(7)
<223> OTHER INFORMATION: an aromatic residue such as a tryptophan or
      phenylalanine residue
<220> FEATURE:
<221> NAME/KEY: MISC_FEATURE
<222> LOCATION: (8)..(8)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (9)..(9)
<223> OTHER INFORMATION: a negatively charged residue such as aspartic
      acid or glutamic acid
<220> FEATURE:
<221> NAME/KEY: MISC_FEATURE
<222> LOCATION: (10)..(10)
<223> OTHER INFORMATION: any residue or a negatively charged residue
      such as glutamic acid or aspartic acid, or a hydroxyl/thiol
      containing residue such as serine, threonine, cysteine or
      tyrosine, or a proline residue
<220> FEATURE:
<221> NAME/KEY: MISC_FEATURE
<222> LOCATION: (11)..(11)
<223> OTHER INFORMATION: any residue or a negatively charged residue
      such as glutamic acid or aspartic acid, or a hydroxyl/thiol
      containing residue such as serine, threonine, cysteine or
      tyrosine, or a proline residue

<400> SEQUENCE: 1172

Xaa Xaa Xaa Xaa Lys Xaa Xaa Xaa Xaa Xaa Xaa
1               5                   10
```

-continued

```
<210> SEQ ID NO 1173
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a hydrophobic residue such as phenylalanine,
      isoleucine, valine or leucine or an aromatic residue
<220> FEATURE:
<221> NAME/KEY: MISC_FEATURE
<222> LOCATION: (2)..(2)
<223> OTHER INFORMATION: a negatively charged residue such as glutamic
      acid or aspartic acid
<220> FEATURE:
<221> NAME/KEY: MISC_FEATURE
<222> LOCATION: (3)..(3)
<223> OTHER INFORMATION: any amino acid or an isoleucine, histidine,
      leucine or arginine residue
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (7)..(7)
<223> OTHER INFORMATION: an aromatic residue such as a tryptophan or
      phenylalanine residue
<220> FEATURE:
<221> NAME/KEY: MISC_FEATURE
<222> LOCATION: (8)..(8)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (9)..(9)
<223> OTHER INFORMATION: a negatively charged residue such as aspartic
      acid or glutamic acid
<220> FEATURE:
<221> NAME/KEY: MISC_FEATURE
<222> LOCATION: (10)..(10)
<223> OTHER INFORMATION: an aliphatic hydrophobic residue such as
      leucine, isoleucine or phenylalanineor a small residue such as
      valine

<400> SEQUENCE: 1173

Xaa Xaa Xaa Xaa Lys Xaa Xaa Xaa Xaa Xaa
1               5                   10

<210> SEQ ID NO 1174
<211> LENGTH: 9
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a hydrophobic residue such as phenylalanine,
      isoleucine, valine or leucine or an aromatic residue
<220> FEATURE:
<221> NAME/KEY: MISC_FEATURE
<222> LOCATION: (2)..(2)
<223> OTHER INFORMATION: a negatively charged residue such as glutamic
      acid or aspartic acid
<220> FEATURE:
<221> NAME/KEY: MISC_FEATURE
<222> LOCATION: (3)..(3)
```

```
<223> OTHER INFORMATION: any amino acid or an isoleucine, histidine,
      leucine or arginine residue
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (7)..(7)
<223> OTHER INFORMATION: an aromatic residue such as a tryptophan or
      phenylalanine residue
<220> FEATURE:
<221> NAME/KEY: MISC_FEATURE
<222> LOCATION: (8)..(8)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (9)..(9)
<223> OTHER INFORMATION: a negatively charged residue such as aspartic
      acid or glutamic acid

<400> SEQUENCE: 1174

Xaa Xaa Xaa Xaa Lys Xaa Xaa Xaa Xaa
1               5

<210> SEQ ID NO 1175
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a hydrophobic residue such as phenylalanine,
      isoleucine, valine or leucine or an aromatic residue
<220> FEATURE:
<221> NAME/KEY: MISC_FEATURE
<222> LOCATION: (2)..(2)
<223> OTHER INFORMATION: a negatively charged residue such as glutamic
      acid or aspartic acid
<220> FEATURE:
<221> NAME/KEY: MISC_FEATURE
<222> LOCATION: (3)..(3)
<223> OTHER INFORMATION: any amino acid or an isoleucine, histidine,
      leucine or arginine residue
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (7)..(7)
<223> OTHER INFORMATION: an aromatic residue such as a tryptophan or
      phenylalanine residue
<220> FEATURE:
<221> NAME/KEY: MISC_FEATURE
<222> LOCATION: (8)..(8)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
```

```
<221> NAME/KEY: MISC_FEATURE
<222> LOCATION: (9)..(9)
<223> OTHER INFORMATION: a negatively charged residue such as aspartic
      acid or glutamic acid
<220> FEATURE:
<221> NAME/KEY: MISC_FEATURE
<222> LOCATION: (10)..(10)
<223> OTHER INFORMATION: a serine or alanine residue

<400> SEQUENCE: 1175

Xaa Xaa Xaa Xaa Lys Xaa Xaa Xaa Xaa Xaa
1               5                   10

<210> SEQ ID NO 1176
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a hydrophobic residue such as phenylalanine,
      isoleucine, valine or leucine or an aromatic residue
<220> FEATURE:
<221> NAME/KEY: MISC_FEATURE
<222> LOCATION: (2)..(2)
<223> OTHER INFORMATION: a negatively charged residue such as glutamic
      acid or aspartic acid
<220> FEATURE:
<221> NAME/KEY: MISC_FEATURE
<222> LOCATION: (3)..(3)
<223> OTHER INFORMATION: any amino acid or an isoleucine, histidine,
      leucine or arginine residue
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (7)..(7)
<223> OTHER INFORMATION: an aromatic residue such as a tryptophan or
      phenylalanine residue
<220> FEATURE:
<221> NAME/KEY: MISC_FEATURE
<222> LOCATION: (8)..(8)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (9)..(9)
<223> OTHER INFORMATION: a negatively charged residue such as aspartic
      acid or glutamic acid
<220> FEATURE:
<221> NAME/KEY: MISC_FEATURE
<222> LOCATION: (10)..(10)
<223> OTHER INFORMATION: any residue or a negatively charged residue
      such as glutamic acid or aspartic acid, or a hydroxyl/thiol
      containing residue such as serine, threonine, cysteine or
      tyrosine, or a proline residue
<220> FEATURE:
<221> NAME/KEY: MISC_FEATURE
<222> LOCATION: (11)..(11)
<223> OTHER INFORMATION: a serine or alanine residue

<400> SEQUENCE: 1176

Xaa Xaa Xaa Xaa Lys Xaa Xaa Xaa Xaa Xaa Xaa
1               5                   10
```

```
<210> SEQ ID NO 1177
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a hydrophobic residue such as phenylalanine,
      isoleucine, valine or leucine or an aromatic residue
<220> FEATURE:
<221> NAME/KEY: MISC_FEATURE
<222> LOCATION: (2)..(2)
<223> OTHER INFORMATION: a negatively charged residue such as glutamic
      acid or aspartic acid
<220> FEATURE:
<221> NAME/KEY: MISC_FEATURE
<222> LOCATION: (3)..(3)
<223> OTHER INFORMATION: any amino acid or an isoleucine, histidine,
      leucine or arginine residue
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (7)..(7)
<223> OTHER INFORMATION: an aromatic residue such as a tryptophan or
      phenylalanine residue
<220> FEATURE:
<221> NAME/KEY: MISC_FEATURE
<222> LOCATION: (8)..(8)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (9)..(9)
<223> OTHER INFORMATION: a negatively charged residue such as aspartic
      acid or glutamic acid
<220> FEATURE:
<221> NAME/KEY: MISC_FEATURE
<222> LOCATION: (10)..(10)
<223> OTHER INFORMATION: an aliphatic hydrophobic residue such as
      leucine, isoleucine or phenylalanineor a small residue such as
      valine
<220> FEATURE:
<221> NAME/KEY: MISC_FEATURE
<222> LOCATION: (11)..(11)
<223> OTHER INFORMATION: a serine or alanine residue

<400> SEQUENCE: 1177

Xaa Xaa Xaa Xaa Lys Xaa Xaa Xaa Xaa Xaa Xaa
1               5                   10

<210> SEQ ID NO 1178
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a hydrophobic residue such as phenylalanine,
      isoleucine, valine or leucine or an aromatic residue
<220> FEATURE:
<221> NAME/KEY: MISC_FEATURE
<222> LOCATION: (2)..(2)
```

```
<223> OTHER INFORMATION: a negatively charged residue such as glutamic
      acid or aspartic acid
<220> FEATURE:
<221> NAME/KEY: MISC_FEATURE
<222> LOCATION: (3)..(3)
<223> OTHER INFORMATION: any amino acid or an isoleucine, histidine,
      leucine or arginine residue
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (7)..(7)
<223> OTHER INFORMATION: an aromatic residue such as a tryptophan or
      phenylalanine residue
<220> FEATURE:
<221> NAME/KEY: MISC_FEATURE
<222> LOCATION: (8)..(8)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (9)..(9)
<223> OTHER INFORMATION: a negatively charged residue such as aspartic
      acid or glutamic acid
<220> FEATURE:
<221> NAME/KEY: MISC_FEATURE
<222> LOCATION: (10)..(10)
<223> OTHER INFORMATION: any residue or a negatively charged residue
      such as glutamic acid or aspartic acid, or a hydroxyl/thiol
      containing residue such as serine, threonine, cysteine or
      tyrosine, or a proline residue

<400> SEQUENCE: 1178

Xaa Xaa Xaa Xaa Lys Xaa Xaa Xaa Xaa Xaa
1               5                   10

<210> SEQ ID NO 1179
<211> LENGTH: 12
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any amino acid or a glycine residue
<220> FEATURE:
<221> NAME/KEY: MISC_FEATURE
<222> LOCATION: (2)..(2)
<223> OTHER INFORMATION: a negatively charged residue such as glutamic
      acid or aspartic acid
<220> FEATURE:
<221> NAME/KEY: MISC_FEATURE
<222> LOCATION: (3)..(3)
<223> OTHER INFORMATION: any amino acid or an isoleucine, histidine,
      leucine or arginine residue
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
```

```
<221> NAME/KEY: MISC_FEATURE
<222> LOCATION: (7)..(7)
<223> OTHER INFORMATION: an aromatic residue such as a tryptophan or
      phenylalanine residue
<220> FEATURE:
<221> NAME/KEY: MISC_FEATURE
<222> LOCATION: (8)..(8)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (9)..(9)
<223> OTHER INFORMATION: a negatively charged residue such as aspartic
      acid or glutamic acid
<220> FEATURE:
<221> NAME/KEY: MISC_FEATURE
<222> LOCATION: (10)..(10)
<223> OTHER INFORMATION: an aliphatic hydrophobic residue such as
      leucine, isoleucine or phenylalanineor a small residue such as
      valine
<220> FEATURE:
<221> NAME/KEY: MISC_FEATURE
<222> LOCATION: (11)..(11)
<223> OTHER INFORMATION: any residue or a negatively charged residue
      such as glutamic acid or aspartic acid, or a hydroxyl/thiol
      containing residue such as serine, threonine, cysteine or
      tyrosine, or a proline residue
<220> FEATURE:
<221> NAME/KEY: MISC_FEATURE
<222> LOCATION: (12)..(12)
<223> OTHER INFORMATION: a serine or alanine residue

<400> SEQUENCE: 1179

Xaa Xaa Xaa Xaa Lys Xaa Xaa Xaa Xaa Xaa Xaa Xaa
1               5                   10

<210> SEQ ID NO 1180
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any amino acid or a glycine residue
<220> FEATURE:
<221> NAME/KEY: MISC_FEATURE
<222> LOCATION: (2)..(2)
<223> OTHER INFORMATION: a negatively charged residue such as glutamic
      acid or aspartic acid
<220> FEATURE:
<221> NAME/KEY: MISC_FEATURE
<222> LOCATION: (3)..(3)
<223> OTHER INFORMATION: any amino acid or an isoleucine, histidine,
      leucine or arginine residue
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (7)..(7)
<223> OTHER INFORMATION: an aromatic residue such as a tryptophan or
      phenylalanine residue
<220> FEATURE:
<221> NAME/KEY: MISC_FEATURE
<222> LOCATION: (8)..(8)
<223> OTHER INFORMATION: an aliphatic hydrophobic residue such as an
      isoleucine, valine, leucine or a threonine residue or an aromatic
```

-continued

```
      residue such as tyrosine, histidine or phenylalanine
<220> FEATURE:
<221> NAME/KEY: MISC_FEATURE
<222> LOCATION: (9)..(9)
<223> OTHER INFORMATION: a negatively charged residue such as aspartic
      acid or glutamic acid
<220> FEATURE:
<221> NAME/KEY: MISC_FEATURE
<222> LOCATION: (10)..(10)
<223> OTHER INFORMATION: an aliphatic hydrophobic residue such as
      leucine, isoleucine or phenylalanineor a small residue such as
      valine
<220> FEATURE:
<221> NAME/KEY: MISC_FEATURE
<222> LOCATION: (11)..(11)
<223> OTHER INFORMATION: any residue or a negatively charged residue
      such as glutamic acid or aspartic acid, or a hydroxyl/thiol
      containing residue such as serine, threonine, cysteine or
      tyrosine, or a proline residue

<400> SEQUENCE: 1180

Xaa Xaa Xaa Xaa Lys Xaa Xaa Xaa Xaa Xaa Xaa
1               5                   10

<210> SEQ ID NO 1181
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any amino acid or a glycine residue
<220> FEATURE:
<221> NAME/KEY: MISC_FEATURE
<222> LOCATION: (2)..(2)
<223> OTHER INFORMATION: a negatively charged residue such as glutamic
      acid or aspartic acid
<220> FEATURE:
<221> NAME/KEY: MISC_FEATURE
<222> LOCATION: (3)..(3)
<223> OTHER INFORMATION: any amino acid or an isoleucine, histidine,
      leucine or arginine residue
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (7)..(7)
<223> OTHER INFORMATION: an aromatic residue such as a tryptophan or
      phenylalanine residue
<220> FEATURE:
<221> NAME/KEY: MISC_FEATURE
<222> LOCATION: (8)..(8)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (9)..(9)
<223> OTHER INFORMATION: a negatively charged residue such as aspartic
      acid or glutamic acid
<220> FEATURE:
<221> NAME/KEY: MISC_FEATURE
<222> LOCATION: (10)..(10)
<223> OTHER INFORMATION: an aliphatic hydrophobic residue such as
      leucine, isoleucine or phenylalanineor a small residue such as
      valine
```

```
<400> SEQUENCE: 1181

Xaa Xaa Xaa Xaa Lys Xaa Xaa Xaa Xaa Xaa
1               5                   10

<210> SEQ ID NO 1182
<211> LENGTH: 9
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any amino acid or a glycine residue
<220> FEATURE:
<221> NAME/KEY: MISC_FEATURE
<222> LOCATION: (2)..(2)
<223> OTHER INFORMATION: a negatively charged residue such as glutamic
      acid or aspartic acid
<220> FEATURE:
<221> NAME/KEY: MISC_FEATURE
<222> LOCATION: (3)..(3)
<223> OTHER INFORMATION: any amino acid or an isoleucine, histidine,
      leucine or arginine residue
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (7)..(7)
<223> OTHER INFORMATION: an aromatic residue such as a tryptophan or
      phenylalanine residue
<220> FEATURE:
<221> NAME/KEY: MISC_FEATURE
<222> LOCATION: (8)..(8)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (9)..(9)
<223> OTHER INFORMATION: a negatively charged residue such as aspartic
      acid or glutamic acid

<400> SEQUENCE: 1182

Xaa Xaa Xaa Xaa Lys Xaa Xaa Xaa Xaa
1               5

<210> SEQ ID NO 1183
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any amino acid or a glycine residue
<220> FEATURE:
<221> NAME/KEY: MISC_FEATURE
<222> LOCATION: (2)..(2)
<223> OTHER INFORMATION: a negatively charged residue such as glutamic
      acid or aspartic acid
<220> FEATURE:
<221> NAME/KEY: MISC_FEATURE
<222> LOCATION: (3)..(3)
<223> OTHER INFORMATION: any amino acid or an isoleucine, histidine,
      leucine or arginine residue
```

```
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (7)..(7)
<223> OTHER INFORMATION: an aromatic residue such as a tryptophan or
      phenylalanine residue
<220> FEATURE:
<221> NAME/KEY: MISC_FEATURE
<222> LOCATION: (8)..(8)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (9)..(9)
<223> OTHER INFORMATION: a negatively charged residue such as aspartic
      acid or glutamic acid
<220> FEATURE:
<221> NAME/KEY: MISC_FEATURE
<222> LOCATION: (10)..(10)
<223> OTHER INFORMATION: a serine or alanine residue

<400> SEQUENCE: 1183

Xaa Xaa Xaa Xaa Lys Xaa Xaa Xaa Xaa Xaa
1               5                   10

<210> SEQ ID NO 1184
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any amino acid or a glycine residue
<220> FEATURE:
<221> NAME/KEY: MISC_FEATURE
<222> LOCATION: (2)..(2)
<223> OTHER INFORMATION: a negatively charged residue such as glutamic
      acid or aspartic acid
<220> FEATURE:
<221> NAME/KEY: MISC_FEATURE
<222> LOCATION: (3)..(3)
<223> OTHER INFORMATION: any amino acid or an isoleucine, histidine,
      leucine or arginine residue
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (7)..(7)
<223> OTHER INFORMATION: an aromatic residue such as a tryptophan or
      phenylalanine residue
<220> FEATURE:
<221> NAME/KEY: MISC_FEATURE
<222> LOCATION: (8)..(8)
<223> OTHER INFORMATION: an aliphatic hydrophobic residue such as an
      isoleucine, valine, leucine or a threonine residue or an aromatic
      residue such as tyrosine, histidine or phenylalanine
```

```
<220> FEATURE:
<221> NAME/KEY: MISC_FEATURE
<222> LOCATION: (9)..(9)
<223> OTHER INFORMATION: a negatively charged residue such as aspartic
      acid or glutamic acid
<220> FEATURE:
<221> NAME/KEY: MISC_FEATURE
<222> LOCATION: (10)..(10)
<223> OTHER INFORMATION: any residue or a negatively charged residue
      such as glutamic acid or aspartic acid, or a hydroxyl/thiol
      containing residue such as serine, threonine, cysteine or
      tyrosine, or a proline residue
<220> FEATURE:
<221> NAME/KEY: MISC_FEATURE
<222> LOCATION: (11)..(11)
<223> OTHER INFORMATION: a serine or alanine residue

<400> SEQUENCE: 1184

Xaa Xaa Xaa Xaa Lys Xaa Xaa Xaa Xaa Xaa Xaa
1               5                   10

<210> SEQ ID NO 1185
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any amino acid or a glycine residue
<220> FEATURE:
<221> NAME/KEY: MISC_FEATURE
<222> LOCATION: (2)..(2)
<223> OTHER INFORMATION: a negatively charged residue such as glutamic
      acid or aspartic acid
<220> FEATURE:
<221> NAME/KEY: MISC_FEATURE
<222> LOCATION: (3)..(3)
<223> OTHER INFORMATION: any amino acid or an isoleucine, histidine,
      leucine or arginine residue
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (7)..(7)
<223> OTHER INFORMATION: an aromatic residue such as a tryptophan or
      phenylalanine residue
<220> FEATURE:
<221> NAME/KEY: MISC_FEATURE
<222> LOCATION: (8)..(8)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (9)..(9)
<223> OTHER INFORMATION: a negatively charged residue such as aspartic
      acid or glutamic acid
<220> FEATURE:
<221> NAME/KEY: MISC_FEATURE
<222> LOCATION: (10)..(10)
<223> OTHER INFORMATION: an aliphatic hydrophobic residue such as
      leucine, isoleucine or phenylalanineor a small residue such as
      valine
<220> FEATURE:
<221> NAME/KEY: MISC_FEATURE
<222> LOCATION: (11)..(11)
<223> OTHER INFORMATION: a serine or alanine residue
```

<400> SEQUENCE: 1185

Xaa Xaa Xaa Xaa Lys Xaa Xaa Xaa Xaa Xaa Xaa
1               5                   10

<210> SEQ ID NO 1186
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Any amino acid or a glycine residue
<220> FEATURE:
<221> NAME/KEY: MISC_FEATURE
<222> LOCATION: (2)..(2)
<223> OTHER INFORMATION: a negatively charged residue such as glutamic
      acid or aspartic acid
<220> FEATURE:
<221> NAME/KEY: MISC_FEATURE
<222> LOCATION: (3)..(3)
<223> OTHER INFORMATION: any amino acid or an isoleucine, histidine,
      leucine or arginine residue
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (7)..(7)
<223> OTHER INFORMATION: an aromatic residue such as a tryptophan or
      phenylalanine residue
<220> FEATURE:
<221> NAME/KEY: MISC_FEATURE
<222> LOCATION: (8)..(8)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (9)..(9)
<223> OTHER INFORMATION: a negatively charged residue such as aspartic
      acid or glutamic acid
<220> FEATURE:
<221> NAME/KEY: MISC_FEATURE
<222> LOCATION: (10)..(10)
<223> OTHER INFORMATION: any residue or a negatively charged residue
      such as glutamic acid or aspartic acid, or a hydroxyl/thiol
      containing residue such as serine, threonine, cysteine or
      tyrosine, or a proline residue

<400> SEQUENCE: 1186

Xaa Xaa Xaa Xaa Lys Xaa Xaa Xaa Xaa Xaa
1               5                   10

<210> SEQ ID NO 1187
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a negatively charged residue such as glutamic
      acid or aspartic acid
<220> FEATURE:

```
<221> NAME/KEY: MISC_FEATURE
<222> LOCATION: (2)..(2)
<223> OTHER INFORMATION: any amino acid or an isoleucine, histidine,
      leucine or arginine residue
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (5)..(5)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (6)..(6)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (7)..(7)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (8)..(8)
<223> OTHER INFORMATION: a negatively charged residue such as aspartic
      acid or glutamic acid
<220> FEATURE:
<221> NAME/KEY: MISC_FEATURE
<222> LOCATION: (9)..(9)
<223> OTHER INFORMATION: an aliphatic hydrophobic residue such as
      leucine, isoleucine or phenylalanineor a small residue such as
      valine
<220> FEATURE:
<221> NAME/KEY: MISC_FEATURE
<222> LOCATION: (10)..(10)
<223> OTHER INFORMATION: any residue or a negatively charged residue
      such as glutamic acid or aspartic acid, or a hydroxyl/thiol
      containing residue such as serine, threonine, cysteine or
      tyrosine, or a proline residue
<220> FEATURE:
<221> NAME/KEY: MISC_FEATURE
<222> LOCATION: (11)..(11)
<223> OTHER INFORMATION: a serine or alanine residue

<400> SEQUENCE: 1187

Xaa Xaa Xaa Lys Xaa Xaa Xaa Xaa Xaa Xaa Xaa
1               5                   10

<210> SEQ ID NO 1188
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a negatively charged residue such as glutamic
      acid or aspartic acid
<220> FEATURE:
<221> NAME/KEY: MISC_FEATURE
<222> LOCATION: (2)..(2)
<223> OTHER INFORMATION: any amino acid or an isoleucine, histidine,
      leucine or arginine residue
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (5)..(5)
```

```
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (6)..(6)
<223> OTHER INFORMATION: an aromatic residue such as a tryptophan or
      phenylalanine residue
<220> FEATURE:
<221> NAME/KEY: MISC_FEATURE
<222> LOCATION: (7)..(7)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (8)..(8)
<223> OTHER INFORMATION: a negatively charged residue such as aspartic
      acid or glutamic acid
<220> FEATURE:
<221> NAME/KEY: MISC_FEATURE
<222> LOCATION: (9)..(9)
<223> OTHER INFORMATION: an aliphatic hydrophobic residue such as
      leucine, isoleucine or phenylalanineor a small residue such as
      valine
<220> FEATURE:
<221> NAME/KEY: MISC_FEATURE
<222> LOCATION: (10)..(10)
<223> OTHER INFORMATION: any residue or a negatively charged residue
      such as glutamic acid or aspartic acid, or a hydroxyl/thiol
      containing residue such as serine, threonine, cysteine or
      tyrosine, or a proline residue

<400> SEQUENCE: 1188

Xaa Xaa Xaa Lys Xaa Xaa Xaa Xaa Xaa Xaa
1               5                   10

<210> SEQ ID NO 1189
<211> LENGTH: 9
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a negatively charged residue such as glutamic
      acid or aspartic acid
<220> FEATURE:
<221> NAME/KEY: MISC_FEATURE
<222> LOCATION: (2)..(2)
<223> OTHER INFORMATION: any amino acid or an isoleucine, histidine,
      leucine or arginine residue
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (5)..(5)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (6)..(6)
<223> OTHER INFORMATION: an aromatic residue such as a tryptophan or
      phenylalanine residue
<220> FEATURE:
<221> NAME/KEY: MISC_FEATURE
<222> LOCATION: (7)..(7)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (8)..(8)
```

```
<223> OTHER INFORMATION: a negatively charged residue such as aspartic
      acid or glutamic acid
<220> FEATURE:
<221> NAME/KEY: MISC_FEATURE
<222> LOCATION: (9)..(9)
<223> OTHER INFORMATION: an aliphatic hydrophobic residue such as
      leucine, isoleucine or phenylalanineor a small residue such as
      valine

<400> SEQUENCE: 1189

Xaa Xaa Xaa Lys Xaa Xaa Xaa Xaa Xaa
1               5

<210> SEQ ID NO 1190
<211> LENGTH: 8
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a negatively charged residue such as glutamic
      acid or aspartic acid
<220> FEATURE:
<221> NAME/KEY: MISC_FEATURE
<222> LOCATION: (2)..(2)
<223> OTHER INFORMATION: any amino acid or an isoleucine, histidine,
      leucine or arginine residue
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (5)..(5)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (6)..(6)
<223> OTHER INFORMATION: an aromatic residue such as a tryptophan or
      phenylalanine residue
<220> FEATURE:
<221> NAME/KEY: MISC_FEATURE
<222> LOCATION: (7)..(7)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (8)..(8)
<223> OTHER INFORMATION: a negatively charged residue such as aspartic
      acid or glutamic acid

<400> SEQUENCE: 1190

Xaa Xaa Xaa Lys Xaa Xaa Xaa Xaa
1               5

<210> SEQ ID NO 1191
<211> LENGTH: 9
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a negatively charged residue such as glutamic
      acid or aspartic acid
<220> FEATURE:
<221> NAME/KEY: MISC_FEATURE
<222> LOCATION: (2)..(2)
<223> OTHER INFORMATION: any amino acid or an isoleucine, histidine,
```

-continued

```
      leucine or arginine residue
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (5)..(5)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (6)..(6)
<223> OTHER INFORMATION: an aromatic residue such as a tryptophan or
      phenylalanine residue
<220> FEATURE:
<221> NAME/KEY: MISC_FEATURE
<222> LOCATION: (7)..(7)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (8)..(8)
<223> OTHER INFORMATION: a negatively charged residue such as aspartic
      acid or glutamic acid
<220> FEATURE:
<221> NAME/KEY: MISC_FEATURE
<222> LOCATION: (9)..(9)
<223> OTHER INFORMATION: a serine or alanine residue

<400> SEQUENCE: 1191

Xaa Xaa Xaa Lys Xaa Xaa Xaa Xaa Xaa
1               5

<210> SEQ ID NO 1192
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a negatively charged residue such as glutamic
      acid or aspartic acid
<220> FEATURE:
<221> NAME/KEY: MISC_FEATURE
<222> LOCATION: (2)..(2)
<223> OTHER INFORMATION: any amino acid or an isoleucine, histidine,
      leucine or arginine residue
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (5)..(5)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (6)..(6)
<223> OTHER INFORMATION: an aromatic residue such as a tryptophan or
      phenylalanine residue
<220> FEATURE:
<221> NAME/KEY: MISC_FEATURE
<222> LOCATION: (7)..(7)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (8)..(8)
```

-continued

```
<223> OTHER INFORMATION: a negatively charged residue such as aspartic
      acid or glutamic acid
<220> FEATURE:
<221> NAME/KEY: MISC_FEATURE
<222> LOCATION: (9)..(9)
<223> OTHER INFORMATION: any residue or a negatively charged residue
      such as glutamic acid or aspartic acid, or a hydroxyl/thiol
      containing residue such as serine, threonine, cysteine or
      tyrosine, or a proline residue
<220> FEATURE:
<221> NAME/KEY: MISC_FEATURE
<222> LOCATION: (10)..(10)
<223> OTHER INFORMATION: a serine or alanine residue

<400> SEQUENCE: 1192

Xaa Xaa Xaa Lys Xaa Xaa Xaa Xaa Xaa Xaa
1               5                   10

<210> SEQ ID NO 1193
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a negatively charged residue such as glutamic
      acid or aspartic acid
<220> FEATURE:
<221> NAME/KEY: MISC_FEATURE
<222> LOCATION: (2)..(2)
<223> OTHER INFORMATION: any amino acid or an isoleucine, histidine,
      leucine or arginine residue
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (5)..(5)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (6)..(6)
<223> OTHER INFORMATION: an aromatic residue such as a tryptophan or
      phenylalanine residue
<220> FEATURE:
<221> NAME/KEY: MISC_FEATURE
<222> LOCATION: (7)..(7)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (8)..(8)
<223> OTHER INFORMATION: a negatively charged residue such as aspartic
      acid or glutamic acid
<220> FEATURE:
<221> NAME/KEY: MISC_FEATURE
<222> LOCATION: (9)..(9)
<223> OTHER INFORMATION: an aliphatic hydrophobic residue such as
      leucine, isoleucine or phenylalanineor a small residue such as
      valine
<220> FEATURE:
<221> NAME/KEY: MISC_FEATURE
<222> LOCATION: (10)..(10)
<223> OTHER INFORMATION: a serine or alanine residue

<400> SEQUENCE: 1193

Xaa Xaa Xaa Lys Xaa Xaa Xaa Xaa Xaa Xaa
1               5                   10
```

-continued

```
<210> SEQ ID NO 1194
<211> LENGTH: 9
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a negatively charged residue such as glutamic
      acid or aspartic acid
<220> FEATURE:
<221> NAME/KEY: MISC_FEATURE
<222> LOCATION: (2)..(2)
<223> OTHER INFORMATION: any amino acid or an isoleucine, histidine,
      leucine or arginine residue
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine residue
<220> FEATURE:
<221> NAME/KEY: MISC_FEATURE
<222> LOCATION: (5)..(5)
<223> OTHER INFORMATION: a hydrophobic residue or valine, isoleucine,
      leucine or phenylalanine or a small residue such as alanine or
      serine, or a non-charged residue
<220> FEATURE:
<221> NAME/KEY: MISC_FEATURE
<222> LOCATION: (6)..(6)
<223> OTHER INFORMATION: an aromatic residue such as a tryptophan or
      phenylalanine residue
<220> FEATURE:
<221> NAME/KEY: MISC_FEATURE
<222> LOCATION: (7)..(7)
<223> OTHER INFORMATION: an aliphatic hydrophobic residue such as an
      isoleucine, valine, leucine or a threonine residue or an aromatic
      residue such as tyrosine, histidine or phenylalanine
<220> FEATURE:
<221> NAME/KEY: MISC_FEATURE
<222> LOCATION: (8)..(8)
<223> OTHER INFORMATION: a negatively charged residue such as aspartic
      acid or glutamic acid
<220> FEATURE:
<221> NAME/KEY: MISC_FEATURE
<222> LOCATION: (9)..(9)
<223> OTHER INFORMATION: any residue or a negatively charged residue
      such as glutamic acid or aspartic acid, or a hydroxyl/thiol
      containing residue such as serine, threonine, cysteine or
      tyrosine, or a proline residue

<400> SEQUENCE: 1194

Xaa Xaa Xaa Lys Xaa Xaa Xaa Xaa Xaa
1               5

<210> SEQ ID NO 1195
<211> LENGTH: 13
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: a hydrophobic or aromatic residue
<220> FEATURE:
<221> NAME/KEY: MISC_FEATURE
<222> LOCATION: (3)..(3)
<223> OTHER INFORMATION: a glutamic acid or aspartic acid
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (5)..(5)
<223> OTHER INFORMATION: an aspartic acid, asparagine, glutamic acid,
      tyrosine or alanine
```

```
<220> FEATURE:
<221> NAME/KEY: MISC_FEATURE
<222> LOCATION: (7)..(7)
<223> OTHER INFORMATION: hydrophobic or serine residue
<220> FEATURE:
<221> NAME/KEY: MISC_FEATURE
<222> LOCATION: (8)..(8)
<223> OTHER INFORMATION: an aromatic residue
<220> FEATURE:
<221> NAME/KEY: MISC_FEATURE
<222> LOCATION: (9)..(9)
<223> OTHER INFORMATION: aromatic, aliphatic hydrophobic, histidine,
      theronine residue
<220> FEATURE:
<221> NAME/KEY: MISC_FEATURE
<222> LOCATION: (10)..(10)
<223> OTHER INFORMATION: a glutamic acid or aspartic acid
<220> FEATURE:
<221> NAME/KEY: MISC_FEATURE
<222> LOCATION: (11)..(11)
<223> OTHER INFORMATION: an aliphatic hydrophobic residue
<220> FEATURE:
<221> NAME/KEY: MISC_FEATURE
<222> LOCATION: (12)..(12)
<223> OTHER INFORMATION: Any amino acid
<220> FEATURE:
<221> NAME/KEY: MISC_FEATURE
<222> LOCATION: (13)..(13)
<223> OTHER INFORMATION: a serine residue, an alanine residue

<400> SEQUENCE: 1195

Gly Xaa Xaa Xaa Xaa Lys Xaa Xaa Xaa Xaa Xaa Xaa Xaa
1               5                   10

<210> SEQ ID NO 1196
<211> LENGTH: 12
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a hydrophobic or aromatic residue
<220> FEATURE:
<221> NAME/KEY: MISC_FEATURE
<222> LOCATION: (2)..(2)
<223> OTHER INFORMATION: a glutamic acid or aspartic acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine
<220> FEATURE:
<221> NAME/KEY: MISC_FEATURE
<222> LOCATION: (6)..(6)
<223> OTHER INFORMATION: a hydrophobic or serine residue
<220> FEATURE:
<221> NAME/KEY: MISC_FEATURE
<222> LOCATION: (7)..(7)
<223> OTHER INFORMATION: an aromatic residue
<220> FEATURE:
<221> NAME/KEY: MISC_FEATURE
<222> LOCATION: (8)..(8)
<223> OTHER INFORMATION: aromatic, aliphatic hydrophobic, histidine,
      theronine residue
<220> FEATURE:
<221> NAME/KEY: MISC_FEATURE
<222> LOCATION: (9)..(9)
<223> OTHER INFORMATION: a glutamic acid or aspartic acid
<220> FEATURE:
<221> NAME/KEY: MISC_FEATURE
<222> LOCATION: (10)..(10)
<223> OTHER INFORMATION: an aliphatic hydrophobic residue
```

```
<220> FEATURE:
<221> NAME/KEY: MISC_FEATURE
<222> LOCATION: (11)..(11)
<223> OTHER INFORMATION: Any amino acid
<220> FEATURE:
<221> NAME/KEY: MISC_FEATURE
<222> LOCATION: (12)..(12)
<223> OTHER INFORMATION: a serine residue, an alanine residue

<400> SEQUENCE: 1196

Xaa Xaa Xaa Xaa Lys Xaa Xaa Xaa Xaa Xaa Xaa Xaa
1               5                   10

<210> SEQ ID NO 1197
<211> LENGTH: 12
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: a glutamic acid or aspartic acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine
<220> FEATURE:
<221> NAME/KEY: MISC_FEATURE
<222> LOCATION: (6)..(6)
<223> OTHER INFORMATION: a hydrophobic or serine residue
<220> FEATURE:
<221> NAME/KEY: MISC_FEATURE
<222> LOCATION: (7)..(7)
<223> OTHER INFORMATION: an aromatic residue
<220> FEATURE:
<221> NAME/KEY: MISC_FEATURE
<222> LOCATION: (8)..(8)
<223> OTHER INFORMATION: aromatic, aliphatic hydrophobic, histidine,
      theronine residue
<220> FEATURE:
<221> NAME/KEY: MISC_FEATURE
<222> LOCATION: (9)..(9)
<223> OTHER INFORMATION: a glutamic acid or aspartic acid
<220> FEATURE:
<221> NAME/KEY: MISC_FEATURE
<222> LOCATION: (10)..(10)
<223> OTHER INFORMATION: an aliphatic hydrophobic residue
<220> FEATURE:
<221> NAME/KEY: MISC_FEATURE
<222> LOCATION: (11)..(11)
<223> OTHER INFORMATION: any amino acid
<220> FEATURE:
<221> NAME/KEY: MISC_FEATURE
<222> LOCATION: (12)..(12)
<223> OTHER INFORMATION: a serine residue, an alanine residue

<400> SEQUENCE: 1197

Gly Xaa Xaa Xaa Lys Xaa Xaa Xaa Xaa Xaa Xaa Xaa
1               5                   10

<210> SEQ ID NO 1198
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a glutamic acid or aspartic acid
```

```
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine
<220> FEATURE:
<221> NAME/KEY: MISC_FEATURE
<222> LOCATION: (5)..(5)
<223> OTHER INFORMATION: a hydrophobic or serine residue
<220> FEATURE:
<221> NAME/KEY: MISC_FEATURE
<222> LOCATION: (6)..(6)
<223> OTHER INFORMATION: an aromatic residue
<220> FEATURE:
<221> NAME/KEY: MISC_FEATURE
<222> LOCATION: (7)..(7)
<223> OTHER INFORMATION: aromatic, aliphatic hydrophobic, histidine,
      theronine residue
<220> FEATURE:
<221> NAME/KEY: MISC_FEATURE
<222> LOCATION: (8)..(8)
<223> OTHER INFORMATION: a glutamic acid or aspartic acid
<220> FEATURE:
<221> NAME/KEY: MISC_FEATURE
<222> LOCATION: (9)..(9)
<223> OTHER INFORMATION: an aliphatic hydrophobic residue
<220> FEATURE:
<221> NAME/KEY: MISC_FEATURE
<222> LOCATION: (10)..(10)
<223> OTHER INFORMATION: Any amino acid
<220> FEATURE:
<221> NAME/KEY: MISC_FEATURE
<222> LOCATION: (11)..(11)
<223> OTHER INFORMATION: a serine residue, an alanine residue

<400> SEQUENCE: 1198

Xaa Xaa Xaa Lys Xaa Xaa Xaa Xaa Xaa Xaa Xaa
1               5                   10

<210> SEQ ID NO 1199
<211> LENGTH: 12
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: a hydrophobic or aromatic residue
<220> FEATURE:
<221> NAME/KEY: MISC_FEATURE
<222> LOCATION: (3)..(3)
<223> OTHER INFORMATION: a glutamic acid or aspartic acid
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (5)..(5)
<223> OTHER INFORMATION: an aspartic acid, asparagine, glutamic acid,
      tyrosine or alanine
<220> FEATURE:
<221> NAME/KEY: MISC_FEATURE
<222> LOCATION: (7)..(7)
<223> OTHER INFORMATION: a hydrophobic or serine residue
<220> FEATURE:
<221> NAME/KEY: MISC_FEATURE
<222> LOCATION: (8)..(8)
<223> OTHER INFORMATION: an aromatic residue
<220> FEATURE:
<221> NAME/KEY: MISC_FEATURE
<222> LOCATION: (9)..(9)
<223> OTHER INFORMATION: aromatic, aliphatic hydrophobic, histidine,
```

```
              theronine residue
<220> FEATURE:
<221> NAME/KEY: MISC_FEATURE
<222> LOCATION: (10)..(10)
<223> OTHER INFORMATION: a glutamic acid or aspartic acid
<220> FEATURE:
<221> NAME/KEY: MISC_FEATURE
<222> LOCATION: (11)..(11)
<223> OTHER INFORMATION: Any amino acid
<220> FEATURE:
<221> NAME/KEY: MISC_FEATURE
<222> LOCATION: (12)..(12)
<223> OTHER INFORMATION: a serine residue, an alanine residue

<400> SEQUENCE: 1199

Gly Xaa Xaa Xaa Xaa Lys Xaa Xaa Xaa Xaa Xaa
1               5                   10

<210> SEQ ID NO 1200
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a hydrophobic or aromatic residue
<220> FEATURE:
<221> NAME/KEY: MISC_FEATURE
<222> LOCATION: (2)..(2)
<223> OTHER INFORMATION: a glutamic acid or aspartic acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine
<220> FEATURE:
<221> NAME/KEY: MISC_FEATURE
<222> LOCATION: (6)..(6)
<223> OTHER INFORMATION: a hydrophobic or serine residue
<220> FEATURE:
<221> NAME/KEY: MISC_FEATURE
<222> LOCATION: (7)..(7)
<223> OTHER INFORMATION: an aromatic residue
<220> FEATURE:
<221> NAME/KEY: MISC_FEATURE
<222> LOCATION: (8)..(8)
<223> OTHER INFORMATION: aromatic, aliphatic hydrophobic, histidine,
      theronine residue
<220> FEATURE:
<221> NAME/KEY: MISC_FEATURE
<222> LOCATION: (9)..(9)
<223> OTHER INFORMATION: a glutamic acid or aspartic acid
<220> FEATURE:
<221> NAME/KEY: MISC_FEATURE
<222> LOCATION: (10)..(10)
<223> OTHER INFORMATION: Any amino acid
<220> FEATURE:
<221> NAME/KEY: MISC_FEATURE
<222> LOCATION: (11)..(11)
<223> OTHER INFORMATION: a serine residue, an alanine residue

<400> SEQUENCE: 1200

Xaa Xaa Xaa Xaa Lys Xaa Xaa Xaa Xaa Xaa Xaa
1               5                   10

<210> SEQ ID NO 1201
<211> LENGTH: 11
<212> TYPE: PRT
<213> ORGANISM: artificial sequence
<220> FEATURE:
```

```
<223> OTHER INFORMATION: synthetic polypeptide
<220> FEATURE:
<221> NAME/KEY: MISC_FEATURE
<222> LOCATION: (2)..(2)
<223> OTHER INFORMATION: a glutamic acid or aspartic acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine
<220> FEATURE:
<221> NAME/KEY: MISC_FEATURE
<222> LOCATION: (6)..(6)
<223> OTHER INFORMATION: a hydrophobic or serine residue
<220> FEATURE:
<221> NAME/KEY: MISC_FEATURE
<222> LOCATION: (7)..(7)
<223> OTHER INFORMATION: an aromatic residue
<220> FEATURE:
<221> NAME/KEY: MISC_FEATURE
<222> LOCATION: (8)..(8)
<223> OTHER INFORMATION: aromatic, aliphatic hydrophobic, histidine,
      theronine residue
<220> FEATURE:
<221> NAME/KEY: MISC_FEATURE
<222> LOCATION: (9)..(9)
<223> OTHER INFORMATION: a glutamic acid or aspartic acid
<220> FEATURE:
<221> NAME/KEY: MISC_FEATURE
<222> LOCATION: (10)..(10)
<223> OTHER INFORMATION: Any amino acid
<220> FEATURE:
<221> NAME/KEY: MISC_FEATURE
<222> LOCATION: (11)..(11)
<223> OTHER INFORMATION: a serine residue, an alanine residue

<400> SEQUENCE: 1201

Gly Xaa Xaa Xaa Lys Xaa Xaa Xaa Xaa Xaa Xaa
1               5                   10

<210> SEQ ID NO 1202
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a glutamic acid or aspartic acid
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine
<220> FEATURE:
<221> NAME/KEY: MISC_FEATURE
<222> LOCATION: (5)..(5)
<223> OTHER INFORMATION: a hydrophobic or serine residue
<220> FEATURE:
<221> NAME/KEY: MISC_FEATURE
<222> LOCATION: (6)..(6)
<223> OTHER INFORMATION: an aromatic residue
<220> FEATURE:
<221> NAME/KEY: MISC_FEATURE
<222> LOCATION: (7)..(7)
<223> OTHER INFORMATION: aromatic, aliphatic hydrophobic, histidine,
      theronine residue
<220> FEATURE:
<221> NAME/KEY: MISC_FEATURE
```

```
<222> LOCATION: (8)..(8)
<223> OTHER INFORMATION: a glutamic acid or aspartic acid
<220> FEATURE:
<221> NAME/KEY: MISC_FEATURE
<222> LOCATION: (9)..(9)
<223> OTHER INFORMATION: Any amino acid
<220> FEATURE:
<221> NAME/KEY: MISC_FEATURE
<222> LOCATION: (10)..(10)
<223> OTHER INFORMATION: a serine residue, an alanine residue

<400> SEQUENCE: 1202

Xaa Xaa Xaa Lys Xaa Xaa Xaa Xaa Xaa Xaa
1               5                   10

<210> SEQ ID NO 1203
<211> LENGTH: 12
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: a hydrophobic or aromatic residue
<220> FEATURE:
<221> NAME/KEY: MISC_FEATURE
<222> LOCATION: (3)..(3)
<223> OTHER INFORMATION: a glutamic acid or aspartic acid
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (5)..(5)
<223> OTHER INFORMATION: an aspartic acid, asparagine, glutamic acid,
      tyrosine or alanine
<220> FEATURE:
<221> NAME/KEY: MISC_FEATURE
<222> LOCATION: (7)..(7)
<223> OTHER INFORMATION: a hydrophobic or serine residue
<220> FEATURE:
<221> NAME/KEY: MISC_FEATURE
<222> LOCATION: (8)..(8)
<223> OTHER INFORMATION: an aromatic residue
<220> FEATURE:
<221> NAME/KEY: MISC_FEATURE
<222> LOCATION: (9)..(9)
<223> OTHER INFORMATION: aromatic, aliphatic hydrophobic, histidine,
      theronine residue
<220> FEATURE:
<221> NAME/KEY: MISC_FEATURE
<222> LOCATION: (10)..(10)
<223> OTHER INFORMATION: a glutamic acid or aspartic acid
<220> FEATURE:
<221> NAME/KEY: MISC_FEATURE
<222> LOCATION: (11)..(11)
<223> OTHER INFORMATION: an aliphatic hydrophobic residue
<220> FEATURE:
<221> NAME/KEY: MISC_FEATURE
<222> LOCATION: (12)..(12)
<223> OTHER INFORMATION: Any amino acid

<400> SEQUENCE: 1203

Gly Xaa Xaa Xaa Xaa Lys Xaa Xaa Xaa Xaa Xaa Xaa
1               5                   10

<210> SEQ ID NO 1204
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
```

```
<222> LOCATION: (1)..(1)
<223> OTHER INFORMATION: a hydrophobic or aromatic residue
<220> FEATURE:
<221> NAME/KEY: MISC_FEATURE
<222> LOCATION: (2)..(2)
<223> OTHER INFORMATION: a glutamic acid or aspartic acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine
<220> FEATURE:
<221> NAME/KEY: MISC_FEATURE
<222> LOCATION: (6)..(6)
<223> OTHER INFORMATION: a hydrophobic or serine residue
<220> FEATURE:
<221> NAME/KEY: MISC_FEATURE
<222> LOCATION: (7)..(7)
<223> OTHER INFORMATION: an aromatic residue
<220> FEATURE:
<221> NAME/KEY: MISC_FEATURE
<222> LOCATION: (8)..(8)
<223> OTHER INFORMATION: aromatic, aliphatic hydrophobic, histidine,
      theronine residue
<220> FEATURE:
<221> NAME/KEY: MISC_FEATURE
<222> LOCATION: (9)..(9)
<223> OTHER INFORMATION: a glutamic acid or aspartic acid
<220> FEATURE:
<221> NAME/KEY: MISC_FEATURE
<222> LOCATION: (10)..(10)
<223> OTHER INFORMATION: an aliphatic hydrophobic residue
<220> FEATURE:
<221> NAME/KEY: MISC_FEATURE
<222> LOCATION: (11)..(11)
<223> OTHER INFORMATION: Any amino acid

<400> SEQUENCE: 1204

Xaa Xaa Xaa Xaa Lys Xaa Xaa Xaa Xaa Xaa Xaa
1               5                   10

<210> SEQ ID NO 1205
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: a glutamic acid or aspartic acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine
<220> FEATURE:
<221> NAME/KEY: MISC_FEATURE
<222> LOCATION: (6)..(6)
<223> OTHER INFORMATION: a hydrophobic or serine residue
<220> FEATURE:
<221> NAME/KEY: MISC_FEATURE
<222> LOCATION: (7)..(7)
<223> OTHER INFORMATION: an aromatic residue
<220> FEATURE:
<221> NAME/KEY: MISC_FEATURE
<222> LOCATION: (8)..(8)
<223> OTHER INFORMATION: an aromatic or aliphatic hydrophobic residue
<220> FEATURE:
<221> NAME/KEY: MISC_FEATURE
```

```
<222> LOCATION: (9)..(9)
<223> OTHER INFORMATION: a glutamic acid or aspartic acid
<220> FEATURE:
<221> NAME/KEY: MISC_FEATURE
<222> LOCATION: (10)..(10)
<223> OTHER INFORMATION: an aliphatic hydrophobic residue
<220> FEATURE:
<221> NAME/KEY: MISC_FEATURE
<222> LOCATION: (11)..(11)
<223> OTHER INFORMATION: Any amino acid

<400> SEQUENCE: 1205

Gly Xaa Xaa Xaa Lys Xaa Xaa Xaa Xaa Xaa Xaa
1               5                   10

<210> SEQ ID NO 1206
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a glutamic acid or aspartic acid
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine
<220> FEATURE:
<221> NAME/KEY: MISC_FEATURE
<222> LOCATION: (5)..(5)
<223> OTHER INFORMATION: a hydrophobic or serine residue
<220> FEATURE:
<221> NAME/KEY: MISC_FEATURE
<222> LOCATION: (6)..(6)
<223> OTHER INFORMATION: an aromatic residue
<220> FEATURE:
<221> NAME/KEY: MISC_FEATURE
<222> LOCATION: (7)..(7)
<223> OTHER INFORMATION: an aromatic or aliphatic hydrophobic residue
<220> FEATURE:
<221> NAME/KEY: MISC_FEATURE
<222> LOCATION: (8)..(8)
<223> OTHER INFORMATION: a glutamic acid or aspartic acid
<220> FEATURE:
<221> NAME/KEY: MISC_FEATURE
<222> LOCATION: (9)..(9)
<223> OTHER INFORMATION: an aliphatic hydrophobic residue
<220> FEATURE:
<221> NAME/KEY: MISC_FEATURE
<222> LOCATION: (10)..(10)
<223> OTHER INFORMATION: Any amino acid

<400> SEQUENCE: 1206

Xaa Xaa Xaa Lys Xaa Xaa Xaa Xaa Xaa Xaa
1               5                   10

<210> SEQ ID NO 1207
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a hydrophobic or aromatic residue
<220> FEATURE:
<221> NAME/KEY: MISC_FEATURE
<222> LOCATION: (2)..(2)
```

```
<223> OTHER INFORMATION: a glutamic acid or aspartic acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine
<220> FEATURE:
<221> NAME/KEY: MISC_FEATURE
<222> LOCATION: (6)..(6)
<223> OTHER INFORMATION: a hydrophobic or serine residue
<220> FEATURE:
<221> NAME/KEY: MISC_FEATURE
<222> LOCATION: (7)..(7)
<223> OTHER INFORMATION: an aromatic residue
<220> FEATURE:
<221> NAME/KEY: MISC_FEATURE
<222> LOCATION: (8)..(8)
<223> OTHER INFORMATION: aromatic, aliphatic hydrophobic, histidine,
      theronine residue
<220> FEATURE:
<221> NAME/KEY: MISC_FEATURE
<222> LOCATION: (9)..(9)
<223> OTHER INFORMATION: a glutamic acid or aspartic acid
<220> FEATURE:
<221> NAME/KEY: MISC_FEATURE
<222> LOCATION: (10)..(10)
<223> OTHER INFORMATION: Any amino acid

<400> SEQUENCE: 1207

Xaa Xaa Xaa Xaa Lys Xaa Xaa Xaa Xaa Xaa
1               5                   10

<210> SEQ ID NO 1208
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: a glutamic acid or aspartic acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine
<220> FEATURE:
<221> NAME/KEY: MISC_FEATURE
<222> LOCATION: (6)..(6)
<223> OTHER INFORMATION: a hydrophobic or serine residue
<220> FEATURE:
<221> NAME/KEY: MISC_FEATURE
<222> LOCATION: (7)..(7)
<223> OTHER INFORMATION: an aromatic residue
<220> FEATURE:
<221> NAME/KEY: MISC_FEATURE
<222> LOCATION: (8)..(8)
<223> OTHER INFORMATION: aromatic, aliphatic hydrophobic, histidine,
      theronine residue
<220> FEATURE:
<221> NAME/KEY: MISC_FEATURE
<222> LOCATION: (9)..(9)
<223> OTHER INFORMATION: a glutamic acid or aspartic acid
<220> FEATURE:
<221> NAME/KEY: MISC_FEATURE
<222> LOCATION: (10)..(10)
<223> OTHER INFORMATION: Any amino acid

<400> SEQUENCE: 1208
```

```
Gly Xaa Xaa Xaa Lys Xaa Xaa Xaa Xaa Xaa
1               5                   10

<210> SEQ ID NO 1209
<211> LENGTH: 9
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a glutamic acid or aspartic acid
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine
<220> FEATURE:
<221> NAME/KEY: MISC_FEATURE
<222> LOCATION: (5)..(5)
<223> OTHER INFORMATION: a hydrophobic or serine residue
<220> FEATURE:
<221> NAME/KEY: MISC_FEATURE
<222> LOCATION: (6)..(6)
<223> OTHER INFORMATION: an aromatic residue
<220> FEATURE:
<221> NAME/KEY: MISC_FEATURE
<222> LOCATION: (7)..(7)
<223> OTHER INFORMATION: aromatic, aliphatic hydrophobic, histidine,
      theronine residue
<220> FEATURE:
<221> NAME/KEY: MISC_FEATURE
<222> LOCATION: (8)..(8)
<223> OTHER INFORMATION: a glutamic acid or aspartic acid
<220> FEATURE:
<221> NAME/KEY: MISC_FEATURE
<222> LOCATION: (9)..(9)
<223> OTHER INFORMATION: Any amino acid

<400> SEQUENCE: 1209

Xaa Xaa Xaa Lys Xaa Xaa Xaa Xaa Xaa
1               5

<210> SEQ ID NO 1210
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: a hydrophobic or aromatic residue
<220> FEATURE:
<221> NAME/KEY: MISC_FEATURE
<222> LOCATION: (3)..(3)
<223> OTHER INFORMATION: a glutamic acid or aspartic acid
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (5)..(5)
<223> OTHER INFORMATION: an aspartic acid, asparagine, glutamic acid,
      tyrosine or alanine
<220> FEATURE:
<221> NAME/KEY: MISC_FEATURE
<222> LOCATION: (7)..(7)
<223> OTHER INFORMATION: a hydrophobic or serine residue
<220> FEATURE:
```

```
<221> NAME/KEY: MISC_FEATURE
<222> LOCATION: (8)..(8)
<223> OTHER INFORMATION: an aromatic residue
<220> FEATURE:
<221> NAME/KEY: MISC_FEATURE
<222> LOCATION: (9)..(9)
<223> OTHER INFORMATION: an aromatic, aliphatic hydrophobic, histidine,
      or threonine residue
<220> FEATURE:
<221> NAME/KEY: MISC_FEATURE
<222> LOCATION: (10)..(10)
<223> OTHER INFORMATION: a glutamic acid or aspartic acid
<220> FEATURE:
<221> NAME/KEY: MISC_FEATURE
<222> LOCATION: (11)..(11)
<223> OTHER INFORMATION: any amino acid

<400> SEQUENCE: 1210

Gly Xaa Xaa Xaa Xaa Lys Xaa Xaa Xaa Xaa Xaa
1               5                   10

<210> SEQ ID NO 1211
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: a hydrophobic or aromatic residue
<220> FEATURE:
<221> NAME/KEY: MISC_FEATURE
<222> LOCATION: (3)..(3)
<223> OTHER INFORMATION: a glutamic acid or aspartic acid residue
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (5)..(5)
<223> OTHER INFORMATION: an aspartic acid, asparagine, glutamic acid,
      tyrosine or alanine
<220> FEATURE:
<221> NAME/KEY: MISC_FEATURE
<222> LOCATION: (7)..(7)
<223> OTHER INFORMATION: a hydrophobic or serine residue
<220> FEATURE:
<221> NAME/KEY: MISC_FEATURE
<222> LOCATION: (8)..(8)
<223> OTHER INFORMATION: an aromatic residue
<220> FEATURE:
<221> NAME/KEY: MISC_FEATURE
<222> LOCATION: (9)..(9)
<223> OTHER INFORMATION: an aromatic, aliphatic hydrophobic, histidine
      or threonine residue
<220> FEATURE:
<221> NAME/KEY: MISC_FEATURE
<222> LOCATION: (10)..(10)
<223> OTHER INFORMATION: a glutamic acid or aspartic acid
<220> FEATURE:
<221> NAME/KEY: MISC_FEATURE
<222> LOCATION: (11)..(11)
<223> OTHER INFORMATION: an aliphatic hydrophobic residue

<400> SEQUENCE: 1211

Gly Xaa Xaa Xaa Xaa Lys Xaa Xaa Xaa Xaa Xaa
1               5                   10

<210> SEQ ID NO 1212
<211> LENGTH: 10
<212> TYPE: PRT
<213> ORGANISM: artificial sequence
<220> FEATURE:
<223> OTHER INFORMATION: synthetic polypeptide
```

```
<220> FEATURE:
<221> NAME/KEY: MISC_FEATURE
<222> LOCATION: (2)..(2)
<223> OTHER INFORMATION: a hydrophobic or aromatic residue
<220> FEATURE:
<221> NAME/KEY: MISC_FEATURE
<222> LOCATION: (3)..(3)
<223> OTHER INFORMATION: a glutamic acid or aspartic acid
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (5)..(5)
<223> OTHER INFORMATION: an aspartic acid, asparagine, glutamic acid,
      tyrosine or alanine
<220> FEATURE:
<221> NAME/KEY: MISC_FEATURE
<222> LOCATION: (7)..(7)
<223> OTHER INFORMATION: a hydrophobic or serine residue
<220> FEATURE:
<221> NAME/KEY: MISC_FEATURE
<222> LOCATION: (8)..(8)
<223> OTHER INFORMATION: an aromatic residue
<220> FEATURE:
<221> NAME/KEY: MISC_FEATURE
<222> LOCATION: (9)..(9)
<223> OTHER INFORMATION: an aromatic, aliphatic hydrophobic, histidine
      or threonine residue
<220> FEATURE:
<221> NAME/KEY: MISC_FEATURE
<222> LOCATION: (10)..(10)
<223> OTHER INFORMATION: a glutamic acid or aspartic acid

<400> SEQUENCE: 1212

Gly Xaa Xaa Xaa Xaa Lys Xaa Xaa Xaa Xaa
1               5                   10

<210> SEQ ID NO 1213
<211> LENGTH: 9
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: a glutamic acid or aspartic acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine
<220> FEATURE:
<221> NAME/KEY: MISC_FEATURE
<222> LOCATION: (6)..(6)
<223> OTHER INFORMATION: a hydrophobic or serine residue
<220> FEATURE:
<221> NAME/KEY: MISC_FEATURE
<222> LOCATION: (7)..(7)
<223> OTHER INFORMATION: an aromatic residue
<220> FEATURE:
<221> NAME/KEY: MISC_FEATURE
<222> LOCATION: (8)..(8)
<223> OTHER INFORMATION: an aromatic, aliphatic hydrophobic, histidine
      or threonine residue
<220> FEATURE:
<221> NAME/KEY: MISC_FEATURE
<222> LOCATION: (9)..(9)
<223> OTHER INFORMATION: a glutamic acid or aspartic acid

<400> SEQUENCE: 1213
```

Gly Xaa Xaa Xaa Lys Xaa Xaa Xaa Xaa
1               5

<210> SEQ ID NO 1214
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: a glutamic acid or aspartic acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine
<220> FEATURE:
<221> NAME/KEY: MISC_FEATURE
<222> LOCATION: (6)..(6)
<223> OTHER INFORMATION: a hydrophobic or serine residue
<220> FEATURE:
<221> NAME/KEY: MISC_FEATURE
<222> LOCATION: (7)..(7)
<223> OTHER INFORMATION: an aromatic residue
<220> FEATURE:
<221> NAME/KEY: MISC_FEATURE
<222> LOCATION: (8)..(8)
<223> OTHER INFORMATION: an aromatic, aliphatic hydrophobic, histidine
      or threonine residue
<220> FEATURE:
<221> NAME/KEY: MISC_FEATURE
<222> LOCATION: (9)..(9)
<223> OTHER INFORMATION: a glutamic acid or aspartic acid
<220> FEATURE:
<221> NAME/KEY: MISC_FEATURE
<222> LOCATION: (10)..(10)
<223> OTHER INFORMATION: an aliphatic hydrophobic residue

<400> SEQUENCE: 1214

Gly Xaa Xaa Xaa Lys Xaa Xaa Xaa Xaa Xaa
1               5                   10

<210> SEQ ID NO 1215
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a hydrophobic or aromatic residue
<220> FEATURE:
<221> NAME/KEY: MISC_FEATURE
<222> LOCATION: (2)..(2)
<223> OTHER INFORMATION: a glutamic acid or aspartic acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine
<220> FEATURE:
<221> NAME/KEY: MISC_FEATURE
<222> LOCATION: (6)..(6)
<223> OTHER INFORMATION: a hydrophobic or serine residue
<220> FEATURE:
<221> NAME/KEY: MISC_FEATURE -continued

```
<222> LOCATION: (7)..(7)
<223> OTHER INFORMATION: an aromatic residue
<220> FEATURE:
<221> NAME/KEY: MISC_FEATURE
<222> LOCATION: (8)..(8)
<223> OTHER INFORMATION: an aromatic, aliphatic hydrophobic, histidine
      or threonine residue
<220> FEATURE:
<221> NAME/KEY: MISC_FEATURE
<222> LOCATION: (9)..(9)
<223> OTHER INFORMATION: a glutamic acid or aspartic acid
<220> FEATURE:
<221> NAME/KEY: MISC_FEATURE
<222> LOCATION: (10)..(10)
<223> OTHER INFORMATION: an aliphatic hydrophobic residue

<400> SEQUENCE: 1215

Xaa Xaa Xaa Xaa Lys Xaa Xaa Xaa Xaa Xaa
1               5                   10

<210> SEQ ID NO 1216
<211> LENGTH: 9
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a hydrophobic or aromatic residue
<220> FEATURE:
<221> NAME/KEY: MISC_FEATURE
<222> LOCATION: (2)..(2)
<223> OTHER INFORMATION: a glutamic acid or aspartic acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine
<220> FEATURE:
<221> NAME/KEY: MISC_FEATURE
<222> LOCATION: (6)..(6)
<223> OTHER INFORMATION: a hydrophobic or serine residue
<220> FEATURE:
<221> NAME/KEY: MISC_FEATURE
<222> LOCATION: (7)..(7)
<223> OTHER INFORMATION: an aromatic residue
<220> FEATURE:
<221> NAME/KEY: MISC_FEATURE
<222> LOCATION: (8)..(8)
<223> OTHER INFORMATION: an aromatic, aliphatic hydrophobic, histidine
      or threonine residue
<220> FEATURE:
<221> NAME/KEY: MISC_FEATURE
<222> LOCATION: (9)..(9)
<223> OTHER INFORMATION: a glutamic acid or aspartic acid

<400> SEQUENCE: 1216

Xaa Xaa Xaa Xaa Lys Xaa Xaa Xaa Xaa
1               5

<210> SEQ ID NO 1217
<211> LENGTH: 9
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a glutamic acid or aspartic acid
<220> FEATURE:
```

```
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine
<220> FEATURE:
<221> NAME/KEY: MISC_FEATURE
<222> LOCATION: (5)..(5)
<223> OTHER INFORMATION: a hydrophobic or serine residue
<220> FEATURE:
<221> NAME/KEY: MISC_FEATURE
<222> LOCATION: (6)..(6)
<223> OTHER INFORMATION: an aromatic residue
<220> FEATURE:
<221> NAME/KEY: MISC_FEATURE
<222> LOCATION: (7)..(7)
<223> OTHER INFORMATION: an aromatic, aliphatic hydrophobic, histidine
      or threonine residue
<220> FEATURE:
<221> NAME/KEY: MISC_FEATURE
<222> LOCATION: (8)..(8)
<223> OTHER INFORMATION: a glutamic acid or aspartic acid
<220> FEATURE:
<221> NAME/KEY: MISC_FEATURE
<222> LOCATION: (9)..(9)
<223> OTHER INFORMATION: an aliphatic hydrophobic residue

<400> SEQUENCE: 1217

Xaa Xaa Xaa Lys Xaa Xaa Xaa Xaa Xaa
1               5

<210> SEQ ID NO 1218
<211> LENGTH: 8
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a glutamic acid or aspartic acid
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine
<220> FEATURE:
<221> NAME/KEY: MISC_FEATURE
<222> LOCATION: (5)..(5)
<223> OTHER INFORMATION: a hydrophobic or serine residue
<220> FEATURE:
<221> NAME/KEY: MISC_FEATURE
<222> LOCATION: (6)..(6)
<223> OTHER INFORMATION: an aromatic residue
<220> FEATURE:
<221> NAME/KEY: MISC_FEATURE
<222> LOCATION: (7)..(7)
<223> OTHER INFORMATION: an aromatic, aliphatic hydrophobic, histidine
      or threonine residue
<220> FEATURE:
<221> NAME/KEY: MISC_FEATURE
<222> LOCATION: (8)..(8)
<223> OTHER INFORMATION: a glutamic acid or aspartic acid

<400> SEQUENCE: 1218

Xaa Xaa Xaa Lys Xaa Xaa Xaa Xaa
1               5

<210> SEQ ID NO 1219
```

```
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a hydrophobic or aromatic residue
<220> FEATURE:
<221> NAME/KEY: MISC_FEATURE
<222> LOCATION: (2)..(2)
<223> OTHER INFORMATION: a glutamic acid or aspartic acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine
<220> FEATURE:
<221> NAME/KEY: MISC_FEATURE
<222> LOCATION: (6)..(6)
<223> OTHER INFORMATION: a hydrophobic or serine residue
<220> FEATURE:
<221> NAME/KEY: MISC_FEATURE
<222> LOCATION: (7)..(7)
<223> OTHER INFORMATION: an aromatic residue
<220> FEATURE:
<221> NAME/KEY: MISC_FEATURE
<222> LOCATION: (8)..(8)
<223> OTHER INFORMATION: an aromatic, aliphatic hydrophobic, histidine
      or threonine residue
<220> FEATURE:
<221> NAME/KEY: MISC_FEATURE
<222> LOCATION: (9)..(9)
<223> OTHER INFORMATION: a glutamic acid or aspartic acid
<220> FEATURE:
<221> NAME/KEY: MISC_FEATURE
<222> LOCATION: (10)..(10)
<223> OTHER INFORMATION: an aliphatic hydrophobic residue
<220> FEATURE:
<221> NAME/KEY: MISC_FEATURE
<222> LOCATION: (11)..(11)
<223> OTHER INFORMATION: an aspartic acid, glutamic acid, serine,
      threonine, cysteine, or tyrosine residue

<400> SEQUENCE: 1219

Xaa Xaa Xaa Xaa Lys Xaa Xaa Xaa Xaa Xaa Xaa
1               5                   10

<210> SEQ ID NO 1220
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a hydrophobic or aromatic residue
<220> FEATURE:
<221> NAME/KEY: MISC_FEATURE
<222> LOCATION: (2)..(2)
<223> OTHER INFORMATION: a glutamic acid or aspartic acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: an aspartic acid, asparagine, glutamic acid,
      tyrosine or alanine
<220> FEATURE:
<221> NAME/KEY: MISC_FEATURE
```

```
<222> LOCATION: (6)..(6)
<223> OTHER INFORMATION: a hydrophobic or serine residue
<220> FEATURE:
<221> NAME/KEY: MISC_FEATURE
<222> LOCATION: (7)..(7)
<223> OTHER INFORMATION: an aromatic residue
<220> FEATURE:
<221> NAME/KEY: MISC_FEATURE
<222> LOCATION: (8)..(8)
<223> OTHER INFORMATION: an aromatic, aliphatic hydrophobic, histidine
      or threonine residue
<220> FEATURE:
<221> NAME/KEY: MISC_FEATURE
<222> LOCATION: (9)..(9)
<223> OTHER INFORMATION: a glutamic acid or aspartic acid
<220> FEATURE:
<221> NAME/KEY: MISC_FEATURE
<222> LOCATION: (10)..(10)
<223> OTHER INFORMATION: an aspartic acid, glutamic acid, serine,
      threonine, cysteine, or tyrosine residue

<400> SEQUENCE: 1220

Xaa Xaa Xaa Xaa Lys Xaa Xaa Xaa Xaa Xaa
1               5                   10

<210> SEQ ID NO 1221
<211> LENGTH: 10
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a glutamic acid or aspartic acid
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine
<220> FEATURE:
<221> NAME/KEY: MISC_FEATURE
<222> LOCATION: (5)..(5)
<223> OTHER INFORMATION: a hydrophobic or serine residue
<220> FEATURE:
<221> NAME/KEY: MISC_FEATURE
<222> LOCATION: (6)..(6)
<223> OTHER INFORMATION: an aromatic residue
<220> FEATURE:
<221> NAME/KEY: MISC_FEATURE
<222> LOCATION: (7)..(7)
<223> OTHER INFORMATION: an aromatic, aliphatic hydrophobic, histidine
      or threonine residue
<220> FEATURE:
<221> NAME/KEY: MISC_FEATURE
<222> LOCATION: (8)..(8)
<223> OTHER INFORMATION: a glutamic acid or aspartic acid
<220> FEATURE:
<221> NAME/KEY: MISC_FEATURE
<222> LOCATION: (9)..(9)
<223> OTHER INFORMATION: an aliphatic hydrophobic residue
<220> FEATURE:
<221> NAME/KEY: MISC_FEATURE
<222> LOCATION: (10)..(10)
<223> OTHER INFORMATION: an aspartic acid, glutamic acid, serine,
      threonine, cysteine, or tyrosine residue

<400> SEQUENCE: 1221

Xaa Xaa Xaa Lys Xaa Xaa Xaa Xaa Xaa Xaa
1               5                   10

<210> SEQ ID NO 1222
```

```
<211> LENGTH: 9
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: a glutamic acid or aspartic acid
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: an aspartic acid, asparagine, glutamic acid,
      tyrosine or alanine
<220> FEATURE:
<221> NAME/KEY: MISC_FEATURE
<222> LOCATION: (5)..(5)
<223> OTHER INFORMATION: a hydrophobic or serine residue
<220> FEATURE:
<221> NAME/KEY: MISC_FEATURE
<222> LOCATION: (6)..(6)
<223> OTHER INFORMATION: an aromatic residue
<220> FEATURE:
<221> NAME/KEY: MISC_FEATURE
<222> LOCATION: (7)..(7)
<223> OTHER INFORMATION: an aromatic, aliphatic hydrophobic, histidine
      or threonine residue
<220> FEATURE:
<221> NAME/KEY: MISC_FEATURE
<222> LOCATION: (8)..(8)
<223> OTHER INFORMATION: a glutamic acid or aspartic acid
<220> FEATURE:
<221> NAME/KEY: MISC_FEATURE
<222> LOCATION: (9)..(9)
<223> OTHER INFORMATION: an aspartic acid, glutamic acid, serine,
      threonine, cysteine, or tyrosine residue

<400> SEQUENCE: 1222

Xaa Xaa Xaa Lys Xaa Xaa Xaa Xaa Xaa
1               5
```

US 8,759,482 B2

KINETICALLY EFFICIENT SUBSTRATE FOR LIPOIC ACID LIGASE

RELATED APPLICATIONS

This application claims the benefit under 35 U.S.C. §119 (e) of U.S. Provisional Application Ser. No. 61/252,881, entitled "Kinetically Efficient Substrate for Lipoic Acid Ligase," filed on Oct. 19, 2009, which is herein incorporated by reference in its entirety.

Government Support

This invention was made with government support under Grant Nos. GM072670 and EY078244 awarded by the National Institutes of Health. The government has certain rights in this invention.

FIELD OF THE INVENTION

The invention pertains to methods and compositions related to the identification of enzyme substrates for protein labeling.

BACKGROUND OF THE INVENTION

Most proteins are evolved to interact with a multitude of cellular molecules and thus contain a number of distinct domains, binding sites, and activities. Often, it is useful to the biochemist to reduce a specific aspect of a protein's function to just a peptide fragment. This can help to determine the minimal features of a protein required for a specific function such as binding, recognition by an enzyme, translocation, or folding.[1-4] It may also be desirable to create a consensus peptide substrate for assay purposes,[5, 6] or to use a peptide in place of a protein to facilitate crystallography of multiprotein complexes.[7,8] For therapeutic applications, replacement of protein drugs with peptides having similar activity can improve tissue penetration and reduce immunogenicity.[9,10]

One application of protein minimization to peptides is for the purpose of developing new protein labeling technologies. Size minimization of protein tags that direct the targeting of fluorescent probes[11] can greatly reduce problems of tag interference with protein trafficking, folding, and interactions. Conversion of proteins to peptides without loss of the function of interest, however, is challenging for a number of reasons. First, the function may require secondary structure that is difficult to recapitulate in a peptide. Second, the function may require contributions from multiple, noncontiguous regions of a protein. Third, structural information is not available for many proteins, and in some cases, even the regions that contribute to a protein's relevant activity are not known. Fourth, due to their more flexible structure, peptide binding is often associated with a greater entropic penalty than is protein binding,[12] making it more difficult to engineer high-affinity interactions. Numerous methods have been used to reduce proteins to peptides. Simple truncation and/or rational design can be successful,[13-15] but is usually associated with at least a partial loss of activity and/or specificity. Peptide scanning[16] or high-throughput screening[17-19] approaches are more exhaustive, but library sizes are limited (typically $10^2$-$10^5$), so it is difficult to identify optimal sequences.

SUMMARY OF THE INVENTION

The invention relates in part to methods and compositions for labeling of proteins. Methods are presented herein for identifying and evolving substrates for enzymes, such as *Escherichia coli* lipoic acid ligase (Lp1A). Using methods associated with the invention, novel, kinetically efficient peptide substrates for Lp1A, or mutants thereof, were identified, with widespread applications for protein labeling in cells.

Aspects of the invention relate to lipoic acid ligase (Lp1A) acceptor peptides that function as substrates for Lp1A, wherein the peptide comprises 8-13 amino acids and a motif $P_{-4}P_{-3}P_{-2}P_{-1}P_0P_{+1}P_{+2}P_{+3}P_{+4}P_{+5}$ (SEQ ID NOs:1151-1154), which includes a central lysine residue at position 0 ($P_0$), a valine residue at position +1 ($P_{+1}$), a tryptophan residue at position +2 ($P_{+2}$), a glutamic acid or aspartic acid residue at position +4 ($P_{+4}$), a hydrophobic residue or no residue at position +5 ($P_{+5}$), a glutamic acid residue at position −3 ($P_{-3}$), and a phenylalanine residue or no residue at position −4 ($P_{-4}$). In some embodiments, the $k_{cat}$ of the peptide is between 0.001 s$^{-1}$ -1.0 s$^{-1}$ and the $K_m$ of the peptide is between 1 μM -500 μM. In some embodiments, the peptide comprises the sequence GFEIDKVWYDLDA (SEQ ID NO:1). In certain embodiments, the peptide consists of the sequence GFEIDKVWYDLDA (SEQ ID NO:1). Aspects of the invention also encompass any nucleic acid that encodes for any of the peptides described herein, and any composition that includes any of the peptides or nucleic acids described herein. Compositions described herein can also include carriers. In some embodiments, the peptide is N- or C-terminally fused to a target protein.

Aspects of the invention relate to lipoic acid ligase (Lp1A) acceptor peptides that function as substrates for Lp1A, wherein the peptide comprises 8-13 amino acids and a motif $P_{-4}P_{-3}P_{-2}P_{-1}P_0P_{+1}P_{+2}P_{+3}P_{+4}P_{+5}$ (SEQ ID NOs:1151-1154), which includes a central lysine residue at position 0 ($P_0$), a hydrophobic residue or serine residue at position +1 ($P_{+1}$), an aromatic residue at position +2 ($P_{+2}$), an aromatic or aliphatic hydrophobic residue, histidine or threonine residue at position +3 ($P_{+2}$), a glutamic acid or aspartic acid residue at position +4 ($P_{+4}$), an aliphatic hydrophobic residue or no residue at position +5 ($P_{+5}$), an aspartic acid, asparagine, glutamic acid, tyrosine or alanine residue at position −1 ($P_{-1}$), a glutamic acid or aspartic acid residue at position −3 ($P_{-3}$), and a hydrophobic or aromatic residue, or no residue at position −4 ($P_{-4}$). In some embodiments, the acceptor peptide comprises a motif $P_{-5}P_{-4}P_{-3}P_{-2}P_{-1}P_0P_{+1}\ P_{+2}P_{+3}P_{+4}P_{+5}P_{+6}P_{+7}$ (SEQ ID NOs:1195-1210), in which position +7 ($P_{+7}$) is a serine residue, an alanine residue, or is absent. In some embodiments, position −5 ($P_{-5}$) is a glycine residue or is absent. In some embodiments, the $k_{cat}$ of the peptide is between 0.001 s$^{-1}$ -1 s$^{-1}$ and the $K_m$ of the peptide is between 500 μM -1 μM.

In some embodiments, the residue at position +1 is a valine, isoleucine, leucine or phenylalanine residue. In some embodiments, the residue at position +2 is a tryptophan or phenylalanine residue. In some embodiments, the residue at position +3 is a tyrosine, histidine, phenylalanine, isoleucine, valine, leucine or threonine residue. In some embodiments, the residue at position +4 is a glutamic acid or aspartic acid residue. In some embodiments, the residue at position +5 is a leucine, isoleucine or phenylalanine residue. In some embodiments, the residue at position +6 is an aspartic acid, glutamic acid, serine, threonine, cysteine or tyrosine residue.

In some embodiments, the residue at position −1 is an aspartic acid, asparagine, glutamic acid, tyrosine or alanine residue. In some embodiments, the residue at position −2 is an isoleucine, histidine, leucine or arginine residue. In some embodiments, the residue at position −3 is a glutamic acid or aspartic acid residue. In some embodiments, the residue at position −4 is a phenylalanine, isoleucine, valine or leucine residue.

In some embodiments, the peptide comprises the sequence GFEIDKVWYDLDA (SEQ ID NO:1). In certain embodiments, the peptide consists of the sequence GFEIDKVWY-DLDA (SEQ ID NO:1). Aspects of the invention also encompass any nucleic acid that encodes for any of the peptides described herein, and any composition that includes any of the peptides or nucleic acids described herein. Compositions described herein can also include carriers. In some embodiments, the peptide is N- or C-terminally fused to a target protein.

Aspects of the invention relate to methods for identifying an acceptor peptide that functions as a substrate for an enzyme, for use in protein labeling, the method including: performing surface display in cells, wherein each cell expresses one acceptor peptide that is fused to a cell surface protein, labeling each cell with the enzyme to ligate the acceptor peptide to a probe, sorting each cell based on the extent of acceptor peptide ligation, and selecting an acceptor peptide that has a $k_{cat}$ between 0.001 s$^{-1}$-1 s$^{-1}$ and a $K_m$ between 500 μM-1 μM, wherein an acceptor peptide that has a $k_{cat}$ between 0.001 s$^{-1}$-1 s$^{-1}$ and a $K_m$ between 500 μM-1 μM is an acceptor peptide that functions as a substrate for the enzyme for use in protein labeling.

In some embodiments, the acceptor peptide is an Lp1A acceptor peptide (LAP) that functions as a substrate for Lp1A, and the enzyme if Lp1A. In some embodiments, the peptide that is selected as a substrate for the enzyme is further optimized through mutagenesis. In some embodiments, the cells are yeast cells. In certain embodiments the probe is lipoic acid, alkyl azide, aryl azide or a halo alkane. In some embodiments, surface display is conducted using a library of acceptor peptides wherein each acceptor peptide within the library has a sequence that is a variation of the sequence of a natural protein substrate for the enzyme.

BRIEF DESCRIPTION OF THE DRAWINGS

FIG. 1A shows natural (lipoic acid) and unnatural (Azide 7 and 11-Br) small-molecule substrates of Lp1A and its W37 mutant. FIG. 1B shows natural and engineered ligation reactions. Top: Lp1A-catalyzed lipoylation of the 9 kD E2p domain of E. coli pyruvate dehydrogenase (structure from PDB 1QJO). Bottom: Lp1A-catalyzed 11-Br ligation onto an engineered LAP ("Lp1A Acceptor Peptide"), which is genetically fused to any protein of interest (POI). Ligated alkyl bromide can be specifically and covalently modified by HaloTag-fluorophore conjugates.[31] The circle represents any probe. FIG. 1C shows a model for interaction between Lp1A (from PDB 1X2H)[33] and E2p (from PBD 1QJO).[34] The lipoylation site on E2p, Lys41, is rendered in stick.

FIG. 2A shows the LAP library displayed on the yeast surface as a fusion to Aga2p protein. A C-terminal myc epitope is used to quantify LAP expression level. In the selection scheme, yeast cells display three sample LAP sequences, with high (LAPx), moderate (LAPy), and low (LAPz) activity shown. The yeast cells are collectively labeled with lipoic acid or 11-Br probe. The former is detected with antilipoic acid; the latter is detected with HaloTag-biotin,[30] followed by streptavidin-fluorophore conjugate. The yeast pool is then sorted (sorting gate is depicted by a solid triangle) on the basis of both ligation extent (probe intensity) and LAP expression level (c-Myc staining intensity), to enrich the most kinetically efficient LAP peptides. FIG. 2B depicts determination of labeling and sorting conditions for model selections. FACS scatter plots are shown for yeast displaying E2p, LAP1,[13] and E2p-Ala (E2p with a Lys41→Ala mutation), after lipoylation with 300 nM Lp1A for 30 min, and staining with antilipoic acid antibody. The plots show the distribution of single yeast cells as a function of phycoerthyrin staining intensity (reflecting extent of lipoylation) and c-Myc staining intensity (reflecting expression level of the Aga2p-LAP fusion). A cell population on the lower left is present in all three samples, and represents untransformed yeast. Optimized sorting gates, used for the model selections, are indicated within each graph. FIG. 2C depicts results of model selections. E2p-displaying yeast and LAP1-displaying yeast were mixed at ratios of 1:10, 1:100, or 1:1000, labeled with 300 nM Lp1A for 30 min, and sorted. PCR analysis gives the ratio of yeast populations pre- and post-selection. E2p enrichment factor was >10$^3$-fold.

FIG. 3A presents a table showing sequences of natural Lp1A protein substrates, a previous rationally designed LAP1,[13] and the LAP library described herein. Lysine modification sites are underlined. For the LAP library, positions −4 and +5 were fixed as hydrophobic amino acids (Val, Ileu, Leu, Phe, Met), positions −3 and +4 as polar amino acids (Glu, Asp, Gln, His), and position +7 as Ser or Ala. Positions −1 and +1 are partially randomized (39% Asp or 49% Val). X represents any amino acid. The sequences in FIG. 3A correspond to SEQ ID NOs: 1110-1119 in descending order. FIG. 3B presents results of four rounds of selection. Selection conditions, including small-molecule substrates used for labeling, are given above each arrow. To analyze amplified yeast pools following each round of selection, uniform lipoylation conditions were used (given in the lower right of each scatter plot). Yeast pools from rounds 3 and 4 were additionally analyzed under milder conditions, with 50 nM Lp1A.

FIG. 4A shows various LAP sequences that were compared to E2p protein, by lipoylation with 50 nM Lp1A for 1 h. Product was detected by HPLC. All LAPs were tested as fusions to the N- or C-terminus of carrier protein HP1, as indicated.[13] Error bars, ±1 s.d. The sequences in FIG. 4A correspond to SEQ ID NOs: 1120, 1121, 1122, 1123, 1, 1 and 1124 respectively. FIG. 4B shows HEK cells expressing LAP2 or LAP1-fused LDL receptor labeled with Lp1AW37A and 11-Br for 5 min, followed by QD605-HaloTag[31] for 5 min. QD605 emission is shown in the top row. Merged GFP and DIC (differential interference contrast) images are shown in the bottom row. Negative controls are shown with ATP or Lp1A omitted. Scale bars, 10 μm.

FIG. 6A presents sequences of LAP clones after rounds 2 and 3. Lipoylated lysine is underlined. The sequences corresponding to "Clones after Round 2" are represented by SEQ ID NOs: 1125-1130 in descending order. The sequences corresponding to "Clones after Round 3" are represented by SEQ ID NOs: 1131-1137 in descending order. FIG. 6B shows a comparison of clones obtained from two different sorting gates in round 4. Several clones from the higher gate (gate A) appeared multiple times. The sequences corresponding to "Clones after Round 4 (Gate A)" are represented by SEQ ID NOs: 1138-1141 in descending order. The sequences corresponding to "Clones after Round 4 (Gate B)" are represented by SEQ ID NOs: 1142-1148 in descending order. FIG. 6C presents diagrams illustrating amino acid frequencies at specific positions in the original library (based on library design), and after rounds 2-4 (based on sequences of isolated clones). Generated using http://weblogo.berkeley.edu/.

FIG. 7A shows the −4 Phe→Val mutant of LAP4.1 compared to LAP4.1 in a yeast cell surface lipoylation assay with 200 nM Lp1A. FIG. 7B shows, for comparison, the same assay performed with Gate A and Gate B yeast pools, obtained from the fourth round of selection.

FIG. 9A shows HEK cells expressing CFP-TM fusions to E2p, LAP2, or LAP1, which were labeled with 1 µM Lp1A for 10 minutes, before staining with anti-lipoic acid antibody followed by fluorescein-conjugated secondary antibody. The surface expression levels of TM fusions to LAP peptides are ~2-fold lower than TM-fused E2p. However, expression levels of intracellular proteins are similar, whether fused to a LAP sequence or E2p. The right column shows fluorescein/CFP ratio images, reflecting lipoylation efficiency. Scale bar, 10 µm. FIG. 9B presents a table showing results from HEK cells expressing CFP-TM fusions to various LAP sequences or E2p, which were labeled and imaged as in (A). Single cell mean fluorescein/CFP intensity ratios were tabulated for >160 cells from >18 fields of view. These ratios were plotted, and the slopes and R2 value are shown in the table.

DETAILED DESCRIPTION OF THE INVENTION

Figure 1:
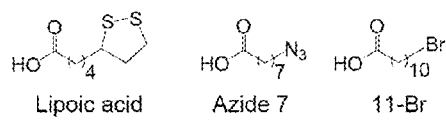
FIG. 1 presents schematics of Lp1A-catalyzed protein and peptide labeling reactions.
Figure 1:
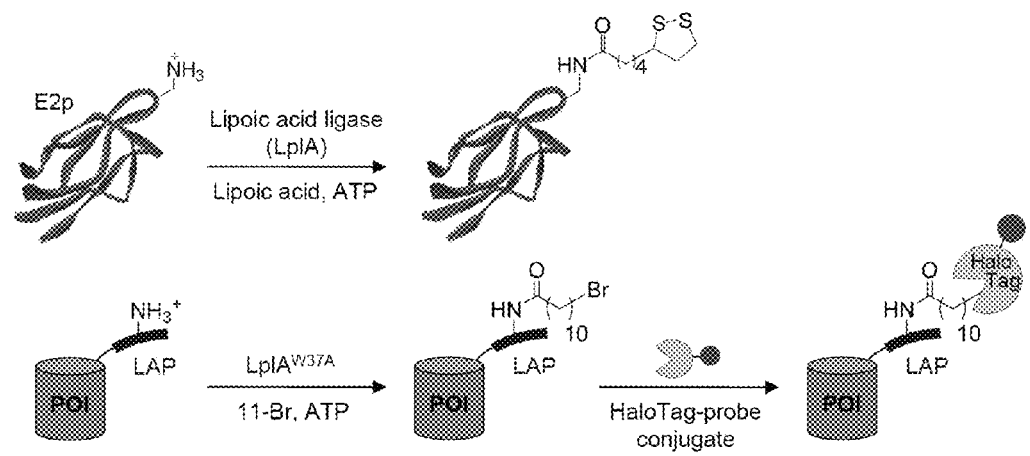
Figure 1:
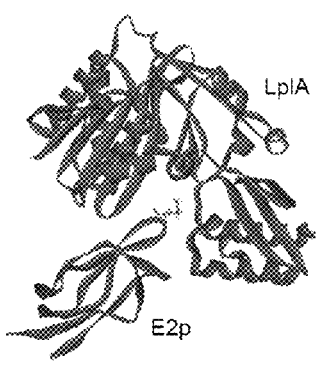

The invention relates, at least in part, to the evolution of peptide substrates. Methods described herein use yeast surface display, optionally combined with rational mutagenesis, to identify optimal peptide substrates for enzymes. Using such methods, lipoic acid ligase (Lp1A) acceptor peptides (LAPs), that function as substrates for Lp1A and/or mutants thereof, were generated that possess optimal kinetic properties for use in protein labeling. Beneficial consequences of kinetic efficiency include the ability to label peptide-tagged cell surface receptors with unnatural probes, and effectiveness in fluorophore-tagging of intracellular proteins.

As one of ordinary skill in the art would appreciate, methods described herein, for identification and optimization of peptide substrates, could be used to identify and/or optimize peptide substrates for any enzyme. In particular, methods described herein are directed to identifying peptide substrates for use in protein labeling in cells. In some embodiments, methods are directed to identifying substrates for the enzyme *E. coli* Lp1A. As used herein, "Lp1A" includes the wild-type *E. coli* protein and any homolog and/or analog and/or functional variant or mutant thereof, including, but not limited to those described further in US Patent Publication 2009/0149631, the entire contents of which is incorporated herein by reference.

Lp1A is a cofactor ligase that can be utilized for fluorescent protein labeling applications.[13,28] The natural function of Lp1A is to catalyze ATP-dependent, covalent ligation of lipoic acid (FIG. 1A) onto specific lysine side chains of three *E. coli* proteins involved in oxidative metabolism: pyruvate dehydrogenase, 2-oxoglutarate dehydrogenase, and the glycine cleavage system.[29] It has previously been shown that Lp1A and engineered mutants thereof can ligate small-molecule probes such as alkyl azides (*Nat. Biotechnol.* 2007, 25, 1483-1487) and photo-cross-linkers (*Angew. Chem., Int. Ed.* 2008, 47, 7018-7021) in place of lipoic acid, facilitating imaging and proteomic studies.

Recombinant fusions of proteins of interest to the 9 kDa E2p domain of pyruvate dehydrogenase (FIG. 1B top),[13] can be labeled with high efficiency and specificity by unnatural probes on the surface and in the cytosol of living mammalian cells,[13,28,31,32] for protein imaging applications. However, fusing a protein to the 9 kDa E2p domain of pyruvate dehydrogenase could potentially interfere with the function of the protein. In an attempt to identify a peptide that would be functional in protein labeling methods with Lp1A but would minimally interfere with the function of the protein of interest, optimization of peptide substrates for Lp1A were investigated herein. As used herein, an Lp1A acceptor polypeptide ("LAP") refers to a peptide sequence that acts as a substrate for Lp1A. Methods described herein identify LAPs with optimal kinetic properties for use with Lp1A in protein labeling.

Aspects of the invention relate to using cell surface display for screening peptides. As used herein, cell surface display refers to a method wherein cells are generated that express proteins of interest fused to a cell-surface protein. In some embodiments, the cells are yeast cells and the cell-surface protein is Aga2p. As described in Example 1, a yeast display library was generated wherein individual yeast cells express LAPs on their cell surfaces and this library was used to screen for substrates of Lp1A. One of the advantages of yeast surface display for enzyme substrate evolution lies in its dynamic range: up to $10^4$-$10^5$ copies of a peptide can be displayed on the surface of each yeast cell.[41] It should be appreciated that the cell surface display methods described herein can also be used in cells other than yeast. For example, such methods could be compatible with bacterial cells, phage, insect cells, plant cells, or mammalian cells.

Aspects of the invention relate to screening a library of peptides to identify optimal substrates for an enzyme. A variety of approaches for library design and construction are compatible with methods of the invention. In some instances, rational design is used in library construction. As used herein, "rational design" refers to incorporating knowledge of the enzyme and/or substrate and/or the interaction between the enzyme and substrate into the design of peptides within the library to be used for screening. For example, in designing a LAP library to identify optimal substrates for Lp1A, rational design methods can be incorporated by examining natural substrates for Lp1A and incorporating conserved residues from these natural substrates into peptides within the library. Random mutagenesis can also be used in library construction.

In some instances, partial randomization of peptides is used for library construction. As used herein, "partial randomization" refers to the use of rational design to select some residues within a peptide and the use of random mutagenesis to select other residues within the same peptide. For example, it was known from natural Lp1A substrates that a central Lys residue is important for the interaction of Lp1A with its substrate, so a LAP can be designed to contain a central lysine residue. Within the context of a 12 amino acid LAP, for example, if complete randomization of the 11 flanking amino acids is employed, this would result in a theoretical diversity of approximately $10^{14}$, a number that is potentially impractical for some experimental approaches. Partial randomization can be used to reduce this number to a more manageable number for experimental purposes. The library described in Example 1 was created using partial randomization. Aspects of rational design included examining alignments of natural Lp1A substrate protein sequences, 3 dimensional structures of such substrates, such as NMR data for E2p,[34] and the structure of a functionally and structurally related biotin acceptor domain in complex with biotin ligase.

Residues relevant for the interaction between Lp1A and its substrates can be ascertained in part by examining the natural substrates for this enzyme. In these proteins (e.g., such as E2o, E2p, or H-protein), the substrate sequence encompasses a lysine lipoylation site at the tip of a sharp β-turn in the substrate. For example in *E. coli* E2o, the lysine at the tip of a sharp β-turn is the lysine that is in position 44 of *E. coli* E2o, see GenBank Accession No. AAA23898. In each of the three lipoyl domains of *E. coli* E2p, the lysines at the tip of the sharp β-turn are the lysine lipoylation sites (e.g., the lysine in position of the lipoyl hybrid domain, see ProteinDataBank Accession No. 1QJO). In *E. coli* H-protein, the lysine at the tip of a sharp β-turn is the lysine that is in position 65 of *E. coli* H-protein, see GenBank Accession No. CAA52145. Testing has shown that although accurate positioning of the target lysine within the β-turn is important for Lp1A recognition, the residues flanking the lysine can be varied.

In Example 1, 250 naturally lipoylated proteins (lipoate acceptor proteins) from >100 distinct species were examined. Trends observed in the sequences of these different species, indicating conserved residues, can be incorporated into peptides within the LAP library. Structural data, such as NMR data on lipoate acceptor domains can also be examined,[34,43,45] and trends observed in this data can be incorporated into a library. In some instances if co-crystallization data is available for an enzyme-substrate pair, this structural data can be examined and used to inform peptide and library design.

It should be appreciated that a LAP library can contain peptides of varying lengths. In some embodiments the peptides are 8-13 amino acids long. For example peptides can be 8, 9, 10, 11, 12 or 13 amino acids long. In other embodiments, peptides can be less than 11 amino acids long. For example, in some embodiment peptides can be 4, 5, 6, 7, or 8 amino acids long. In other embodiments, peptides can be longer than 13 amino acids. For example, peptides can be 14, 15, 16, 17, 18, 19, 20, 21, 22, 23, 24, 25, 26, 27, 28, 29, 30, or greater than 30 amino acids long. A library can have peptides that are all the same length, or peptides of varying lengths.

It should be appreciated that, once peptides have been selected for screening, basic molecular biology techniques known to one of ordinary skill in the art can be employed for constructing and screening a peptide library. Yeast surface display screening can employ one round of selection or multiple rounds of selection, and can be combined with other selection techniques. In some embodiments, the concentration of the enzyme such as Lp1A is modified between each round of selection. For example, if multiple rounds of selection are conducted, the enzyme concentration can be reduced in later rounds relative to earlier rounds in order to increase the selectivity of the selection process. Also, different Lp1A mutants or a mixture of them can be used within one or more of the rounds of selection, including a negative selection for generating an acceptor peptide.

Yeast surface display screens described herein to identify acceptor peptides (such as LAPs) for an enzyme (such as Lp1A), involve labeling each cell with the enzyme to ligate the peptide to a probe. It should be appreciated that a variety of probes are compatible with methods of the invention, as discussed further in US Patent Publication 2009/0149631, the entire contents of which is incorporated herein by reference. In some embodiments, lipoic acid or analogs thereof are used as a probe. In certain embodiments, the probe is alkyl azide or aryl azide. Probes, such as lipoic acid or analogs thereof, may be directly detectable or may be reacted with a detectable moiety. Examples of such lipoic acid analogs include but are not limited to those conjugated to coumarin, fluorescein, aryl azides, diazirines, benzophenones, resorufins, various xanthene-type fluorophores, haloalkanes, metal-binding ligands, or derivatives thereof. A lipoic acid analog can also be fluorogenic. As used herein, a fluorogenic compound is one that is not detectable (e.g., fluorescent) by itself, but when conjugated to another moiety becomes fluorescent. An example of this is non-fluorescent coumarin phosphine which reacts with azides to produce fluorescent coumarin. Fluorogenic lipoic acid analogs are especially useful to keeping background to a minimum (e.g., cellular imaging applications). Lipoic acid and its analogs, labeling of such molecules, and the use of such molecules in imaging, are all incorporated by reference from US Patent Publication 2009/0149631.

Yeast surface display screens described herein involve sorting cells to determine which cells contain peptides of interest. Any method for cell sorting familiar to one of ordinary skill in the art could be compatible with methods associated with the invention. In some embodiments, cells are sorted using fluorescence-activated cell sorting (FACS), using standard techniques. The selection scheme developed herein is generalizable to other classes of enzyme substrates, such as those for kinases and glycosyltransferases. In some embodiments, the enzymatic products are detected by fluorescence.

Aspects of the invention relate to identification and selection of optimal peptide substrates (LAPs) for Lp1A. LAPs, at least in part, can be selected based on kinetic properties, including $k_{cat}$ and/or $K_m$ values. In some embodiments, a LAP is selected that has a $k_{cat}$ value in the range of 0.001 s$^{-1}$-1.0 s$^{-1}$ and/or a $K_m$ value in the range of 1μM-500 μM and/or a $k_{cat}/K_m$ ratio in the range of 0.0001-10 μM$^{-1}$min$^{-1}$. In some embodiments, a LAP is selected that has a $k_{cat}$ value of approximately 0.22±0.01 s$^{-1}$ and/or a $K_m$ value of approximately 13.32±1.78 μM.

LAPs associated with the invention have a conserved central lysine residue at position 0, but can have varying flanking residues. In some embodiments, the residue at position +1 is hydrophobic. For example, the residue at position +1 can be valine, isoleucine, leucine or phenylalanine. In other embodiments, the residue at position +1 can be a small residue such as alanine or serine. In some embodiments, the residue at position +1 is not a charged residue. In some embodiments, the residue at position +2 position is an aromatic residue such as a tryptophan or phenylalanine residue. In some embodiments, the residue at position +3 position is an aromatic residue such as tyrosine, histidine or phenylalanine. In some embodiments, the residue at position +3 position is an aliphatic hydrophobic residue such as an isoleucine, valine, leucine or threonine residue.

LAPs associated with the invention comprise a motif $P_{-5}P_{-4}P_{-3}P_{-2}P_{-1}P_0P_{+1}P_{+2}P_{+3}P_{+4}P_{+5}P_{+6}P_{+7}$ (SEQ ID NOs: 1163-1194) and have a conserved central lysine residue at position 0 ($P_0$), but can have varying flanking residues. In some embodiments, the residue at position +1 ($P_{+1}$) hydrophobic. For example, the residue at position +1 ($P_{+1}$) can be valine, isoleucine, leucine or phenylalanine. In other embodiments, the residue at position +1 ($P_{+1}$) can be a small residue such as alanine or serine. In some embodiments, the residue at position +1 ($P_{+1}$) is not a charged residue. In some embodiments, the residue at position +2 ($P_{+2}$) position is an aromatic residue such as a tryptophan or phenylalanine residue. In some embodiments, the residue at position +3 ($P_{+3}$) position is an aromatic residue such as tyrosine, histidine or phenylalanine. In some embodiments, the residue at position +3 ($P_{+3}$) position is an aliphatic hydrophobic residue such as an isoleucine, valine, leucine or threonine residue.

In some embodiments, the residue at position +4 ($P_{+4}$) is a negatively charged residue such as aspartic acid or glutamic acid. In some embodiments, the residue at position +5 ($P_{+5}$) is an aliphatic hydrophobic residue such as leucine, isoleucine or phenylalanine. In some embodiments, the residue at position +5 ($P_{+5}$) is a small residue such as valine. In some embodiments, there is no residue at position +5 ($P_5$). The residue at position +6 ($P_{+6}$) can be any residue. In some embodiments, the residue at position +6 ($P_{+6}$) can be a negatively charged residue such as glutamic acid or aspartic acid. In some embodiments, the residue at position +6 ($P_{+6}$) is a hydroxyl/thiol containing residue such as serine, threonine, cysteine or tyrosine. In some embodiments, the residue at position +6 ($P_{+6}$) is a proline residue. In some embodiments, there is no residue at position +6 ($P_{+6}$) In some embodiments there is no residue in position +7 ($P_{+7}$). In other embodiments there is a residue at position +7 ($P_{+7}$). In certain embodiments, the residue at position +7 ($P_{+1}$) is a serine or alanine residue.

In some embodiments the residue at position −1 ($P_{-1}$) is an aspartic acid, asparagine, glutamic acid, tyrosine or alanine residue. The residue at position −2 ($P_{-2}$), can be any residue. In some embodiments, the residue at position −2 ($P_{-2}$), is an isoleucine, histidine, leucine or arginine residue. In some embodiments the residue at position −3 ($P_{-3}$) is a negatively charged residue such as glutamic acid or aspartic acid. In some embodiments, the residue at position −4 ($P_{-4}$) is a hydrophobic residue such as phenylalanine, isoleucine, valine or leucine. In some embodiments, the residue at position −4 ($P_{-4}$) is an aromatic residue. In some embodiments, there is no residue at position −4 ($P_{-4}$). In some embodiments, there is no residue in position −5 ($P_{-5}$) In other embodiments, there is a residue in position −5 ($P_{-5}$) In certain embodiments, the residue at position −5 ($P_{-5}$) is a glycine residue.

In some embodiments the LAP comprises the sequence GFEIDKVWYDLDA (SEQ ID NO:1), with the central lysine (K) residue indicated by underlining. In certain embodiments, the LAP sequence consists of the sequence GFEIDKVWYDLDA (SEQ ID NO:1), and is referred to as "LAP2." Other non-limiting examples of peptides consistent with aspects of the invention, wherein the central lysine (K) residue is indicated by underlining include peptides that comprise or consist of the following:

```
FEIDKVWYDLD,      (SEQ ID NO: 2)
GFEIDKVWYDLD,     (SEQ ID NO: 3)
FEIDKVWYDLDA,     (SEQ ID NO: 4)
GFEIDKIWYDLDA,    (SEQ ID NO: 5)
FEIDKIWYDLD,      (SEQ ID NO: 6)
GFEIDKIWYDLD,     (SEQ ID NO: 7)
FEIDKIWYDLDA,     (SEQ ID NO: 8)
GFEIDKLWYDLDA,    (SEQ ID NO: 9)
FEIDKLWYDLD,      (SEQ ID NO: 10)
GFEIDKLWYDLD,     (SEQ ID NO: 11)
FEIDKLWYDLDA,     (SEQ ID NO: 12)
GFEIDKFWYDLDA,    (SEQ ID NO: 13)
FEIDKFWYDLD,      (SEQ ID NO: 14)
GFEIDKFWYDLD,     (SEQ ID NO: 15)
FEIDKFWYDLDA,     (SEQ ID NO: 16)
GFEIDKAWYDLDA,    (SEQ ID NO: 17)
FEIDKAWYDLD,      (SEQ ID NO: 18)
GFEIDKAWYDLD,     (SEQ ID NO: 19)
FEIDKAWYDLDA,     (SEQ ID NO: 20)
GFEIDKSWYDLDA,    (SEQ ID NO: 21)
FEIDKSWYDLD,      (SEQ ID NO: 22)
GFEIDKSWYDLD,     (SEQ ID NO: 23)
FEIDKSWYDLDA,     (SEQ ID NO: 24)
GFEIDKVFYDLDA,    (SEQ ID NO: 25)
FEIDKVFYDLD,      (SEQ ID NO: 26)
GFEIDKVFYDLD,     (SEQ ID NO: 27)
FEIDKVFYDLDA,     (SEQ ID NO: 28)
GFEIDKIFYDLDA,    (SEQ ID NO: 29)
FEIDKIFYDLD,      (SEQ ID NO: 30)
```

-continued

| | |
|---|---|
| GFEIDKIFYDLD, | (SEQ ID NO: 31) |
| FEIDKIFYDLDA, | (SEQ ID NO: 32) |
| GFEIDKLFYDLDA, | (SEQ ID NO: 33) |
| FEIDKLFYDLD, | (SEQ ID NO: 34) |
| GFEIDKLFYDLD, | (SEQ ID NO: 35) |
| FEIDKLFYDLDA, | (SEQ ID NO: 36) |
| GFEIDKFFYDLDA, | (SEQ ID NO: 37) |
| FEIDKFFYDLD, | (SEQ ID NO: 38) |
| GFEIDKFFYDLD, | (SEQ ID NO: 39) |
| FEIDKFFYDLDA, | (SEQ ID NO: 40) |
| GFEIDKAFYDLDA, | (SEQ ID NO: 41) |
| FEIDKAFYDLD, | (SEQ ID NO: 42) |
| GFEIDKAFYDLD, | (SEQ ID NO: 43) |
| FEIDKAFYDLDA, | (SEQ ID NO: 44) |
| GFEIDKSFYDLDA, | (SEQ ID NO: 45) |
| FEIDKSFYDLD, | (SEQ ID NO: 46) |
| GFEIDKSFYDLD, | (SEQ ID NO: 47) |
| FEIDKSFYDLDA, | (SEQ ID NO: 48) |
| GFEIDKVWHDLDA, | (SEQ ID NO: 49) |
| FEIDKVWHDLD, | (SEQ ID NO: 50) |
| GFEIDKVWHDLD, | (SEQ ID NO: 51) |
| FEIDKVWHDLDA, | (SEQ ID NO: 52) |
| GFEIDKIWHDLDA, | (SEQ ID NO: 53) |
| FEIDKIWHDLD, | (SEQ ID NO: 54) |
| GFEIDKIWHDLD, | (SEQ ID NO: 55) |
| FEIDKIWHDLDA, | (SEQ ID NO: 56) |
| GFEIDKLWHDLDA, | (SEQ ID NO: 57) |
| FEIDKLWHDLD, | (SEQ ID NO: 58) |
| GFEIDKLWHDLD, | (SEQ ID NO: 59) |
| FEIDKLWHDLDA, | (SEQ ID NO: 60) |
| GFEIDKFWHDLDA, | (SEQ ID NO: 61) |
| FEIDKFWHDLD, | (SEQ ID NO: 62) |
| GFEIDKFWHDLD, | (SEQ ID NO: 63) |
| FEIDKFWHDLDA, | (SEQ ID NO: 64) |
| GFEIDKAWHDLDA, | (SEQ ID NO: 65) |
| FEIDKAWHDLD, | (SEQ ID NO: 66) |
| GFEIDKAWHDLD, | (SEQ ID NO: 67) |
| FEIDKAWHDLDA, | (SEQ ID NO: 68) |
| GFEIDKSWHDLDA, | (SEQ ID NO: 69) |
| FEIDKSWHDLD, | (SEQ ID NO: 70) |
| GFEIDKSWHDLD, | (SEQ ID NO: 71) |

-continued

| | |
|---|---|
| FEIDKSWHDLDA, | (SEQ ID NO: 72) |
| GFEIDKVFHDLDA, | (SEQ ID NO: 73) |
| FEIDKVFHDLD, | (SEQ ID NO: 74) |
| GFEIDKVFHDLD, | (SEQ ID NO: 75) |
| FEIDKVFHDLDA, | (SEQ ID NO: 76) |
| GFEIDKIFHDLDA, | (SEQ ID NO: 77) |
| FEIDKIFHDLD, | (SEQ ID NO: 78) |
| GFEIDKIFHDLD, | (SEQ ID NO: 79) |
| FEIDKIFHDLDA, | (SEQ ID NO: 80) |
| GFEIDKLFHDLDA, | (SEQ ID NO: 81) |
| FEIDKLFHDLD, | (SEQ ID NO: 82) |
| GFEIDKLFHDLD, | (SEQ ID NO: 83) |
| FEIDKLFHDLDA, | (SEQ ID NO: 84) |
| GFEIDKFFHDLDA, | (SEQ ID NO: 85) |
| FEIDKFFHDLD, | (SEQ ID NO: 86) |
| GFEIDKFFHDLD, | (SEQ ID NO: 87) |
| FEIDKFFHDLDA, | (SEQ ID NO: 88) |
| GFEIDKAFHDLDA, | (SEQ ID NO: 89) |
| FEIDKAFHDLD, | (SEQ ID NO: 90) |
| GFEIDKAFHDLD, | (SEQ ID NO: 91) |
| FEIDKAFHDLDA, | (SEQ ID NO: 92) |
| GFEIDKSFHDLDA, | (SEQ ID NO: 93) |
| FEIDKSFHDLD, | (SEQ ID NO: 94) |
| GFEIDKSFHDLD, | (SEQ ID NO: 95) |
| FEIDKSFHDLDA, | (SEQ ID NO: 96) |
| GFEIDKVWFDLDA, | (SEQ ID NO: 97) |
| FEIDKVWFDLD, | (SEQ ID NO: 98) |
| GFEIDKVWFDLD, | (SEQ ID NO: 99) |
| FEIDKVWFDLDA, | (SEQ ID NO: 100) |
| GFEIDKIWFDLDA, | (SEQ ID NO: 101) |
| FEIDKIWFDLD, | (SEQ ID NO: 102) |
| GFEIDKIWFDLD, | (SEQ ID NO: 103) |
| FEIDKIWFDLDA, | (SEQ ID NO: 104) |
| GFEIDKLWFDLDA, | (SEQ ID NO: 105) |
| FEIDKLWFDLD, | (SEQ ID NO: 106) |
| GFEIDKLWFDLD, | (SEQ ID NO: 107) |
| FEIDKLWFDLDA, | (SEQ ID NO: 108) |
| GFEIDKFWFDLDA, | (SEQ ID NO: 109) |
| FEIDKFWFDLD, | (SEQ ID NO: 110) |
| GFEIDKFWFDLD, | (SEQ ID NO: 111) |

-continued

| | |
|---|---|
| FEIDKFWFDLDA, | (SEQ ID NO: 112) |
| GFEIDKAWFDLDA, | (SEQ ID NO: 113) |
| FEIDKAWFDLD, | (SEQ ID NO: 114) |
| GFEIDKAWFDLD, | (SEQ ID NO: 115) |
| FEIDKAWFDLDA, | (SEQ ID NO: 116) |
| GFEIDKSWFDLDA, | (SEQ ID NO: 117) |
| FEIDKSWFDLD, | (SEQ ID NO: 118) |
| GFEIDKSWFDLD, | (SEQ ID NO: 119) |
| FEIDKSWFDLDA, | (SEQ ID NO: 120) |
| GFEIDKVFFDLDA, | (SEQ ID NO: 121) |
| FEIDKVFFDLD, | (SEQ ID NO: 122) |
| GFEIDKVFFDLD, | (SEQ ID NO: 123) |
| FEIDKVFFDLDA, | (SEQ ID NO: 124) |
| GFEIDKIFFDLDA, | (SEQ ID NO: 125) |
| FEIDKIFFDLD, | (SEQ ID NO: 126) |
| GFEIDKIFFDLD, | (SEQ ID NO: 127) |
| FEIDKIFFDLDA, | (SEQ ID NO: 128) |
| GFEIDKLFFDLDA, | (SEQ ID NO: 129) |
| FEIDKLFFDLD, | (SEQ ID NO: 130) |
| GFEIDKLFFDLD, | (SEQ ID NO: 131) |
| FEIDKLFFDLDA, | (SEQ ID NO: 132) |
| GFEIDKFFFDLDA, | (SEQ ID NO: 133) |
| FEIDKFFFDLD, | (SEQ ID NO: 134) |
| GFEIDKFFFDLD, | (SEQ ID NO: 135) |
| FEIDKFFFDLDA, | (SEQ ID NO: 136) |
| GFEIDKAFFDLDA, | (SEQ ID NO: 137) |
| FEIDKAFFDLD, | (SEQ ID NO: 138) |
| GFEIDKAFFDLD, | (SEQ ID NO: 139) |
| FEIDKAFFDLDA, | (SEQ ID NO: 140) |
| GFEIDKSFFDLDA, | (SEQ ID NO: 141) |
| FEIDKSFFDLD, | (SEQ ID NO: 142) |
| GFEIDKSFFDLD, | (SEQ ID NO: 143) |
| FEIDKSFFDLDA, | (SEQ ID NO: 144) |
| GFEIDKVWIDLDA, | (SEQ ID NO: 145) |
| FEIDKVWIDLD, | (SEQ ID NO: 146) |
| GFEIDKVWIDLD, | (SEQ ID NO: 147) |
| FEIDKVWIDLDA, | (SEQ ID NO: 148) |
| GFEIDKVWVDLDA, | (SEQ ID NO: 149) |
| FEIDKVWVDLD, | (SEQ ID NO: 150) |
| GFEIDKVWVDLD, | (SEQ ID NO: 151) |
| FEIDKVWVDLDA, | (SEQ ID NO: 152) |
| GFEIDKVWLDLDA, | (SEQ ID NO: 153) |
| FEIDKVWLDLD, | (SEQ ID NO: 154) |
| GFEIDKVWLDLD, | (SEQ ID NO: 155) |
| FEIDKVWLDLDA, | (SEQ ID NO: 156) |
| GFEIDKVWLDLDA, | (SEQ ID NO: 157) |
| FEIDKVWLDLD, | (SEQ ID NO: 158) |
| GFEIDKVWLDLD, | (SEQ ID NO: 159) |
| FEIDKVWLDLDA, | (SEQ ID NO: 160) |
| GFEIDKVWTDLDA, | (SEQ ID NO: 161) |
| FEIDKVWTDLD, | (SEQ ID NO: 162) |
| GFEIDKVWTDLD, | (SEQ ID NO: 163) |
| FEIDKVWTDLDA, | (SEQ ID NO: 164) |
| GFEIDKVWYELDA, | (SEQ ID NO: 165) |
| FEIDKVWYELD, | (SEQ ID NO: 166) |
| GFEIDKVWYELD, | (SEQ ID NO: 167) |
| FEIDKVWYELDA, | (SEQ ID NO: 168) |
| GFEIDKIWYELDA, | (SEQ ID NO: 169) |
| FEIDKIWYELD, | (SEQ ID NO: 170) |
| GFEIDKIWYELD, | (SEQ ID NO: 171) |
| FEIDKIWYELDA, | (SEQ ID NO: 172) |
| GFEIDKLWYELDA, | (SEQ ID NO: 173) |
| FEIDKLWYELD, | (SEQ ID NO: 174) |
| GFEIDKLWYELD, | (SEQ ID NO: 175) |
| FEIDKLWYELDA, | (SEQ ID NO: 176) |
| GFEIDKFWYELDA, | (SEQ ID NO: 177) |
| FEIDKFWYELD, | (SEQ ID NO: 178) |
| GFEIDKFWYELD, | (SEQ ID NO: 179) |
| FEIDKFWYELDA, | (SEQ ID NO: 180) |
| GFEIDKAWYELDA, | (SEQ ID NO: 181) |
| FEIDKAWYELD, | (SEQ ID NO: 182) |
| GFEIDKAWYELD, | (SEQ ID NO: 183) |
| FEIDKAWYELDA, | (SEQ ID NO: 184) |
| GFEIDKSWYELDA, | (SEQ ID NO: 185) |
| FEIDKSWYELD, | (SEQ ID NO: 186) |
| GFEIDKSWYELD, | (SEQ ID NO: 187) |
| FEIDKSWYELDA, | (SEQ ID NO: 188) |
| GFEIDKVWYDIDA, | (SEQ ID NO: 189) |
| FEIDKVWYDID, | (SEQ ID NO: 190) |
| GFEIDKVWYDID, | (SEQ ID NO: 191) |
| FEIDKVWYDIDA, | (SEQ ID NO: 192) |

| | |
|---|---|
| GFEIDKIWYDIDA, | (SEQ ID NO: 193) |
| FEIDKIWYDID, | (SEQ ID NO: 194) |
| GFEIDKIWYDID, | (SEQ ID NO: 195) |
| FEIDKIWYDIDA, | (SEQ ID NO: 196) |
| GFEIDKLWYDIDA, | (SEQ ID NO: 197) |
| FEIDKLWYDID, | (SEQ ID NO: 198) |
| GFEIDKLWYDID, | (SEQ ID NO: 199) |
| FEIDKLWYDIDA, | (SEQ ID NO: 200) |
| GFEIDKFWYDIDA, | (SEQ ID NO: 201) |
| FEIDKFWYDID, | (SEQ ID NO: 202) |
| GFEIDKFWYDID, | (SEQ ID NO: 203) |
| FEIDKFWYDIDA, | (SEQ ID NO: 204) |
| GFEIDKAWYDIDA, | (SEQ ID NO: 205) |
| FEIDKAWYDID, | (SEQ ID NO: 206) |
| GFEIDKAWYDID, | (SEQ ID NO: 207) |
| FEIDKAWYDIDA, | (SEQ ID NO: 208) |
| GFEIDKSWYDIDA, | (SEQ ID NO: 209) |
| FEIDKSWYDID, | (SEQ ID NO: 210) |
| GFEIDKSWYDID, | (SEQ ID NO: 211) |
| FEIDKSWYDIDA, | (SEQ ID NO: 212) |
| GFEIDKVWYDFDA, | (SEQ ID NO: 213) |
| FEIDKVWYDFD, | (SEQ ID NO: 214) |
| GFEIDKVWYDFD, | (SEQ ID NO: 215) |
| FEIDKVWYDFDA, | (SEQ ID NO: 216) |
| GFEIDKIWYDFDA, | (SEQ ID NO: 217) |
| FEIDKIWYDFD, | (SEQ ID NO: 218) |
| GFEIDKIWYDFD, | (SEQ ID NO: 219) |
| FEIDKIWYDFDA, | (SEQ ID NO: 220) |
| GFEIDKLWYDFDA, | (SEQ ID NO: 221) |
| FEIDKLWYDFD, | (SEQ ID NO: 222) |
| GFEIDKLWYDFD, | (SEQ ID NO: 223) |
| FEIDKLWYDFDA, | (SEQ ID NO: 224) |
| GFEIDKFWYDFDA, | (SEQ ID NO: 225) |
| FEIDKFWYDFD, | (SEQ ID NO: 226) |
| GFEIDKFWYDFD, | (SEQ ID NO: 227) |
| FEIDKFWYDFDA, | (SEQ ID NO: 228) |
| GFEIDKAWYDFDA, | (SEQ ID NO: 229) |
| FEIDKAWYDFD, | (SEQ ID NO: 230) |
| GFEIDKAWYDFD, | (SEQ ID NO: 231) |
| FEIDKAWYDFDA, | (SEQ ID NO: 232) |
| GFEIDKSWYDFDA, | (SEQ ID NO: 233) |
| FEIDKSWYDFD, | (SEQ ID NO: 234) |
| GFEIDKSWYDFD, | (SEQ ID NO: 235) |
| FEIDKSWYDFDA, | (SEQ ID NO: 236) |
| GFEIDKVWYDVDA, | (SEQ ID NO: 237) |
| FEIDKVWYDVD, | (SEQ ID NO: 238) |
| GFEIDKVWYDVD, | (SEQ ID NO: 239) |
| FEIDKVWYDVDA, | (SEQ ID NO: 240) |
| GFEIDKIWYDVDA, | (SEQ ID NO: 241) |
| FEIDKIWYDVD, | (SEQ ID NO: 242) |
| GFEIDKIWYDVD, | (SEQ ID NO: 243) |
| FEIDKIWYDVDA, | (SEQ ID NO: 244) |
| GFEIDKLWYDVDA, | (SEQ ID NO: 245) |
| FEIDKLWYDVD, | (SEQ ID NO: 246) |
| GFEIDKLWYDVD, | (SEQ ID NO: 247) |
| FEIDKLWYDVDA, | (SEQ ID NO: 248) |
| GFEIDKFWYDVDA, | (SEQ ID NO: 249) |
| FEIDKFWYDVD, | (SEQ ID NO: 250) |
| GFEIDKFWYDVD, | (SEQ ID NO: 251) |
| FEIDKFWYDVDA, | (SEQ ID NO: 252) |
| GFEIDKAWYDVDA, | (SEQ ID NO: 253) |
| FEIDKAWYDVD, | (SEQ ID NO: 254) |
| GFEIDKAWYDVD, | (SEQ ID NO: 255) |
| FEIDKAWYDVDA, | (SEQ ID NO: 256) |
| GFEIDKSWYDVDA, | (SEQ ID NO: 257) |
| FEIDKSWYDVD, | (SEQ ID NO: 258) |
| GFEIDKSWYDVD, | (SEQ ID NO: 259) |
| FEIDKSWYDVDA, | (SEQ ID NO: 260) |
| GFEIDKVWYDLDS, | (SEQ ID NO: 261) |
| FEIDKVWYDLDS, | (SEQ ID NO: 262) |
| GFEIDKIWYDLDS, | (SEQ ID NO: 263) |
| FEIDKIWYDLDS, | (SEQ ID NO: 264) |
| GFEIDKLWYDLDS, | (SEQ ID NO: 265) |
| FEIDKLWYDLDS, | (SEQ ID NO: 266) |
| GFEIDKFWYDLDS, | (SEQ ID NO: 267) |
| FEIDKFWYDLDS, | (SEQ ID NO: 268) |
| GFEIDKAWYDLDS, | (SEQ ID NO: 269) |
| FEIDKAWYDLDS, | (SEQ ID NO: 270) |
| GFEIDKSWYDLDS, | (SEQ ID NO: 271) |
| FEIDKSWYDLDS, | (SEQ ID NO: 272) |
| GFEINKVWYDLDA, | (SEQ ID NO: 273) |

-continued

| | |
|---|---|
| FEINKVWYDLD, | (SEQ ID NO: 274) |
| GFEINKVWYDLD, | (SEQ ID NO: 275) |
| FEINKVWYDLDA, | (SEQ ID NO: 276) |
| GFEINKIWYDLDA, | (SEQ ID NO: 277) |
| FEINKIWYDLD, | (SEQ ID NO: 278) |
| GFEINKIWYDLD, | (SEQ ID NO: 279) |
| FEINKIWYDLDA, | (SEQ ID NO: 280) |
| GFEINKLWYDLDA, | (SEQ ID NO: 281) |
| FEINKLWYDLD, | (SEQ ID NO: 282) |
| GFEINKLWYDLD, | (SEQ ID NO: 283) |
| FEINKLWYDLDA, | (SEQ ID NO: 284) |
| GFEINKFWYDLDA, | (SEQ ID NO: 285) |
| FEINKFWYDLD, | (SEQ ID NO: 286) |
| GFEINKFWYDLD, | (SEQ ID NO: 287) |
| FEINKFWYDLDA, | (SEQ ID NO: 288) |
| GFEINKAWYDLDA, | (SEQ ID NO: 289) |
| FEINKAWYDLD, | (SEQ ID NO: 290) |
| GFEINKAWYDLD, | (SEQ ID NO: 291) |
| FEINKAWYDLDA, | (SEQ ID NO: 292) |
| GFEINKSWYDLDA, | (SEQ ID NO: 293) |
| FEINKSWYDLD, | (SEQ ID NO: 294) |
| GFEINKSWYDLD, | (SEQ ID NO: 295) |
| FEINKSWYDLDA, | (SEQ ID NO: 296) |
| GFEIEKVWYDLDA, | (SEQ ID NO: 297) |
| FEIEKVWYDLD, | (SEQ ID NO: 298) |
| GFEIEKVWYDLD, | (SEQ ID NO: 299) |
| FEIEKVWYDLDA, | (SEQ ID NO: 300) |
| GFEIEKIWYDLDA, | (SEQ ID NO: 301) |
| FEIEKIWYDLD, | (SEQ ID NO: 302) |
| GFEIEKIWYDLD, | (SEQ ID NO: 303) |
| FEIEKIWYDLDA, | (SEQ ID NO: 304) |
| GFEIEKLWYDLDA, | (SEQ ID NO: 305) |
| FEIEKLWYDLD, | (SEQ ID NO: 306) |
| GFEIEKLWYDLD, | (SEQ ID NO: 307) |
| FEIEKLWYDLDA, | (SEQ ID NO: 308) |
| GFEIEKFWYDLDA, | (SEQ ID NO: 309) |
| FEIEKFWYDLD, | (SEQ ID NO: 310) |
| GFEIEKFWYDLD, | (SEQ ID NO: 311) |
| FEIEKFWYDLDA, | (SEQ ID NO: 312) |
| GFEIEKAWYDLDA, | (SEQ ID NO: 313) |
| FEIEKAWYDLD, | (SEQ ID NO: 314) |

-continued

| | |
|---|---|
| GFEIEKAWYDLD, | (SEQ ID NO: 315) |
| FEIEKAWYDLDA, | (SEQ ID NO: 316) |
| GFEIEKSWYDLDA, | (SEQ ID NO: 317) |
| FEIEKSWYDLD, | (SEQ ID NO: 318) |
| GFEIEKSWYDLD, | (SEQ ID NO: 319) |
| FEIEKSWYDLDA, | (SEQ ID NO: 320) |
| GFEIYKVWYDLDA, | (SEQ ID NO: 321) |
| FEIYKVWYDLD, | (SEQ ID NO: 322) |
| GFEIYKVWYDLD, | (SEQ ID NO: 323) |
| FEIYKVWYDLDA, | (SEQ ID NO: 324) |
| GFEIYKIWYDLDA, | (SEQ ID NO: 325) |
| FEIYKIWYDLD, | (SEQ ID NO: 326) |
| GFEIYKIWYDLD, | (SEQ ID NO: 327) |
| FEIYKIWYDLDA, | (SEQ ID NO: 328) |
| GFEIYKLWYDLDA, | (SEQ ID NO: 329) |
| FEIYKLWYDLD, | (SEQ ID NO: 330) |
| GFEIYKLWYDLD, | (SEQ ID NO: 331) |
| FEIYKLWYDLDA, | (SEQ ID NO: 332) |
| GFEIYKFWYDLDA, | (SEQ ID NO: 333) |
| FEIYKFWYDLD, | (SEQ ID NO: 334) |
| GFEIYKFWYDLD, | (SEQ ID NO: 335) |
| FEIYKFWYDLDA, | (SEQ ID NO: 336) |
| GFEIYKAWYDLDA, | (SEQ ID NO: 337) |
| FEIYKAWYDLD, | (SEQ ID NO: 338) |
| GFEIYKAWYDLD, | (SEQ ID NO: 339) |
| FEIYKAWYDLDA, | (SEQ ID NO: 340) |
| GFEIYKSWYDLDA, | (SEQ ID NO: 341) |
| FEIYKSWYDLD, | (SEQ ID NO: 342) |
| GFEIYKSWYDLD, | (SEQ ID NO: 343) |
| FEIYKSWYDLDA, | (SEQ ID NO: 344) |
| GFEIAKVWYDLDA, | (SEQ ID NO: 345) |
| FEIAKVWYDLD, | (SEQ ID NO: 346) |
| GFEIAKVWYDLD, | (SEQ ID NO: 347) |
| FEIAKVWYDLDA, | (SEQ ID NO: 348) |
| GFEIAKIWYDLDA, | (SEQ ID NO: 349) |
| FEIAKIWYDLD, | (SEQ ID NO: 350) |
| GFEIAKIWYDLD, | (SEQ ID NO: 351) |
| FEIAKIWYDLDA, | (SEQ ID NO: 352) |
| GFEIAKLWYDLDA, | (SEQ ID NO: 353) |
| FEIAKLWYDLD, | (SEQ ID NO: 354) |

-continued

| | |
|---|---|
| GFEIAKLWYDLD, | (SEQ ID NO: 355) |
| FEIAKLWYDLDA, | (SEQ ID NO: 356) |
| GFEIAKFWYDLDA, | (SEQ ID NO: 357) |
| FEIAKFWYDLD, | (SEQ ID NO: 358) |
| GFEIAKFWYDLD, | (SEQ ID NO: 359) |
| FEIAKFWYDLDA, | (SEQ ID NO: 360) |
| GFEIAKAWYDLDA, | (SEQ ID NO: 361) |
| FEIAKAWYDLD, | (SEQ ID NO: 362) |
| GFEIAKAWYDLD, | (SEQ ID NO: 363) |
| FEIAKAWYDLDA, | (SEQ ID NO: 364) |
| GFEIAKSWYDLDA, | (SEQ ID NO: 365) |
| FEIAKSWYDLD, | (SEQ ID NO: 366) |
| GFEIAKSWYDLD, | (SEQ ID NO: 367) |
| FEIAKSWYDLDA, | (SEQ ID NO: 368) |
| GFDIDKVWYDLDA, | (SEQ ID NO: 369) |
| FDIDKVWYDLD, | (SEQ ID NO: 370) |
| GFDIDKVWYDLD, | (SEQ ID NO: 371) |
| FDIDKVWYDLDA, | (SEQ ID NO: 372) |
| GFDIDKIWYDLDA, | (SEQ ID NO: 373) |
| FDIDKIWYDLD, | (SEQ ID NO: 374) |
| GFDIDKIWYDLD, | (SEQ ID NO: 375) |
| FDIDKIWYDLDA, | (SEQ ID NO: 376) |
| GFDIDKLWYDLDA, | (SEQ ID NO: 377) |
| FDIDKLWYDLD, | (SEQ ID NO: 378) |
| GFDIDKLWYDLD, | (SEQ ID NO: 379) |
| FDIDKLWYDLDA, | (SEQ ID NO: 380) |
| GFDIDKFWYDLDA, | (SEQ ID NO: 381) |
| FDIDKFWYDLD, | (SEQ ID NO: 382) |
| GFDIDKFWYDLD, | (SEQ ID NO: 383) |
| FDIDKFWYDLDA, | (SEQ ID NO: 384) |
| GFDIDKAWYDLDA, | (SEQ ID NO: 385) |
| FDIDKAWYDLD, | (SEQ ID NO: 386) |
| GFDIDKAWYDLD, | (SEQ ID NO: 387) |
| FDIDKAWYDLDA, | (SEQ ID NO: 388) |
| GFDIDKSWYDLDA, | (SEQ ID NO: 389) |
| FDIDKSWYDLD, | (SEQ ID NO: 390) |
| GFDIDKSWYDLD, | (SEQ ID NO: 391) |
| FDIDKSWYDLDA, | (SEQ ID NO: 392) |
| GIEIDKVWYDLDA, | (SEQ ID NO: 393) |
| IEIDKVWYDLD, | (SEQ ID NO: 394) |
| GIEIDKVWYDLD, | (SEQ ID NO: 395) |
| IEIDKVWYDLDA, | (SEQ ID NO: 396) |
| GIEIDKIWYDLDA, | (SEQ ID NO: 397) |
| IEIDKIWYDLD, | (SEQ ID NO: 398) |
| GIEIDKIWYDLD, | (SEQ ID NO: 399) |
| IEIDKIWYDLDA, | (SEQ ID NO: 400) |
| GIEIDKLWYDLDA, | (SEQ ID NO: 401) |
| IEIDKLWYDLD, | (SEQ ID NO: 402) |
| GIEIDKLWYDLD, | (SEQ ID NO: 403) |
| IEIDKLWYDLDA, | (SEQ ID NO: 404) |
| GIEIDKFWYDLDA, | (SEQ ID NO: 405) |
| IEIDKFWYDLD, | (SEQ ID NO: 406) |
| GIEIDKFWYDLD, | (SEQ ID NO: 407) |
| IEIDKFWYDLDA, | (SEQ ID NO: 408) |
| GIEIDKAWYDLDA, | (SEQ ID NO: 409) |
| IEIDKAWYDLD, | (SEQ ID NO: 410) |
| GIEIDKAWYDLD, | (SEQ ID NO: 411) |
| IEIDKAWYDLDA, | (SEQ ID NO: 412) |
| GIEIDKSWYDLDA, | (SEQ ID NO: 413) |
| IEIDKSWYDLD, | (SEQ ID NO: 414) |
| GIEIDKSWYDLD, | (SEQ ID NO: 415) |
| IEIDKSWYDLDA, | (SEQ ID NO: 416) |
| GVEIDKVWYDLDA, | (SEQ ID NO: 417) |
| VEIDKVWYDLD, | (SEQ ID NO: 418) |
| GVEIDKVWYDLD, | (SEQ ID NO: 419) |
| VEIDKVWYDLDA, | (SEQ ID NO: 420) |
| GVEIDKIWYDLDA, | (SEQ ID NO: 421) |
| VEIDKIWYDLD, | (SEQ ID NO: 422) |
| GVEIDKIWYDLD, | (SEQ ID NO: 423) |
| VEIDKIWYDLDA, | (SEQ ID NO: 424) |
| GVEIDKLWYDLDA, | (SEQ ID NO: 425) |
| VEIDKLWYDLD, | (SEQ ID NO: 426) |
| GVEIDKLWYDLD, | (SEQ ID NO: 427) |
| VEIDKLWYDLDA, | (SEQ ID NO: 428) |
| GVEIDKFWYDLDA, | (SEQ ID NO: 429) |
| VEIDKFWYDLD, | (SEQ ID NO: 430) |
| GVEIDKFWYDLD, | (SEQ ID NO: 431) |
| VEIDKFWYDLDA, | (SEQ ID NO: 432) |
| GVEIDKAWYDLDA, | (SEQ ID NO: 433) |
| VEIDKAWYDLD, | (SEQ ID NO: 434) |
| GVEIDKAWYDLD, | (SEQ ID NO: 435) |

VEIDKAWYDLDA, (SEQ ID NO: 436)
GVEIDKSWYDLDA, (SEQ ID NO: 437)
VEIDKSWYDLD, (SEQ ID NO: 438)
GVEIDKSWYDLD, (SEQ ID NO: 439)
VEIDKSWYDLDA, (SEQ ID NO: 440)
GLEIDKVWYDLDA, (SEQ ID NO: 441)
LEIDKVWYDLD, (SEQ ID NO: 442)
GLEIDKVWYDLD, (SEQ ID NO: 443)
LEIDKVWYDLDA, (SEQ ID NO: 444)
GLEIDKIWYDLDA, (SEQ ID NO: 445)
LEIDKIWYDLD, (SEQ ID NO: 446)
GLEIDKIWYDLD, (SEQ ID NO: 447)
LEIDKIWYDLDA, (SEQ ID NO: 448)
GLEIDKLWYDLDA, (SEQ ID NO: 449)
LEIDKLWYDLD, (SEQ ID NO: 450)
GLEIDKLWYDLD, (SEQ ID NO: 451)
LEIDKLWYDLDA, (SEQ ID NO: 452)
GLEIDKFWYDLDA, (SEQ ID NO: 453)
LEIDKFWYDLD, (SEQ ID NO: 454)
GLEIDKFWYDLD, (SEQ ID NO: 455)
LEIDKFWYDLDA, (SEQ ID NO: 456)
GLEIDKAWYDLDA, (SEQ ID NO: 457)
LEIDKAWYDLD, (SEQ ID NO: 458)
GLEIDKAWYDLD, (SEQ ID NO: 459)
LEIDKAWYDLDA, (SEQ ID NO: 460)
GLEIDKSWYDLDA, (SEQ ID NO: 461)
LEIDKSWYDLD, (SEQ ID NO: 462)
GLEIDKSWYDLD, (SEQ ID NO: 463)
LEIDKSWYDLDA, (SEQ ID NO: 464)
FEIDKVWYD, (SEQ ID NO: 465)
FEIDKIWYD, (SEQ ID NO: 466)
FEIDKLWYD, (SEQ ID NO: 467)
FEIDKFWYD, (SEQ ID NO: 468)
FEIDKAWYD, (SEQ ID NO: 469)
FEIDKSWYD, (SEQ ID NO: 470)
FEIDKVFYD, (SEQ ID NO: 471)
FEIDKIFYD, (SEQ ID NO: 472)
FEIDKLFYD, (SEQ ID NO: 473)
FEIDKFFYD, (SEQ ID NO: 474)
FEIDKAFYD, (SEQ ID NO: 475)
FEIDKSFYD, (SEQ ID NO: 476)
FEIDKVWHD, (SEQ ID NO: 477)
FEIDKIWHD, (SEQ ID NO: 478)
FEIDKLWHD, (SEQ ID NO: 479)
FEIDKFWHD, (SEQ ID NO: 480)
FEIDKAWHD, (SEQ ID NO: 481)
FEIDKSWHD, (SEQ ID NO: 482)
FEIDKVFHD, (SEQ ID NO: 483)
FEIDKIFHD, (SEQ ID NO: 484)
FEIDKLFHD, (SEQ ID NO: 485)
FEIDKFFHD, (SEQ ID NO: 486)
FEIDKAFHD, (SEQ ID NO: 487)
FEIDKSFHD, (SEQ ID NO: 488)
FEIDKVWFD, (SEQ ID NO: 489)
FEIDKIWFD, (SEQ ID NO: 490)
FEIDKLWFD, (SEQ ID NO: 491)
FEIDKFWFD, (SEQ ID NO: 492)
FEIDKAWFD, (SEQ ID NO: 493)
FEIDKSWFD, (SEQ ID NO: 494)
FEIDKVFFD, (SEQ ID NO: 495)
FEIDKIFFD, (SEQ ID NO: 496)
FEIDKLFFD, (SEQ ID NO: 497)
FEIDKFFFD, (SEQ ID NO: 498)
FEIDKAFFD, (SEQ ID NO: 499)
FEIDKSFFD, (SEQ ID NO: 500)
FEIDKVWLD, (SEQ ID NO: 501)
FEIDKIWLD, (SEQ ID NO: 502)
FEIDKLWLD, (SEQ ID NO: 503)
FEIDKFWLD, (SEQ ID NO: 504)
FEIDKAWLD, (SEQ ID NO: 505)
FEIDKSWLD, (SEQ ID NO: 506)
FEIDKVFLD, (SEQ ID NO: 507)
FEIDKIFLD, (SEQ ID NO: 508)
FEIDKLFLD, (SEQ ID NO: 509)
FEIDKFFLD, (SEQ ID NO: 510)
FEIDKAFLD, (SEQ ID NO: 511)
FEIDKSFLD, (SEQ ID NO: 512)
FEIDKVWID, (SEQ ID NO: 513)
FEIDKIWID, (SEQ ID NO: 514)
FEIDKLWID, (SEQ ID NO: 515)
FEIDKFWID, (SEQ ID NO: 516)

-continued

FEIDKAWID, (SEQ ID NO: 517)
FEIDKSWID, (SEQ ID NO: 518)
FEIDKVFID, (SEQ ID NO: 519)
FEIDKIFID, (SEQ ID NO: 520)
FEIDKLFID, (SEQ ID NO: 521)
FEIDKFFID, (SEQ ID NO: 522)
FEIDKAFID, (SEQ ID NO: 523)
FEIDKSFID, (SEQ ID NO: 524)
FEIDKVWVD, (SEQ ID NO: 525)
FEIDKIWVD, (SEQ ID NO: 526)
FEIDKLWVD, (SEQ ID NO: 527)
FEIDKFWVD, (SEQ ID NO: 528)
FEIDKAWVD, (SEQ ID NO: 529)
FEIDKSWVD, (SEQ ID NO: 530)
FEIDKVFVD, (SEQ ID NO: 531)
FEIDKIFVD, (SEQ ID NO: 532)
FEIDKLFVD, (SEQ ID NO: 533)
FEIDKFFVD, (SEQ ID NO: 534)
FEIDKAFVD, (SEQ ID NO: 535)
FEIDKSFVD, (SEQ ID NO: 536)
FEIDKVWTD, (SEQ ID NO: 537)
FEIDKIWTD, (SEQ ID NO: 538)
FEIDKLWTD, (SEQ ID NO: 539)
FEIDKFWTD, (SEQ ID NO: 540)
FEIDKAWTD, (SEQ ID NO: 541)
FEIDKSWTD, (SEQ ID NO: 542)
FEIDKVFTD, (SEQ ID NO: 543)
FEIDKIFTD, (SEQ ID NO: 544)
FEIDKLFTD, (SEQ ID NO: 545)
FEIDKFFTD, (SEQ ID NO: 546)
FEIDKAFTD, (SEQ ID NO: 547)
FEIDKSFTD, (SEQ ID NO: 548)
FEIDKVWYE, (SEQ ID NO: 549)
FEIDKIWYE, (SEQ ID NO: 550)
FEIDKLWYE, (SEQ ID NO: 551)
FEIDKFWYE, (SEQ ID NO: 552)
FEIDKAWYE, (SEQ ID NO: 553)
FEIDKSWYE, (SEQ ID NO: 554)
FEIDKVFYE, (SEQ ID NO: 555)
FEIDKIFYE, (SEQ ID NO: 556)
FEIDKLFYE, (SEQ ID NO: 557)

-continued

FEIDKFFYE, (SEQ ID NO: 558)
FEIDKAFYE, (SEQ ID NO: 559)
FEIDKSFYE, (SEQ ID NO: 560)
FEIDKVWHE, (SEQ ID NO: 561)
FEIDKIWHE, (SEQ ID NO: 562)
FEIDKLWHE, (SEQ ID NO: 563)
FEIDKFWHE, (SEQ ID NO: 564)
FEIDKAWHE, (SEQ ID NO: 565)
FEIDKSWHE, (SEQ ID NO: 566)
FEIDKVFHE, (SEQ ID NO: 567)
FEIDKIFHE, (SEQ ID NO: 568)
FEIDKLFHE, (SEQ ID NO: 569)
FEIDKFFHE, (SEQ ID NO: 570)
FEIDKAFHE, (SEQ ID NO: 571)
FEIDKSFHE, (SEQ ID NO: 572)
FEIDKVWFE, (SEQ ID NO: 573)
FEIDKIWFE, (SEQ ID NO: 574)
FEIDKLWFE, (SEQ ID NO: 575)
FEIDKFWFE, (SEQ ID NO: 576)
FEIDKAWFE, (SEQ ID NO: 577)
FEIDKSWFE, (SEQ ID NO: 578)
FEIDKVFFE, (SEQ ID NO: 579)
FEIDKIFFE, (SEQ ID NO: 580)
FEIDKLFFE, (SEQ ID NO: 581)
FEIDKFFFE, (SEQ ID NO: 582)
FEIDKAFFE, (SEQ ID NO: 583)
FEIDKSFFE, (SEQ ID NO: 584)
FEIDKVWLE, (SEQ ID NO: 585)
FEIDKIWLE, (SEQ ID NO: 586)
FEIDKLWLE, (SEQ ID NO: 587)
FEIDKFWLE, (SEQ ID NO: 588)
FEIDKAWLE, (SEQ ID NO: 589)
FEIDKSWLE, (SEQ ID NO: 590)
FEIDKVFLE, (SEQ ID NO: 591)
FEIDKIFLE, (SEQ ID NO: 592)
FEIDKLFLE, (SEQ ID NO: 593)
FEIDKFFLE, (SEQ ID NO: 594)
FEIDKAFLE, (SEQ ID NO: 595)
FEIDKSFLE, (SEQ ID NO: 596)
FEIDKVWIE, (SEQ ID NO: 597)

-continued

| | |
|---|---|
| FEIDKIWIE, | (SEQ ID NO: 598) |
| FEIDKLWIE, | (SEQ ID NO: 599) |
| FEIDKFWIE, | (SEQ ID NO: 600) |
| FEIDKAWIE, | (SEQ ID NO: 601) |
| FEIDKSWIE, | (SEQ ID NO: 602) |
| FEIDKVFIE, | (SEQ ID NO: 603) |
| FEIDKIFIE, | (SEQ ID NO: 604) |
| FEIDKLFIE, | (SEQ ID NO: 605) |
| FEIDKFFIE, | (SEQ ID NO: 606) |
| FEIDKAFIE, | (SEQ ID NO: 607) |
| FEIDKSFIE, | (SEQ ID NO: 608) |
| FEIDKVWVE, | (SEQ ID NO: 609) |
| FEIDKIWVE, | (SEQ ID NO: 610) |
| FEIDKLWVE, | (SEQ ID NO: 611) |
| FEIDKFWVE, | (SEQ ID NO: 612) |
| FEIDKAWVE, | (SEQ ID NO: 613) |
| FEIDKSWVE, | (SEQ ID NO: 614) |
| FEIDKVFVE, | (SEQ ID NO: 615) |
| FEIDKIFVE, | (SEQ ID NO: 616) |
| FEIDKLFVE, | (SEQ ID NO: 617) |
| FEIDKFFVE, | (SEQ ID NO: 618) |
| FEIDKAFVE, | (SEQ ID NO: 619) |
| FEIDKSFVE, | (SEQ ID NO: 620) |
| FEIDKVWTE, | (SEQ ID NO: 621) |
| FEIDKIWTE, | (SEQ ID NO: 622) |
| FEIDKLWTE, | (SEQ ID NO: 623) |
| FEIDKFWTE, | (SEQ ID NO: 624) |
| FEIDKAWTE, | (SEQ ID NO: 625) |
| FEIDKSWTE, | (SEQ ID NO: 626) |
| FEIDKVFTE, | (SEQ ID NO: 627) |
| FEIDKIFTE, | (SEQ ID NO: 628) |
| FEIDKLFTE, | (SEQ ID NO: 629) |
| FEIDKFFTE, | (SEQ ID NO: 630) |
| FEIDKAFTE, | (SEQ ID NO: 631) |
| FEIDKSFTE, | (SEQ ID NO: 632) |
| FEINKVWYD, | (SEQ ID NO: 633) |
| FEIEKVWYD, | (SEQ ID NO: 634) |
| FEIYKVWYD, | (SEQ ID NO: 635) |
| FEHDKVWYD, | (SEQ ID NO: 636) |
| FELDKVWYD, | (SEQ ID NO: 637) |
| FERDKVWYD, | (SEQ ID NO: 638) |

-continued

| | |
|---|---|
| FEEDKVWYD, | (SEQ ID NO: 639) |
| FDIDKVWYD, | (SEQ ID NO: 640) |
| LEIDKVWYD, | (SEQ ID NO: 641) |
| IEIDKVWYD, | (SEQ ID NO: 642) |
| VEIDKVWYD, | (SEQ ID NO: 643) |
| FERDKVWHD, | (SEQ ID NO: 644) |
| FERDKAWYD, | (SEQ ID NO: 645) |
| FERDKAWHD, | (SEQ ID NO: 646) |
| GFERDKVWHDLDS, | (SEQ ID NO: 647) |
| GFERDKAWHDLDS, | (SEQ ID NO: 648) |
| GFEHDKVWHDLDS, | (SEQ ID NO: 649) |
| GFERDKVWYDLDA, | (SEQ ID NO: 650) |
| EIDKVWYD, | (SEQ ID NO: 651) |
| DIDKVWYD, | (SEQ ID NO: 652) |
| EHDKVWYD, | (SEQ ID NO: 653) |
| DHDKVWYD, | (SEQ ID NO: 654) |
| ELDKVWYD, | (SEQ ID NO: 655) |
| DLDKVWYD, | (SEQ ID NO: 656) |
| ERDKVWYD, | (SEQ ID NO: 657) |
| DRDKVWYD, | (SEQ ID NO: 658) |
| EEDKVWYD, | (SEQ ID NO: 659) |
| DEDKVWYD, | (SEQ ID NO: 660) |
| EINKVWYD, | (SEQ ID NO: 661) |
| EHNKVWYD, | (SEQ ID NO: 662) |
| ELNKVWYD, | (SEQ ID NO: 663) |
| ERNKVWYD, | (SEQ ID NO: 664) |
| DINKVWYD, | (SEQ ID NO: 665) |
| DHNKVWYD, | (SEQ ID NO: 666) |
| DLNKVWYD, | (SEQ ID NO: 667) |
| DRNKVWYD, | (SEQ ID NO: 668) |
| DENKVWYD, | (SEQ ID NO: 669) |
| EIEKVWYD, | (SEQ ID NO: 670) |
| EHEKVWYD, | (SEQ ID NO: 671) |
| ELEKVWYD, | (SEQ ID NO: 672) |
| EREKVWYD, | (SEQ ID NO: 673) |
| EEEKVWYD, | (SEQ ID NO: 674) |
| DIEKVWYD, | (SEQ ID NO: 675) |
| DHEKVWYD, | (SEQ ID NO: 676) |
| DLEKVWYD, | (SEQ ID NO: 677) |
| DREKVWYD, | (SEQ ID NO: 678) |

DEEKVWYD, (SEQ ID NO: 679)
EIYKVWYD, (SEQ ID NO: 680)
EHYKVWYD, (SEQ ID NO: 681)
ELYKVWYD, (SEQ ID NO: 682)
ERYKVWYD, (SEQ ID NO: 683)
EEYKVWYD, (SEQ ID NO: 684)
DIYKVWYD, (SEQ ID NO: 685)
DHYKVWYD, (SEQ ID NO: 686)
DLYKVWYD, (SEQ ID NO: 687)
DRYKVWYD, (SEQ ID NO: 688)
DEYKVWYD, (SEQ ID NO: 689)
EIDKIWYD, (SEQ ID NO: 690)
DIDKIWYD, (SEQ ID NO: 691)
EHDKIWYD, (SEQ ID NO: 692)
DHDKIWYD, (SEQ ID NO: 693)
ELDKIWYD, (SEQ ID NO: 694)
DLDKIWYD, (SEQ ID NO: 695)
ERDKIWYD, (SEQ ID NO: 696)
DRDKIWYD, (SEQ ID NO: 697)
EEDKIWYD, (SEQ ID NO: 698)
DEDKIWYD, (SEQ ID NO: 699)
EINKIWYD, (SEQ ID NO: 700)
EHNKIWYD, (SEQ ID NO: 701)
ELNKIWYD, (SEQ ID NO: 702)
ERNKIWYD, (SEQ ID NO: 703)
DINKIWYD, (SEQ ID NO: 704)
DHNKIWYD, (SEQ ID NO: 705)
DLNKIWYD, (SEQ ID NO: 706)
DRNKIWYD, (SEQ ID NO: 707)
DENKIWYD, (SEQ ID NO: 708)
EIEKIWYD, (SEQ ID NO: 709)
EHEKIWYD, (SEQ ID NO: 710)
ELEKIWYD, (SEQ ID NO: 711)
EREKIWYD, (SEQ ID NO: 712)
EEEKIWYD, (SEQ ID NO: 713)
DIEKIWYD, (SEQ ID NO: 714)
DHEKIWYD, (SEQ ID NO: 715)
DLEKIWYD, (SEQ ID NO: 716)
DREKIWYD, (SEQ ID NO: 717)
DEEKIWYD, (SEQ ID NO: 718)
EIYKIWYD, (SEQ ID NO: 719)
EHYKIWYD, (SEQ ID NO: 720)
ELYKIWYD, (SEQ ID NO: 721)
ERYKIWYD, (SEQ ID NO: 722)
EEYKIWYD, (SEQ ID NO: 723)
DIYKIWYD, (SEQ ID NO: 724)
DHYKIWYD, (SEQ ID NO: 725)
DLYKIWYD, (SEQ ID NO: 726)
DRYKIWYD, (SEQ ID NO: 727)
DEYKIWYD, (SEQ ID NO: 728)
EIDKLWYD, (SEQ ID NO: 729)
DIDKLWYD, (SEQ ID NO: 730)
EHDKLWYD, (SEQ ID NO: 731)
DHDKLWYD, (SEQ ID NO: 732)
ELDKLWYD, (SEQ ID NO: 733)
DLDKLWYD, (SEQ ID NO: 734)
ERDKLWYD, (SEQ ID NO: 735)
DRDKLWYD, (SEQ ID NO: 736)
EEDKLWYD, (SEQ ID NO: 737)
DEDKLWYD, (SEQ ID NO: 738)
EINKLWYD, (SEQ ID NO: 739)
EHNKLWYD, (SEQ ID NO: 740)
ELNKLWYD, (SEQ ID NO: 741)
ERNKLWYD (SEQ ID NO: 742)
DINKLWYD, (SEQ ID NO: 743)
DHNKLWYD, (SEQ ID NO: 744)
DLNKLWYD, (SEQ ID NO: 745)
DRNKLWYD, (SEQ ID NO: 746)
DENKLWYD, (SEQ ID NO: 747)
EIEKLWYD, (SEQ ID NO: 748)
EHEKLWYD, (SEQ ID NO: 749)
ELEKLWYD, (SEQ ID NO: 750)
EREKLWYD, (SEQ ID NO: 751)
EEEKLWYD, (SEQ ID NO: 752)
DIEKLWYD, (SEQ ID NO: 753)
DHEKLWYD, (SEQ ID NO: 754)
DLEKLWYD, (SEQ ID NO: 755)
DREKLWYD, (SEQ ID NO: 756)
DEEKLWYD, (SEQ ID NO: 757)
EIYKLWYD, (SEQ ID NO: 758)
EHYKLWYD, (SEQ ID NO: 759)

-continued

| | |
|---|---|
| ELYKLWYD, | (SEQ ID NO: 760) |
| ERYKLWYD, | (SEQ ID NO: 761) |
| EEYKLWYD, | (SEQ ID NO: 762) |
| DIYKLWYD, | (SEQ ID NO: 763) |
| DHYKLWYD, | (SEQ ID NO: 764) |
| DLYKLWYD, | (SEQ ID NO: 765) |
| DRYKLWYD, | (SEQ ID NO: 766) |
| DEYKLWYD, | (SEQ ID NO: 767) |
| EIDKFWYD, | (SEQ ID NO: 768) |
| DIDKFWYD, | (SEQ ID NO: 769) |
| EHDKFWYD, | (SEQ ID NO: 770) |
| DHDKFWYD, | (SEQ ID NO: 771) |
| ELDKFWYD, | (SEQ ID NO: 772) |
| DLDKFWYD, | (SEQ ID NO: 773) |
| ERDKFWYD, | (SEQ ID NO: 774) |
| DRDKFWYD, | (SEQ ID NO: 775) |
| EEDKFWYD, | (SEQ ID NO: 776) |
| DEDKFWYD, | (SEQ ID NO: 777) |
| EINKFWYD, | (SEQ ID NO: 778) |
| EHNKFWYD, | (SEQ ID NO: 779) |
| ELNKFWYD, | (SEQ ID NO: 780) |
| ERNKFWYD, | (SEQ ID NO: 781) |
| DINKFWYD, | (SEQ ID NO: 782) |
| DHNKFWYD | (SEQ ID NO: 783) |
| DLNKFWYD, | (SEQ ID NO: 784) |
| DRNKFWYD, | (SEQ ID NO: 785) |
| DENKFWYD, | (SEQ ID NO: 786) |
| EIEKFWYD, | (SEQ ID NO: 787) |
| EHEKFWYD, | (SEQ ID NO: 788) |
| ELEKFWYD, | (SEQ ID NO: 789) |
| EREKFWYD, | (SEQ ID NO: 790) |
| EEEKFWYD, | (SEQ ID NO: 791) |
| DIEKFWYD, | (SEQ ID NO: 792) |
| DHEKFWYD, | (SEQ ID NO: 793) |
| DLEKFWYD, | (SEQ ID NO: 794) |
| DREKFWYD, | (SEQ ID NO: 795) |
| DEEKFWYD, | (SEQ ID NO: 796) |
| EIYKFWYD, | (SEQ ID NO: 797) |
| EHYKFWYD, | (SEQ ID NO: 798) |
| ELYKFWYD, | (SEQ ID NO: 799) |
| ERYKFWYD, | (SEQ ID NO: 800) |
| EEYKFWYD, | (SEQ ID NO: 801) |
| DIYKFWYD, | (SEQ ID NO: 802) |
| DHYKFWYD, | (SEQ ID NO: 803) |
| DLYKFWYD, | (SEQ ID NO: 804) |
| DRYKFWYD, | (SEQ ID NO: 805) |
| DEYKFWYD, | (SEQ ID NO: 806) |
| EIDKAWYD, | (SEQ ID NO: 807) |
| DIDKAWYD, | (SEQ ID NO: 808) |
| EHDKAWYD, | (SEQ ID NO: 809) |
| DHDKAWYD, | (SEQ ID NO: 810) |
| ELDKAWYD, | (SEQ ID NO: 811) |
| DLDKAWYD, | (SEQ ID NO: 812) |
| ERDKAWYD, | (SEQ ID NO: 813) |
| DRDKAWYD, | (SEQ ID NO: 814) |
| EEDKAWYD, | (SEQ ID NO: 815) |
| DEDKAWYD, | (SEQ ID NO: 816) |
| EINKAWYD, | (SEQ ID NO: 817) |
| EHNKAWYD, | (SEQ ID NO: 818) |
| ELNKAWYD, | (SEQ ID NO: 819) |
| ERNKAWYD, | (SEQ ID NO: 820) |
| DINKAWYD, | (SEQ ID NO: 821) |
| DHNKAWYD, | (SEQ ID NO: 822) |
| DLNKAWYD, | (SEQ ID NO: 823) |
| DRNKAWYD, | (SEQ ID NO: 824) |
| DENKAWYD, | (SEQ ID NO: 825) |
| EIEKAWYD, | (SEQ ID NO: 826) |
| EHEKAWYD, | (SEQ ID NO: 827) |
| ELEKAWYD, | (SEQ ID NO: 828) |
| EREKAWYD, | (SEQ ID NO: 829) |
| EEEKAWYD, | (SEQ ID NO: 830) |
| DIEKAWYD, | (SEQ ID NO: 831) |
| DHEKAWYD, | (SEQ ID NO: 832) |
| DLEKAWYD, | (SEQ ID NO: 833) |
| DREKAWYD, | (SEQ ID NO: 834) |
| DEEKAWYD, | (SEQ ID NO: 835) |
| EIYKAWYD, | (SEQ ID NO: 836) |
| EHYKAWYD, | (SEQ ID NO: 837) |
| ELYKAWYD, | (SEQ ID NO: 838) |
| ERYKAWYD, | (SEQ ID NO: 839) |
| EEYKAWYD, | (SEQ ID NO: 840) |

-continued

| | |
|---|---|
| DIYKAWYD, | (SEQ ID NO: 841) |
| DHYKAWYD, | (SEQ ID NO: 842) |
| DLYKAWYD, | (SEQ ID NO: 843) |
| DRYKAWYD, | (SEQ ID NO: 844) |
| DEYKAWYD, | (SEQ ID NO: 845) |
| EIDKSWYD, | (SEQ ID NO: 846) |
| DIDKSWYD, | (SEQ ID NO: 847) |
| EHDKSWYD, | (SEQ ID NO: 848) |
| DHDKSWYD, | (SEQ ID NO: 849) |
| ELDKSWYD, | (SEQ ID NO: 850) |
| DLDKSWYD, | (SEQ ID NO: 851) |
| ERDKSWYD, | (SEQ ID NO: 852) |
| DRDKSWYD, | (SEQ ID NO: 853) |
| EEDKSWYD, | (SEQ ID NO: 854) |
| DEDKSWYD, | (SEQ ID NO: 855) |
| EINKSWYD, | (SEQ ID NO: 856) |
| EHNKSWYD, | (SEQ ID NO: 857) |
| ELNKSWYD, | (SEQ ID NO: 858) |
| ERNKSWYD, | (SEQ ID NO: 859) |
| DINKSWYD, | (SEQ ID NO: 860) |
| DHNKSWYD, | (SEQ ID NO: 861) |
| DLNKSWYD, | (SEQ ID NO: 862) |
| DRNKSWYD, | (SEQ ID NO: 863) |
| DENKSWYD, | (SEQ ID NO: 864) |
| EIEKSWYD, | (SEQ ID NO: 865) |
| EHEKSWYD, | (SEQ ID NO: 866) |
| ELEKSWYD, | (SEQ ID NO: 867) |
| EREKSWYD, | (SEQ ID NO: 868) |
| EEEKSWYD, | (SEQ ID NO: 869) |
| DIEKSWYD, | (SEQ ID NO: 870) |
| DHEKSWYD, | (SEQ ID NO: 871) |
| DLEKSWYD, | (SEQ ID NO: 872) |
| DREKSWYD, | (SEQ ID NO: 873) |
| DEEKSWYD, | (SEQ ID NO: 874) |
| EIYKSWYD, | (SEQ ID NO: 875) |
| EHYKSWYD, | (SEQ ID NO: 876) |
| ELYKSWYD, | (SEQ ID NO: 877) |
| ERYKSWYD, | (SEQ ID NO: 878) |
| EEYKSWYD, | (SEQ ID NO: 879) |
| DIYKSWYD, | (SEQ ID NO: 880) |
| DHYKSWYD, | (SEQ ID NO: 881) |

-continued

| | |
|---|---|
| DLYKSWYD, | (SEQ ID NO: 882) |
| DRYKSWYD, | (SEQ ID NO: 883) |
| DEYKSWYD, | (SEQ ID NO: 884) |
| EIDKSFYD, | (SEQ ID NO: 885) |
| DIDKSFYD, | (SEQ ID NO: 886) |
| EHDKSFYD, | (SEQ ID NO: 887) |
| DHDKSFYD, | (SEQ ID NO: 888) |
| ELDKSFYD, | (SEQ ID NO: 889) |
| DLDKSFYD, | (SEQ ID NO: 890) |
| ERDKSFYD, | (SEQ ID NO: 891) |
| DRDKSFYD, | (SEQ ID NO: 892) |
| EEDKSFYD, | (SEQ ID NO: 893) |
| DEDKSFYD, | (SEQ ID NO: 894) |
| EINKSFYD, | (SEQ ID NO: 895) |
| EHNKSFYD, | (SEQ ID NO: 896) |
| ELNKSFYD, | (SEQ ID NO: 897) |
| ERNKSFYD, | (SEQ ID NO: 898) |
| DINKSFYD, | (SEQ ID NO: 899) |
| DHNKSFYD, | (SEQ ID NO: 900) |
| DLNKSFYD, | (SEQ ID NO: 901) |
| DRNKSFYD, | (SEQ ID NO: 902) |
| DENKSFYD, | (SEQ ID NO: 903) |
| EIEKSFYD, | (SEQ ID NO: 904) |
| EHEKSFYD, | (SEQ ID NO: 905) |
| ELEKSFYD, | (SEQ ID NO: 906) |
| EREKSFYD, | (SEQ ID NO: 907) |
| EEEKSFYD, | (SEQ ID NO: 908) |
| DIEKSFYD, | (SEQ ID NO: 909) |
| DHEKSFYD, | (SEQ ID NO: 910) |
| DLEKSFYD, | (SEQ ID NO: 911) |
| DREKSFYD, | (SEQ ID NO: 912) |
| DEEKSFYD, | (SEQ ID NO: 913) |
| EIYKSFYD, | (SEQ ID NO: 914) |
| EHYKSFYD, | (SEQ ID NO: 915) |
| ELYKSFYD, | (SEQ ID NO: 916) |
| ERYKSFYD, | (SEQ ID NO: 917) |
| EEYKSFYD, | (SEQ ID NO: 918) |
| DIYKSFYD, | (SEQ ID NO: 919) |
| DHYKSFYD, | (SEQ ID NO: 920) |
| DLYKSFYD, | (SEQ ID NO: 921) |

-continued

DRYKSFYD, (SEQ ID NO: 922)

DEYKSFYD, (SEQ ID NO: 923)

EIDKSFHD, (SEQ ID NO: 924)

DIDKSFHD, (SEQ ID NO: 925)

EHDKSFHD, (SEQ ID NO: 926)

DHDKSFHD, (SEQ ID NO: 927)

ELDKSFHD, (SEQ ID NO: 928)

DLDKSFHD, (SEQ ID NO: 929)

ERDKSFHD, (SEQ ID NO: 930)

DRDKSFHD, (SEQ ID NO: 931)

EEDKSFHD, (SEQ ID NO: 932)

DEDKSFHD, (SEQ ID NO: 933)

EINKSFHD, (SEQ ID NO: 934)

EHNKSFHD, (SEQ ID NO: 935)

ELNKSFHD, (SEQ ID NO: 936)

ERNKSFHD, (SEQ ID NO: 937)

DINKSFHD, (SEQ ID NO: 938)

DHNKSFHD, (SEQ ID NO: 939)

DLNKSFHD, (SEQ ID NO: 940)

DRNKSFHD, (SEQ ID NO: 941)

DENKSFHD, (SEQ ID NO: 942)

EIEKSFHD, (SEQ ID NO: 943)

EHEKSFHD, (SEQ ID NO: 944)

ELEKSFHD, (SEQ ID NO: 945)

EREKSFHD, (SEQ ID NO: 946)

EEEKSFHD, (SEQ ID NO: 947)

DIEKSFHD, (SEQ ID NO: 948)

DHEKSFHD, (SEQ ID NO: 949)

DLEKSFHD, (SEQ ID NO: 950)

DREKSFHD, (SEQ ID NO: 951)

DEEKSFHD, (SEQ ID NO: 952)

EIYKSFHD, (SEQ ID NO: 953)

EHYKSFHD, (SEQ ID NO: 954)

ELYKSFHD, (SEQ ID NO: 955)

ERYKSFHD, (SEQ ID NO: 956)

EEYKSFHD, (SEQ ID NO: 957)

DIYKSFHD, (SEQ ID NO: 958)

DHYKSFHD, (SEQ ID NO: 959)

DLYKSFHD, (SEQ ID NO: 960)

DRYKSFHD, (SEQ ID NO: 961)

DEYKSFHD, (SEQ ID NO: 962)

-continued

EIDKSFFD, (SEQ ID NO: 963)

DIDKSFFD, (SEQ ID NO: 964)

EHDKSFFD, (SEQ ID NO: 965)

DHDKSFFD, (SEQ ID NO: 966)

ELDKSFFD, (SEQ ID NO: 967)

DLDKSFFD, (SEQ ID NO: 968)

ERDKSFFD, (SEQ ID NO: 969)

DRDKSFFD, (SEQ ID NO: 970)

EEDKSFFD, (SEQ ID NO: 971)

DEDKSFFD, (SEQ ID NO: 972)

EINKSFFD, (SEQ ID NO: 973)

EHNKSFFD, (SEQ ID NO: 974)

ELNKSFFD, (SEQ ID NO: 975)

ERNKSFFD, (SEQ ID NO: 976)

DINKSFFD, (SEQ ID NO: 977)

DHNKSFFD, (SEQ ID NO: 978)

DLNKSFFD, (SEQ ID NO: 979)

DRNKSFFD, (SEQ ID NO: 980)

DENKSFFD, (SEQ ID NO: 981)

EIEKSFFD, (SEQ ID NO: 982)

EHEKSFFD, (SEQ ID NO: 983)

ELEKSFFD, (SEQ ID NO: 984)

EREKSFFD, (SEQ ID NO: 985)

EEEKSFFD, (SEQ ID NO: 986)

DIEKSFFD, (SEQ ID NO: 987)

DHEKSFFD, (SEQ ID NO: 988)

DLEKSFFD, (SEQ ID NO: 989)

DREKSFFD, (SEQ ID NO: 990)

DEEKSFFD, (SEQ ID NO: 991)

EIYKSFFD, (SEQ ID NO: 992)

EHYKSFFD, (SEQ ID NO: 993)

ELYKSFFD, (SEQ ID NO: 994)

ERYKSFFD, (SEQ ID NO: 995)

EEYKSFFD, (SEQ ID NO: 996)

DIYKSFFD, (SEQ ID NO: 997)

DHYKSFFD, (SEQ ID NO: 998)

DLYKSFFD, (SEQ ID NO: 999)

DRYKSFFD, (SEQ ID NO: 1000)

DEYKSFFD, (SEQ ID NO: 1001)

EIDKSFLD, (SEQ ID NO: 1002)

```
DIDKSFLD,           (SEQ ID NO: 1003)
EHDKSFLD,           (SEQ ID NO: 1004)
DHDKSFLD,           (SEQ ID NO: 1005)
ELDKSFLD,           (SEQ ID NO: 1006)
DLDKSFLD,           (SEQ ID NO: 1007)
ERDKSFLD,           (SEQ ID NO: 1008)
DRDKSFLD,           (SEQ ID NO: 1009)
EEDKSFLD,           (SEQ ID NO: 1010)
DEDKSFLD,           (SEQ ID NO: 1011)
EINKSFLD,           (SEQ ID NO: 1012)
EHNKSFLD,           (SEQ ID NO: 1013)
ELNKSFLD,           (SEQ ID NO: 1014)
ERNKSFLD,           (SEQ ID NO: 1015)
DINKSFLD,           (SEQ ID NO: 1016)
DHNKSFLD,           (SEQ ID NO: 1017)
DLNKSFLD,           (SEQ ID NO: 1018)
DRNKSFLD,           (SEQ ID NO: 1019)
DENKSFLD,           (SEQ ID NO: 1020)
EIEKSFLD,           (SEQ ID NO: 1021)
EHEKSFLD,           (SEQ ID NO: 1022)
ELEKSFLD,           (SEQ ID NO: 1023)
EREKSFLD,           (SEQ ID NO: 1024)
EEEKSFLD,           (SEQ ID NO: 1025)
DIEKSFLD,           (SEQ ID NO: 1026)
DHEKSFLD,           (SEQ ID NO: 1027)
DLEKSFLD,           (SEQ ID NO: 1028)
DREKSFLD,           (SEQ ID NO: 1029)
DEEKSFLD,           (SEQ ID NO: 1030)
EIYKSFLD,           (SEQ ID NO: 1031)
EHYKSFLD,           (SEQ ID NO: 1032)
ELYKSFLD,           (SEQ ID NO: 1033)
ERYKSFLD,           (SEQ ID NO: 1034)
EEYKSFLD,           (SEQ ID NO: 1035)
DIYKSFLD,           (SEQ ID NO: 1036)
DHYKSFLD,           (SEQ ID NO: 1037)
DLYKSFLD,           (SEQ ID NO: 1038)
DRYKSFLD,           (SEQ ID NO: 1039)
DEYKSFLD,           (SEQ ID NO: 1040)
EIDKSFLE,           (SEQ ID NO: 1041)
DIDKSFLE,           (SEQ ID NO: 1042)
EHDKSFLE,           (SEQ ID NO: 1043)
DHDKSFLE,           (SEQ ID NO: 1044)
ELDKSFLE,           (SEQ ID NO: 1045)
DLDKSFLE,           (SEQ ID NO: 1046)
ERDKSFLE,           (SEQ ID NO: 1047)
DRDKSFLE,           (SEQ ID NO: 1048)
EEDKSFLE,           (SEQ ID NO: 1049)
DEDKSFLE,           (SEQ ID NO: 1050)
EINKSFLE,           (SEQ ID NO: 1051)
EHNKSFLE,           (SEQ ID NO: 1052)
ELNKSFLE,           (SEQ ID NO: 1053)
ERNKSFLE,           (SEQ ID NO: 1054)
DINKSFLE,           (SEQ ID NO: 1055)
DHNKSFLE,           (SEQ ID NO: 1056)
DLNKSFLE,           (SEQ ID NO: 1057)
DRNKSFLE,           (SEQ ID NO: 1058)
DENKSFLE,           (SEQ ID NO: 1059)
EIEKSFLE,           (SEQ ID NO: 1060)
EHEKSFLE,           (SEQ ID NO: 1061)
ELEKSFLE,           (SEQ ID NO: 1062)
EREKSFLE,           (SEQ ID NO: 1063)
EEEKSFLE,           (SEQ ID NO: 1064)
DIEKSFLE,           (SEQ ID NO: 1065)
DHEKSFLE,           (SEQ ID NO: 1066)
DLEKSFLE,           (SEQ ID NO: 1067)
DREKSFLE,           (SEQ ID NO: 1068)
DEEKSFLE,           (SEQ ID NO: 1069)
EIYKSFLE,           (SEQ ID NO: 1070)
EHYKSFLE,           (SEQ ID NO: 1071)
ELYKSFLE,           (SEQ ID NO: 1072)
ERYKSFLE,           (SEQ ID NO: 1073)
EEYKSFLE,           (SEQ ID NO: 1074)
DIYKSFLE,           (SEQ ID NO: 1075)
DHYKSFLE,           (SEQ ID NO: 1076)
DLYKSFLE,           (SEQ ID NO: 1077)
DRYKSFLE,           (SEQ ID NO: 1078)
DEYKSFLE            (SEQ ID NO: 1079)
and
FEIDKVWY.           (SEQ ID NO: 1109)
```

Figure 12:
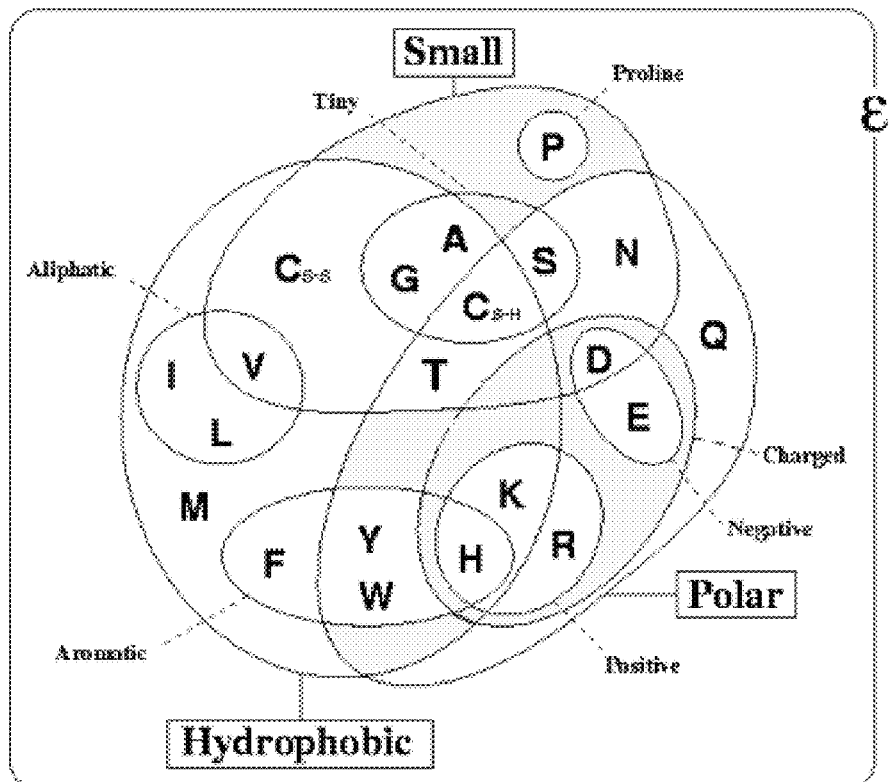
FIG. 12 presents a diagram depicting sequences confirmed to be or expected to be active towards modification by lipoic acid ligase and its mutants. The peptide GFEIDKVWY-DLDA corresponds to SEQ ID NO:1, the peptide LDHN corresponds to SEQ ID NO:1149 and the peptide IFHEIES corresponds to SEQ ID NO:1150.
Figure 13:
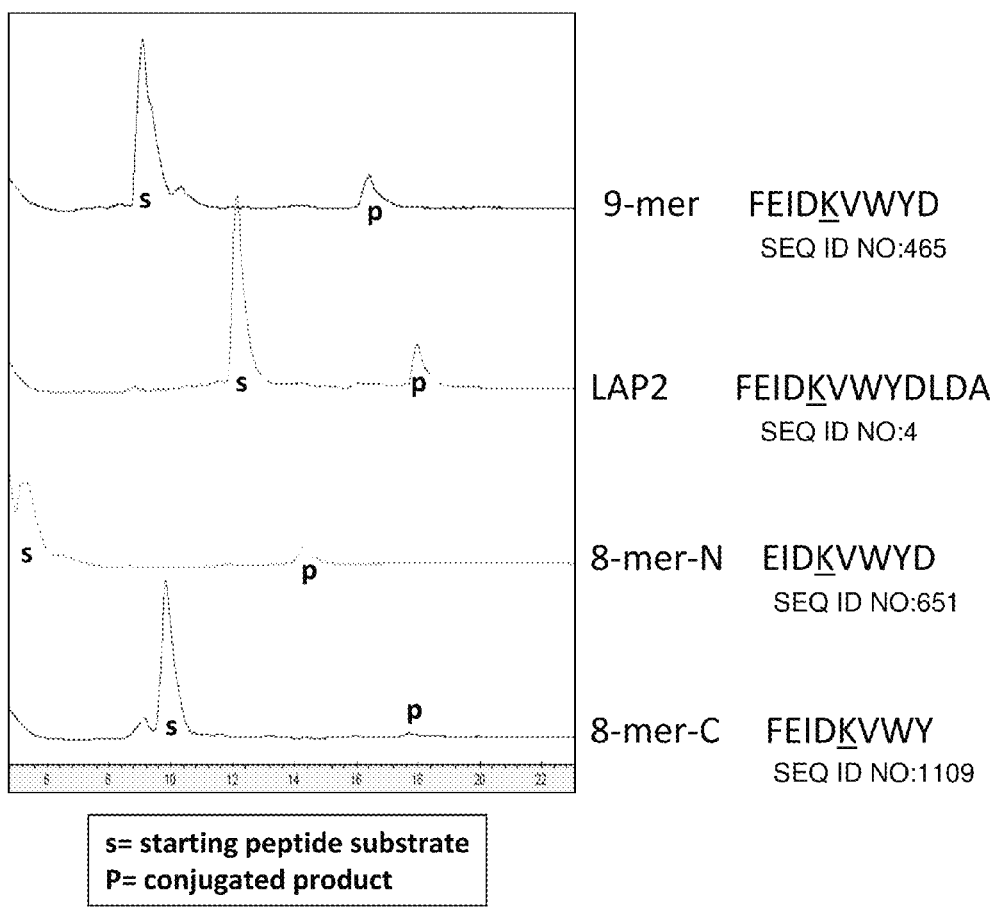
FIG. 13 presents a graph depicting lipoylation of 8-mer LAP2 substrates by Lp1A. The peptides listed correspond to SEQ ID NOs: 465, 4, 651 and 1109.

One of ordinary skill in the art will appreciate that other peptides can be designed that are compatible with the invention, based in part on the data presented in Example 1 and the schematics presented in FIG. 12. In some embodiments of the invention, an acceptor peptide that functions as a substrate for a lipoic acid ligase or mutant thereof comprises an amino acid sequence of GFEIDKVWYDLDA or a functional variant thereof. In some embodiments, an acceptor peptide functional variant comprises an amino acid sequence that has up to 90%, 95%, or 99% identity to GFEIDKVWYDLDA and is a substrate for a lipoic acid ligase or mutant thereof. It should be appreciated that the invention also encompasses nucleic acids that encode for any of the peptides described herein, and composition that comprise any of the peptides and/or nucleic acids described herein.

LAPs are used in methods associated with the invention to tag target proteins that are to be labeled by Lp1A. The acceptor peptide and target protein may be fused to each other either at the nucleic acid or amino acid level. Recombinant DNA technology for generating fusion nucleic acids that encode both the target protein and the acceptor peptide are known in the art. Additionally, the acceptor peptide may be fused to the target protein post-translationally. Such linkages may include cleavable linkers or bonds which can be cleaved once the desired labeling is achieved. Such bonds may be cleaved by exposure to a particular pH, or energy of a certain wavelength, and the like. Cleavable linkers are known in the art. Examples include thiol-cleavable cross-linker 3,3'-dithiobis(succinimidyl proprionate), amine-cleavable linkers, and succinyl-glycine spontaneously cleavable linkers.

The acceptor peptide can be fused to the target protein at any position. In some instances, it is preferred that the fusion not interfere with the activity of the target protein, accordingly, the acceptor peptide is fused to the protein at positions that do not interfere with the activity of the protein. Generally, the acceptor peptides can be C- or N-terminally fused to the target proteins. In still other instances, it is possible that the acceptor peptide is fused to the target protein at an internal position (e.g., a flexible internal loop). These proteins are then susceptible to specific tagging by lipoic acid ligase and/or mutants thereof in vivo and in vitro. This specificity is possible because neither lipoic acid ligase nor the acceptor peptide react with other enzymes or peptides in a cell.

Methods and compositions described herein can be used for protein labeling and imaging. Protein labeling encompasses in vitro and in vivo methods. As used herein, protein labeling in vitro means labeling of a protein in a cell-free environment. As an example, protein labeling can be conducted in a test tube or a well of a multiwell plate. As used herein, protein labeling in vivo means labeling of a protein in the context of a cell. The method can be used to label proteins that are intracellular proteins or cell surface proteins. The cell may be present in a subject or it may be present in culture.

Labeling of proteins allows one to track the movement and activity of such proteins. Protein labeling permits cells expressing such proteins to be tracked and imaged. Examples of types of proteins that can be labeled using LAPs of the invention include, but are not limited to, signal transduction proteins (e.g., cell surface receptors, kinases, adapter proteins), nuclear proteins (transcription factors, histones), mitochondrial proteins (cytochromes, transcription factors) and hormone receptors.

As used herein, a subject shall mean an organism such as an insect, a yeast cell, a worm, a fish, or a human or animal including but not limited to a dog, cat, horse, cow, pig, sheep, goat, chicken, rodent e.g., rats and mice, primate, e.g., monkey. Subjects include vertebrate and invertebrate species. Subjects can be house pets (e.g., dogs, cats, fish, etc.), agricultural stock animals (e.g., cows, horses, pigs, chickens, etc.), laboratory animals (e.g., mice, rats, rabbits, etc.), zoo animals (e.g., lions, giraffes, etc.), but are not so limited. Methods and compositions of the invention may be used to introduce labels for MRI, PET, or multiphoton imaging, etc. into and for detection in live animals. Methods and compositions of the invention may be applied to living animals, for example, transgenic animals, thus subjects of the invention may be transgenic animals.

The compositions, as described above, are administered in effective amounts for labeling of the target proteins. The effective amount will depend upon the mode of administration, the location of the cells being targeted, the amount of target protein present and the level of labeling desired.

Methods for identifying an acceptor polypeptide having specificity for a lipoic acid ligase or mutant thereof are provided. Such methods may include combining an candidate acceptor peptide with a labeled lipoic acid or analog thereof in the presence of a lipoic acid ligase or mutant thereof and determining a level of lipoic acid or lipoic acid analog incorporation, wherein lipoic acid or lipoic acid analog incorporation is indicative of a candidate acceptor peptide having specificity for a lipoic acid ligase or mutant thereof.

Methods of the invention, generally speaking, may be practiced using any mode of administration that is medically acceptable, meaning any mode that produces effective levels of the active compounds without causing clinically unacceptable adverse effects. A variety of administration routes are available including but not limited to oral, rectal, topical, nasal, intradermal, or parenteral routes. The term "parenteral" includes subcutaneous, intravenous, intramuscular, or infusion.

When peptides are used, in certain embodiments one desirable route of administration is by pulmonary aerosol. Techniques for preparing aerosol delivery systems containing peptides are well known to those of skill in the art. Generally, such systems should utilize components which will not significantly impair the biological properties of the peptides or proteins (see, for example, Sciarra and Cutie, "Aerosols," in *Remington's Pharmaceutical Sciences,* 18th edition, 1990, pp 1694-1712; incorporated by reference). Those of skill in the art can readily determine the various parameters and conditions for producing protein or peptide aerosols without resort to undue experimentation.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that subject tolerance permits. Multiple doses per day are contemplated to achieve appropriate systemic levels of compounds.

The agents may be combined, optionally, with a pharmaceutically-acceptable carrier. The term "pharmaceutically-acceptable carrier" as used herein means one or more compatible solid or liquid filler, diluents or encapsulating substances which are suitable for administration into a subject. The term "carrier" denotes an organic or inorganic ingredient, natural or synthetic, with which the active ingredient is combined to facilitate the application. The components of the pharmaceutical compositions also are capable of being commingled with the molecules of the present invention, and with each other, in a manner such that there is no interaction that would substantially impair the desired pharmaceutical efficacy.

The invention in other aspects includes pharmaceutical compositions. When administered, the pharmaceutical preparations of the invention are applied in pharmaceutically-acceptable amounts and in pharmaceutically-acceptably compositions. Such preparations may routinely contain salt, buffering agents, preservatives, compatible carriers, and the like. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

Other delivery systems can include time-release, delayed release or sustained release delivery systems. Such systems can avoid repeated administrations of the labeling reagents. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480.

A preferred delivery system of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 µm can encapsulate large macromolecules. RNA, DNA, and intact virions can be encapsulated within the aqueous interior and be delivered to cells in a biologically active form (Fraley, et al., *Trends Biochem. Sci.,* (1981) 6:77). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2, 3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, (1985) 3:235-241.

In one important embodiment, the preferred vehicle is a biocompatible microparticle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System"). PCT/US/03307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the fugetactic agents described herein are encapsulated or dispersed within the biocompatible, preferably biodegradable polymeric matrix disclosed in PCT/US/03307.

The polymeric matrix preferably is in the form of a microparticle such as a microsphere (wherein an agent is dispersed throughout a solid polymeric matrix) or a microcapsule (wherein an agent is stored in the core of a polymeric shell). Other forms of the polymeric matrix for containing an agent include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used. Preferably when an aerosol route is used the polymeric matrix and agent are encompassed in a surfactant vehicle. The polymeric matrix composition can be selected to have both favorable degradation rates and also to be formed of a material which is bioadhesive, to further increase the effectiveness of transfer. The matrix composition also can be selected not to degrade, but rather, to release by diffusion over an extended period of time.

In another important embodiment the delivery system is a biocompatible microsphere that is suitable for local, site-specific delivery. Such microspheres are disclosed in Chickering et al., *Biotech. And Bioeng.,* (1996) 52:96-101 and Mathiowitz et al., *Nature,* (1997) 386:.410-414.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

Examples of non-biodegradable polymers include ethylene vinyl acetate, poly(meth)acrylic acid, polyamides, copolymers and mixtures thereof.

Bioadhesive polymers of particular interest include bio-erodible hydrogels described by H. S. Sawhney, C. P. Pathak and J. A. Hubell in *Macromolecules,* (1993) 26:581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The invention will be more fully understood by reference to the following examples. These examples, however, are merely intended to illustrate the embodiments of the invention and are not to be construed to limit the scope of the invention.

EXAMPLES

Example 1

Yeast Display Evolution of a Kinetically Efficient 13-Amino Acid Substrate for Lipoic Acid Ligase Introduction Described herein is the identification of novel, kinetically efficient peptide substrates for *Escherichia coli* lipoic acid ligase (LplA) (FIG. 1). LplA is a cofactor ligase that can be harnessed for fluorescent protein labeling applications.[13,28] The natural function of LplA is to catalyze ATP-dependent, covalent ligation of lipoic acid (FIG. 1A) onto specific lysine side chains of three *E. coli* proteins involved in oxidative metabolism: pyruvate dehydrogenase, 2-oxoglutarate dehydrogenase, and the glycine cleavage system.[29] Previously, it was shown that LplA and engineered variants could ligate unnatural probes such as an alkyl azide (a functional group handle for fluorophore introduction; FIG. 1A),[13] a fluorinated aryl azide photo-cross-linker,[28] bromoalkanoic acid (a ligand for HaloTag;[30] FIG. 1A),[31] and a coumarin fluorophore[32] in place of lipoic acid. To utilize these ligation reactions for protein imaging applications, recombinant fusions were prepared of proteins of interest (POIs) to the 9 kD E2p domain of pyruvate dehydrogenase (FIG. 1B top).[13] Such fusions could be labeled with high efficiency and specificity by unnatural probes on the surface and in the cytosol of living mammalian cells.[13,28,31,32]

Even though 9 kD (85 amino acids) E2p is considerably smaller than green fluorescent protein (27 kD) and other protein labeling tags such as HaloTag (33 kD)[30] and SNAP tag (20 kD),[35] further reducing its size would be preferred, to minimize steric interference with POI function. This was previously attempted by rational design of an "Lp1A acceptor peptide" (LAP1),[13] based mostly on the sequence of Lp1A's natural protein substrate 2-oxoglutarate dehydrogenase, with a few additional rational mutations. LAP1 is 17 amino acids long, or 22 amino acids with the recommended linker [13]. It was found that LAP1 fusion proteins could be ligated by Lp1A to some probes (lipoic acid,[13] alkyl azide,[13] and aryl azide[28]) in vitro and in cell lysate, but not on the cell surface except under conditions of high LAP1-POI overexpression.[13,28] LAP1 labeling was not detected in the cytosol, using the visualization methods described herein.[32] Other probes (bromoalkanoic acid and coumarin) were not found to ligate to LAP1 fusions, at least using methods tested thus far.[31,32] By contrast, E2p fusions could be labeled by all probes on the cell surface and in the cytosol.[13,28,31,32] Since the measured $k_{cat}$ values for Azide 7 ligation, for instance, are similar for LAP1 and E2p (0.048 (0.001 s$^{-1}$ and 0.111 (0.003 s$^{-1}$, respectively[13]), the difference in labeling outcomes is likely to be attributable to the gap in their $K_m$ values. H-protein of the glycine cleavage system has a $K_m$ of 1.2 µM,[36] which is likely to be similar to E2p's $K_m$, due to their sequence and structural similarity.[37] On the other hand, based on HPLC measurements, the $K_m$ for LAP1 is estimated to be >200 µM.

Yeast surface display[38] was selected as the platform to evolve a novel peptide substrate for Lp1A (called "LAP2"), with kinetic properties comparable to those of Lp1A's natural protein substrates. Yeast display was preferred relative to other evolution platforms for a number of reasons. Selections in bacterial cytosol[24] do not allow fine adjustment of protein concentrations and selection conditions. Phage display has limited dynamic range, both due to displayed peptide copy number (3-5 on pIII or 2700 on pVIII[39]), and due to the all-or-nothing nature of affinity-based product capture. The limited dynamic range makes it very difficult to enrich kinetically efficient peptide substrates, as was discovered in phage display evolution of yAP, a peptide substrate for yeast biotin ligase.[21] Mammalian cell surface display is challenging due to the need for viral transfection to control the multiplicity of infection, and the low viability of cells after fluorescence activated cell sorting (FACS).[40]

By careful library design, tuning of selection conditions with the help of a model selection, four rounds of selection with decreasing Lp1A concentrations, and additional rational mutagenesis, a 13-amino acid LAP2 peptide was engineered that had a $k_{cat}$ of 0.22 (0.01 s$^{-1}$ and a $K_m$ of 13.32±1.78 µM for lipoic acid ligation. The catalytic efficiency ($k_{cat}/K_m$) 0.99 µM$^{-1}$ min$^{-1}$) is closer to that of Lp1A's natural protein substrate H-protein ($k_{cat}/K_m$) 7.95 µM$^{-1}$ min$^{-1}$)[33] than that of LAP1 (est. $k_{cat}/K_m$<0.0135 µM$^{-1}$ min$^{-1}$ for azide ligation).[13] As a consequence of this improvement, cell surface LAP2 fusion proteins could be easily lipoylated, even at low expression levels. Lp1A-mediated specific quantum dot targeting to LAP2-LDL receptor was also performed. In comparison, quantum dot labeling was undetectable when using the same receptor fused to LAP1.

Results
Model Selections

Figure 2:
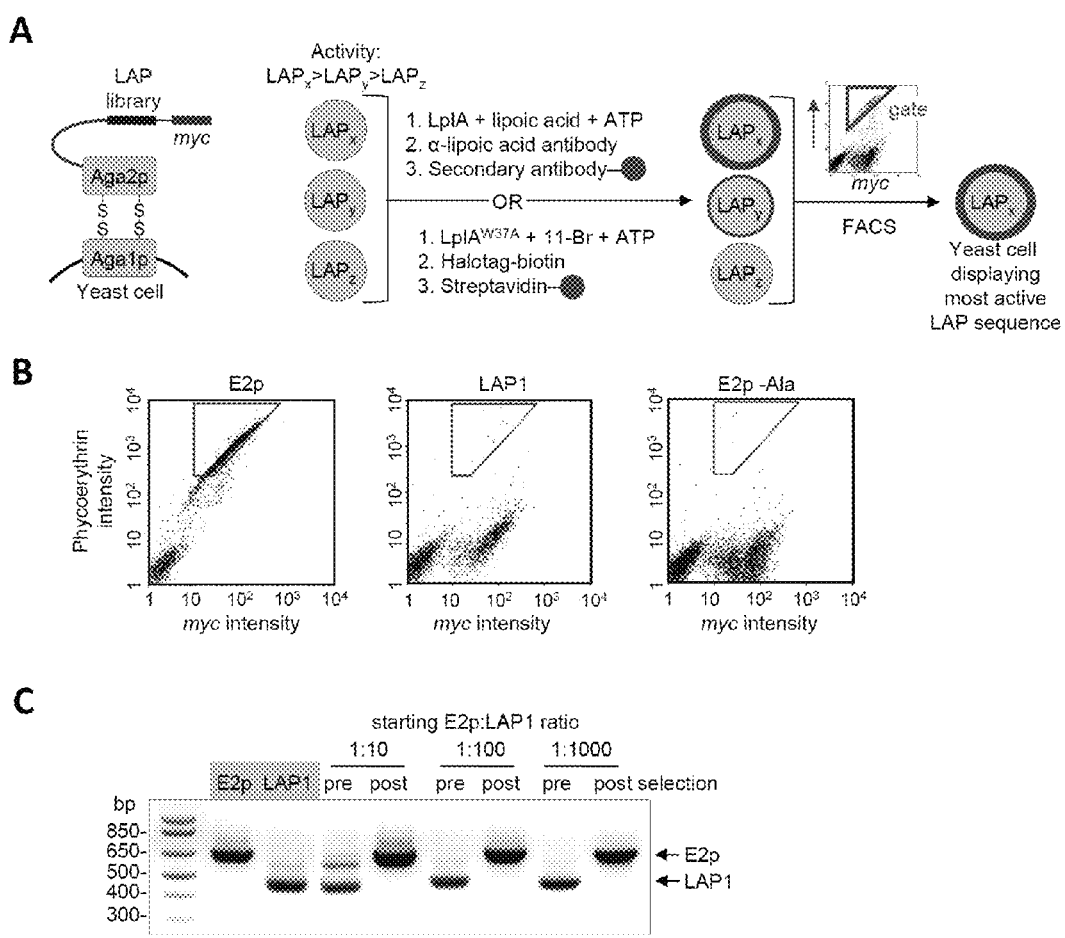
FIG. 2 presents a schematic of a yeast display selection scheme and results of model selections.

The selection scheme is shown in FIG. 2A. A library of LAP variants was displayed on the C-terminus of Aga2p, a cell surface mating agglutinin protein commonly used for yeast display.[38] A c-Myc epitope tag was also introduced to allow measurement of LAP expression levels by immunofluorescence staining. Each of $10^6$-$10^8$ yeast cells expressed a single LAP mutant. Three hypothetical LAP mutants (LAPx, LAPy, and LAPz) with diminishing activity toward Lp1A are shown in FIG. 2A. They were collectively labeled by Lp1A (e.g., with lipoic acid), and ligated probe is detected with a suitable fluorescent reagent (e.g., antilipoic acid antibody followed by phycoerythrin-conjugated secondary antibody). Since LAPx is the most active mutant in this scheme, yeast cells displaying this mutant should become brightly fluorescent. On the other hand, LAPy and LAPz-displaying yeast will be dimmer or unlabeled. To normalize for variations in expression level, the yeast pool was also collectively labeled with anti-c-Myc antibody, detected with a secondary antibody conjugated to Alexa Fluor 488, which is easily resolvable from phycoerythrin fluorescence. The double-labeled yeast cells were subjected to two-dimensional fluorescence activated cell sorting (FACS). Yeast cells displaying a high ratio of phycoerythrin intensity to Alexa Fluor 488 intensity (sorting gate shown by a solid triangle in FIG. 2A) represent the most efficiently labeled yeast, with the largest fraction of labeled LAPs, and were isolated by FACS. The captured yeast cells were amplified, sequenced, and subjected to further rounds of selection.

Before initiating selections on a LAP library, the selection scheme was tested and optimized using a model system consisting of mixtures of E2p-expressing yeast and LAP1-expressing yeast. Since LAP1 represents the best that can be achieved by rational design and E2p represents Lp1A's natural substrate with evolutionarily optimized $k_{cat}/K_m$, the goal was to design a selection that could maximally enrich E2p-yeast over LAP1-yeast. Lipoylation of E2p or LAP1 expressed on yeast surface was performed by adding purified Lp1A, ATP, and lipoic acid to the media. FACS scanning showed that, for a 30 min reaction time, the largest difference in signal between E2p-yeast and LAP1-yeast could be obtained using 300 nM Lp1A (FIG. 2B). Higher Lp1A concentrations increased LAP1 intensity without increasing E2p intensity, diminishing the difference between them. To check the site-specificity of Lp1A labeling on the yeast surface, a negative control was also performed using an E2p-Aga2p construct with a Lys→Ala mutation at the lipoylation site. No phycoerythrin staining was observed (FIG. 2B).

Using 300 nM Lp1A, 30-min labeling was performed on 1:10, 1:100, and 1:1000 mixtures of E2p-yeast and LAP1-yeast (E2p yeast in the minority). FACS was performed as shown in FIG. 2B. A PCR assay was used to determine the ratio of yeast before and after a single round of selection, capitalizing on the different sizes of the E2p and LAP1 genes. FIG. 2C shows that for all starting mixtures, the selection protocol enriched E2p yeast and depleted LAP1 yeast so completely that it could not be detected. Thus, this selection can enrich kinetically efficient Lp1A substrates (e.g., E2p) over active but inefficient substrates (e.g., LAP1) by >1000-fold in a single round.

In addition to a selection based on lipoylation, it was also a goal to develop a selection scheme based on ligation of an unnatural probe. This would serve two purposes. First, by using two different sets of probes and detection reagents in alternating rounds of selection, the possibility of inadvertently isolating LAPs with affinity for one of our detection reagents would be minimized. Second, the probability of isolating a LAP sequence that would be effective not just for lipoylation, but also for ligation of unnatural probes such as photo-cross-linkers and fluorophores would be increased.

In separate work,[31] mutants of Lp1A that catalyze ligation of bromoalkanoic acids have been identified. Once ligated to E2p or LAP, such probes can covalently react with the commercial protein HaloTag,[30] which is derived from a microbial dehalogenase. Thus, herein, 11-bromoundecanoic acid (11-Br, FIG. 1A) was used to target HaloTag-conjugated fluorophores to specific cell surface proteins (FIG. 1B, bottom).[31] For yeast display selections, cell surface E2p or LAP1 were labeled with the Trp37fAla mutant of Lp1A mutant (Lp1AW37A), ATP, and the 11-Br probe. Then, ligated bromoalkane was detected with HaloTag protein, conjugated to biotin, and that in turn was detected with streptavidin conjugated to phycoerythrin (FIG. 2A). As with the lipoylation assay, a large difference was detected in phycoerythrin staining between E2p-yeast and LAP1-yeast, using 500 nM mutant Lp1A, and no labeling of E2p (LysfAla)-yeast (data not shown). Thus, 11-Br probe is also suitable for LAP selections on yeast cells.

Construction of LAP Library and Yeast Display Selections

In order to shorten LAP, from LAP1's 17-22 amino acids,[13,28] a 12-mer peptide library was used. With complete randomization of the 11 residues flanking the central Lys, the theoretical diversity would be ~$10^{14}$, far greater than the experimentally achievable library size, which is limited by yeast transformation efficiency to $10^7$-$10^8$.[41] Thus, a partially randomized 12-mer library was created, guided by alignments of natural lipoate acceptor protein sequences, the NMR structure of E2p,[34] and the structure of a functionally and structurally related biotin acceptor domain in complex with biotin ligase.[42]

Figure 3:
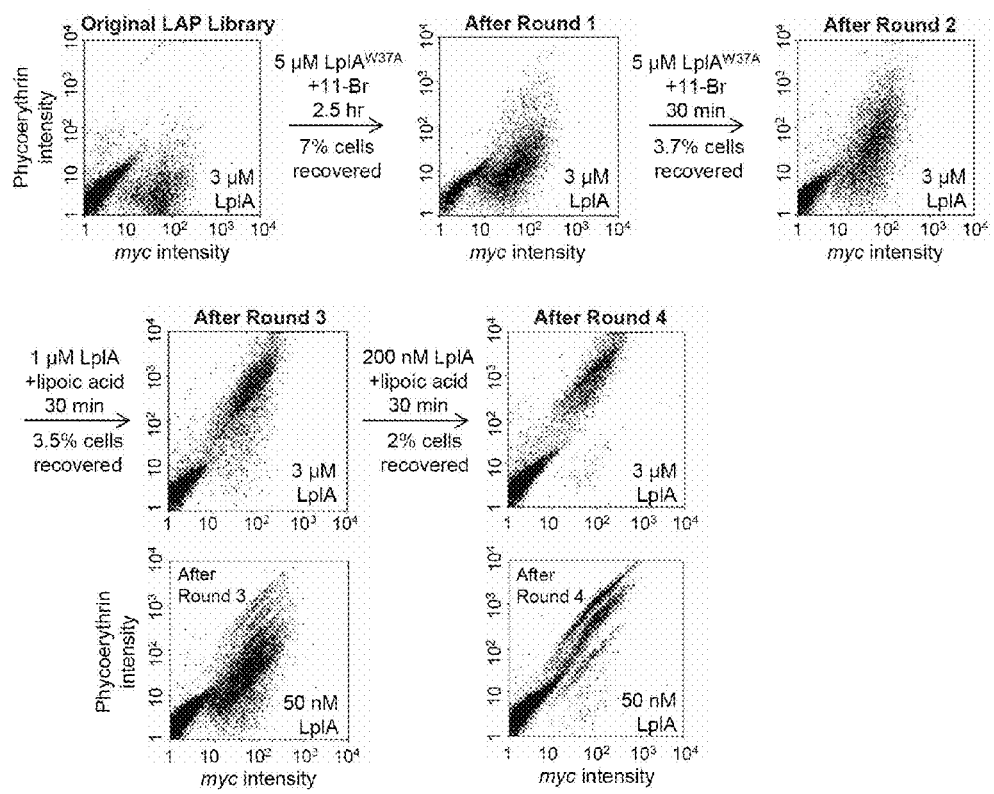
FIG. 3 depicts library design and selection results.

The sequences of 250 naturally lipoylated proteins (lipoate acceptor proteins) from >100 distinct species were aligned. The five lipoyl domains from E. coli (present in Lp1A acceptor proteins), along with lipoyl domains from three other species are shown in FIG. 3A. Several trends were apparent from the alignment: (1) the −1 Asp is highly conserved; (2) positions +1, +5, and −4 are usually hydrophobic; (3) Glu and Asp are enriched at positions −3 and +4; and (4) position +6 is usually Ser or Ala. These preferences were introduced into the LAP library design, shown in FIG. 3A.

Figure 5:
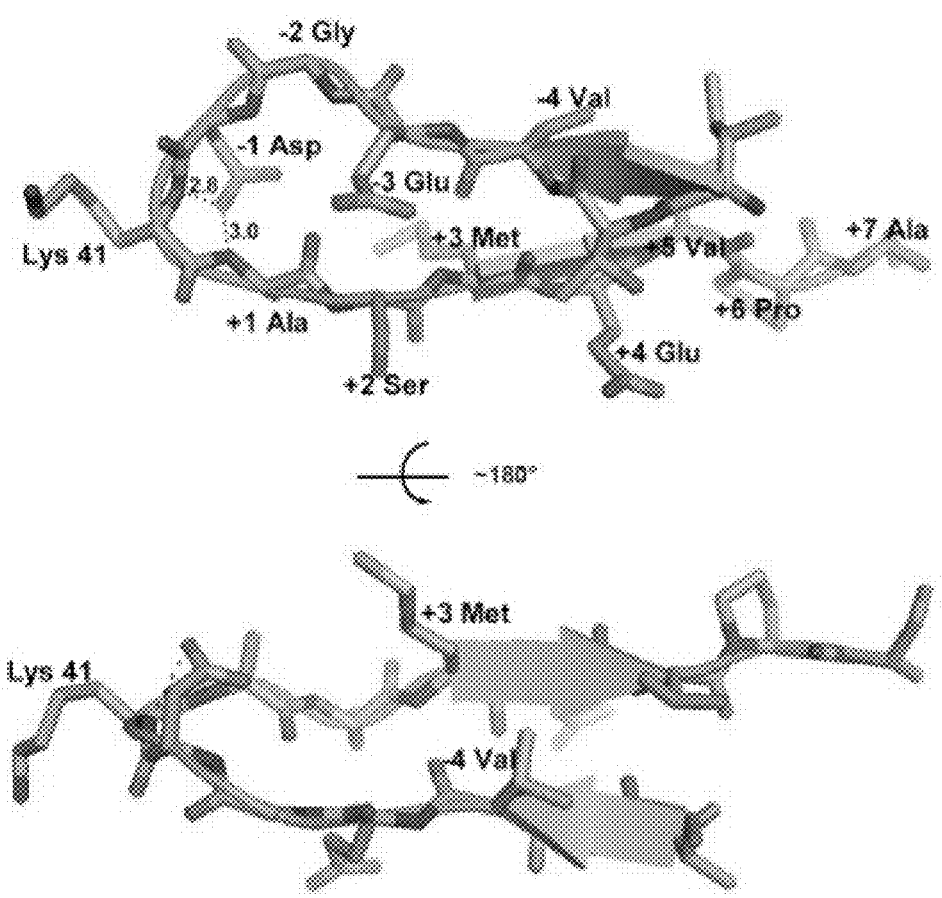
FIG. 5 depicts the NMR structure of the E2p domain of E. coli pyruvate dehydrogenase (PDB 1QJO).[52] (β-strands 4 and 5 are shown with the lipoylation site at Lys41. (Top) Hydrogen bonds between the sidechain of −1 Asp and the backbone NH groups of Lys41 and +1 Ala are indicated by dashed lines. (Bottom) β-strands 4 and 5 are shown in a different orientation. +3 Met and −4 Val sidechains point in the same direction. These data suggest that the sidechains of +3 Tyr and −4 Phe in the engineered LAP2 sequence described herein, may stack together.

In addition, structural data was used to inform the LAP library design. NMR structures are available for several lipoate acceptor domains.[34,43-45] All of them show that the lipoylated lysine is presented at the tip of a β-hairpin turn. Though this is a challenging structure to recapitulate in a peptide, a cue was taken from the structure of E. coli E2p, which shows that the −1 Asp side-chain hydrogen bonds with backbone amide N—H groups of both the central lysine and +1 Ala (FIG. 5).[34] To promote this loop-favoring interaction, Asp was installed at the −1 position with 39% frequency in the LAP library (FIG. 3A).

There is no cocrystal structure of a lipoate acceptor domain with Lp1A, to indicate which residues might be important for interactions with the enzyme. However, lipoate domains are structurally similar to biotin acceptor domains,[46,47] and Lp1A is structurally related to biotin ligase as well.[48] The cocrystal structure of Pyrococcus horikoshii biotin ligase with its biotin acceptor protein shows a hydrogen bond between the +4 Glu of the acceptor and Lys27 of the enzyme.[42] In addition, the authors of the Thermoplasma acidophilum Lp1A structure created a computationally docked model of their enzyme with E2p.[37] The docked structure also predicts a hydrogen bond between the +4 Glu of E2p and Lys155 of the enzyme, which corresponds to Lys143 in E. coli Lp1A. FIG. 1C shows a docked model of *E. coli* Lp1A with its E2p lipoate acceptor. Because these structures and models suggest that +4 Glu is important for interactions with Lp1A, the +4 position of the LAP library was restricted to polar residues (Glu, Asp, Gln, and His) to promote intermolecular hydrogen bonding (FIG. 3A).

The LAP library was cloned by Klenow-mediated fill-in of a synthetic oligonucleotide library. The insert was introduced into pCTCON2,[41] containing Aga2p and the c-Myc tag, by homologous recombination. The yeast transformation efficiency was ~$10^7$, $10^3$-fold under the theoretical diversity of ~$10^{10}$.

For reasons described above, both lipoic acid and bromoalkanoic acid (11-Br) probes were used for selections. The latter was used for the first two rounds of selection, and lipoic acid was used for rounds 3 and 4 (FIG. 3B). To successively increase selection stringency, Lp1A concentration was decreased throughout the selection, from 5 µM in rounds 1 and 2, to 1 µM in round 3, to 200 nM Lp1A in the final round. Reaction times were 2.5 h for the first round, and 30 min for all subsequent rounds.

To compare the activities of recovered yeast from each round of selection, the yeast pools were reamplified and labeled with lipoic acid under identical conditions. FIG. 3B shows that c-Myc intensities remained constant, while phycoerythrin intensities gradually increased. With 3 µM Lp1A, yeast recovered from rounds 3 and 4 looked identical; thus analysis was also performed under milder conditions (FIG. 3B). With 50 nM Lp1A, it can be seen that yeast cells from round 4 were more extensively labeled by lipoic acid than yeast cells from round 3.

Characterization of Selection Results

Figure 6:
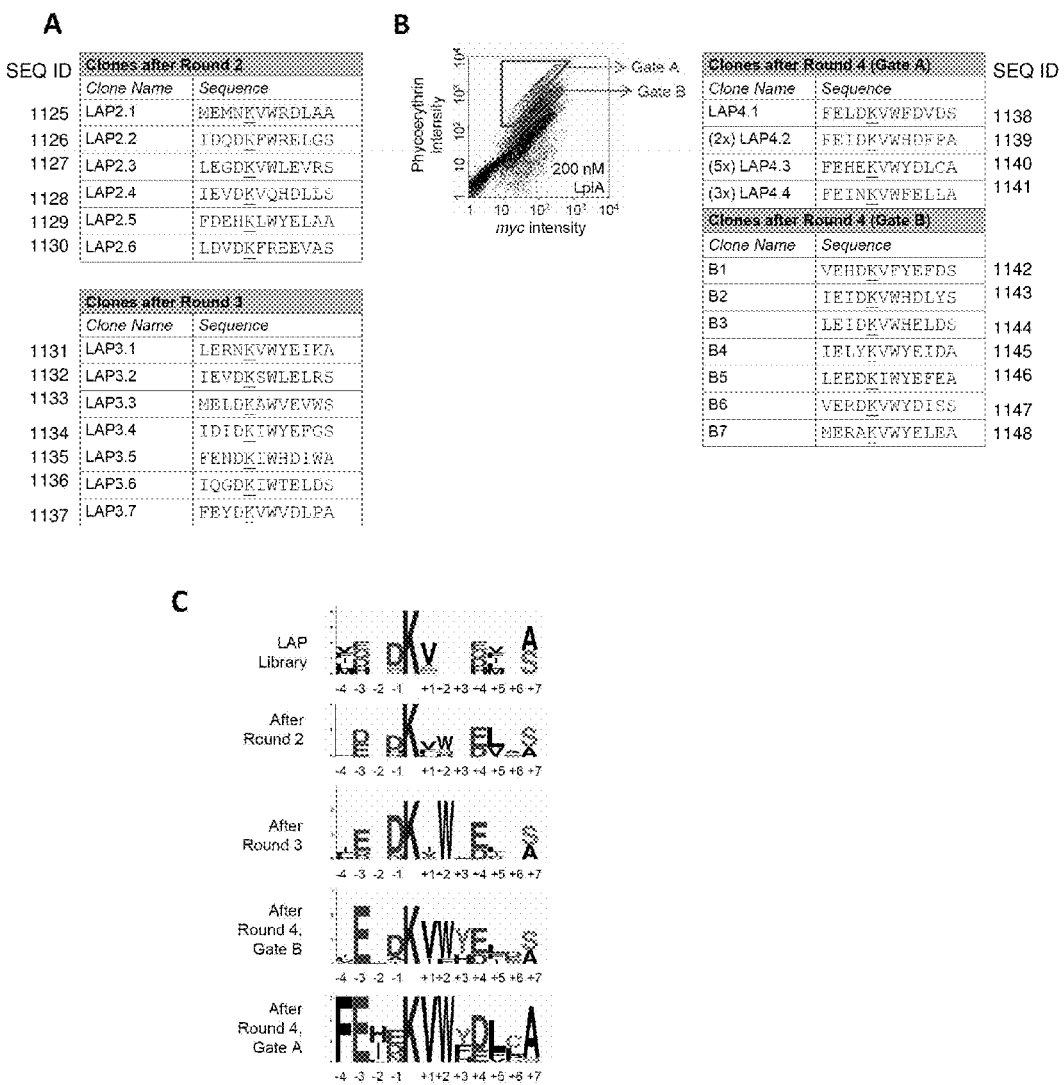
FIG. 6 depicts LAP sequences after each round of selection.

The sequences of selected LAP clones from rounds 2, 3, and 4 are shown in FIG. 6. In addition, FIG. 6 shows graphical representations of amino acid frequencies. The following trends were observed: (1) In general, selected LAP clones had interlaced hydrophobic and negatively charged side chains flanking the central lysine. (2) Position +2, which was fully randomized in the LAP library, became 100% Trp. This enrichment was apparent after just a single round of selection. (3) Position +3, which was also fully randomized, showed a preference for aromatic side chains. (4) Positions −3 and +4 were limited to one of 4 polar side chains in the LAP library. Position −3 became 100% Glu. Position +4 became exclusively Glu or Asp, already by round 2. (5) Positions −4 and +5 were limited to hydrophobic residues in the LAP library. Position +5 did not converge, but position −4 became 100% Phe. (6) Position +1, which was 49% Val in the library, became 100% Val. After round 4, only 4 distinct clones were observed, and further rounds of selection did not reveal any additional diversity.

Figure 7:
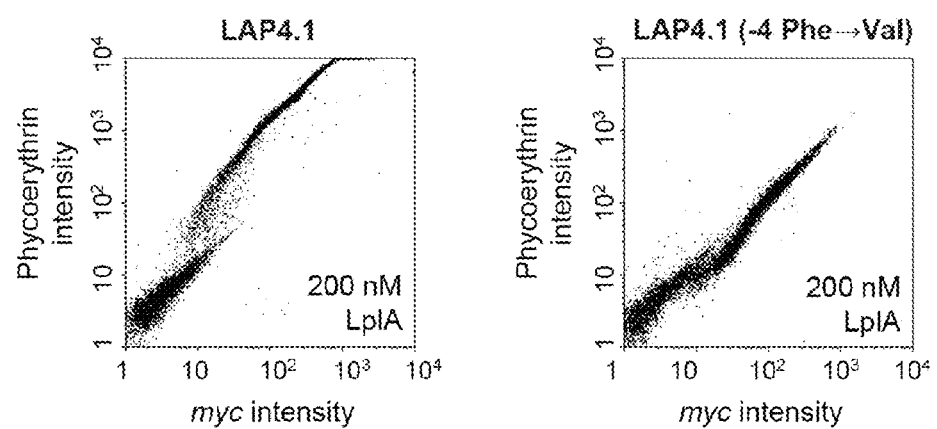
FIG. 7 presents results showing the contribution of −4 Phe to LAP recognition by Lp1A.
Figure 7:
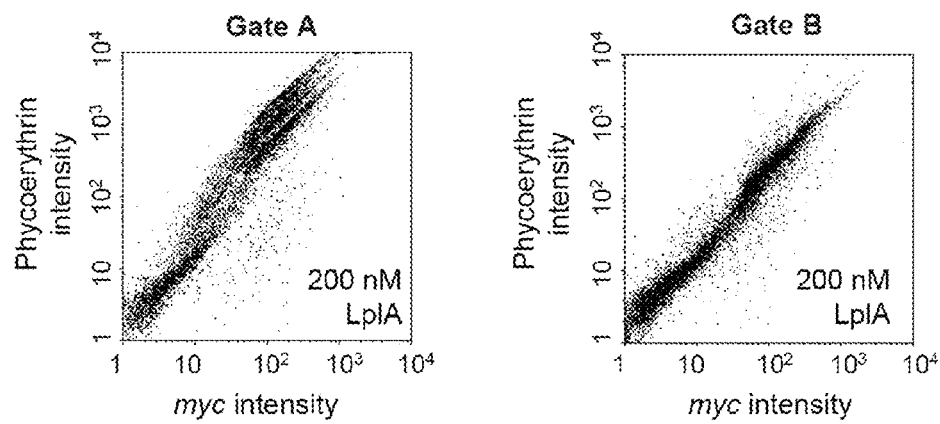

A powerful feature of FACS-based selection is its dynamic range. For a single round of selection, different sorting gates can be used, and the sequences of clones obtained via different gates can be compared, to infer sequence-activity relationships. For round 4, in addition to the standard high phycoerthyrin gate ("Gate A"), yeast was also collected from a slightly lower gate ("Gate B"). FIG. 6 shows that the major difference between Gate A clones and Gate B clones is the presence of Phe at the −4 position in Gate A clones, suggesting that the selection of −4 Phe may account for much of the jump in LAP activity between rounds 3 and 4. Indeed, when the −4 Phe of one of the Gate A clones, LAP4.1, was mutated to Val, its activity in a yeast surface lipoylation assay dropped to a level comparable to the Gate B clones (FIG. 7).

The information from Gate A and Gate B clones (FIG. 6) was utilized to rationally design a new LAP sequence, called "LAP2". Since Gate A clones showed clear amino acid preferences at positions −4, −3, −2, +1, +2, +4, +5, and +7, these preferred residues were introduced into the LAP2 sequence. Positions −1, +3, and +6 did not show consensus in Gate A clones, so these amino acids in LAP2 were based on preferences seen in the Gate B clones. This rationally designed LAP2 was characterized alongside the four evolved LAP clones from round 4, in cell-based and in vitro assays, described below.

Comparison of LAP Sequences

To compare the round 4 LAP sequences and LAP2, genetic fusions were created to CFP-TM (cyan fluorescent protein fused to a transmembrane helix from PDGF receptor)[13] for mammalian cell surface expression, and HP1 (heterochromatin protein 1)[13] for bacterial expression. In all constructs, an N-terminal glycine from the Aga2p fusion was carried over, making the total LAP length 13 amino acids.

Figure 8:
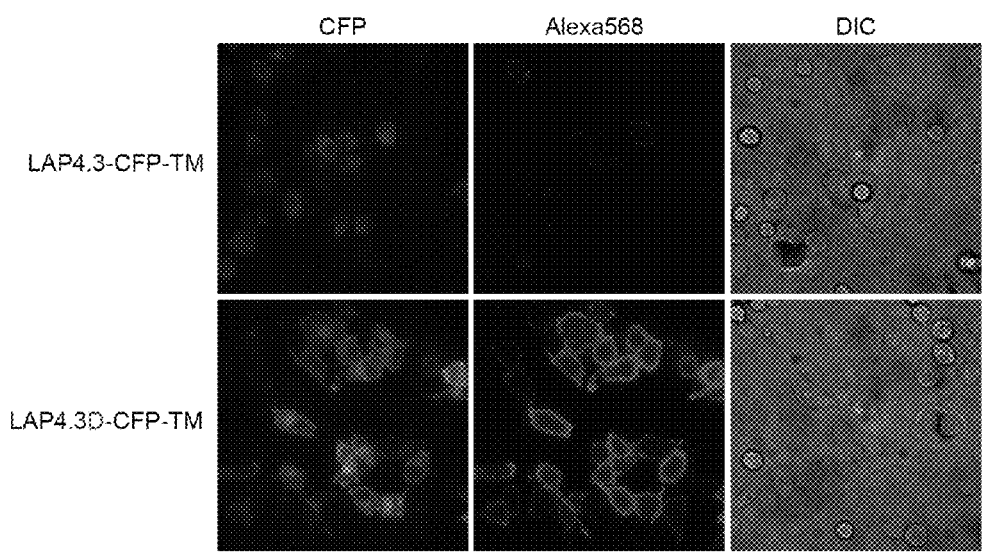
FIG. 8 depicts cell surface lipoylation of LAP4.3 vs. LAP4.3D. HeLa cells expressing either LAP4.3-CFP-TM or LAP4.3D-CFP-TM were lipoylated with 1 µM Lp1A for 10 minutes. Lipoylation was detected with Alexa568-conjugated anti-lipoic acid antibody.

First, the surface expression levels of the LAP fusions in HeLa mammalian cells was compared. Whereas LAP4.1, LAP4.2, and LAP2 gave clear cell surface expression, both LAP4.3 and LAP4.4 showed poor expression. Without wishing to be bound by any theory, LAP4.3 expression might be hindered by its +6 Cys, due to intermolecular disulfide bond formation in the oxidizing secretory pathway. Since Gate B clones showed a preference for Asp at this position, a point mutant of LAP4.3 with a +6CysfAsp mutation (LAP4.3D) was prepared. FIG. 8 shows that LAP4.3D gives improved cell surface expression compared to LAP4.3, as indicated by the pattern of CFP fluorescence. In addition, cell surface lipoylation with exogenous Lp1A gives a strong signal with LAP4.3D-CFP-TM, whereas little signal is detected under the same conditions with LAP4.3-CFP-TM. *E. coli* expression of the HP1 fusion protein also improved significantly upon introduction of the +6Cysf Asp mutation in LAP4.3. Based on these observations, LAP4.3D was carried into subsequent analyses, while LAP4.3 and LAP4.4 were not characterized further.

Figure 9:
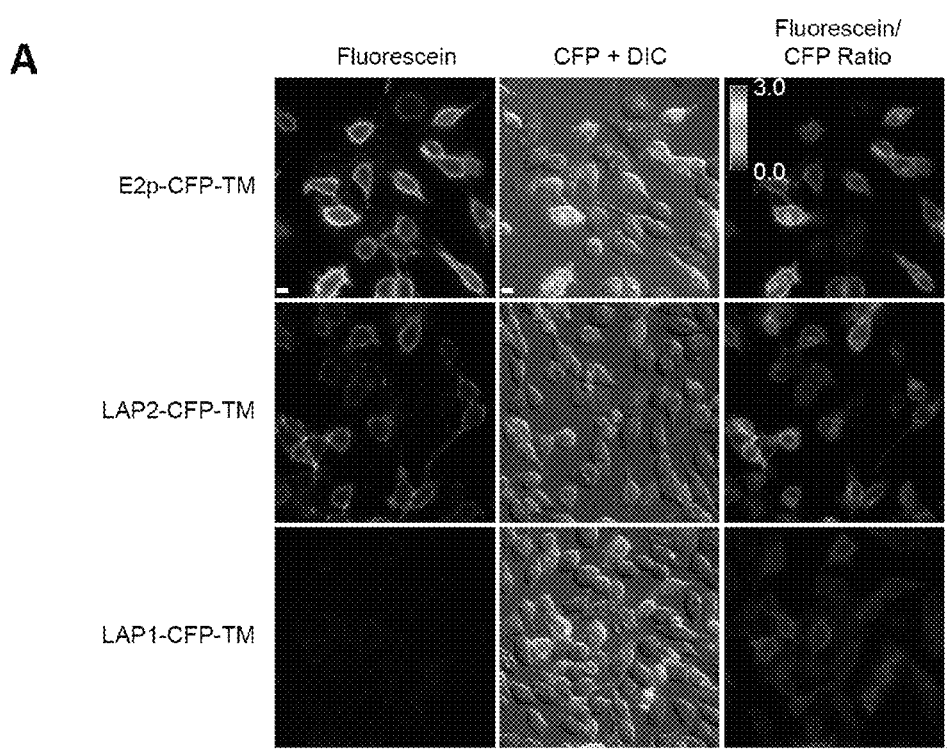
FIG. 9 depicts cell surface lipoylation of LAP sequences and E2p.
Figure 10:
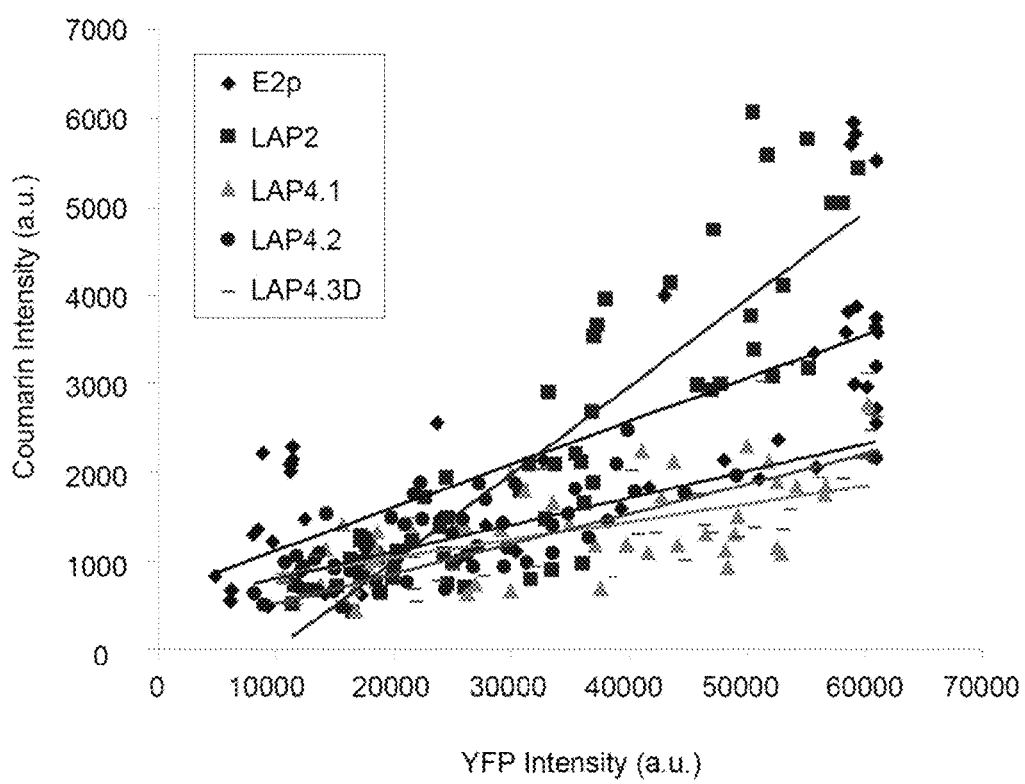
FIG. 10 shows a comparison of LAP sequences for intracellular protein labeling with a coumarin fluorophore ligase.[53] Various LAP sequences or E2p were fused to Yellow Fluorescent Protein (YFP) and expressed in the nuclei of HEK293T cells. The fusion proteins were labeled for 10 minutes with 7-hydroxycoumarin using an engineered coumarin fluorophore ligase.[53] To evaluate labeling efficiency, the mean coumarin intensity was plotted against the mean YFP intensity, for single cells. A high coumarin/YFP ratio signifies high labeling yield. LAP2-YFP expression levels were comparable to E2p-YFP expression levels in this assay.

Second, the LAPs were compared in a cell surface lipoylation assay (FIG. 9). CFP-TM fusion constructs were expressed in human embryonic kidney 293 (HEK) cells, and lipoylation was carried out by purified Lp1A enzyme added to the media. After 10 min of labeling, lipoylated cell surface proteins were imaged using antilipoic acid antibody. FIG. 9A shows representative images of labeled E2p, LAP2, and LAP1. The surface expression levels of TM fusions to LAP peptides are ~2-fold lower than TM fusions to E2p. However, expression levels of intracellular proteins are similar, whether fused to a LAP sequence or E2p (FIG. 10). Whereas E2p and LAP2 were lipoylated to a similar degree, labeling was not detected under these conditions for LAP1. To quantitatively compare the labeling efficiencies of all the LAP sequences, lipoylation signal (as measured by antibody staining intensity) was plotted against CFP signal for single cells. Average signal ratios listed in FIG. 9 indicate that LAP2 is labeled more efficiently than the other LAP sequences, and is comparable even to E2p.

Third, the LAP sequences were compared in an intracellular labeling assay. In separate work, a coumarin fluorophore ligase was engineered for labeling of recombinant proteins in living mammalian cells.[32] To compare the LAP sequences using this assay, fusions were prepared to nuclear-localized yellow fluorescent protein (YFP), and transfected cells were labeled with the coumarin probe for 10 min. Afterward, images were analyzed by plotting mean single cell coumarin intensities against mean single cell YFP intensities. FIG. 10 shows that LAP2 is labeled more efficiently than the other LAP sequences in the cytosol, and gives even higher signal intensities than E2p, at high expression levels.

Figure 4:
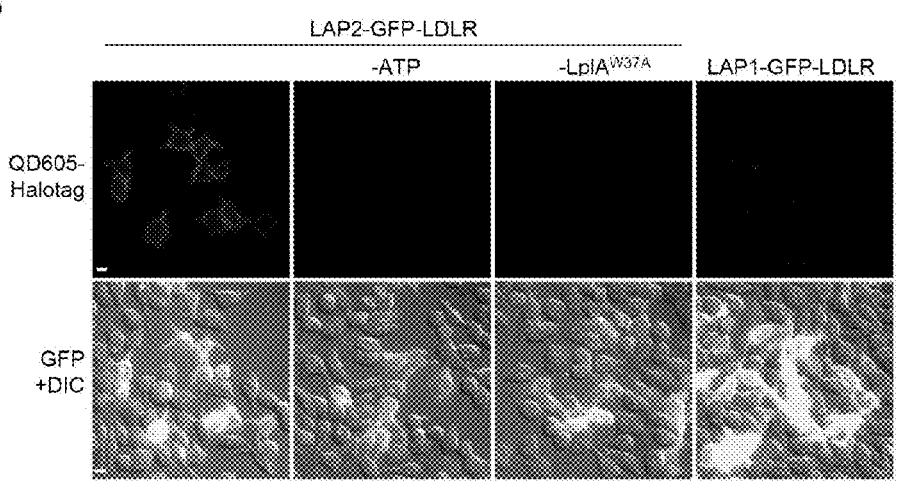
FIG. 4 presents a comparison of LAP clones and demonstrates an application of such clones to cell surface quantum dot tagging.

Fourth, LAP sequences were compared in vitro in an HPLC assay,[13] after expressing and purifying the HP1 fusion proteins[13] from bacteria. FIG. 4A shows the percent conversion to lipoylated product under identical reaction conditions. As in the cellular assays, LAP2 is the best sequence. When fused to the C- rather than N-terminus of HP1, the activity of LAP2 decreased somewhat, but was still higher than all other LAP sequences at the N-terminus. HPLC assays were also performed using other probes (azide 7, 11-Br, and coumarin) and LAP2 was found to be the best substrate for these also.

Characterization of LAP2 and Application to Receptor Labeling

Figure 11:
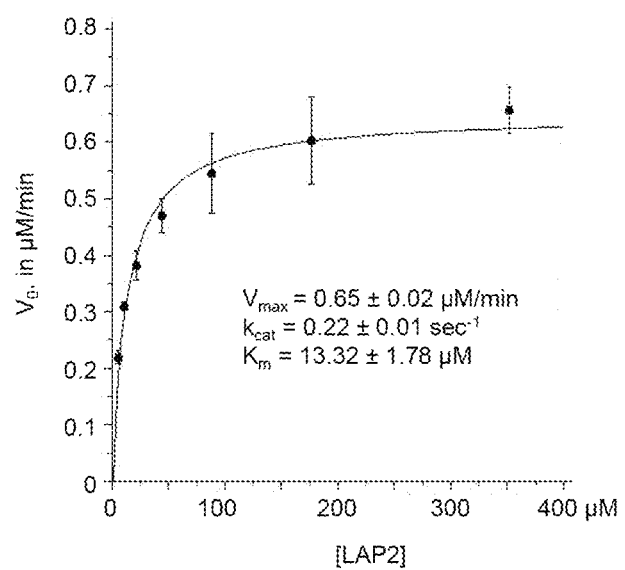
FIG. 11 presents a graph depicting LAP2 kinetics. Various concentrations of synthetic LAP2 peptide (not a fusion protein) were lipoylated with 50 nM Lp1A, 750 µM lipoic acid, and 3 mM ATP, and initial reaction rates were measured by HPLC. The Michaelis-Menten curve shows the initial rates plotted as a function of LAP2 concentration. Measurements were performed in triplicate. Error bars, ±1 s.d.

Using HPLC to quantify product formation, the $k_{cat}$ and $K_m$ values were measured for Lp1A-catalyzed lipoylation of a synthetic LAP2 peptide (without an attached fusion protein). FIG. 11 shows that the $k_{cat}$ is $0.22 \pm 0.01$ s$^{-1}$, slightly lower than that of E2p ($k_{cat}$ $0.253 \pm 0.003$ s$^{-1}$ [13]). The $K_m$ is $13.32 \pm 1.78$ μM, closer to that of Lp1A's natural substrate H-protein ($K_m$ 1.2 μM[33]) than that of LAP1 (est. $K_m$ >200 μM).

To utilize LAP2 for receptor imaging, a fusion was prepared to the low density lipoprotein (LDL) receptor. LAP2-LDL receptor expressed in HEK cells was labeled with Lp1AW37A and 11-Br probe. Ligated bromoalkane was derivatized with HaloTag-conjugated quantum dot 605 (QD605). FIG. 4B shows specific QD605 labeling of LAP2-LDL receptor at the cell surface. Omission of ATP or Lp1A eliminated labeling. The same experiment performed with LAP1-fused LDL receptor did not produce any detectable QD605 signal.

Lp1A labeling can be used in conjunction with biotin ligase (BirA) labeling, for two-color imaging applications.[13,31] HPLC was used to test the cross-reactivity of LAP2 with BirA. No biotinylation was found after a 12 h reaction with 5 μM BirA.

TABLE 1

Forward oligonucleotide sequences

| Peptide | Forward Oligos |
|---|---|
| LAP4.1 | 5'CTAGCGGATTTGAACTTGATAAAGTATGGTTTGATGTCGATTCAC (SEQ ID NO: 1080) |
| LAP4.2 | 5'CTAGCGGATTCGAGATTGATAAAGTATGGCATGATTTCCCTGCAC (SEQ ID NO: 1081) |
| LAP4.3D | 5'CTAGCGGATTTGAGCATGAGAAAGTTTGGTATGATCTCGATGCGC (SEQ ID NO: 1082) |
| LAP2 | 5'CTAGCGGCTTCGAGATCGACAAGGTGTGGTACGACCTGGACGCCC (SEQ ID NO: 1083) |
| LAP2-C | 5'CTAGCGGCTTCGAGATCGACAAGGTGTGGTACGACCTGGACGCCTAAGAG (SEQ ID NO: 1084) |

TABLE 2

Reverse oligonucleotide sequences

| Peptide | Reverse Oligos |
|---|---|
| LAP4.1 | 5'AATTGTGAATCGACATCAAACCATACTTTATCAAGTTCAAATCCG (SEQ ID NO: 1085) |
| LAP4.2 | 5'AATTGTGCAGGGAAATCATGCCATACTTTATCAATCTCGAATCCG (SEQ ID NO: 1086) |
| LAP4.3D | 5'AATTGCGCATCGAGATCATACCAAACTTTCTCATGCTCAAATCCG (SEQ ID NO: 1087) |
| LAP2 | 5'AATTGGGCGTCCAGGTCGTACCACACCTTGTCGATCTCGAAGCCG (SEQ ID NO: 1088) |
| LAP2-C | 5'GATCCTCTTAGGCGTCCAGGTCGTACCACACCTTGTCGATCTCGAAGCCG (SEQ ID NO: 1089) |

Discussion

In summary, a new peptide substrate for Lp1A has been engineered herein using a novel selection platform based on yeast display. The peptide, LAP2, is lipoylated with a $k_{cat}$ similar to that of Lp1A's protein substrate E2p, and has a $K_m$ much closer to that of Lp1A's protein substrates than that of the previous rationally designed LAP1.[13] The consequence of this improvement in kinetic efficiency is the ability to label peptide-tagged cell surface receptors with unnatural probes, even at low or medium receptor expression levels. In other work, LAP2 also allows fluorophore tagging of intracellular proteins.[32] In contrast, LAP1 fusions are difficult to label at the cell surface,[13,28] and have not thus far been found to label inside of living cells.[32] LAP2 is also shorter than LAP1 (13 amino acids instead of 17-22 amino acids) and can be recognized by Lp1A at the N-terminus, C-terminus, and internally.[32]

Comparing LAP2 to Lp1A's natural protein substrates, the negatively charged residues at positions −1, −3, and +4, and the hydrophobic residues at positions −4 and +5 are shared. Since −1 Asp of E2p may promote loop formation (FIG. 5), and +4 Glu in E2p may interact with Lys143 in Lp1A's binding pocket (see above), LAP2 may interact with Lp1A in a manner similar to E2p. When overlaying the LAP2 sequence onto the E2p NMR structure (FIG. 5),[34] the −4 Phe and the +3 Tyr are positioned to interact in an intramolecular manner. Without wishing to be bound by any theory, this interaction may help to stabilize LAP2 in a loop conformation that promotes high affinity binding to Lp1A. Additionally, the +2 Trp that emerged in the selections described herein may be positioned to interact with a hydrophobic patch on the Lp1A surface that includes Phe24.

This study also introduces a new selection scheme for evolution of peptide substrates. Previously, yeast display has been used to evolve enzyme specificity,[35,50] binding peptides,[26] and binding proteins,[38] but, to our knowledge, no enzymatic substrates have been evolved by this method. Also, previously, two generations of phage display selections were used (as opposed to the single generation of selections used here) to produce a peptide substrate for yeast biotin ligase with a $k_{cat}/K_m$ of only 0.00078 μM$_{-1}$ min$^{-1}$,[21] >1000-fold worse than the $k_{cat}/K_m$ obtained here for LAP2. Yin et al. have also used phage display to evolve peptide substrates for phosphopantetheinyl transferases, and obtained $K_m$ values in the 51-117 μM range, with $k_{cat}/K_m$ in the range of 0.015-0.19

µM⁻¹ min⁻¹ [23]. Again, these values are poorer than the corresponding values for LAP2. The selection scheme developed herein should be generalizable to other classes of enzyme substrates, such as those for kinases and glycosyltransferases, as long as the enzymatic products can be detected by fluorescence. Future work will involve the engineering of even shorter LAP sequences, performing biochemical assays and crystallography to determine the mode of LAP binding to Lp1A, and evolving orthogonal LAP/Lp1A pairs for multicolor imaging applications.

Materials and Methods

Cloning of Aga2p Fusions to LAP1 and E2p for Yeast Display

The E2p gene was amplified from E2p-CFP-TM[13] using the primers E2p-NheI-PCR (5'GCATC GCTAGC ATG GCT ATC GAA ATC AAA GTA CCG G (SEQ ID NO:1090); incorporates an NheI site) and E2p-BamHI-PCR (5'GGTGA GGATCC CGC AGG AGC TGC CGC AG (SEQ ID NO:1091); incorporates a BamHI site). The resulting PCR product was digested with NheI and BamHI and ligated inframe to NheI/BamHI-digested pCTCON2 vector.[41] To clone the Aga2p fusion to LAP1, the oligos LAP1-NheIBamHI-F (5'CTAGC GAC GAA GTA CTG GTT GAA ATC GAA ACC GAC AAA GCA GTT CTG GAA GTA CCG GGC GGT GAG GAG GAG G (SEQ ID NO:1092)) and LAP1-NheIBamHI-R (5'GATCC CTC CTC CTC ACC GCC CGG TAC TTC CAG AAC TGC TTT GTC GGT TTC GAT TTC AAC CAG TAC TTC GTC G (SEQ ID NO:1093)) were hybridized. The annealed oligos encode the 22-amino acid LAP1 sequence DEVLVEIETDKAVLEVPGGEEE (SEQ ID NO:1094).[13] The duplex DNA was then ligated in-frame to NheI/BamHI-digested pCTCON2 vector. The E2p-Ala mutant was generated by Lys40fAla mutagenesis using the QuikChange oligo 5' GATCACCGTA-GAAGGCGAC GCT GCTTCTATGGAAGTTCCGGC (SEQ ID NO:1095) and its reverse complement.

Model Selections on Yeast with LAP1 and E2p

Aga2p-E2p and Aga2p-LAP1 plasmids were transformed into *Saccharomyses cerevisiae* EBY100 using the Frozen-EZ Yeast Transformation II kit (Zymo Research). After transformation, cells were grown in SDCAA media[41] at 30° C. with shaking for 20 h. The culture was then diluted to a cell density of 10⁶ cells/mL in SGCAA media[41] to induce protein expression for 20 h with shaking at room temperature. Cells were harvested by centrifugation and washed with PBSB (phosphate buffered saline, pH 7.4+0.5% BSA).

To lipoylate the yeast, 10⁶-10⁷ cells were pelleted at 14,000g for 30 s in a 1.5 mL Eppendorf tube, then resuspended in 100 µL of PBSB. To these cells, 750 µM (±)-α-lipoic acid, 300 nM Lp1A, 3 mM ATP, and 5 mM magnesium acetate were added. The cells were incubated on a rotator for 30 mM at 30° C. After washing the cells once with PBSB, cells were incubated with rabbit antilipoic acid antibody (1:300 dilution, Calbiochem) and mouse anti-c-Myc antibody (1:50 dilution, Calbiochem) for 40 mM at 4° C. The cells were washed again with PBSB followed by incubation with phycoerythrin-antirabbit antibody (1:100 dilution, Invitrogen) and Alexa Fluor 488-antimouse antibody (1:100 dilution, Invitrogen) for 40 mM at 4° C. Finally, cells were rinsed twice with PBSB and resuspended in 600 µL of PBSB for FACS analysis on a FACScan instrument, or FACS sorting on an Aria FACS instrument, both from BD Biosciences, and housed in the Koch Institute flow cytometry core facility.

For c-Myc tag detection, initially a chicken anti-c-Myc antibody was used. However, that anti-chicken antibody was found to cross-react with rabbit antibodies, and thus a mouse anti-c-Myc antibody was used instead, which gives a lower signal, but does not bind to the rabbit antilipoic acid antibody.

To implement the model selections, E2p-displaying yeast and LAP1-displaying yeast were combined in various ratios. A total of 10⁷ cells were lipoylated as described above in 100 µL PBSB. Following labeling, cells were sorted using a typical polygonal gate as shown in FIG. 2B. ~5% of cells were recovered from the 1:10 mixture of E2p:LAP1, 0.5% of cells from the 1:100 mixture, and <0.1% of cells from the 1:1000 mixture. Collected cells were amplified in SDCAA media for 24-48 h. Plasmids were isolated using Zymoprep II (Zymo Research). For PCR analysis of enrichment factors, the primers pctPCR•F (5'GCGGTTCTCACCCCTCAACAAC (SEQ ID NO:1096)) and pctPCR•R (5'GTATGTGTAAAGTTG-GTAACGGAACG (SEQ ID NO:1097)) were used.

Cloning of LAP Library

A partially randomized oligo with the following sequence: 5'A AAT AAG CTT TTG TTC GGA TCC NGM MNN NAN NTS MNN MNN AAC TTT ATC MNN NTS NAN TCC GCT AGC CGA CCC TCC (SEQ ID NO:1098) was ordered from IDT (Integrated DNA Technologies). Underlined nucleotides were synthesized from mixtures containing 70% of the indicated base +10% of each of the other bases. N designates an equimolar mixture of all bases. S designates a 1:1 mixture of G and C. M designates a 1:1 mixture of A and C.

This oligo was annealed with another oligo, Con2For•F (5'CT AGT GGT GGA GGA GGC TCT GGT GGA GGC GGT AGC GGA GGC GGA GGG TCG GCT AGC GGA (SEQ ID NO:1099)), which overlaps with both pCTCON2 vector and the library oligo. The 5' overhangs were filled in using Klenow polymerase. The resulting product was PCR-amplified using the primers Con2For•F and Con2Rev•R (5'TA TCA GAT CTC GAG CTA TTA CAAGTC CTC TTC AGA AAT AAG CTT TTG TTC GGA TCC (SEQ ID NO:1100)). Meanwhile, pCT-CON2 vector was prepared by digestion with NheI and BamHI, and gel-purified. PCR insert and pCTCON2 vector were transformed together into *S. cerevisiae* EBY100 (Invitrogen) by electroporation as described by Colby et al.[51] Homologous recombination occurred inside the yeast. Serial dilutions of transformed yeast were plated on SDCAA plates and colonies were counted, to determine transformation efficiency.

Yeast Display Selection on LAP Library

Yeast displaying the LAP library were prepared as described above (see Model Selections). The cells (~7×10⁷) were washed and resuspended in 700 µL of PBSB. For the first round, HaloTag labeling was performed. Cells were combined with 1 mM 11-Br, 5 µM Lp1A(W37A), 3 mM ATP, and 5 mM magnesium acetate for 2.5 h at 30° C. After washing with PBSB, 700 nM biotinylated-HaloTag protein[31] was incubated with the cells in 50 µL of PBSB for 30 min at 30° C. HaloTag protein was biotinylated by EZ-Link Sulfo-NHS-LC-Biotin (sulfosuccinimidyl-6-(biotinamido)hexanoate) (Thermo Fisher Scientific) as described by the manufacturer. Then, cells were rinsed once with PBSB and labeled with streptavidin-phycoerythrin (1:100 dilution, Jackson ImmunoResearch) for 40 min at 4° C. For detection of the c-Myc tag, chicken anti-c-Myc antibody (1:200 dilution, Invitrogen) and Alexa Fluor 488-anti-mouse antibody (1:100 dilution, Invitrogen) were used. Labeled cells were rinsed twice with PBSB and resuspended in 1 mL of PBSB for FACS sorting. After sorting, collected yeast cells were amplified in SDCAA media at 30° C. for 36-48 h and induced with SGCAA media at 30° C. for 20 h, for the next round.

Rounds 2-4 were implemented with 11-Br or lipoic acid labeling, under the conditions indicated in FIG. 3B. Lipoylation was carried out as described above under Model Selections.

Analysis of Yeast Pools after Each Round of Selection

Yeast harvested from each round of selection were amplified and induced as described above. All pools were then treated identically with 3 µM Lp1A or 50 nM Lp1A, 750 µM (±)-α-lipoic acid, and 3 mM ATP for 30 min. To sequence individual clones, yeast were plated on SDCAA plates, single colonies were amplified in SDCAA media, and plasmid was isolated using the Zymoprep Yeast Plasmid Miniprep kit (Zymo Research). To increase DNA concentration, LAP genes were PCR-amplified from plasmid using the primers PctPCR • F and PctPCR • R (sequences under Model Selections). Sequencing was completed using the primer PctSeq (5'GGCAGCCCCATAAACACAC (SEQ ID NO:1101)).

Cloning and Expression of LAP-HP1 Fusion Proteins

First, an MfeI restriction site was introduced into the previously described[13] LAP1-HP1 expression plasmid, at the C-terminal end of the LAP1 sequence, using the QuikChange primer 5' AAGCAGTTCTGGAAGTACCG CAATTG GGCGGTGAGGAGGAGTACGCC (SEQ ID NO:1102) and its reverse complement. The forward and reverse oligos shown in Table 1 and 2 were then annealed, and the duplex DNA was ligated in-frame into NheI/MfeI-digested LAP1-(MfeI)-HP1 vector. The vector introduced a C-terminal His$_6$ tag. Bacterial expression and purification were carried out as previously described.[13]

C-terminal fusion of LAP2 to HP1 was performed by annealing LAP2-C forward and reverse oligos (Table 1 and 2), and ligating the duplex in-frame to NdeI/BamHI digested pET15b vector, which introduces an N-terminal His$_6$ tag.

Comparison of LAP Clones by HPLC Assay

To compare the labeling efficiencies of the different LAP-HP1 fusion proteins, labeling reactions were assembled as follows: 50 nM Lp1A, 60 µM LAP-HP1 or E2p, 750 µM (±)-α-lipoic acid, 3 mM ATP, and 5 mM magnesium acetate in Dulbecco's phosphate buffered saline (DPBS). Reactions were incubated at 30° C. for 1 h, and then quenched with 180 mM EDTA (final concentration). The extent of conversion to lipoylated product was determined by HPLC as described in previous work.[13,28]

Cloning of LAP Fusion Proteins for Mammalian Expression

Three QuikChange mutations were made on the published pEGFP-LAP-LDLR construct.[13] 5'GAAGTACCATCAG-CAGACGGCCAATTG ACTGTGAGCAAGGGCGAGG (SEQ ID NO:1103) and its reverse complement were used to introduce MfeI site to 3' end of LAP1. Subsequently, 5'GCACCTCGGTTCTATCGATA ACGCGT AC-CATGGGGCCCTGGGGC (SEQ ID NO:1104) and its reverse complement were used to mutate upstream (outside of the gene) NheI site to MluI. A new NheI site was then introduced to 5' end of LAP1 using 5'CTG-CAGTTGGCGACA-GAAGT GCTAGC GACGAAGTACTGGT-TGAAATC (SEQ ID NO:1105) and its reverse complement. This expression vector was named LAP1-GFP-LDLR.

LAP2-GFP-LDLR was obtained by annealing LAP2 forward and reverse oligos used for LAP2 HP1 fusion protein and ligating the duplex DNA in-frame into NheI/MfeI-digested LAP1-GFP-LDLR. LAP2-CFP-TM was generated by annealing LAP2-BglIIAscI-F (5'GATCT GGC TTC GAG ATC GAC AAG GTG TGG TAC GAC CTG GAC GCC GG (SEQ ID NO:1106)) and LAP2-BglIIAscI-R (5'CGCGCC GGC GTC CAG GTC GTA CCA CAC CTT GTC GAT CTC GAA GCC A (SEQ ID NO:1107)) and ligating the duplex DNA in-frame into BglII/AscI digested LAP-CFP-TM (renamed as LAP1-CFP-TM).[13] E2p-CFP-TM has previously been described.[13]

Cell Surface Quantum Dot Labeling of LAP2 with Lp1A

HEK 293T cells were transfected with LAP2-GFP-LDLR plasmid using Lipofectamine 2000. After 24 h in growth media (Dulbecco's Modified Eagle Medium (DMEM) with 10% fetal bovine serum (FBS)) at 37° C., enzymatic ligation of 11-Br was performed in DPBS containing 10 µM Lp1A (W37A), 500 µM 11-Br, 1 mM ATP, 5 mM Mg(OAc)2 and 1% (w/v) BSA (Fraction V, EMD) as a blocking agent for 5 min at room temperature. Cells were then rinsed three times with DPBS followed by treatment with 50 nM HaloTag-QD60531 in DPBS containing 1% BSA for 5 min at room temperature. After another three rinses with DPBS, cells were imaged in the same buffer on a Zeiss Axio Observer.Z1 inverted epifluorescence microscope using a 40X oil-immersion lens. GFP (493/16 excitation, 525/30 emission, 488 dichroic, 300 ms exposure), QD605 (400/120 excitation, 605/30 emission, 488 dichroic, 200 ms exposure), and DIC images were collected and analyzed using Slidebook software (Intelligent Imaging Innovations). Fluorescence images were normalized to the same intensity ranges.

Cloning and Analysis of −4 Phe→Val Mutant of LAP4.1 pCTCON2 plasmid carrying LAP4.1 was isolated from yeast clone using the Zymoprep Yeast Plasmid Miniprep kit. Phe at position −4 was mutated to Val using the QuikChange primer 5'GGAGGGTCGGCTAGCGGA GTG GAACT-TGATAAAGTATGGTTTGATGTCG (SEQ ID NO:1108) and its reverse complement primer. This construct was subsequently transformed into S. cerevisiae EBY100, grown and induced as described above (see "Model selections"). To compare the yeast cell surface lipoylation of the Phe→Val mutant with the original LAP4.1 clone, clones from Gate A and the clones from Gate B, cells were lipoylated as described above except that 200 nM Lp1A was used.

Cell Surface Lipoylation of LAP Constructs

HEK 293T or HeLa cells were transfected with LAP4.1-, LAP4.3D-, E2p, LAP2-, or LAP1-CFP-TM13 plasmids using Lipofectamine 2000. After 24 h in growth media (DMEM with 10% FBS) at 37° C., lipoylation was performed in growth media containing 1 µM Lp1A, 100 µM (±)-α-lipoic acid, 1 mM ATP, 5 mM Mg(OAc)$_2$ and 1% (w/v) BSA for 10 min at room temperature. Cells were then rinsed three times with DPBS followed by incubation with rabbit antilipoic acid antibody (1:300 dilution, Calbiochem) in DPBS containing 1-2% BSA for 10 min at room temperature. Fluorescence staining was achieved by treatment with either fluorescein-conjugated goat antirabbit antibody (1:100 dilution, Calbiochem) or Alexa Fluor 568-conjugated goat antirabbit antibody (1:100 dilution, Invitrogen) for 10 min at room temperature in DPBS with 1-2% BSA. Cells were imaged as described above using CFP (420/20 excitation, 475/40 emission, 450 dichroic, 500 ms exposure), fluorescein (493/120 excitation, 525/30 emission, 488 dichroic, 100 ms exposure) and Alexa Fluor 568 (570/20 excitation, 605/30 emission, 585 dichroic, 200 ms exposure) filter sets. Slidebook software was used for emission intensity ratio quantitation. Average across-cell fluorescein and CFP intensities were used, after background subtraction.

Measurement of LAP2 Kinetics

Synthetic LAP2 peptide (sequence GFEIDKVWYDLDA (SEQ ID NO:1)) was prepared by the Tufts University Core Facility. To measure the $k_{cat}$ and $K_m$ values for lipoylation, 50 nM Lp1A was combined with 750 µM lipoic acid, 2 mM ATP, and 5 mM magnesium acetate in DPBS. Varying concentrations of LAP2 (5.5, 11, 22, 44, 88, 176, or 352 µM) were used;

60 μL aliquots were removed from the 30° C. reactions at 5 min intervals, up to 20 min, and quenched with 180 mM EDTA (final concentration). HPLC was used to determine the amount of product in each aliquot, and kinetic parameters were extracted using the Michaelis-Menten equation as described previously.[13,28]

REFERENCES (1) Feng, S. B.; Kasahara, C.; Rickles, R. J.; Schreiber, S. L. *Proc. Natl. Acad. Sci. U.S.A.* 1995, 92, 12408-12415.
(2) Rowland, R. R. R.; Schneider, P.; Fang, Y.; Wootton, S.; Yoo, D.; Benfield, D. A. *Virology* 2003, 316, 135-145.
(3) Hall, J. G.; Frieden, C. *Proc. Natl. Acad. Sci. U.S.A.* 1989, 86, 3060-3064.
(4) Zerella, R.; Chen, P. Y.; Evans, P. A.; Raine, A.; Williams, D. H. *Protein Sci.* 2000, 9, 2142-2150.
(5) Toomik, R.; Ek, P. *Biochem. J.* 1997, 322, 455-460.
(6) Cummings, R. T.; Salowe, S. P.; Cunningham, B. R.; Wiltsie, J.; Park, Y. W.; Sonatore, L. M.; Wisniewski, D.; Douglas, C. M.; Hermes, J. D.; Scolnick, E. M. *Proc. Natl. Acad. Sci. U.S.A.* 2002, 99, 6603-6606.
(7) Shamoo, Y.; Steitz, T. A. *Cell* 1999, 99, 155-166.
(8) Ghose, R.; Shekhtman, A.; Goger, M. J.; Ji, H.; Cowburn, D. *Nat. Struct. Biol.* 2001, 8, 998-1004.
(9) Borghouts, C.; Kunz, C.; Groner, B. *J. Pept. Sci.* 2005, 11, 713-726.
(10) Sato, A. K.; Viswanathan, M.; Kent, R. B.; Wood, C. R. *Curr. Opin. Biotechnol.* 2006, 17, 638-642.
(11) Lin, M. Z.; Wang, L. *Physiology* 2008, 23, 131-141.
(12) Khan, A. R.; Parrish, J. C.; Fraser, M. E.; Smith, W. W.; Bartlett, P. A.; James, M. N. G. *Biochemistry* 1998, 37, 16839-16845.
(13) Fernandez-Suarez, M.; Baruah, H.; Martinez-Hernandez, L.; Xie, K. T.;
(14) Mitchell, R. D.; Glass, D. B.; Wong, C. W.; Angelos, K. L.; Walsh, D. A. *Biochemistry* 1995, 34, 528-534.
(15) Viguera, A. R.; Arrondo, J. L. R.; Musacchio, A.; Saraste, M.; Serrano, L. *Biochemistry* 1994, 33, 10925-10933.
(16) Rudiger, S.; Schneider-Mergener, J.; Bukau, B. *EMBO J.* 2001, 20, 1042-1050.
(17) Lam, K. S.; Wu, J. Z.; Lou, Q. *Int. J. Pept. Protein Res.* 1995, 45, 587-592.
(18) Reineke, U.; Volkmer-Engert, R.; Schneider-Mergener, J. *Curr. Opin. Biotechnol.* 2001, 12, 59-64.
(19) Marani, M. M.; Ceron, M. C. M.; Giudicessi, S. L.; de Oliveira, E.; Cote, S.; Erra-Balsells, R.; Albericio, F.; Cascone, O.; Camperi, S. A. *J. Comb. Chem.* 2009, 11, 146-150.
(20) Herman, R. E.; Badders, D.; Fuller, M.; Makienko, E. G.; Houston, M. E.; Quay, S. C.; Johnson, P. H. *J. Biol. Chem.* 2007, 282, 9813-9824.
(21) Chen, I.; Choi, Y. A.; Ting, A. Y. *J. Am. Chem. Soc.* 2007, 129, 6619-6625.
(22) Sidhu, S. S.; Koide, S. *Curr. Opin. Struct. Biol.* 2007, 17, 481-487.
(23) Zhou, Z.; Cironi, P.; Lin, A. J.; Xu, Y. Q.; Hrvatin, S.; Golan, D. E.; Silver, P. A.; Walsh, C. T.; Yin, J. *ACS Chem. Biol.* 2007, 2, 337-346.
(24) Schatz, P. J. *Biotechnology* 1993, 11, 1138-1143.
(25) Dane, K. Y.; Chan, L. A.; Rice, J. J.; Daugherty, P. S. *J. Immunol. Methods* 2006, 309, 120-129.
(26) Krauland, E. M.; Peelle, B. R.; Wittrup, K. D.; Belcher, A. M. *Biotechnol. Bioeng.* 2007, 97, 1009-1020.
(27) Wolkowicz, R.; Jager, G. C.; Nolan, G. P. *J. Biol. Chem.* 2005, 280, 15195-15201.
(28) Baruah, H.; Puthenveetil, S.; Choi, Y. A.; Shah, S.; Ting, A. Y. *Angew. Chem., Int. Ed.* 2008, 47, 7018-7021.
(29) Cronan, J. E.; Zhao, X.; Jiang, Y. *Adv. Microb. Physiol.* 2005, 50, 103-146.
(30) Los, G. V.; Encell, L. P.; McDougall, M. G.; Hartzell, D. D.; Karassina, N.; Zimprich, C.; Wood, M. G.; Learish, R.; Ohana, R. F.; Urh, M.; Simpson, D.; Mendez, J.; Zimmerman, K.; Otto, P.; Vidugiris, G.; Zhu, J.; Darzins, A.; Klaubert, D. H.; Bulleit, R. F.; Wood, K. V. *ACS Chem. Biol.* 2008, 3, 373-382.
(31) Liu, D. S.; Phipps, W. S.; Howarth, M.; Puthenveetil, S.; Ting, A. Y. Irreversible targeting to a peptide in living cells using lipoate ligase and Halotag: Application to two-color quantum dot tracking of receptors, 2009. Unpublished work.
(32) Baruah, H.; Uttamapinant, C.; White, K. A.; Fernández-Suárez, M.; Puthenveetil, S.; Thompson, S.; Ting, A. Y. *A fluorophore ligase for site-specific protein labeling in living cells*, 2009. Unpublished work.
(33) Fujiwara, K.; Toma, S.; Okamura-Ikeda, K.; Motokawa, Y.; Nakagawa, A.; Taniguchi, H. *J. Biol. Chem.* 2005, 280, 33645-33651.
(34) Jones, D. D.; Stott, K. M.; Howard, M. J.; Perham, R. N. *Biochemistry* 2000, 39, 8448-8459.
(35) Gautier, A.; Juillerat, A.; Heinis, C.; Correa, I. R., Jr.; Kindermann, M.; Beaufils, F.; Johnsson, K. *Chem. Biol.* 2008, 15, 128-136.
(36) Fujiwara, K.; Suzuki, M.; Okumachi, Y.; Okamura-Ikeda, K.; Fujiwara, T.; Takahashi, E.; Motokawa, Y. *Eur. J. Biochem.* 1999, 260, 761-767.
(37) Kim, D. J.; Kim, K. H.; Lee, H. H.; Lee, S. J.; Ha, J. Y.; Yoon, H. J.; Suh, S. W. *J. Biol. Chem.* 2005, 280, 38081-38089.
(38) Gai, S. A.; Wittrup, K. D. *Curr. Opin. Struct. Biol.* 2007, 17, 467-473.
(39) Paschke, M. *Appl. Microbiol. Biotechnol.* 2006, 70, 2-11.
(40) Martin, B. R.; Giepmans, B. N.; Adams, S. R.; Tsien, R. Y. *Nat. Biotechnol.* 2005, 23, 1308-1314.
(41) Chao, G.; Lau, W. L.; Hackel, B. J.; Sazinsky, S. L.; Lippow, S. M.; Wittrup, K. D. *Nat. Protoc.* 2006, 1, 755-768.
(42) Bagautdinov, B.; Matsuura, Y.; Bagautdinova, S.; Kunishima, N. *J. Biol. Chem.* 2008, 283, 14739-14750.
(43) Dardel, F.; Davis, A. L.; Laue, E. D.; Perham, R. N. *J. Mol. Biol.* 1993, 229, 1037-1048.
(44) Howard, M. J.; Chauhan, H. J.; Domingo, G. J.; Fuller, C.; Perham, R. N. *J. Mol. Biol.* 2000, 295, 1023-1037.
(45) Ricaud, P. M.; Howard, M. J.; Roberts, E. L.; Broadhurst, R. W.; Perham, R. N. *J. Mol. Biol.* 1996, 264, 179-190.
(46) Reche, P.; Perham, R. N. *EMBO J.* 1999, 18, 2673-2682.
(47) Cui, G. F.; Nan, B. Y.; Hu, J. C.; Wang, Y. P.; Jin, C. W.; Xia, B. *J. Biol. Chem.* 2006, 281, 20598-20607.
(48) Reche, P. A. *Protein Sci.* 2000, 9, 1922-1929.
(49) Beckett, D.; Kovaleva, E.; Schatz, P. J. *Protein Sci.* 1999, 8, 921-929.
(50) Antipov, E.; Cho, A. E.; Wittrup, K. D.; Klibanov, A. M. *Proc. Natl. Acad. Sci. U.S.A.* 2008, 105, 17694-17699.
(51) Colby, D. W.; Kellogg, B. A.; Graff, C. P.; Yeung, Y. A.; Swers, J. S.; Wittrup, K. D. *Protein Eng.* 2004, 388, 348-358.
(52) Jones, D. D.; Stott, K. M.; Howard, M. J.; Perham, R. N. *Biochemistry* 2000, 39, 8448-8459.
(53) Baruah, H., Uttamapinant, C., White, K. A., Fernández-Suárez, M., Puthenveetil, S., Thompson, S, and Ting, A. Y.

A fluorophore ligase for site-specific protein labeling in living cells. 2009. Ref Type: Submitted

EQUIVALENTS

It should be understood that the preceding is merely a detailed description of certain embodiments. It therefore should be apparent to those of ordinary skill in the art that various modifications and equivalents can be made without departing from the spirit and scope of the invention, and with no more than routine experimentation. It is intended to encompass all such modifications and equivalents within the scope of the appended claims.

All references, patents and patent applications that are recited in this application are incorporated by reference herein in their entirety.

What is claimed is:

1. A lipoic acid ligase (Lp1A) acceptor peptide, wherein the peptide comprises 8-13 amino acids and a motif $P_{-4}P_{-3}P_{-2}P_{-1}P_0P_{+1}P_{+2}P_{+3}P_{+4}P_{+5}$ set forth as SEQ ID NOs:1151-1154, which includes, a central lysine residue at position 0 ($P_0$), a valine residue at position +1 ($P_{+1}$), a tryptophan residue at position +2 ($P_{+2}$), a glutamic acid or aspartic acid residue at position +4 ($P_{+4}$), a hydrophobic residue or no residue at position +5 ($P_{+5}$), a glutamic acid residue at position −3 ($P_{-3}$), a phenylalanine residue or no residue at position −4 ($P_{-4}$), and any amino acid residue in each of positions +3 ($P_{+3}$), −1 ($P_{-1}$), and −2 ($P_{-2}$).

2. The peptide of claim 1, wherein the peptide comprises the sequence GFEIDKVWYDLDA (SEQ ID NO: 1).

3. The peptide of claim 2, wherein the peptide consists of the sequence GFEIDKVWYDLDA (SEQ ID NO: 1).

4. A nucleic acid encoding the peptide of claim 1.

5. A composition comprising the peptide of claim 1 and a carrier.

6. A composition comprising the peptide of claim 1 wherein the peptide is N- or C-terminally fused to a target protein, and a carrier.

7. A lipoic acid ligase (Lp1A) acceptor peptide, wherein the peptide comprises 8-13 amino acids and a motif $P_{-4}P_{-3}P_{-2}P_{-1}P_0P_{+1}P_{+2}P_{+3}P_{+4}P_{+5}$ set forth as SEQ ID NOs:1155-1158, which includes, a central lysine residue at position 0 ($P_0$), a hydrophobic or serine residue at position +1 ($P_{+1}$), an aromatic residue at position +2 ($P_{+2}$), an aromatic, aliphatic hydrophobic, histidine, or threonine residue at position +3 ($P_{+3}$), a glutamic acid or aspartic acid residue at position +4 ($P_{+4}$), an aliphatic hydrophobic residue or no residue at position +5 ($P_{+5}$), an aspartic acid, asparagine, glutamic acid, tyrosine or alanine residue at position −1 ($P_{-1}$), a glutamic acid or aspartic acid residue at position −3 ($P_{-3}$), a hydrophobic or aromatic residue, or no residue at position −4 ($P_{-4}$), and any amino acid residue at position −2 ($P_{-2}$).

8. The peptide of claim 7, wherein the peptide comprises a motif $P_{-4}P_{-3}P_{-2}P_{-1}P_0 \ P_{+1}P_{+2}P_{+3}P_{+4}P_{+5} \ P_{+6}P_{+7}$ set forth as SEQ ID NOs: 1196, 1198, 1200, 1202, 1204, 1206, 1207, and 1209, in which position +7 ($P_{+7}$) is a serine residue, an alanine residue, or is absent, and position +6 ($P_{+6}$) is any amino acid residue.

9. The peptide of claim 7, wherein the peptide comprises a motif $P_{-5}P_{-4}P_{-3}P_{-2}P_{-1}P_0P_{+1}P_{+2}P_{+3}P_{+4}P_{+5}$ set forth as SEQ ID NOs: 1211-1214, in which position −5 ($P_{-5}$) is a glycine residue.

10. The peptide of claim 7, wherein the residue at position +1 is a valine, isoleucine, leucine, alanine, serine, or phenylalanine residue.

11. The peptide of claim 7, wherein the residue at position +2 is a tryptophan or phenylalanine residue.

12. The peptide of claim 7, wherein the residue at position +3 is a tyrosine, histidine, phenylalanine, isoleucine, valine, leucine, or threonine residue.

13. The peptide of claim 7, wherein the residue at position +5 is a leucine, isoleucine, or phenylalanine residue.

14. The peptide of claim 7, wherein the peptide comprises a motif $P_{-4}P_{-3}P_{-2}P_{-1}P_0P_{+1}P_{+2}P_{+3}P_{+4}P_{+5}P_{+6}$ set forth as SEQ ID NOs:1219-1222, in which the residue at position +6 ($P_{+6}$) is an aspartic acid, glutamic acid, serine, threonine, cysteine, or tyrosine residue.

15. The peptide of claim 7, wherein the residue at position −2 is an isoleucine, histidine, leucine, or arginine residue.

16. The peptide of claim 7, wherein the residue at position −4 is a phenylalanine, valine, leucine, or an isoleucine residue.

17. A nucleic acid encoding the peptide of claim 7.

18. A composition comprising the peptide of claim 7 and a carrier.

19. A composition comprising the peptide of claim 7, wherein the peptide is N- or C-terminally fused to a target protein, and a carrier.

\* \* \* \* \*